US009492521B2

(12) United States Patent
Liles et al.

(10) Patent No.: US 9,492,521 B2
(45) Date of Patent: Nov. 15, 2016

(54) **VACCINES FOR CONTROL OF EPIDEMIC *AEROMONAS HYDROPHILA* GENERATED BY MARKERLESS GENE DELETION**

(71) Applicant: Auburn Univeristy, Auburn, AL (US)

(72) Inventors: Mark R. Liles, Auburn, AL (US); Jeffery S. Terhune, Auburn, AL (US); Joseph C. Newton, Auburn, AL (US); Mohammad J. Hossain, Auburn, AL (US); Dawei Sun, Auburn, AL (US); Charles Thurlow, Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 14/724,388

(22) Filed: May 28, 2015

(65) Prior Publication Data

US 2015/0343045 A1    Dec. 3, 2015

Related U.S. Application Data

(60) Provisional application No. 62/003,953, filed on May 28, 2014.

(51) Int. Cl.
| | | |
|---|---|---|
| *C12N 1/20* | (2006.01) | |
| *A61K 39/02* | (2006.01) | |
| *C12N 15/74* | (2006.01) | |
| *C07K 16/18* | (2006.01) | |
| *A61K 39/00* | (2006.01) | |

(52) U.S. Cl.
CPC ........... *A61K 39/0208* (2013.01); *A61K 39/02* (2013.01); *C07K 16/18* (2013.01); *C12N 15/74* (2013.01); *A61K 2039/521* (2013.01); *A61K 2039/522* (2013.01); *A61K 2039/523* (2013.01); *A61K 2039/54* (2013.01); *A61K 2039/545* (2013.01); *A61K 2039/55* (2013.01); *A61K 2039/552* (2013.01)

(58) Field of Classification Search
CPC ................................................. A61K 39/0208
See application file for complete search history.

(56) References Cited

U.S. PATENT DOCUMENTS 7,302,913 B2    12/2007   Salonius et al.

OTHER PUBLICATIONS

Overstreet, R. M., S. S. Curran, et al. (2002). "*Bolbophorus damnificus* n. sp.(Digenea: Bolbophoridae) from the channel catfish Ictalurus punctatus and American white pelican Pelecanus erythrorhynchos in the USA based on life-cycle and molecular data." Systematic Parasitology 52(2): 81-96.
Padnos, M. and R. F. Nigrelli (1942). "Trichodina spheroidesi and Trichodina halli spp. nov. parasitic on the gills and skin of marine fishes, with special reference to the life-history of T. spheroidesi." Zoologica 27: 65-72.
Papema, I. (1972). "Infection by Ichthyophthirius multifiliis of fish in Uganda." The Progressive Fish-Culturist 34(3): 162-164.
Papema, I. 1991). "Diseases caused by parasites in the aquaculture of warm water fish." Annual Review of Fish Diseases 1: 155-194.
Pirhonen, J. and C. B. Schreck (2003). "Effects of anaesthesia with MS-222, clove oil and CO2 on feed intake and plasma cortisol in steelhead trout (Oncorhynchus mykiss)." Aquaculture 220(1): 507-514.
Pridgeon, J. W. and P. H. Klesius (2010). "Identification and expression profile of multiple genes in channel catfish fry 10min after modified live Flavobacterium columnare vaccination." Veterinary immunology and immunopathology 138 (1): 25-33.
Raupach, B. and S. H. Kaufmann (2001). "Bacterial virulence, proinflammatory cytokines and host immunity: how to choose the appropriate *Salmonella* vaccine strain?" Microbes and infection 3(14): 1261-1269.
Reeves, P. R., M. Hobbs, et al. (1996). "Bacterial polysaccharide synthesis and gene nomenclature." Trends in microbiology 4(12): 495-503.
Rogge, M.L., Dubytska, L., Jung; T.S., Wiles, J., Elkamel, A.A., Rennhoff, A., Oanh, D.T. and Thune, R.L. (2013) Comparison of Vietnamese and US isolates of Edwardsiella ictaluri. Diseases of aquatic organisms, 106, 17-29.
Sambrook, J., E. F. Fritsch, et al. (1989). Molecular cloning, Cold spring harbor laboratory press New York.
Schreier, T. M., J. J. Rach, et al. (1996). "Efficacy of formalin, hydrogen peroxide, and sodium chloride on fungal-infected rainbow trout eggs." Aquaculture 140(4): 323-331.
Sheehan. R. J. and W. M. Lewis (1986). "Influence of pH and ammonia salts on ammonia toxicity and water balance in young channel catfish." Transactions of the American fisheries Society 115(6): 891-899.
Shoemaker, C. A., P. H. Klesius, et al. (2002). "In vivo methods for utilizing the modified live Edwardsiella ictaluri vaccine against enteric septicemia in channel catfish." Aquaculture 203(3): 221-227.
Shoemaker, C. A., P. H. Klesius, et al. (2007). "Immunization of eyed channel catfish, Ictalurus punctatus, eggs with monovalent Flavobacterium columnare vaccine and bivalent F. columnare and Edwardsiella ictaluri vaccine." Vaccine 25(6): 1126-1131.
Shoemaker, C. A., P. H. Klesius, et al. (2009). "Use of modified live vaccines in aquaculture." Journal of the World Aquaculture Society 40(5): 573-585.
Skirpstunas, R. T. and T. J. Baldwin (2002). "Edwardsiella ictaluri invasion of IEC-6, Henle 407, fathead minnow and channel catfish enteric epithelial cells." Diseases of Aquatic Organisms 51(3): 161-167.

(Continued)

*Primary Examiner* — Albert Navarro
(74) *Attorney, Agent, or Firm* — Andrus Intellectual Property Law, LLP

(57) ABSTRACT

Disclosed are attenuated bacteria, compositions comprising attenuated bacteria, and vectors and methods for preparing attenuated bacteria. The attenuated bacteria may include attenuated *Aeromonas hydrophila* for use in vaccinating aquatic animals such as channel catfish against Motile *Aeromonas* Septicemia (MAS).

20 Claims, 24 Drawing Sheets

(56) References Cited

OTHER PUBLICATIONS

Stevens, R. E. (1959). The white and channel catfishes of the Santee-Cooper Reservoir and tailrace sanctuary. Proceedings of the Annual Conference Southeastern Association of Game and Fish Commissioners.

Subasinghe, R. (2005). "Aquaculture topics and activities—State of world aquaculture." FAO 2005-2014 FAO Fisheries and Aquaculture Department [online].

Thomason, L., D. L. Court, et al. (2007). "Recombineering: genetic engineering in bacteria using homologous recombination." Current protocols in molecular biology: 1.16. 11-11.16. 24.

Thune, R. L., L. A. Stanley, et al. (1993). "Pathogenesis of gram-negative bacterial infections in warm water fish." Annual Review of Fish Diseases 3: 37-68.

Tomasso, J., C. A. Goudie, et al. (1980). "Effects of environmental pH and calcium on ammonia toxicity in channel catfish." Transactions of the American fisheries Society 109(2): 229-234.

Tucker, C. S. and J. A. Hargreaves (2004). Biology and culture of channel catfish, Elsevier.

Urawa, S. (1992). "Epidermal responses of chum salmon (Oncorhynchus keta) fry to the ectoparasitic flagellate of Ichthyobodo necator." Canadian Journal of Zoology 70(8): 1567-1575.

Vignesh, R., B. Karthikeyan, et al. (2011). "Antibiotics in aquaculture: an overview." South Asian Journal of Experimental Biology 1(3): 114-120.

Wagner, B. A., D. J. Wise, et al. (2002). "The epidemiology of bacterial diseases in food-size channel catfish." Journal of Aquatic Animal Health 14(4): 263-272.

Wards, B., G. De Lisle, et al. (2000). "An esat6 knockout mutant of Mycobacterium bovis produced by homologous recombination will contribute to the development of a live tuberculosis vaccine." Tubercle and Lung Disease 80(4): 185-189.

West, N. P., P. Sansonetti, et al. (2005). "Optimization of virulence functions through glucosylation of Shigella LPS." Science 307(5713): 1313-1317.

Wolters, W. R. and M. R. Johnson (1994). "Enteric septicemia resistance in blue catfish and three channel catfish strains." Journal of Aquatic Animal Health 6(4): 329-334.

Zhang, D., J. W. Pridgeon, et al. (2013). "Expression and activity of recombinant proaerolysin derived from Aeromonas hydrophila cultured from diseased channel catfish." Veterinary microbiology 165(3): 478-482.

Zhang, L., J. Radziejewska-Lebrecht, et al. (1997). "Molecular and chemical characterization of the lipopolysaccharide O-antigen and its role in the virulence of Yersinia enterocolitica serotype O: 8." Molecular microbiology 23(1): 63-76.

Arber, W. and Dussoix, D. (1962) Host specificity of DNA produced by Escherichia coli. I. Host controlled modification of bacteriophage lambda. Journal of molecular biology, 5, 18-36.e 1: protozoan and metazoan infections.. 181-227.

Arber, W. and Linn, S. (1969) DNA modification and restriction. Annual review of biochemistry, 38, 467-500.

Cherepanov, P.P. and Wackemagel, W. (1995) Gene disruption in Escherichia coli: TcR and KmR cassettes with the option of Flp-catalyzed excision of the antibiotic-resistance determinant. Gene, 158, 9-14.

Copeland, N.G., Jenkins, N.A. and Court, D.L. (2001) Recombineering: a powerful new tool for mouse functional genomics. Nature reviews. Genetics, 2, 769-779.

Court, D.L., Sawitzke, J.A. and Thomason, L.C. (2002) Genetic Engineering Using Homologous Recombination. Annual Review of Genetics, 36, 361-388.

Dawoud, T.M., Jiang, T., Mandal, R.K., Ricke, S.C. and Kwon, Y.M. (2014) Improving the efficiency of transposon mutagenesis in Salmonella entenditis by overcoming host-restriction barriers. Molecular biotechnology, 56, 1004-1010.

Dickerson, H., D. Dawe, et al. (1995). "Ichthyophthirius multifiliis and Cryptocaryon irritans (Phylum Ciliophora)." Fish diseases and disorders. vol. 1: protozoan and metazoan infections.. 181-227.

Eden, P.A. and Blakemore, R.P. (1991) Electroporation and conjugal plasmid transfer to members of the genus Aquaspirillum. Archives of microbiology, 155, 449-452.

Elhai, J. and Wolk, C.P. (1988) Conjugal transfer of DNA to cyanobacteria. Methods in enzymology, 167, 747-754.

Griffin, B. (1991). "Characteristics of a chondroitin AC lyase produced by Cytophaga columnaris." Transactions of the American fisheries Society 120(3): 391-395.

He, P., Hao, K., Blom, J., Ruckert, C., Vater, J., Mao, Z., Wu, Y., Hou, M., He, P., He, Y. et al. (2012) Genome sequence of the plant growth promoting strain Bacillus amyloliquefaciens subsp. plantarum B9601-Y2 and expression of mersacidin and other secondary metabolites. J Biotechnol, 164, 281-291.

Hossain, M.J., Rahman Kh, S., Terhune, J.S. and Liles, M.R. (2012) An outer membrane porin protein modulates phase susceptibility in Edwardsiella ictaluri. Microbiology (Reading, England), 158, 474-487.

Jost, B.H., Homchampa, P., Strugnell, R.A. and Adler, B. (1997) The sacB gene cannot be used as a counter-selectable marker in Pasteurella multocida. Molecular biotechnology, 8, 189-191.

Karakousis, G., Ye, N., Li, Z., Chiu, S.K., Reddy, G. and Radding, C.M. (1998) The beta protein of phage binds preferentially to an intermediate in DNA renaturation. Journal of Molecular Biology, 276, 721-731.

Matsuda, T., Freeman, T.A., Hilbert, D.W., Duff, M., Fuortes, M., Stapleton, P.P. and Daly, J.M. (2005) Lysis-deficient bacteriophage therapy decreases endotoxin and inflammatory mediator release and improves survival in a murine peritonitis model. Surgery, 137, 639-646.

Murphy, K.C., Campellone, K.G. and Poteete, A.R. (2000) PCR-mediated gene replacement in Escherichia coli. Gene, 246, 321-330.

Pridgeon, J.W. and Klesius, P.H. (2011) Molecular identification and virutence of three Aeromonas hydrophila isolates cultured from infected channel catfish during a disease outbreak in west Alabama (USA) in 2009. Diseases of aquatic organisms, 94, 249-253.

Robert, F. and C. Gabrion (1991). "Experimental approach to the specificity in first intermediate hosts of Bothriocephalids (Cestoda, Pseudophyllidae) from marine fish." Acta oecologica:(1990) 12(5): 617-632.

Szewczyk, E., Nayak, T., Oakley, C.E., Edgerton, H., Xiong, Y., Taheri-Talesh, N., Osmani, S.A. and Oakley, B.R. (2007) Fusion PCR and gene targeting in Aspergillus nidulans. Nat. Protocols, 1, 3111-3120.

Thomas, C.M. and Nielsen, K.M. (2005) Mechanisms of, and barriers to, horizontal gene transfer between bacteria. Nature reviews Microbiology, 3, 711-721.

Via, P., Badia, J., Baldoma, L., Obradors, N. and Aguilar, J. (1996) Transcriptional regulation of the Escherichia coli thaT gene Microbiology (Reading, England), 142 ( Pt 7), 1833-1840.

Williams, M.L. and Lawrence, M.L. (2005) Identification and characterization of a two-component hemolysin from Edwardsiella ictaluri. Veterinary Microbiology, 108, 281-289.

Wolters, W.R., D. J. Wise, et al. (1996). "Survival and antibody response of channel catfish, blue catfish, and channel catfish femalex blue catfish male hybrides after exposure to Edwardsiella ictaluri." Journal of Aquatic Animal Health 8 (3): 249-254.

Alexeyev, M. (1999). "The pKNOCK series of broad-host-range mobilizable suicide vectors for gene knockout and targeted DNA insertion into the chromosome of gram-negative bacteria." Biotechniques 26(5): 824-827.

Allison, R. and H. Kelly (1963). "An epizootic of Ichthyophthirius multifiliis in a river fish population." The Progressive Fish-Culturist 25(3): 149-150.

Alper, H., K. Miyaoku, et al. (2005). "Construction of lycopene-overproducing E. coli strains by combining systematic and combinatorial gene knockout targets." Nature biotechnology 23(5): 612-616.

(56) References Cited

OTHER PUBLICATIONS

Anthony, J. (1963). "Parasites of eastern Wisconsin fishes." Transactions of the Wisconsin Academy of Sciences, Arts and Letters 52: 83-95.
Arias, C. R., W. Cai, et al. (2012). "Catfish hybrid Ictalurus punctatus × I. furcatus exhibits higher resistance to columnaris disease than the parental species." Marine Ecology Progress Series 100(1): 77-81.
Bader, J. A. and J. M. Grizzle (1992). "Effects of ammonia on growth and survival of recently hatched channel catfish." Journal of Aquatic Animal Health 4(1): 17-23.
Baker, J. C. and J. L. Crites (1976). Parasites of channel catfish, Ictalurus punctatus Rafinesque, from the island region of Lake Erie. Proc. Helminthol. Soc. Wash.
Beck, B. H., B. D. Farmer, et al. (2012). "Putative roles for a rhamnose binding lectin in Flavobacterium columnare pathogenesis in channel catfish Ictalurus punctatus." Fish & shellfish immunology 33(4): 1008-1015.
Berman, T. and B. Magasanik (1966). "The Pathway of myo-Inositol Degradation in Aerobacter aerogenes Dehydrogenation and Dehydration." Journal of Biological Chemistry 241(4): 800-806.
Buentello, J. A., D. M. Gatlin III, et al. (2000). "Effects of water temperature and dissolved oxygen on daily feed consumption, feed utilization and growth of channel catfish ( Ictalurus punctatus )." Aquaculture 182(3): 339-352.
Chassy, B. M., A. Mercenier, et al. (1988). "Transformation of bacteria by electroporation." Trends in Biotechnology 6 (12): 303-309.
Chen, Y.-L., S. Kauffman, et al. (2008). "Candida albicans uses multiple mechanisms to acquire the essential metabolite inositol during infection." Infection and immunity 76(6): 2793-2801.
Choi, S. H. and K. H. Kim (2011). "Generation of two auxotrophic genes knock-out Edwardsiella tarda and assessment of its potential as a combined vaccine in olive flounder ( Paralichthys olivaceus )." Fish & shellfish immunology 31(1): 58-65.
Cole, B. A. and C. E. Boyd (1986). "Feeding rate, water quality, and channel catfish production in ponds." The Progressive Fish-Culturist 48(1): 25-29.
Colt, J. and G. Tchobanoglous (1976). "Evaluation of the short-term toxicity of nitrogenous compounds to channel catfish, Ictalurus punctatus ." Aquaculture 8(3): 209-224.
Cooper, R. K., E. B. Shotts Jr, et al. (1996). "Use of a mini-transposon to study chondroitinase activity associated with Edwardsiella ictaluri." Journal of Aquatic Animal Health 8(4): 319-324.
Davison, J. (1999). "Genetic exchange between bacteria in the environment." Plasmid 42(2): 73-91.
Declercq, A., F. Boyen, et al. (2013). "Antimicrobial susceptibility pattern of Flavobacterium columnare isolates collected worldwide from 17 fish species." Journal of fish diseases 36(1): 45-55.
Edwards, R. A., L. H. Keller, et al. (1998). "Improved allelic exchange vectors and their use to analyze 987P fimbria gene expression." Gene 207(2): 149-157.
Esquivel, J. R., S. Z. Gomes, et al. (1998). "Growth of channel catfish, Ictalurus punctatus, in southern Brazil." Journal of Applied Aquaculture 8(3): 71-78.
Frost, P. and A. Ness (1997). "Vaccination of Atlantic salmon with recombinant VP2 of infectious pancreatic necrosis virus (IPNV), added to a multivalent vaccine, suppresses viral replication following IPNV challenge." Fish & shellfish immunology 7(8): 609-619.
Gauchat-Feiss, D., J. Frey, et al. (1985). "Cloning of genes involved in myo-inositol transport in a *Pseudomonas* sp." Journal of bacteriology 162(1): 324-327.
Goodwin, A. E. (1999). "Massive Lernaea cyprinacea infestations damaging the gills of channel catfish polycultured with bighead carp." Journal of Aquatic Animal Health 11(4): 406-408.
Gudding, R., A. Lillehaug, et al. (1999). "Recent developments in fish vaccinology." Veterinary immunology and immunopathology 72(1): 203-212.

Hargreaves, J. A. (2002). "Channel catfish farming in ponds: lessons from a maturing industry." Reviews in Fisheries Science 10(3-4): 499-528.
Harris, N. J., J. W. Neal, et al. (2011). "Notes on hatchery spawning methods for bigmouth sleeper Gobiomorus dormitor." Aquaculture Research 42(8): 1145-1152.
Hawke, J. P. (1979). "A bacterium associated with disease of pond cultured channel catfish, Ictalurus punctatus." Journal of the Fisheries Board of Canada 36(12): 1508-1512.
Hawke, J., R. Durborow, et al. (1998). "ESC—Enteric Septicemia of Catfish."
Hawke, J. P., A. C. McWhorter, et al. (1981). "*Edwardsiella ictaluri* sp. nov., the causative agent of enteric septicemia of catfish." International Journal of Systematic Bacteriology 31(4): 396-400.
Hildreth, M. B. and R. D. Lumsden (1985). "Description of Otobothrium insigne plerocercus (Cestoda: Trypanorhyncha) and its incidence in catfish from the gulf coast of Louisiana." Proceedings of the Helminthological Society of Washington 52(1): 44-50.
Horton, R. M., H. D. Hunt, et al. (1989). "Engineering hybrid genes without the use of restriction enzymes: gene splicing by overlap extension." Gene 77(1): 61-68.
Inoue, H., H. Nojima, et al. (1990). "High efficiency transformation of *Escherichia coli* with plasmids." Gene 96(1): 23-28.
Kieman, J. A. (1999). "Histological and histochemical methods: theory and practice." Shock 12(6): 479.
Kinnucan, H. (1995). "Catfish aquaculture in the United States: five propositions about industry growth and policy." World Aquaculture-Baton Rouge—26: 13-13.
Knepp, G. and G. F. Arkin (1973). "Ammonia toxicity levels and nitrate tolerance of channel catfish." The Progressive Fish-Ctilturist 35(4): 221-224.
Koonin, E. V., K. S. Makarova, et al. (2001). "Horizontal gene transfer in prokaryotes: quantification and classification 1." Annual Reviews in Microbiology 55(1): 709-742.
Lawrence, M. L., M. M. Banes, et al. (2001). "Phenotype and virulence of a transposon-derived lipopolysaccharide O side-chain mutant strain of Edwardsiella ictaluri." Journal of Aquatic Animal Health 13(4): 291-299.
Le, T. X. and Y. Munekage (2004). "Residues of selected antibiotics in water and mud from shrimp ponds in mangrove areas in Viet Nam." Marine pollution bulletin 49(11): 922-929.
Lugo, J. Z., S. Price, et al. (2007). "Lipopolysaccharide O-antigen promotes persistent murine bacteremia." Shock 27 (2): 186-191.
Maiden, M. C. (1998). "Horizontal genetic exchange, evolution, and spread of antibiotic resistance in bacteria." Clinical Infectious Diseases 27(Supplement 1): S12-S20.
Martin, K. and T. Smith (2005). "The myo-inositol-1-phosphate synthase gene is essential in Trypanosome brucei." Biochemical Society Transactions 33(Pt 5): 983-985.
Meyer; F. P. (1966). "A new control for the anchor parasite, Lernaea cyprinacea." The Progressive Fish-Culturist 28(1): 33-39.
Mischke, C. C. (2003). "Evaluation of Two Bio-Stimulants for Improving Water Quality in Channel Catfish, Ictalurus punctatus, Production Ponds." Journal of Applied Aquaculture 14(1-2): 163-169.
Mitchell, S. and H. Rodger (2011). "A review of infectious gill disease in marine salmonid fish." Journal of fish diseases 34(6): 411-432.
Miyazaki, T. and J. Plumb (1985). "Histopathology of Edwardsiella ictaluri in channel catfish, Ictalurus punctatus (Rafinesque)." Journal of fish diseases 8(4): 389-392.
Morand, S., F. Robert, et al. (1995). "Complexity in parasite life cycles: population biology of cestodes in fish." Journal of animal ecology: 256-264.
MSU (2010). "Commercial Catfish Production: Disease." http://msucares.com/aquaculture/catfish/disease.html.
Murray, G. L., S. R. Attridge, et al. (2003). "Regulation of *Salmonella typhimurium* lipopolysaccharide O antigen chain length is required for virulence; identification of FepE as a second Wzz." Molecular microbiology 47(5): 1395-1406.
Norton, V. M. and K. B. Davis (1977). "Effect of abrupt change in the salinity of the environment on plasma electrolytes, urine vol-

(56) References Cited

OTHER PUBLICATIONS ume, and electrolyte excretion in channel catfish, Ictalurus punctatus ." Comparative Biochemistry and Physiology Part A: Physiology 56(3): 425-431.
Ochman, H., J. G. Lawrence, et al. (2000). "Lateral gene transfer and the nature of bacterial innovation." Nature 405 (6784): 299-304.
Ando, T., Xu, Q., Torres, M., Kusugami, K., Israel, D.A. and Blaser, M.J. (2000) Restriction-modification system differenes in Helicobacter pylori are a barrier to interstrain plasmid transfer. Mol Microbiol, 37, 1052-1065.
Baba, T., T. Ara, et al. (2006). "Construction of *Escherichia coli* K-12 in-frame, single-gene knockout mutants: the Keio collection." Molecular systems biology 2(1).
Badgett, M. R., A. Auer, et al. (2002). "Evolutionary dynamics of viral attenuation." Journal of virology 76(20): 10524-10529.
Baxa, D., J. Groff, et al. (1990). "Susceptibility of nonictalurid fishes to experimental infection with Edwardsiella ctaluri." Diseases of Aquatic Organisms 8(2): 113-117.
Bebak, J., M. Matthews, et al. (2009). "Survival of vaccinated, feed-trained largemouth bass fry ( Micropterus salmoides floridanus ) during natural exposure to Flavobacterium columnare ." Vaccine 27(32): 4297-4301.
Bengoechea, J. A., H. Najdenski, et al. (2004). "Lipopolysaccharide O antigen status of Yersinia enterocolitica O: 8 is essential for virulence and absence of O antigen affects the expression of other Yersinia virulence factors." Molecular microbiology 52(2): 451-469.
Bhende, P.M. and Egan, S.M. (2000) Genetic Evidence that Transcription Activation by RhaS Involves Specific Amino Acid Contacts with Sigma 70. Journal of Bacteriology, 182, 4959-4969.
Booth, N. J., J. B. Beekman, et al. (2009). "Edwardsiella ictaluri encodes an acid-activated urease that is required for intracellular replication in channel catfish (Ictalurus punctatus) macrophages." Applied and environmental microbiology 75(21): 6712-6720.
Branda, S. S., J. E. González-Pastor, et al. (2004). "Genes involved in formation of structured multicellular communities by Bacillus subtilis." Journal of bacteriology 186(12): 3970-3979.
Branda, S. S., F. Chu, et al. (2006). "A major protein component of the Bacillus subtilis biofilm matrix." Molecular microbiology 59(4): 1229-1238.
Brüggemann, H., S. Bäumer, et al. (2003). "The genome sequence of Clostridium tetani, the causative agent of tetanus disease." Proceedings of the National Academy of Sciences 100(3): 1316-1321.
Cameron, D. E., J. M. Urbach, et al. (2008). "A defined transposon mutant library and its use in identifying motility genes in Vibrio cholerae." Proceedings of the National Academy of Sciences 105(25): 8736-8741.
Cartman, S.T. and Minton, N.P. (2010) A mariner-based transposon system for in vivo random rnutagenesis of Clostridium difficile. Appl Environ Microbiol, 76, 1103-1109.
Cassuto, E., Lash, T., Sriprakash, K.S. and Radding, C.M. (1971) Role of Exonuclease and β Protein of Phage in Genetic Recombination, V. Recombination of DNA in Vitro. Proceedings of the National Academy of Sciences, 68, 1639-1643.
Chambrier, A. d. and T. Scholz (2008). "Tapeworms (Cestoda: Proteocephalidea) of firewood catfish Sorubimichthys planiceps (Siluriformes: Pimelodidae) from the Amazon River." Folia Parasitologica 55(1): 17-28.
Collins, D. M. (2000). "New tuberculosis vaccines based on attenuated strains the *Mycobacterium tubeculosis* complex." Immunology and cell biology 78(4): 342-348.
Datsenko, K.A. and Wanner, B.L. (2000) One-step inactivation of chromosomal genes in *Escherichia coli* K-12 using PCR products. Proceedings of the National Academy of Sciences of the United States of America, 97, 6640-6645.
Datsenko, K.A. and Wanner, B.L. (2000) One-step inactivation of chromosomal genes in *Escherichia coli* K-12 using PCR products. Proceedings of the National Academy of Sciences, 97, 6640-6645.

Declercq, A. M., F. Haesebrouck, et al. (2013). "Columnaris disease in fish: a review with emphasis on bacterium-host interactions." Vet Res 44(27): 10.1186.
Deshazer, D., P. J. Brett, et al. (1998). "The type II O-antigenic polysaccharide moiety of Burkholderia pseudomallei ipopolysaccharide is required for serum resistance, and virulence." Molecular microbiology 30(5): 1081-1100.
Donahue, J.P., Israel, D.A., Peek, R.M., Blaser, M.J. and Miller, G.G. (2000) Overcoming the restriction barrier to plasmid transformation of Helicobacter pylori. Mol Microbiol, 37, 1066-1074.
Dower, W. J., J. F. Miller, et al. (1988). "High efficiency transformation of *E. coli* by high voltage electroporation." Nucleic acids research 16(13): 6127-6145.
Durborow, R. (1998). "Columnaris disease." A bacterial infection caused by Flavobacterium Columnare South Regional Aquaculture Centre SRAC, Texas A & M University, Publication(479).
Esteve, C., Alcaide, E. and Blasco, M.D. (2012) *Aeromonas hydrophila* subsp. dhakensis Isolated from Feces, Water and Fish in Mediterranean Spain. Microbes and Environments, 27, 367-373.
FAO (2012). "The state of world fisheries and aquaculture 2012." FAO Fisheries and Aquaculture Dept.
Flett, F., Mersinias, V. and Smith, C.P. (1997) High efficiency intergerieric conjugal transfer of plasmid DNA from *Escherichia coli* to methyl DNA-restricting streptomycetes. FEMS Microbiol Lett, 155, 223-229.
Galli-Taliadoros, L., J. Sedgwick, et al. (1995). "Gene knock-out technology: a methodological overview for the interested novice." Journal of immunological methods 181(1): 1-15.
Hadjifrangiskou, M., Gu, A.P., Pinkner, J.S., Kostakioti, M., Zhang, E.W., Greene, S.E. and Hultgren, S.J. (2012) Transposon mutagenesis identifies uropathogenic *Escherichia coli* biofilm factors. J Bacteriol, 194, 6195-6205.
Hanson, T. and M. D. Sites (2012). "2011 US Catfish Database." Fisheries.
He, J., J. Deng, et al. (2006). "A synergistic effect on the production of S -adenosyl-I-methionine in Pichia pastoris by knocking in of S -adenosyl-I-methionine synthase and knocking out of cystathionine-β synthase." Journal of biotechnology 126(4).
Hirayama, Y., Sakanaka, M., Fukuma, H., Murayama, H., Kano, Y., Fukiya, S and Yokota, A. (2012) Development of a Double-Crossover Markerless Gene Deletion System in Bifidobacterium longum: Functional Analysis of the a-Galactosidase Gene for Raffinose Assimilation. Applied and Environmental Microbiology, 78, 4984-4994.
Hossain, M.J., Sun, D., McGarey, D.J., Wrenn, S., Alexander, L.M., Martino, M.E., Xing, Y., Terhune, J.S. and Liles, M.R. (2014) An Asian Origin of Virulent Aeromonas hydrophila Responsible for Disease Epidemics in United States—Farmed Catfish. mBio, 5.
Hossain, M.J., Waldbieser, G.C., Sun, D., Capps, N.K., Hemstreet, W.B., Carlisle, K., Griffin, M.J., Khoo, L., Goodwin, A.E., Sonstegard, T.S. et al. (2013) Implication of Lateral Genetic Transfer in the Emergence of Aeromonas hydrophila Isolates of Epidemic Outbreaks in Channel Catfish. PLoS ONE, 8, e80943.
Hossain, M.J., Rahman, K.S., Terhune, J.S. and Liles, M.R. (2012) An outer membrane porin protein modulates phage susceptibility in Edwardsiella ictalurii. Microbiol-Sgm, 158, 474-487.
Hung, K., R. Hayashi, et al. (1998). "The central role of CD4+ T cells in the antitumor immune response." The Journal of experimental medicine 188(12): 2357-2368.
Iredell, J. R., U. H. Stroeher, et al. (1998). "Lipopolysaccharide O-antigen expression and the effect of its absence on virulence in rfb mutants of Vibrio cholerae O1." FEMS Immunology & Medical Microbiology 20(1): 45-54.
Ishikawa, M. and K. Hori (2013). "A new simple method for introducing an unmarked mutation into a large gene of non-competent Gram-negative bacteria by FLP/FRT recombination." BMC microbiology 13(1): 86.
Jansson, P. E., B. Lindberg, et al. (1981). "Structural studies on the hexose region of the core in lipopolysaccharides from Enterobacteriaceae." European journal of biochemistry 115(3): 571-577.

(56) References Cited

OTHER PUBLICATIONS

Jasin, M. and Schimmel, P. (1984) Deletion of an essential gene in *Escherichia coli* by site-specific recombination with linear DNA fragments. Journal of Bacteriology, 159, 783-786.

Kakirde, K.S., Wild, J., Godiska, R., Mead, D.A., Wiggins, A.G., Goodman, R.M., Szybalski, W. and Liles, M.R. (2011) Gram negative shuttle BAC vector for heterologous expression of metagenomic libraries. Gene, 475, 57-62.

Karpf, A. R. (2006). "A potential role for epigenetic modulatory drugs in the enhancement of cancer/germ-line antigen vaccine efficacy." Epigenetics 1(3): 116-120.

Kawsar, H. I., K. Ohtani, et al. (2004). "Organization and transcnptional reglulation of myo-inositol operon in Clostridium perfringens." FEMS microbiology letters 235(2): 289-295.

Kobayashi, K. (2007). "Gradual activation of the response regulator DegU controls serial expression of genes for flagellum formation and biofilm formation in Bacillus subtilis." Molecular microbiology 88(2): 395-409.
Kohler, P. R., E.-L. Choong, et al. (2011). "The RpiR-like repressor lolR regulates inositol catabolism in Sinorhizobium meliloti." Journal of bacteriology 193(19): 5155-5163.
Krings, E., K. Krumbach, et al. (2006). "Characterization of myo-inositol utilization by Corynebacterium glutamicum: the stimulon, identification of transporters, and influence on L-lysine formation." Journal of bacteriology 188(23): 8054-8061.
Kröger, C., S. Srikumar, et al. (2011). "Bistability in myo-inositol utilization by *Salmonella* enterica serovar Typhimurium." Journal of bacteriology 193(6): 1427-1435.
Kurosawa, N. and Grogan, D.W. (2005) Homologous recombination of exogenous DNA with the Sulfolobus acidocaldarius genome: properties and uses. FEMS Microbiol Lett, 253, 141-149.
Lee, D.J., Bingle, L.E., Heurlier, K., Pallen, M.J., Penn, C.W., Busby, S.J. and Hobman, J.L. (2009) Gene doctoring: a method for recombineering in laboratory and pathogenic *Escherichia coli* strains. BMC microbiology, 9, 252.
Li, X.-t., Thomason, L.C., Sawitzke, J.A., Costantino, N. and Court, D.L. (2013) Positive and negative selection using the tetA-sacB cassette: recombineering and P1 transduction in *Escherichia coli*. Nucleic Acids Research.
Little, J.W. (1976) An Exonuclease Induced by Bacteriophage. Journal of Biological Chemistry, 242, 679-686.
Lorenzen, N. and S. LaPatra (2005). "DNA vaccines for aquacultured fish." Revue Scientifique Et Technique-Office International Des Epizooties 24(1): 201.
Lucas, J. S. and P. C. Southgate (2012). Aquaculture: Farming aquatic animals and plants, John Wiley & Sons.
Matsuura, S.-i., Komatsu, J., Hirano, K., Yasuda, H., Takashima, K., Katsura, S. and Mizuno, A. (2001) Real-time observation of a single DNA digestion by exonuclease under a fluorescence microscope field. Nucleic Acids Research, 29, e79.
Merabishvili, M., Pimay, J.-P., Verbeken, G., Chanishvili, N., Tediashvili, M., Lashkhi, N., Glonti, T., Krylov, V., Mast, J., Van Parys, L. et al. (2009) Quality-Controlled Small-Scale Production of a Well-Defined Bacteriophage Cocktail for Use in Human Clinical Trials. PLoS ONE, 4, e4944.
Merino S., X. Rubires, et al. (1996). "The O: 34-antigen lipopolysaccharide as an adhesin in Aeromonas hydrophila." FEMS microbiology letters 139(2-3): 97-101.
Miwa, Y. and Y. Fujita (2001). "Involvement of two distinct catabolite-responsive elements in catabolite repression of the Bacillus subtilis myo-inositol (iol) operon." Journal of bacteriology 183(20): 5877-5884.
Monk, I.R., Shah, I.M., Xu, M., Tan, M.W. and Foster, T.J. (2012) Transforming the untransformable: application of direct transformation to manipulate genetically *Staphylococcus aureus* and *Staphylococcus epidermidis*. MBio, 3.
Morris, J. E. (1993). "Pond Culture of Channel Catfish in the North Central Region." North Central Regional Aquaculture Center in cooperation with USDA and the NCR Educational Materials Project.
Movahedzadeh, F., D. A. Smith, et al. (2004). "The *Mycobacterium tuberculosis* ino1 gene is essential for growth and virulence." Molecular microbiology 51(4): 1003-1014.
Muniyappa, K. and Radding, C.M. (1986) The homologous recombination system of phage lambda. Pairing activities of beta protein. Journal of Biological Chemistry, 261, 7472-7478.
Murphy, K.C. (1998) Use of Bacteriophage Recombination Functions To Promote Gene Replacement in *Escherichia coli*. Journal of Bacteriology, 180, 2063-2071.
Muyrers, J.P., Zhang, Y., Benes, V., Testa, G., Ansorge, W. and Stewart, A.F. (2000) Point mutation of bacterial artificial chromosomes by ET recombination. EMBO reports, 1, 239-243.
Mylonas, C. C., A. Fostier, et al. (2010). "Broodstock management and hormonal manipulations of fish reproduction." General and comparative endocrinology 165(3): 516-534.
Nagy, G., V. Danino, et al. (2006). "Down-regulation of key virulence factors makes the *Salmonella enterica* serovar Typhimurium rfaH mutant a promising live-attenuated vaccine candidate." Infection and immunity 14(10): 5914-5925.
Nevola, J. J., D. C. Laux, et al. (1987). "In vivo colonization of the mouse large intestine and in vitro penetration of intestinal mucus by an avirulent smooth strain of *Salmonella typhimurium* and its lipopolysaccharide-deficient mutant." Infection and immunity 55(12): 2884-2890.
Pádua, S., M. Martins, et al. (2013). "First record of Chilodonella hexasticha (Ciliophora: Chilodonellidae) in Brazilian cultured fish: A morphological and pathological assessment." Veterinary parasitology 191(1): 154-160.
Peleg, A., Y. Shifrin, et al. (2005). "Identification of an *Escherichia coli* operon required for formation of the O-antigen capsule." Journal of bacteriology 187(15): 5259-5266.
Poteete, A.R., Fenton, A.C. and Murphy, K.C. (1988) Modulation of *Escherichia coli* RecBCD activity by the bacteriophage lambda Gam and P22 Abc functions. Journal of Bacteriology, 170, 2012-2021.
Reynolds, T. B. (2009). "Strategies for acquiring the phospholipid metabolite inositol in pathogenic bacteria, fungi and protozoa: making it and taking it." Microbiology 155(5): 1386-1396.
Rocha, E. P., E. Cornet, et al. (2005). "Comparative and evolutionary analysis of the bacterial homologous recombination systems." PLoS genetics 1(2).
Rogge, M. L. and R. L. Thune (2011). "Regulation of the Edwardsiella ictaluri type III secretion system by pH and phosphale concentration through EsrA, EsrB, and EsrC." Applied and environmental microbiology 17(13): 4293-4302.
Serra-Moreno, R., Acosta, S., Hernalsteens, J., Jofre, J. and Muniesa, M. (2006) Use of the lambda Red recombinase system to produce recombinant prophages carrying antibiotic resistance genes. BMC Molecular Biology, 7, 31.
Sha, J., E. Kozlova, et al. (2002). "Role of various enterotoxins in Aeromonas hydrophila-induced gastroenteritis: generation of enterotoxin gene-deficient mutants and evaluation of their enterotoxic activity." Infection and immunity 70 (4): 1924-1935.
Sharan, S.K., Thomason, L.C., Kuznetsov, S.G. and Court, D.L. (2009) Recombineering: A Homologous Recombination-Based Method of Genetic Engineering. Nature protocols, 4, 206-223.
Shimizu, T., K. Ohtani, et al. (2002). "Complete genome sequence of Clostridium perfringens, an anaerobic flesh-eater." Proceedings of the National Academy of Sciences 99(2): 996-1001.
Shoemaker, C., O. Olivares-Fuster, et al. (2008). "Flavobacterium columnare genomovar influences mortality in channel catfish ( Ictalurus punctatus )." Veterinary microbiology 127(3): 353-359.
Sitaraman, R. and Leppla, S.H. (2012) Methylation-dependent DNA restriction in Bacillus anthracis. Gene, 494, 44-50.
Stickley, A. and K. Andrews (1989). Survey of Mississippi catfish farmers on means, effort, and costs to repel fish-eating birds from ponds. Fourth Eastern Wildlife Damage Control Conference, 1989.
Sun, Q., R. Lan, et al. (2012). "Identification of a divergent O-acetyltransferase gene oac1b from Shigella flexneri serotype 1b strains." Emerging Microbes & Infections 1(9): e21.
Thomas, R. M., R. W. Titball, et al. (2007). "The immunologically distinct O antigens from *Francisella tularensis* subspecies

(56) References Cited

OTHER PUBLICATIONS tularensis and Francisella novicida are both virulence determinants and protective antigens." Infection and immunity 75(1): 311-378.
Thune, R. L., D. H. Fernandez, et al. (2007). "Signature-tagged mutagenesis of Edwardsiella ictaluri identifies virulence-related genes, including a Salmonella pathogenicity island 2 class of type III secretion systems." Applied and environmental microbiology 73(24): 7934-7946.
Torkitdsen, L., O. B. Samuelsen, et al. (2000). "Minimum inhibitory concentrations of chloramphenicol, florfenicol, trimethoprim/sulfadiazine and flumequine in seawater of bacteria associated with scallops ( Pecten maximus ) larvae." Aquaculture 185(1): 1-12.
USDA (2014). "Catfish Production." the National Agricultural Statistics Service (NASS), Agricultural Statistics Board, United States Department of Agriculture (USDA).
USDA (2010). "Catfish 2010 Part I: Reference of Gatfish Health and Production Practices in the United States, 2009."
USDA (2010). "Catfish 2010 Part II: Health and Production Practices for Foodsize Catfish in the United States, 2009."
Uzzau, S., Figueroa-Bossi, N., Rubino, S. and Bossi, L. (2001) Epitope tagging of chromosomal genes in Salmonella. Proceedings of the National Academy of Sciences of the United States of America, 98, 15264-15269.
Van Den Bosch, L., P. A. Manning, et al. (1997). "Regulation of O-antigen chain length is required for Shigella flexneri virulence." Molecular microbiology 23(4): 765-775.
Welch, T.J., Evenhuis, J., White, D. G., McDermott P.F., Harbottle, H., Miller, R.A., Griffin, M. and Wise, D. (2009) IncA/C Plasmid-Mediated Florfenicol Resistance in the Catfish Pathogen Edwardsiella ictaluri. Antimicrobial Agents and Chemotherapy, 53, 845-846.
Wellbom, T. L. (1988). "Channel catfish: life history and biology." SRAC publication (USA).
Xue, C. (2012). "Cryptococcus and Beyond—Inositol Utilization and Its Implications for the Emergence of Fungal Virulence." PLoS pathogens 8(9): e1002869.
Yebra, M. J., M. Zúñiga, et al. (2007). "Identification of a gene cluster enabling Lactobacillus casei BL23 to utilize myo-inositol." Applied and environmental microbiology 73(12): 3850-3858.
Yoshida, K.-I., D. Aoyama, et al. (1997). "Organization and transcription of the myo-inositol operon, iol, of Bacillus subtilis." Journal of bacteriology 179(14): 4591-4598.
Yu, D., Ellis, H.M., Lee, E.-C., Jenkins, N.A., Copeland, N.G. and Court, D.L. (2000) An efficient recombination system for chromosome engineering in Escherichia coli Proceedings of the National Academy of Sciences, 97, 5978-5983.
Hossain et al., "Implication of lateral genetic transfer in the emergence of aeromonas hydrophila isolates of epidemic outbreaks in channel catfish", Plos One, Nov. 2013, 8(11):8.
Kang et al., "Knockout and pullout recombineering for naturally transformable Burkholderia thailandesis and Burkholderia pseudornallei", Nature Protocols, Aug. 2011, 6(8):1085-1104.
Liang et al., "Scarless and sequential gene modification in Pseudomonas using PCR product flanked by short homology region", BMC Microbiology, Aug. 3, 2010, 10(1):209.
Moral et al., "Molecular characterization of the Aeromonas hydrophila aroA gene and potential use of an auxotrophic aroA mutant as a live attenttuated vaccine", Infection and Immunity, May 1998, 66(5):1813-1821.
Pridgeon et al., "Identification of gyrB and rpoB gene mutations and differentially expressed proteins between a novobiocin-resistant Aeromonas hydrophila catfish vaccine strain and its virulent parent strain", Veterinary Microbiology, Oct. 25, 2013, 166:3-4.
Pridgeon et al., "Biochemical and molecular characterization of the novobiocin and rifampicin resistant Aeromonas hydrophila vaccine strain AL09-71N+R compared to its virulent parent strain AL09-71", Veterinary Microbiology, Aug. 2013, 165:3-4.
Pridgeon et al., "Development and efficacy of novobiocin and rifampicin-resistantas novel vaccines in channel catfish and Nile tilapia", Vaccine, Aug. 15, 2011, 29(45):7896-7904.

International Search Report for PCT/US2015/032961 dated Oct. 8, 2015.
Written Opinion for PCT/US2015/032961 dated Oct. 8, 2015.
Humphrey, J.D., C. Lancaster, et al. (1986). "Exotic bacterial pathogens Edwardsiella tarda and Edwardsiella ictaluri from imported ornamental firsh Betta splendens and Puntius conchonius, respectively: isolation and quarantine significance." Australian Veterinary Journal 63(11): 369-371.
Jiang, X. M., B. Neal, et al. (1991). "Structure and sequence of the rfb (O antigen) gene cluster of Salmonella serovar typhimurium (strain LT2)." Molecular microbiology 5(3): 695-713.
Matthews, R. (1994). "Ichthyophthirius multifiliis Fouquet, 1876: infection and protective response within the fish host." Parasitic diseases of fish. Samara Publishers, Dyfed, UK: 17-42.
Meyer, F. P. and S. Snieszko (1970). A symposium on diseases of fishes and shellfishes. Seasonal fluctuations in the incidence of disease on fish farms. A symposium on diseases of fishes and shellfishes. Seasonal fluctuations in the incidence of disease on fish farms.
Plumb, J. and D. Sanchez (1983). "Susceptibility of five species of fish to Edwardsiella ictaluri." Journal of fish diseases 6(3): 261-266.
Roberts, M. F. (2006). Inositol in bacteria and archaea. Biology of inositols and phosphoinositides, Springer: 103-133.
Robertson, D. A. (1985). A review of Ichthyobodo necator (Henneguy, 1883) an important and damaging fish parasite. Recent advances in aquaculture, Springer: 1-30.
Roubal, F., A. Bullock, et al. (1987). "Ultrastructural aspects of infestation by Ichthyobodo necator (Henneguy, 1883) on the skin and gills of the salmonids Salmo salar L . and Salmo gairdneri Richardson." Journal of fish diseases 10(3): 181-192.
Teichert-Coddington, D. R. and B. W. Green (1997). "Experimental and commercial culture of tilapia in Honduras." Tilapia aquaculture in the Americas 1: 142-162.
Walters, G. and J. Plumb (1980). "Environmental stress and bacterial infection in channel catfish, Ictalurus punctatus Rafinesque." Journal of fish biology 17(2): 177-185.
Invitation to Pay Additional Fees and, Where Applicable, Protest Fee for International Patent Application No. PCT/US2015/032961 dated Jul. 31, 2015.
Moral, C.H. et al. "Molecular characterization of the Aeromonas hydrophila aroA gene and potential use of an auxotrophic aroA mutant as a live attenuated vaccine," Infection and Immunity (1998) 66(5): 1813-1821.
Pridgeon, J.W. et al. "Identification of byrB and rpoB gene mutations and differentially expressed proteins between a novobiocin-resistant Aeromonas hydrophila catfish vaccine strain and its virulent parent strain," Veterinary Microbiology (2013) 166(3-4): 624-630.
Pridgeon, J.W. et al. "Biochemical and molecular characterization of the novobiocin and rifampicin resistant Aeromonas hydrophila vaccine strain AL09-71N+R compared to its virulent parent strain AL09-71," Veterinary Microbiology, (2013) 165(3-4): 349-357.
Pridgeon, J.W. et al. "Development and efficacy of novobiocin and rifampicin-resistantas novel vaccines in channel catfish and Nile i" Vaccine, Elsevier Ltd, GB (2011) 29(45): 7896-7904.
Hossain M.J. et al. "Implication of Lateral Genetic Transfer in the Emergence of Aeromonas hydrophila Isolates of Epidemic Outbreaks in Channel Catfish," Plos One (2013) 8(11): 8.
Lang R. et al. "Scarless and sequential gene modification in Pseudomonas using PCR product flanked by short homology regions," BMC Microbiology, Biomed Central Ltd, GB (2010) 10(1): 209.
Kang Y. et al. "Knockout and pullout recombineering for naturally transformable Burkholderia thailandensis and Burkholderia pseudomallei," Nature Protocols (2011) 6(8): 1085-1104.
Bergerhouse, D.L. (1994). "Lethal effects of elevated pH and ammonia on early life stages of hybrid striped bass." Journal of Applied Aquaculture 2(3-4): 81-100.
Coon, T. G. and H. R. Dames (1989). Catfish movement and habitat use in a Missouri River tributary. Proceedings of the Annual Conference Southeastern Association of Fish and Wildlife Agencies.

(56) References Cited

OTHER PUBLICATIONS

Moriarty, D. J. (1997). "The role of microorganisms in aquaculture ponds." Aquaculture 151(1): 333-349.

Simon, R., Priefer, U. and Puhler, A. (1983) A Broad Host Range Mobilization System for In Vivo Genetic Engineering: Transposon Mutagenesis in Gram Negative Bacteria. Nat Biotech, 1, 784-791.

Tucker, C. S. and S. W. Lloyd (1985). "Evaluation of a commercial bacterial amendment for improving water quality in channel catfish ponds." Research repo.

| Means with the same letter are not significantly different. | | | |
|---|---|---|---|
| Duncan Grouping | Mean | N | strain |
| A | 1.00000 | 4 | ML09-119 |
| A | | | |
| A | 0.87955 | 4 | iolARec3 |
| A | | | |
| A | 0.82727 | 4 | iolARec4 |
| B | | | |
| B | 0.27500 | 4 | $\Delta iolA_{trs}$ |
| B | | | |
| B | 0.16667 | 3 | control |

Figure 11

Subchallenge of the survivors of each treatment after 21 days with wild type ML09-119

VACCINES FOR CONTROL OF EPIDEMIC *AEROMONAS HYDROPHILA* GENERATED BY MARKERLESS GENE DELETION

CROSS-REFERENCE TO RELATED APPLICATIONS

The present application claims the benefit of priority under 35 U.S.C. §119(e) to U.S. Provisional Applications No. 62/003,953, filed on May 28, 2014, the content of which is incorporated herein by reference in its entirety.

STATEMENT REGARDING FEDERALLY SPONSORED RESEARCH OR DEVELOPMENT

This invention was made with U.S. government support under grant nos. 2012-38500-19665, 2013-67015-21313, and 2014-38500-22308 awarded by the U.S. Department of Agriculture. The U.S. government has certain rights in the invention.

BACKGROUND

The field of the present invention relates to compositions and methods for treating or preventing disease in aquatic animals such as farmed fish (e.g. catfish or tilapia) and crustaceans (e.g., shrimp). In particular, the present invention relates to compositions and methods comprising or utilizing attenuated strains of *Aeromonas hydrophila* for treating or preventing diseases such as Motile *Aeromonas* Septicemia (MAS) in aquatic animals such as farmed fish.

Aquaculture is one of the fastest growing industries in the world. It is developing, expanding and intensifying in almost all regions of the world due to the vast global population demand of aquatic food products and the leveling-off of the capture fisheries. According to FAO, in 2010 alone, the World aquaculture production reached 60 million tons (excluding aquatic plants and non-food products), with an estimated, total value of US $119 billion. In 2010, 181 countries and territories had aquaculture production, with Asia accounting for 89 percent of world aquaculture production by volume, in which 61.4 percent was from China. During the last thirty years, the production of global food fish protein has expanded by almost 12 times, at a rate of 8.8 percent more per year (FAO 2012) According to FAO, global aquaculture production will need to achieve 80 million tons by 2050 just to maintain the current level of per capita consumption. It is not possible for the capture fisheries industry itself to meet this big global aquatic food need. Even with the fast growing rate and the significant contribution of the aquaculture industry, it is still a big challenge for the aquaculture to achieve this goal. (FAO 2005).

In United States, the aquaculture industry is dominated by finfish production (FAO 2012). Being the largest sector of the aquaculture industry, channel catfish farming produced more than 400 million dollars which accounts for approximately half of the total aquaculture production in U.S. in 2010, in the top 10 fish and seafood that consumed among Americans rank, Catfish raised by farm was sixth, about 0.8 pound per person per year. (Hanson & Sites, 2012). Most catfish are produced in the south of the United States and Mississippi, Alabama, Arkansas, and Texas are the top four States for catfish in the United States, which accounts for 94 percent of total sales (USDA, 2014).

Even though the U.S. catfish industry is the dominant aquaculture practiced in the United States, catfish production is vulnerable to adverse impacts of disease and environmental conditions. Before the 1990's, the strategy of management practices was 'low-density', which resulted in good pond water quality, lower overall stress on fish populations and less efficient pathogen transmission. However, due to the great competition from the Asian countries especially China, the producers applied much more intense production strategies, such as multiple batch cropping systems, higher stocking density, more feed put into the culture systems. All of these practices lead to the emergence of the infectious diseases which now becomes the primary limiting factor in catfish production. Disease outbreaks in recent years are very common even on efficient and well-built catfish farming facilities. According to MSU (Mississippi State University) reports, infectious diseases have caused approximately 45 percent of inventory losses on catfish fingerling farms, and about 60 percent of the overall catfish losses are attributed to single or mixed bacterial infections, 30 percent due to parasitic infection, 9 percent from fungal infection, and 1 percent result from viral etiology. Economic losses resulting from infectious diseases are believed to cost producers millions of dollars in direct fish losses each year. Furthermore, infectious diseases can also impact the profitability by increasing treatment costs, reducing food consumption by fish due to the flavor change and appearance, increasing feed conversion ratios, and causing harvesting delays.

The major bacterial diseases in catfish that affect the catfish industry are: Enteric septicemia of catfish (ESC), caused by *Edwardsiella ictaluri* (Hawke, 1979); Motile *Aeromonas* septicemia (MAS), which is caused by *Aeromonas* species (Austin & Adams, 1996) and Columnaris (also referred to as cottonmouth) which is caused by *Flavobacterium columnare* (Wagner, 2002). The economic losses due to the ESC, according to USDA were about 30 to 50 million dollars each year (Shoemaker et al., 2007; USDA, 2010a, 2010b). The yearly losses caused by the Columnaris are estimated to be 30 million dollars (Declercq, 2013). MAS also causes huge amount of economic losses which are not limited to channel catfish but also including tilapia, catfish, goldfish, common carp, and eel (Pridgeon et al., 2011).

Prior to 2009, MAS in channel catfish caused by *A. hydrophila* was not a significant concern because the catfish aquaculture operations in the southeastern United States had not experienced a major outbreak (Hemstreet, 2010). However In 2009, catfish farmers in west Alabama reported severe disease outbreaks which were then proved to be caused by a highly virulent strain of *A. hydrophila*, ML09-119, to channel catfish (*Ictalurus punctatus*). From 2009-2011, Alabama catfish famers lost more than 7.5 million pounds of catfish that were market-size and estimated to be $3 million due to this epidemic strain of *A. hydrophila* (Pridgeon, 2011; Liles, 2011). It is reported that *A. hydrophila* epidemic strain, ML09-119, is highly virulent to channel catfish, causing severe mortality within 24 h post exposure with certain amount of dose (Pridgeon, 2011). The epidemic MAS outbreaks caused by *Aeromonas hydrophila* are so devastating that it is highly essential to investigate the virulence nature of this pathogen, identify the virulence related genes and create live avirulent bacterial mutants that are vaccine candidates for this bacterial disease. So far there are only a few factors identified for the *A. hydrophila* epidemic strain, and no commercial vaccine or treatment for the epidemic MAS are available right now. Three attenuated *A. hydrophila* vaccines were reported to offered 86-100% protection against their virulent parents at 14 days post vaccination (dpv), when the channel catfish were vaccinated with the mutants at dosage of $4\times10^5$ CFU/fish. These mutants were developed from the virulent 2009 West Alabama isolates through selection for resistance to both novobiocin and rifampicin (Julia and Klesius, 2011). But these antibiotic resistant mutants are spontaneous mutants that could more readily revert to a virulent strain compared to targeted, stable genetic deletions in gene(s) responsible for virulence.

Therefore, there is a need for a better understanding of the virulence of *A. hydrophila* in order for vaccine development to progress. Here, the inventors disclose methods for identifying virulence factors of *A. hydrophila* and producing attenuated strains of *A. hydrophila* that have been made deficient in one or more virulence factors.

SUMMARY

Disclosed are attenuated bacteria, compositions comprising attenuated bacteria, and vectors and methods for preparing attenuated bacteria. The attenuated bacteria may include attenuated *Aeromonas hydrophila* for use in vaccinating aquatic animals such as channel catfish against Motile *Aeromonas* Septicemia (MAS).

The attenuated bacteria may be attenuated by making the bacteria deficient in one or more target genes that are associated with pathogenicity. Suitable genes may include but are not limited to the genes associated with the pathway for O-antigen and/or O-antigen capsule synthesis and secretion and myo-inositol catabolism and regulation. Genes associated with the pathway for O-antigen and/or O-antigen capsule synthesis and secretion may include, but are not limited too ymcA, ymcB, ymcC, waaL, wzy, polysaccharide export protein, and wzz. (See FIG. 19). Genes associated with myo-inositol catabolism and regulation may include, but are not limited to iolA, iolB, iolC, iolD, iolE, iolG1, and iolG2 (See FIG. 8).

The bacteria may be made deficient of the one or more target genes (e.g., target genes associated with pathogenicity) by a method that includes deleting at least a portion of the target gene by recombination and insertion of a selectable marker in place of the deleted portion of the target gene. Subsequently, the selectable marker may be deleted in order to prepare a markerless bacterium that is deficient in the target gene.

Suitable methods for preparing the markerless bacteria that are deficient in the one or more target genes may include recombineering systems. The recombineering systems may include: (a) a mobilizable recombineering vector that expresses protein components for facilitating homologous recombination; and (b) a linear DNA molecule that is configured for recombining at a target gene and replacing at least a portion of the target gene with a selectable marker that is flanked by recombinase recognition target sequences. After the linear DNA molecule is recombined at the target sequence, a recombinase that recognizes the recombinase recognition target sequences may be expressed in order to recombine the target sequences and remove the selectable marker that is flanked by recombinase recognition target sequences.

Also disclosed are vaccine compositions comprising the attenuated bacteria disclosed herein, preferably together with a suitable carrier. The vaccine compositions may include live attenuated bacteria or attenuated bacteria that have been killed, for example by chemical treatment or heat treatment. Optionally, the vaccines may include an adjuvant.

Preferably, the vaccine compositions comprise an effective concentration of the bacteria for treating and/or preventing disease in an aquatic animal after the vaccine compositions are administered to the aquatic animal. Accordingly, also contemplated herein are methods of vaccinating an aquatic animal against infection by the bacteria that include administering the vaccine composition to the aquatic animal.

Also disclosed herein are vectors and kits comprising one or more vectors for preparing the bacteria disclosed herein. Contemplated vectors include recombineering vectors as disclosed herein, and contemplated kits may include one or more recombineering vectors.

BRIEF DESCRIPTION OF THE DRAWINGS

FIG. 11. SAS Duncan comparisons. Significant differences were observed between $iolA_{tra}$ and ML09-119 treatment groups ($P=5.23E^{-06}$), indicating that the $\Delta iolA_{tra}$ is an attenuated mutant of ML09-119. No significant differences were observed between the $iolA_{Rec3}$ or $iolA_{Rec4}$ treatment groups and the wild type (P=0.09).

DETAILED DESCRIPTION

Disclosed herein are microbiocidal compositions. The disclosed microbiocidal compositions may be described using several definitions as discussed below.

Unless otherwise specified or indicated by context, the terms "a", "an", and "the" mean "one or more." In addition, singular nouns such as "a bacterium," "a carrier," and "a vector" should be interpreted to mean "bacteria," "carriers," and "vectors," unless otherwise specified or indicated by context.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

As used herein, a "subject" or an "individual" and means an animal in need of treatment or prevention. Animals may include aquatic animals such as farmed fish (e.g. catfish or tilapia) and crustaceans (e.g., shrimp) having or at risk for developing an infection by a pathogenic microorganism such as *Aeromonas hydrophila, Edwardsiella ictaluri, Edwardsiella tarda, Flavobacterium columnare, Streptococcus iniae, Yersinia ruckeri, Vibrio* species and/or the oomycete fungus *Saprolegnia*. An animal may include a catfish at risk for developing Motile *Aeromonas* Septicemia (MAS).

Disclosed herein is a bacterium that has been made deficient in one or more genes associated with virulence. As used herein, "deficient" means that the bacterium does not express a functional form of a protein encoded by the gene. As such, deficiencies may include deletions, insertion, premature stop codons and the like, but preferably the bacteria disclosed herein have been made deficient in one or more genes associated with virulence via deletion of at least a portion of the gene, and preferably the entirety of the gene. For example, bacteria contemplated herein may be made deficient in one or more genes associated with the pathway for O-antigen and/or O-antigen capsule synthesis and secretion and myo-inositol catabolism and regulation.

Figure 19:
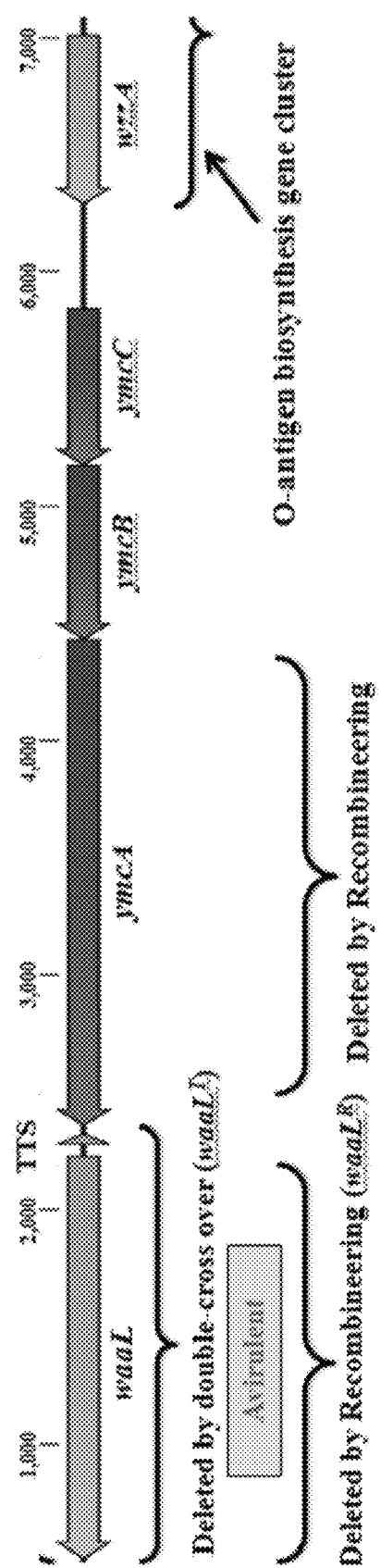
FIG. 19. Organization of O-antigen Biosynthesis Gene Cluster

Genes associated with the pathway for O-antigen and/or O-antigen capsule synthesis and secretion may include, but are not limited to ymcA, ymcB, ymcC, waaL (O-antigen ligase), wzy (O-antigen length determinant protein), polysaccharide export protein, and wzz (O-antigen length determinant protein). (See FIG. 19). Genes associated with myo-inositol catabolism and regulation may include, but are not limited to iolA (methylmalonate-semialdehyde dehydrogenase), iolB (5-deoxy-glucuronate isomerase), iolC (5-dehydro-2-deoxygluconokinase), iolD (COG3962 acetolactate synthase), iolE (myo-inosose-2-dehdratase), iolG1 (myo-inositol 2-dehdrogenase), and iolG2 (myo-inositol 2-dehdrogenase). (See FIG. 8). As such, bacteria contemplated herein may be made deficient in a gene encoding any of the polypeptides of SEQ ID NOs:11 (YmcA), 15 (unknown), 17 (YmcB), 19 (YmcC), 21 (O-antigen ligase), 23 (O-antigen length determinant protein Wzy), 25 (Polysaccharide Export Protein), 27 (O-antigen length determinant protein Wzz), 29 (methylmalonate-semialdehyde dehydrogenase IolA), 31 (COG3962 acetolactate synthase IolD), 33 (myo-inositol 2-dehydrogenase IolG1), 35 (myo-inositol 2-dehydrogenase IolG1), 37 (5-dehydro-2-deoxygluconokinase IolC), 39 (myo-inosose 2-dehdratase IolE), or 41 (5-deoxy-glucuronate isomerase IolB) or encoding a variant polypeptide having at least about 95% sequence identity to the polypeptide of any of SEQ ID NOs:11, 15, 17, 19, 21, 23, 25, 27, 29, 31, 33, 35, 37, 39, or 41, wherein the variant polypeptide maintains or lacks the biological activity associated with any of 11, 15, 17, 19, 21, 23, 25, 27, 29, 31, 33, 35, 37, 39, or 41. Accordingly, bacteria contemplated herein, may be made deficient in a gene (or one or more genes) comprising a polynucleotide sequence of any of SEQ ID NOs:12 (ymcA), 16 (unknown), 18 (ymcB), 20 (ymcC), 22 (waaL), 24 (wzy), 26 (polysaccharide export protein), 28 (wzz), 30 (iolA), 32 (iolD), 34 (iolG2), 36 (ioG1), 38 (iolC), 40 (iolE), or 42 (iolB), or a gene comprising a polnucleotide sequence having at least 95% sequence identity to any of SEQ ID NOs:12, 16, 18, 20, 22, 24, 26, 28, 30, 32, 34, 36, 38, 40, or 42.

Reference may be made herein to polypeptides and proteins, which terms may used interchangeably herein. For example, polypeptides contemplated herein may comprise the amino acid sequences of any of SEQ ID NOs:2, 3, 4, 5, 8, 11 or 13, or may comprise an amino acid sequence having at least about 80%, 90%, 95%, 96%, 97%, 98%, or 99% sequence identity to any of SEQ ID NOs:2, 3, 4, 5, 8, 11 or 13. Mutant polypeptides or variant polypeptides may include one or more amino acid substitutions, deletions, additions and/or amino acid insertions relative to the wild-type polypeptide, where optionally the mutant polypeptides or variant polypeptide may exhibit the biological activity of the wild-type polypeptide or alternatively may lack the biological activity of the wild-type polypeptide.

Reference also is made herein to polynucleotides and nucleotide sequences, which terms may be used interchangeably herein. For example, polynucleotides that encode the polypeptides disclosed herein are contemplated (e.g., polynucleotides that encode the polypeptide of any of SEQ ID NOs:2, 3, 4, 5, 8, 11 or 13 or mutants or variants thereof). For example, contemplated herein are polynucleotides (e.g., DNA or RNA) comprising the nucleotide sequence of any of SEQ ID NOs:1, 6, 7, 12, or 14, or mutants or variants thereof, for example polynucleotides having at least about 80%, 90%, 95%, 96%, 97%, 98%, or 99% sequence identity to any of SEQ ID NOs:1, 6, 7, 12, or 14.

Also contemplated are bacterial expression vectors that express the disclosed polypeptides or variants or mutants thereof. Vectors may include plasmids or other related vectors that may be used to transform appropriate host cells (e.g., *E. coli* and/or *A. hydrophila*), and the terms "vector" and "plasmid" may be used interchangeably in some embodiments disclosed herein. The transformed host cell may be cultured such that the polypeptide is expressed constitutively or after adding a reagent that induces expression (e.g., via an inducible promoter). Expression vectors as contemplated herein may include control sequences that modulate expression of the encoded polypeptide. Expression control sequences may include constitutive or inducible promoters (e.g., T3, T7, Lac, trp, or phoA, arabinose-inducible promoters, rhamnose-inducible promoters), ribosome binding sites, or transcription terminators.

The vectors disclosed herein may be utilized to transform host cells. Suitable host cells include bacterial. Suitable bacteria include, but are not limited to: Gram-negative bacteria such as *Escherichia* species (e.g., *E. coli*) and *Aeromonas* species (e.g. *Aeromonas hydrophila*), and other Gram-negative bacteria, (e.g., *Edwardsiella* species such as *Edwardsiella ictaluri*)

The terms "nucleic acid" and "nucleic acid sequence" refer to a nucleotide, oligonucleotide, polynucleotide (which terms may be used interchangeably), or any fragment thereof. These phrases also refer to DNA or RNA of genomic or synthetic origin (which may be single-stranded or double-stranded and may represent the sense or the antisense strand).

The terms "amino acid" and "amino acid sequence" refer to an oligopeptide, peptide, polypeptide, or protein sequence (which terms may be used interchangeably), or a fragment of any of these, and to naturally occurring or synthetic molecules. Where "amino acid sequence" is recited to refer to a sequence of a naturally occurring protein molecule, "amino acid sequence" and like terms are not meant to limit the amino acid sequence to the complete native amino acid, sequence associated with the recited protein molecule.

The amino acid sequences contemplated herein may include conservative amino acid substitutions relative to a reference amino acid sequence. For example, a variant, mutant, or derivative polypeptide may include conservative amino acid substitutions relative to a reference polypeptide. "Conservative amino acid substitutions" are those substitutions that are predicted to interfere least with the properties of the reference polypeptide. In other words, conservative amino acid substitutions substantially conserve the structure and the function of the reference protein. Table 1 provides a list of exemplary conservative amino acid substitutions.

TABLE 1

| Original Residue | Conservative Substitution |
| --- | --- |
| Ala | Gly, Ser |
| Arg | His, Lys |
| Asn | Asp, Gln, His |
| Asp | Asn, Glu |

TABLE 1-continued

| Original Residue | Conservative Substitution |
|---|---|
| Cys | Ala, Ser |
| Gln | Asn, Glu, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

A "deletion" refers to a change in the amino acid or nucleotide sequence that results in the absence of one or more amino acid residues or nucleotides. A deletion removes at least 1, 2, 3, 4, 5, 10, 20, 50, 100, or 200 amino acids residues or nucleotides. A deletion may include an internal deletion or a terminal deletion (e.g., an N-terminal truncation or a C-terminal truncation of a reference polypeptide or a 5'-terminal or 3'-terminal truncation of a reference polynucleotide).

A "fragment" is a portion of an amino acid sequence or a polynucleotide which is identical in sequence to but shorter in length than a reference sequence. A fragment may comprise up to the entire length of the reference sequence, minus at least one nucleotide/amino acid residue. For example, a fragment may comprise from 5 to 1000 contiguous nucleotides or contiguous amino acid residues of a reference polynucleotide or reference polypeptide, respectively. In some embodiments, a fragment may comprise at least 5, 10, 15, 20, 25, 30, 40, 50, 60, 70, 80, 90, 100, 150, 250, or 500 contiguous nucleotides or contiguous amino acid residues of a reference polynucleotide or reference polypeptides respectively. Fragments may be preferentially selected from certain regions of a molecule. The term "at least a fragment" encompasses the full length polynucleotide or full length polypeptide.

A "full length" polynucleotide sequence is one containing at least a translation initiation codon (e.g., methionine) followed by an open reading frame and a translation termination codon. A "full length" polynucleotide sequence encodes a "full length" polypeptide sequence.

"Homology" refers to sequence similarity or, interchangeably, sequence identity, between two or more polynucleotide sequences or two or more polypeptide sequences. Homology, sequence similarity, and percentage sequence identity may be determined using methods in the art and described herein.

The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences, "BLAST 2 Sequences" can be accessed and used interactively at the NCBI website. The "BLAST 2 Sequences" tool can be used for both blastn and blastp (discussed below).

Percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

A "variant," "mutant," or "derivative" of a particular nucleic acid sequence may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

Nucleic acid sequences that do not show a high degree of identity may nevertheless encode similar amino acid sequences due to the degeneracy of the genetic code. It is understood that changes in a nucleic acid sequence can be made using this degeneracy to produce multiple nucleic acid sequences that all encode substantially the same protein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. Percent identity for amino acid sequences may be determined as understood in the art. (See. e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases.

Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence listing, may be used to describe a length over which percentage identity may be measured.

A "variant," "mutant," or "derivative" of a particular polypeptide sequence is defined as a polypeptide sequence having at least 50% sequence identity to the particular polypeptide sequence over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of polypeptides may show, for example, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides. A "variant" or a "derivative" may have substantially the same functional activity as a reference polypeptide. For example, a variant or derivative of a cysteine protease may have cysteine protease activity (e.g., autoproteolytic cysteine protease activity).

The words "insertion" and "addition" refer to changes in an amino acid or nucleotide sequence resulting in the addition of one or more amino acid residues or nucleotides, respectively. An insertion or addition may refer to 1, 2, 3, 4, 5, 10, 20, 30, 40, 50, 60, 70, 80, 90, 100, 150, or 200 amino acid residues or nucleotides.

"Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame.

A "recombinant nucleic acid" is a sequence that is not naturally occurring or has a sequence that is made by an artificial combination of two or more otherwise separated segments of sequence. This artificial, combination is often, accomplished by chemical synthesis or, more commonly, by the artificial manipulation of isolated segments of nucleic acids, e.g., by genetic engineering techniques such as those described in Sambrook, J. et al. (1989) Molecular Cloning: A Laboratory Manual, 2$^{nd}$ ed., vol. I 3, Cold Spring Harbor Press, Plainview N.Y. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

"Substantially isolated or purified" nucleic acid or amino acid sequences are contemplated herein. The term "substantially isolated or purified" refers to nucleic acid or amino acid sequences that are removed from their natural environment, and are at least 60% free, preferably at least 75% free, and more preferably at least 90% free, even more preferably at least 95% free from other components with which they are naturally associated.

"Transformation" describes a process by which exogenous DNA is introduced into a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, bacteriophage or viral infection, electroporation, heat shock, lipofection, and particle bombardment. The term "transformed cells" includes stably transformed cells in which the inserted DNA is capable of replication either as an autonomously replicating plasmid or as part of the host chromosome, as well as transiently transformed cells which express the inserted DNA or RNA for limited periods of time.

A "composition comprising a given amino acid sequence" and a "composition comprising a given polynucleotide sequence" refer broadly to any composition containing the given polynucleotide or amino acid sequence. The composition may comprise a dry formulation or an aqueous solution. The compositions may be stored in any suitable form including, but not limited to, freeze-dried form and may be associated with a stabilizing agent such as a carbohydrate. The compositions may be aqueous solution containing salts (e.g., NaCl), detergents (e.g., sodium dodecyl sulfate; SDS), and other components (e.g., Denhardt's solution, dry milk, salmon sperm DNA, and the like).

The presently disclosed composition and methods may include or utilize Gram negative bacteria such as *Aeromonas* spp, and *Edwarsiella* spp. *Aeromonas* spp. may include but are not limited to *Aeromonas hydrophila*, *Aeromonas caviae*, and *Aeromonas veronii*. (See also *Aeromonas* spp, disclosed in Martino et al., "Determination of Microbial Diversity of *Aeromonas* Strains on the Basis of Multilocus Sequence Typing, Phenotype, and Presence of Putative Virulence Genes," Applied Environmental Microbiology. 2011 July; 77)14): 4986-5000). The complete genome of *Aeromonas hydrophila* ML09-110 (5,024,500 bp) has been sequenced and is deposited in GenBank under accession number CP005966.1. *Edwarsiella* spp. may include but are not limited to *Edwardsiella ictaluri*. The complete genome of *Edwardsiella ictaluri* 93-146 (3,812,301 bp) has been sequenced and is deposited in the National Center for Biotechnology Information (NCBI) database under accession number NC_012779.2.

The disclosed compositions and methods may include or utilize *Aeromonas hydrophila* or an *Aeromonas* species that is closely related to *Aeromonas* spp. an *Aeromonas* species that is closely related to *Aeromonas hydrophila* may be defined as a species comprising a 16S rDNA sequence comprising SEQ ID NO:9 or comprising a 16S rDNA sequence having at least about 90%, 91%, 92%, 93%, 94%, 95%, 96%, 97%, 98%, or 99% sequence identity to SEQ ID NO:9.

The disclosed compositions and methods may include or utilize *Edwarsiella ictaluri* or an *Edwarsiella* species that is closely related to *Edwarsiella ictaluri*. An *Edwardsiella* species that is closely related to *Edwarsiella ictaluri* may be defined as a species comprising a 16S rDNA sequence comprising SEQ ID NO: 10 or comprising a 16s rDNA sequence having at least about 90%, 91%, 92%, 93%, 94%, 95%, 96%, 97%, 98%, or 99% sequence identity to SEQ ID NO:10.

"Percentage sequence identity" between two polynucleotide sequences may be determined by aligning two sequences using the Basic Local Alignment Search Tool (BLAST) available at the National Center for Biotechnology Information (NCBI) website (i.e., "bl2seq" as described in Tatiana A. Tatusova, Thomas L. Madden (1999), "Blast 2 sequences—a new tool for comparing protein and nucleotide sequences", FEMS Microbiol Lett. 174:247-250, incorporated herein by reference in its entirety). For example, percentage sequence identity between nucleotide sequences disclosed herein may be determined by aligning these two sequences using the online BLAST software provided at the NCBI website.

"Percentage sequence identity" between two deoxyribonucleotide sequences may also be determined using the Kimura 2-parameter distance model which corrects for multiple hits, taking into account transitional and transversional substitution rates, while assuming that the four nucleotide frequencies are the same and that rates of substitution do not vary among sites (Nei and Kumar, 2000) as implemented in the MEGA 4 (Tamura K, Dudley J, Nei M & Kumar S (2007) MEGA4: Molecular Evolutionary Genetics Analysis (MEGA) software version 4.0. *Molecular Biology and Evolution* 24:1596-1599), preferably version 4.0.2 or later. The gap opening and extension penalties are set to 15 and 6.66 respectively. Terminal gaps are not penalized. The delay divergent sequences switch is set to 30. The transition weight score is 35 set to 0.5, as a balance between a complete mismatch and a matched pair score. The DMA weight matrix used is the IUB scoring matrix where x's and n's are matches to any IUB ambiguity symbol, and all matches score 1.9, and all mismatched score O.

The presently disclosed vaccine composition may be administered to treat or prevent infection by bacterial pathogens of aquatic animals such as farmed fish (e.g. catfish or tilapia) and crustaceans (e.g., shrimp). In particular, the methods may be utilized to control or prevent the infection or colonization of catfish (e.g., *Ictaluri punctatus* Rafinesque) by pathogenic bacteria or fungi or colonization of environments in which catfish live or are raised (e.g., aquaculture ponds).

The term "sample" is used herein in its broadest sense. A sample may comprise a biological sample from an animal (e.g., a biological sample obtained from aquatic animals such as farmed fish (e.g. catfish or tilapia) and crustaceans (e.g., shrimp)) or a sample taken from an environment, (e.g., a water sample from a pond or a swabbed surface sample taken from a container or instrument).

*Aeromonas hydrophila*, a free-living, Gram-negative bacterium, is one of the most common bacteria in freshwater habitats worldwide. *A. hydrophila* infection results in hemorrhagic septicemia and heavy mortalities in cultured and wild fish. Antibiotics and chemotherapeutic drugs have been used for disease management in feed additives and in direct administration into fish pond water; however, there has been an increase in drug resistant strains (Son et al. 1997. Letters in Appl. Microbiol. 24: 479-482; (Harikrishnan and Balasundaram. 2005. Reviews in Fisheries Science 13: 281-320). Extensive research efforts and strategies have not yet resulted in the development of a safe and effective vaccine. There is still no product that has been licensed for use against the motile aeromonads within the United States (Cipriano, R. C. 2001. Revision of Fish Disease Leaflet 68, U.S. Dept. Interior, Fish and Wildlife Service Div. of Fishery Res., Washington, D.C.). Thus, there is a need, particularly in the aquaculture industry, for an efficacious and safe vaccine.

The disclosed vaccine compositions may be administered to aquatic animals by any suitable method. Suitable administration methods may include injection (e.g., intraperitoneal injection), oral administration, or by administering the compositions to an aqueous environment in which the aquatic animal resides (e.g., bath immersion).

The disclosed vaccines preferably may be administered to protect an aquatic animal from infection by a homologous strain of bacteria that was used to prepare the vaccine composition and/or to protect the aquatic animal from infection by a heterologous strain of bacteria (i.e., strains which are different from those used in the preparation of the vaccine composition). Moreover, the vaccine compositions may include live attenuated bacteria, or killed attenuated bacteria where the killed bacteria has been inactivated by chemical treatment (e.g., treatment with formalin, phenol, or beta-propiolactone) or by physical treatment (e.g., treatment with heat and/or pressure). Preferably, the disclosed vaccine compositions induce both antibody and cellular immune responses and can provide years of protection after the vaccine compositions are administered to an aquatic animal.

The vaccine compositions preferably control infection by *A. hydrophila* in a variety of aquatic animals when administered thereto, including channel catfish (*Ictaluri punctutus*). In addition, the vaccine compositions preferably control infection by *A. hydrophila* in a variety of other aquatic animals, including but not limited to tilapia (*Oreochromis* sp.), American, European, and Japanese eels (*Anguilla* sp), salmonids (*Oncorhynchus* sp. and *Salmo* sp.), striped bass and hybrid-striped bass (*Morone chrysops×M. saxatilis*), flounders (*Seriola* sp.), seabream (*Sparus* sp.), sea perch (*Lates calcarifer*), and the estuarine grouper (*Epinephelus tawine*), walleye (*Zander vitreum*), centrachids (such as large-mouth bass, *Micropterus salmoides*), brown bullheads (*Nebulosus* sp.) bait minnows (*Pimephales promelas*), golden shiners (*Netemigonus crysoleucas*), goldfish (*Carassius auratus*), carp (*Cyprinus carpio*) and aquarium fish species such as black mollies (*Poecilia sphenops*) and platies (*Xiphophorus maculates*).

"Vaccine" is defined herein in its broad sense to refer to any type of biological agent in an administrable form capable of stimulating a protective immune response in an animal inoculated with the vaccine. For purposes of this invention, the vaccine may comprise one or more live attenuated mutants of *A. hydrophila* or killed or inactivated mutants of *A. hydrophila*.

Vaccination may be accomplished by administering a vaccine composition by injection or through oral ingestion or by means of aqueous immersion. The bacterial agent is prepared for administration by formulation in an effective immunization dosage with an acceptable carrier, diluent, or excipient. The expressions "effective immunization dosage" and "immunologically effective amount or dosage" may be defined as being that amount which will induce complete or partial immunity in a treated fish against subsequent challenge by a virulent strain of *A. hydrophila*. Immunity is considered as having been induced in a population of fish when the level of protection for the population (evidenced by a decrease in the number of infected fish or a decrease in the severity of infection) is significantly higher than that of an unvaccinated control group (measured at a confidence level of at least 80%, preferably measured at a confidence level of 95%). One measure of protection following experimental challenge is relative percent survival (RPS) as described by Amend (1981, Dev. Bio. Stand. 49: 447-454) herein incorporated by reference. RPS is calculated according to the following formula:

$$RPS = 1 - \frac{\% \text{ vaccinate mortality}}{\% \text{ control mortality}} \times 100$$

In some embodiments, a positive vaccine effect is indicated by a RPS equal to or greater than about 50%, 60%, 70%, 80%, 90%, or higher. The vaccine may be administered to 7-10 day old aquatic animals such as fish by bath immersion, injection, and/or any oral delivery or immersion device. For example, fish may be vaccinated by immersion in water containing about $1 \times 10^4$ to about $1 \times 10^8$ colony forming units (CFU)/mL of attenuated A. hydrophila for 10 min at a density of about 50/L and a temperature of about 25° C. However, these parameters may be varied such that a sufficient level of vaccination is obtained without inducing stressful conditions or loss of fish. Suitable concentrations of A. hydrophila may range from about $1 \times 10^4$ CFU/ml, $1 \times 10^5$ CFU/ml, $1 \times 10^6$ CFU/ml, or $1 \times 10^7$ CFU/ml, to about $1 \times 10^8$ CFU/ml of immersion medium. Suitable vaccination times may range from about 1 min, 2 min, 5 min, 10 min, 20 min, 30 min, 40 min, or 50 min to about 60 min, preferably from about 2 min to about 15 min. Temperature of the inoculation media may range within the physiologically acceptable limits of the fish involved, channel catfish at tilapia preferably from about 18° C. to about 32° C., most preferably from about 20° C. to about 30° C. Concentrations of fish treated in the inoculation medium typically range from about 10, 20, 30, 40, 50, 60, 70, 80, or 90, to about 100 fish/L, but, in the alternative, may be determined on a weight basis and range from about 0.1, 0.2, 0.5, 1.0, 1.5, or 2.0 to about 2.5 kg/L.

The vaccine compositions also may be administered to aquatic animals such as fish by intraperitoneal injection using about $1 \times 10^4$ CFU, $1 \times 10^5$ CFU, $1 \times 10^6$ CFU or $1 \times 10^7$ CFU to about $1 \times 10^8$ CFU per fish. The vaccine can be effectively administered any time after the fish attains immunocompetence, which for channel catfish, after 7-10 days post-hatch and for tilapia is at about two to fourteen days post-hatch. Other species of fish susceptible to A. hydrophila can be immunized after 21-30 days post-hatch or when they become immunocompetent to modified live vaccine administered by immersion.

To produce large amounts of the recombinant A. hydrophila bacteria for preparation of a vaccine composition, the bacteria may be cultivated under any conventional conditions and on media which promote growth of A. hydrophila. Without being limited thereto, the recombinant A hydrophila may be grown on a variety of solid or liquid media types, including but not limited to tryptic soy agar or Helellea agar. In the alternative to growth on solid media, it is also envisioned that the strain may be grown in liquid culture. Without being limited thereto, conventional tryptic soy broth is preferred.

Following propagation, the recombinant A hydrophila may be recovered for use as a vaccine composition. Cells, particularly those produced by liquid culture, may be optionally concentrated, for example, by centrifugation or filtration. Live cells of the A. hydrophila strain are prepared for administration by formulation in an immunologically effective amount or dosage to the fish. The dose may further include pharmaceutically acceptable carriers and adjuvants known in the art such as water, physiological saline, mineral, oil, vegetable oils, aqueous sodium carboxymethyl cellulose, or aqueous polyvinylpyrrolidone. The vaccine formulations may also contain optional adjuvants, antibacterial agents or other pharmaceutically active agents as are conventional in the art. Without being limited thereto, suitable adjuvants include but are not limited to mineral oil, vegetable oils, alum, and Freund's incomplete adjuvant. Still other preferred adjuvants include microparticles or beads of biocompatible matrix materials. The microparticles may be composed of any biocompatible matrix materials as are conventional in the art, including but not limited to, agar and polyacrylate. The practitioner skilled in the art will recognize that other carriers or adjuvants may be used as well. For example, other adjuvants which may be used are described by Webb and Winkelstein (In: Basic & Clinical Immunology, 1984. Stites et al. (Eds.), Fifth Edition, Lange Medical Publications, Los Altos, Calif., pages 282-285), the contents of which are incorporated by reference herein.

ILLUSTRATIVE EMBODIMENTS

The following embodiments are illustrative and are not intended to limit the claimed subject matter.

Embodiment 1

An attenuated Aeromonas spp. bacterium that has been genetically modified by recombination to be deficient of gene encoding the polypeptide of any of SEQ ID NOs:11, 15, 17, 19, 21, 23, 25, 27, 29, 31, 33, 35, 37, 39, and 41 or to be deficient of a gene encoding a polypeptide having at least 80%, 85%, 90%, 95%, 96%, 97%, 98%, or 99% sequence identity to the polypeptide of any of SEQ ID NOs:11, 15, 17, 19, 21, 23, 25, 27, 29, 31, 33, 35, 37, 39, and 41, optionally where the gene encoding the polypeptide is a gene comprising the polynucleotide of any of SEQ ID NOs: 12, 16, 18, 20, 22, 24, 26, 28, 30, 32, 34, 36, 38, 40, and 42 or a polynucleotide having at least about 80%, 85%, 90%, 95%, 96%, 97%, 98%, or 99% sequence identity to the polynucleotide of any of SEQ ID NOs:12, 16, 18, 20, 22, 24, 26, 28, 30, 32, 34, 36, 38, 40, and 42.

Embodiment 2

The attenuated Aeromonas spp. of embodiment 1, wherein the bacterium is selected from the group consisting of Aeromonas hydrophila, Aeromonas caviae, and Aeromonas veronii.

Embodiment 3

The attenuated Aeromonas spp. bacterium of embodiment 1 or 2, wherein the bacterium has been genetically modified by a method that includes (a) deleting at least a portion of the gene ymcA by recombination and inserting a selectable marker in place of the deleted portion of the ymcA gene, and (b) subsequently deleting the selectable marker to create a markerless bacterium deficient of gene ymcA, wherein optionally the selectable marker is a gene expressing a protein for antibiotic resistance (e.g., chloramphenicol resistance gene (SEQ ID NO:7) expressing the chloramphenicol resistance protein (SEQ ID NO:8).

Embodiment 4

The attenuated Aeromonas spp. bacterium of embodiment 3, wherein the bacterium has been genetically modified by (a) transferring a recombineering system into the bacterium, wherein the recombineering system deletes at least a portion of the ymcA gene (e.g. SEQ ID NO:12) and replaces the portion with the selectable marker flanked by two recombinase recognition target sites (e.g., SEQ ID NO:6 or SEQ ID NO:14); (b) selecting the bacterium for expression of the selectable marker; (c) curing the selected bacterium of the recombineering system; (d) transferring a vector that expresses a recombinase into the selected bacterium (e.g., flp recombinase (SEQ ID NO:5) or cre recombinase (SEQ ID NO:13)), wherein the recombinase recognizes the two recombinase recognition target sites (e.g., SEQ ID NO:6 or SEQ ID NO:14); (e) selecting the bacterium for lack of expression of the selectable marker; and (f) curing the selected bacterium of the vector that expresses the recombinase.

Embodiment 5

The attenuated *Aeromonas* spp. bacterium of embodiment 4, wherein the recombineering system comprises: a mobilizable recombineering vector; and a linear DNA molecule comprising the following contiguous sequences in 5' to 3' order: (i) a first nucleotide sequence of at least 10 nucleotides (or at least 20, 30, 40, 50 or more nucleotides) having sequence identity with the gene ymcA (SEQ ID NO:2), (ii) a second nucleotide sequence comprising the first of the recombinase recognition target sites (e.g., SEQ ID NO:6 or SEQ ID NO:14), (iii) a third nucleotide sequence that expresses a selectable marker (e.g., chloramphenicol resistance gene (e.g., (SEQ ID NO:7) expressing the chloramphenicol resistance protein (SEQ ID NO:8)), (iv) a fourth nucleotide sequence comprising the second of the recombinase recognition target sites (e.g., SEQ ID NO:6 or SEQ ID NO:14), and (v), a fifth nucleotide sequence of at least 10 nucleotides (or at least 20, 30, 40, 50 or more nucleotides) having sequence identity with the gene ymcA (SEQ ID NO:2) that is different than the first nucleotide sequence of (i) and is upstream or downstream of the first nucleotide sequence of (i), wherein after a recombinase is expressed in the bacteria (e.g., flp recombinase (SEQ ID NO:5) or cre recombinase (SEQ ID NO:13)), the recombinase recombines the recombinases recognition target sites (e.g., SEQ ID NO:6 or SEQ ID NO:14) to remove the selectable marker (e.g., (SEQ ID NO:7) expressing the chloramphenicol resistance protein (SEQ ID NO:8)) and the portion of the ymcA gene (e.g., SEQ ID NO:2) that is deleted is replaced with one recombinase recognition target site (e.g., SEQ ID NO:6 or SEQ ID NO:14).

Embodiment 6

A vaccine composition comprising the attenuated *Aeromonas* spp. bacterium of any of embodiments 1-5 and a suitable carrier, diluent, or excipient, and optionally an adjuvant.

Embodiment 7

The vaccine composition of embodiment 6, wherein the attenuated *Aeromonas* spp. bacterium has been inactivated by chemical treatment, such as formalin treatment, phenol treatment, or beta-propriolactone treatment, and/or by physical treatment such as heat and/or pressure.

Embodiment 8

The vaccine composition of embodiment 7, wherein the attenuated *Aeromonas* spp. bacterium has been inactivated by formalin treatment.

Embodiment 9

A method for vaccinating an aquatic animal against infection by an *Aeromonas* spp. bacterium, the method comprising administering the attenuated *Aeromonas* spp. of any of claims 1-5 to the animal or administering a vaccine composition of any of claims 6-8 to the aquatic animal.

Embodiment 10

The method of embodiment 9, wherein the aquatic animal is a channel catfish (*Ictaluri punctata*).

Embodiment 11

The method of embodiment 9 or 10, wherein the aquatic animal is administered the vaccine composition by intraperitoneal injection.

Embodiment 12

The method of any of embodiments 9-11, wherein the aquatic animal is administered the vaccine composition at a dose that delivers $10^4$-$10^8$ CFU of attenuated *Aeromonas* spp. bacteria per aquatic animal.

Embodiment 13

The method of embodiment 9 or 10, wherein the aquatic animal is administered the vaccine composition by immersing the aquatic animal in an aqueous medium comprising the vaccine composition.

Embodiment 14

The method of embodiment 13, wherein the aqueous medium has a concentration of $10^4$-$10^8$ CFU/ml of attenuated *Aeromonas* spp. bacteria.

Embodiment 15

A mobilizable recombineering vector: (a) that comprises a polynucleotide sequence comprising oriT (SEQ ID NO:1) or a polynucleotide sequence having at least about 95% sequence identity with oriT (SEQ ID NO:1) wherein the polynucleotide sequence functions as an origin of transfer; and (b) a polynucleotide sequence that expresses lambda Gam polypeptide (SEQ ID NO:2) or a polypeptide having at least 95% sequence identity to lambda Gam polypeptide (SEQ ID NO:2), wherein the polypeptide functions as an inhibitor of *E. coli* RecBCD exonuclease; (c) a polynucleotide sequence that expresses lambda Exo polypeptide (SEQ ID NO:3) or a polypeptide having at least 95% sequence identity to lambda Exo polypeptide (SEQ ID NO:3), wherein the polypeptide functions as a 5'→3' double-stranded DNA specific nuclease; and (d) a polynucleotide sequence that expresses lambda Beta polypeptide (SEQ ID NO:4) or a polypeptide having at least 95% sequence identity to lambda Beta polypeptide (SEQ ID NO:4), wherein the polypeptide functions as a ssDNA annealing protein.

Embodiment 16

The vector of embodiment 13, wherein the aqueous medium has a concentration of $10^4$-$10^8$ CFU/ml of attenuated Aero 15, wherein the lambda Gam polypeptide (SEQ ID NO:2), the lambda Exo polypeptide (SEQ ID NO:3), and the lambda Beta polypeptide (SEQ ID NO:4) are inducibly expressed from the vector.

Embodiment 17

The vector of embodiment 15 or 16, wherein the vector further expresses a recombinase selected from bacteriophage P1 cre recombinase (SEQ ID NO:13) or a recombinase having at least about 95% sequence identity to bacteriophage P1 cre recombinase (SEQ ID NO:13), and *Saccharomyces cerevisiae* flp recombinase (SEQ ID NO:5) or a recombinase having at least about 95% sequence identify to *Saccharomyces cerevisiae* flp recombinase (SEQ ID NO:5).

Embodiment 18

The vector of embodiment 17, wherein the recombinase is inducibly expressed.

Embodiment 19

A method for genetically modifying an *Aeromonas* spp. bacterium to obtain a recombinant bacterium, the method comprising one or more of the following steps: (a) transferring a recombineering system into the bacterium, wherein the recombineering system deletes at least a portion of a target sequence and replaces the portion with a selectable marker flanked by two recombinase recognition target sites; (b) selecting the bacterium for expression of the selectable marker; (c) curing the selected bacterium of the recombineering system; (d) transferring a vector that expresses a recombinase into the selected bacterium, wherein the recombinase recognizes the two recombinase recognition target sites; (e) selecting the bacterium for lack of expression of the selectable marker; and (f) curing the selected bacterium of the vector that expresses the recombinase.

Embodiment 20

The method of embodiment 19, wherein deletion of the target sequence results in attenuating the bacterium.

EXAMPLES

The following examples are illustrative and are not intended to limit the claimed subject matter.

Example 1

Conjugal Transfer of a Recombineering System to Generate and Complement Markerless Genome Modifications\

Abstract

The genetic modification of primary bacterial disease isolates is challenging due to the lack of highly efficient genetic tools. In this study, we were unable to use an available recombineering system to construct genetic mutants in the fish pathogens *Edwardsiella ictaluri* and *Aeromonas hydrophila* due to an inability to introduce plasmids into these disease isolates via electroporation. Herein we describe the development of a modified PCR-based λ Red-mediated recombineering system for efficient deletion of genes in gram-negative bacteria, which we have used in different *E. ictaluria* and *A. hydrophila* strains. A series of conjugally transferrable plasmids were constructed by cloning oriT sequence and different antibiotic resistance genes into recombinogenic plasmid pKD46. Using this system we knocked out a total of 16 different genes from the genomes of three different strains of *E. ictaluri* and *A. hydrophila*. To generate a markerless mutant, we engineered the λ Red cassette and flp recombinase under the control of arabinose- and rhamnose-inducible promoters, respectively, and introduced this construct onto a conjugally transferrable and temperature sensitive plasmid. Using this system, we generated markerless gene deletion mutants in *A. hydrophila* including a mutant in a genetic operon. In order to formally demonstrate the contribution of this specific operon to virulence, we needed to complement this entire operon. To accomplish this we developed a highly efficient and novel PCR-free cloning system to capture larger bacterial genetic elements and clone them into a conjugally transferable plasmid. This system should be applicable in diverse Gram-negative bacteria for modification and complementation of genomic elements including larger elements such as operons, genomic islands, and prophages in bacterial isolates that cannot be manipulated using currently available genetic tools.

Introduction

Genetic manipulation of bacterial strains provides critical information on the contributions of specific loci to virulence or other cellular functions, and many systems have been developed to achieve genetic knockouts and modifications (1-3). The modification of bacterial genomes using counter-selectable plasmid-based double-crossover methods are labor intensive and sometimes very difficult to achieve due to the low frequency of the recombination events (4-6). In contrast, the λ Red recombineering system (7,8) has many advantages as a fast, efficient and reliable means of generating targeted genetic modifications in prokaryotes (9,10) and eukaryotes (11). The λ Red system expresses Exo, Beta and Gam proteins that work coordinately to recombine single and double stranded DNA (9, 10, 12, 13), and has been exploited for genome modifications in *Escherichia coli* and other Gram-negative bacteria (9, 10, 12). Exo has a 5' to 3' double stranded DNA (dsDNA)-dependent exonuclease activity for generating 3' single stranded DNA (ssDNA) overhangs (14-16) which then serve as a substrate for ssDNA-binding protein. Beta to anneal complementary DNA strands for recombination (17-19). Gam, an inhibitor of host exonuclease activity due to RecBCD (20), helps to improve the efficiency of λ Red-mediated recombination with linear double-strand DNA. Unlike recA-dependent homologous recombination which requires longer regions of sequence homology with the targeted genetic region (21), the λ Red apparatus can efficiently recombine DNA with homologous regions as short as 30 to 50 bp which can directly be incorporated into oligonucleotide primers in a PCR (9,10). The recombineering technique is widely used to generate precise deletions (10), substitutions (22), insertions (23) or tagging (24) of targeted genes. One of the biggest advantages of the recombineering method is that modifying DNA can precisely eliminate the antibiotic selection markers for subsequent modification of the targeted DNA (9, 10, 25).

While this recombineering system works well in a model bacterium such as E. coli (7,8) bacteria often express restriction endonucleases that make them recalcitrant to foreign DNA even among naturally competent strains (26,27). In fact, it was through experimental infections of E. coli strains with bacteriophage λ that led to the discovery of restriction-modification (RM) systems (28). Overcoming host RM systems can be accomplished via the passage of plasmids through a methylation-minus E. coli strain (29), but in highly methylated bacterial strains it may be necessary to use an in vitro or in vivo methylation strategy to achieve more efficient electroporation (30-32). However, modulating the plasmid DNA methylation status is inefficient and labor-intensive compared to using conjugal transfer to introduce foreign DNA into a bacterial strain using a broad host range plasmid like IncP when electroporation is problematic (33-35).

Our need to generate target genetic deletions in gram-negative bacterial pathogens of farmed catfish led to the development of recombinogenic plasmids that could be introduced via conjugation. Our studies focused on two bacterial pathogens, including Edwardsiella ictaluri, causative agent of enteric septicemia of catfish (ESC), which is responsible for significant economic loss to the channel catfish industry in the Southeastern United States (36). Fish diseases caused by strains of E. ictaluri are also frequently reported in catfish farming in Asia (37). In addition to E. ictaluri, we also had an interest in studying the pathogenesis of Aeromonas hydrophila, because beginning in 2009 US catfish farmers experienced epidemic disease outbreaks of motile Aeromonas septicemia (MAS) caused by a highly virulent Aeromonas hydrophila strain (38). This newly emergent and virulent A. hydrophila strain, which has been implicated to have an Asian origin (39), is responsible for killing millions of pounds of food-sized channel catfish in the US (39). Though, both E. ictaluri and A. hydrophila pose serious threats to the US catfish industry (36, 40, 41) as well as global fish farming (37,42), highly efficient genome modification techniques have not been developed yet to study the virulence mechanisms and permit generation of markerless vaccines for these two pathogens.

Though recombineering techniques are widely being used for genome modification of domesticated laboratory isolates, the implementation of these techniques for primary pathogenic isolates is quite challenging. In this study, we modified the available λ Red recombination tools (13,43) to generate markerless mutants of E. ictaluri and A. hydrophila. A novel dual inducible Redαβλγ and Flp recombinase plasmid was constructed to facilitate the removal of antibiotic resistance marker followed by recombineering. In addition, we also developed a novel in vivo error-free cloning system that can be used to clone large fragments of genomic DNA without PCR amplification of the inserts and used to complement larger genomic regions.

Materials and Methods

Bacterial Strains and Plasmids.

The list of bacterial strains and plasmids used in this study is presented in Table 2. E. ictaluri and A. hydrophila strains were routinely grown on Trypticase Soy Broth or Agar (TSB/TSA) medium at 28° C. and 30° C., respectively. E. coli SM10λpir (44) was routinely used for the conjugal transfer of mobilizable plasmids to strains of E. ictaluri and A. hydrophila. E. coli BW25141 and BT340 (10) were received from the Yale University Genetic Stock Center. When antibiotic selection was required, bacterial growth media were supplemented with chloramphenicol (15.0 and 25.0 µg/ml for strains of E. ictaluri and A. hydrophila, respectively), tetracycline (10.0 µg/ml) and/or colistin (10.0 µg/ml).

Recombinant DNA Techniques, and Conjugal Transfer of Recombinogenic Plasmids.

The list of primers used in this study are presented in Table 3. All primers were purchased from Eurofins MWG Operon (Huntsville, Ala.). For cloning purposes, we routinely used electrocompetent E. coli ("E. cloni 10G", Lucigen Corp., Middleton, Wis.). PCR amplifications were carried out using EconoTaq DNA polymerase (Lucigen Corp.), Pfu DNA polymerase (Life Technologies, Grand Island, N.Y.) and TaKaRa Ex Taq (Clontech, Mountain View, Calif.) as appropriate. Genomic DNAs and plasmids were extracted using E.Z.N.A. DNA Isolation Kit (Omega Biotek, Atlanta, Ga.) and FastPlasmid Mini Kit (5 Prime, Gaithersburg, Md.), respectively. Restriction enzymes and T4 DNA Ligase (Quick ligase) used for restriction digestion of DNAs, and cloning, respectively were purchased from New England Biolabs (Ipswich, Me.). Restriction digested DNAs with sticky ends were blunt-ended using a DNA Terminator kit (Lucigen Corp.). Digested DNAs and ligation mix were purified using DNA Clean and Concentrator-5 (Zymo Research, Irvine, Calif.). DNA samples were quantitated using a Qubit 2.0 Fluorometer (Life Technologies). The mobilizable recombinogenic plasmids pMJH46 and pMJH65, and dual expression plasmid pMJH95 bearing the λ-Red cassette were introduced into E. coli SM10λpir by electroporation according to a previous published method (45). Plasmids were conjugally transferred into E. ictaluri and A. hydrophila by filter mating experiments according to the methods described previously (Maurer et al., 2001). E. ictaluri and A. hydrophila transconjugants were selected of LB plates supplemented with chloramphenicol and colistin, or tetracycline and colistin, respectively. The introduction of plasmids into E. ictaluri or A. hydrophila was confirmed by their growth in the presence of appropriate antibiotics and by conducting PCR with a plasmid-specific printer set.

Construction of Broad Host Range Recombinogenic Plasmids.

A list of primers used in this study is presented in Table 3. The mobilizable plasmid pMJH46 was constructed by introducing the oriT sequence and chloramphenicol acetyltransferase (cat) into the recombinogenic plasmid pKD46 (46) which contains an arabinose-inducible λ-Red cassette (exo, bet and gam genes) required for recombineering (FIG. 1). The oriT sequence and cat gene were PCR amplified from pGNS-BAC (47) using primers MobF and MobR, and CatF and CatR, respectively. Amplicons for the oriT sequence and cat gene were fused by splicing by overlap extension (SOE) PCR (48) using primers Mob-intF (forward) and Cat-intR (reverse). The oriT-cat cassette and pKD46 plasmid were digested with EcoRV and NcoI, respectively. NcoI digested pKD46 plasmid was blunt-ended and ligated to oriT-cat cassette using a DNA Terminator kit (Lucigen Corp., Middleton, Wis.) and T4 DNA ligase (Promega, Wis.), respectively. The ligation mixture was then transformed into electrocompetent E. coli (E. cloni 10G, Lucigen, Corp.). Transformants were selected on 2×YT medium supplemented with ampicillin and chloramphenicol after incubation overnight at 30° C. The introduction of the oriT-cat cassette into pKD46, resulting in pMJH46, was confirmed by PCR and sequencing. To construct the recombinogenic plasmid pMJH65, plasmid pMJH46 was digested with BstZ17I and SfiI, and blunt-ended using the DNA Terminator kit. A tetracycline resistance gene (tetA)

cassette was PCR amplified from pACYC184 using primers TetAF and TetAR and ligated to blunt-ended pMJH46 using T4 DNA ligase. The ligation mixture was then transformed into electrocompetent *E. coli* (E. cloni 10G, Lucigen Corp.), Transformants were selected on 2×YT medium supplemented with tetracycline after overnight incubation at 30° C. The construction of recombinogenic plasmid pMJH65 was confirmed by PCR and sequencing.

Construction of Dual Inducible Plasmid for Red and flp/FRT Recombination.

Figure 1A:
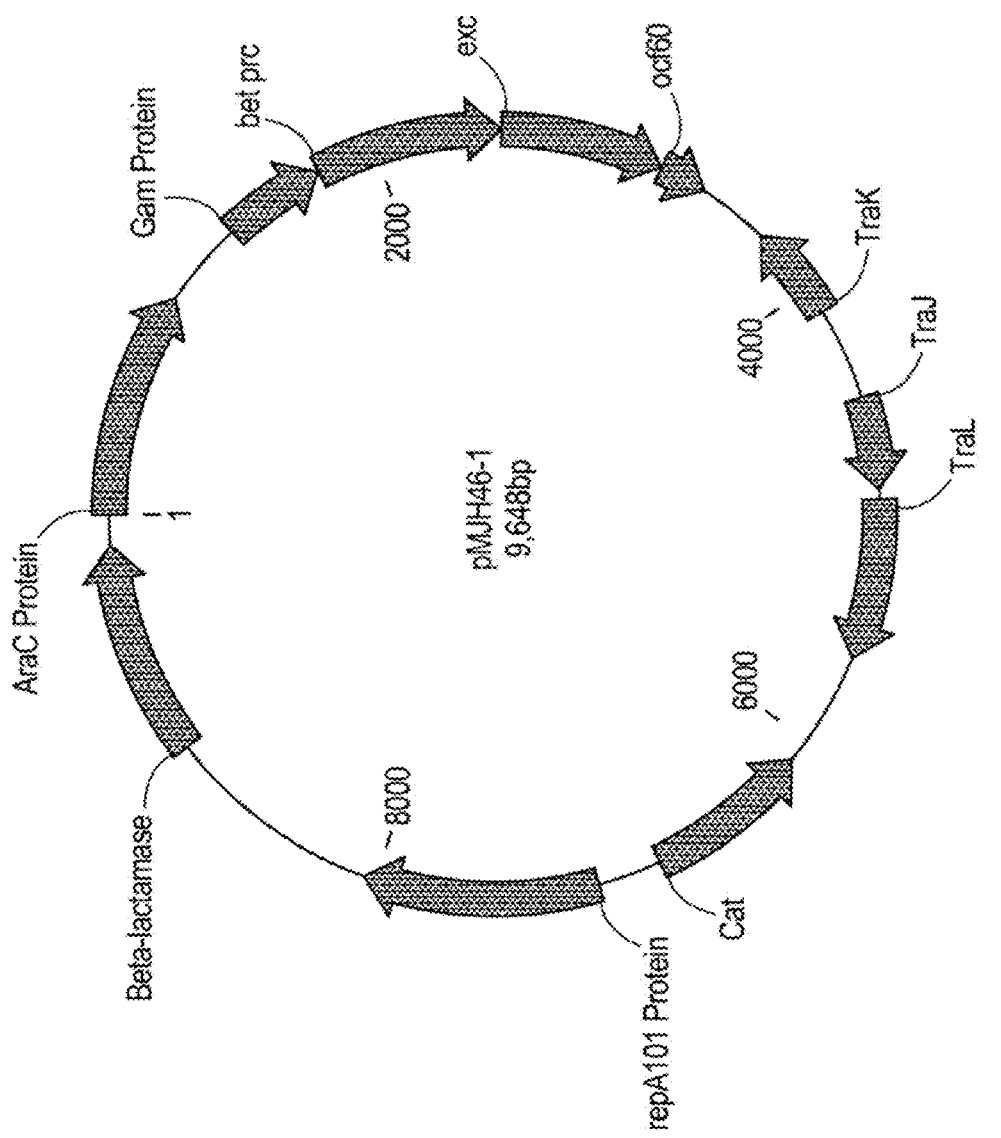
FIG. 1 (A)-(D) Schematic map of conjugally transferable recombinogenic and flp recombinase plasmids constructed in this study. The plasmid map was generated by CLC Genomics Workbench (Version 4.7.1).
Figure 1B:
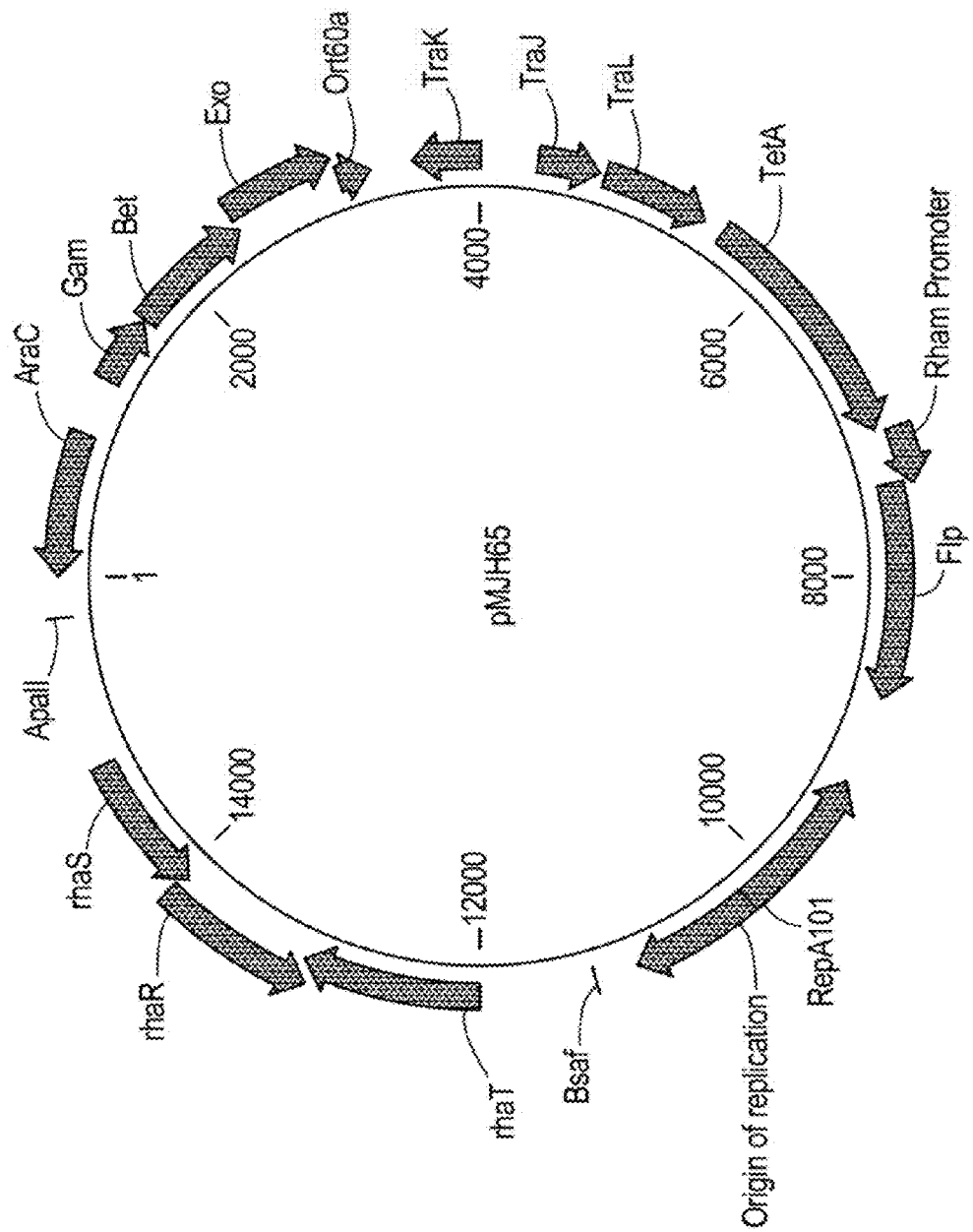
Figure 1C:
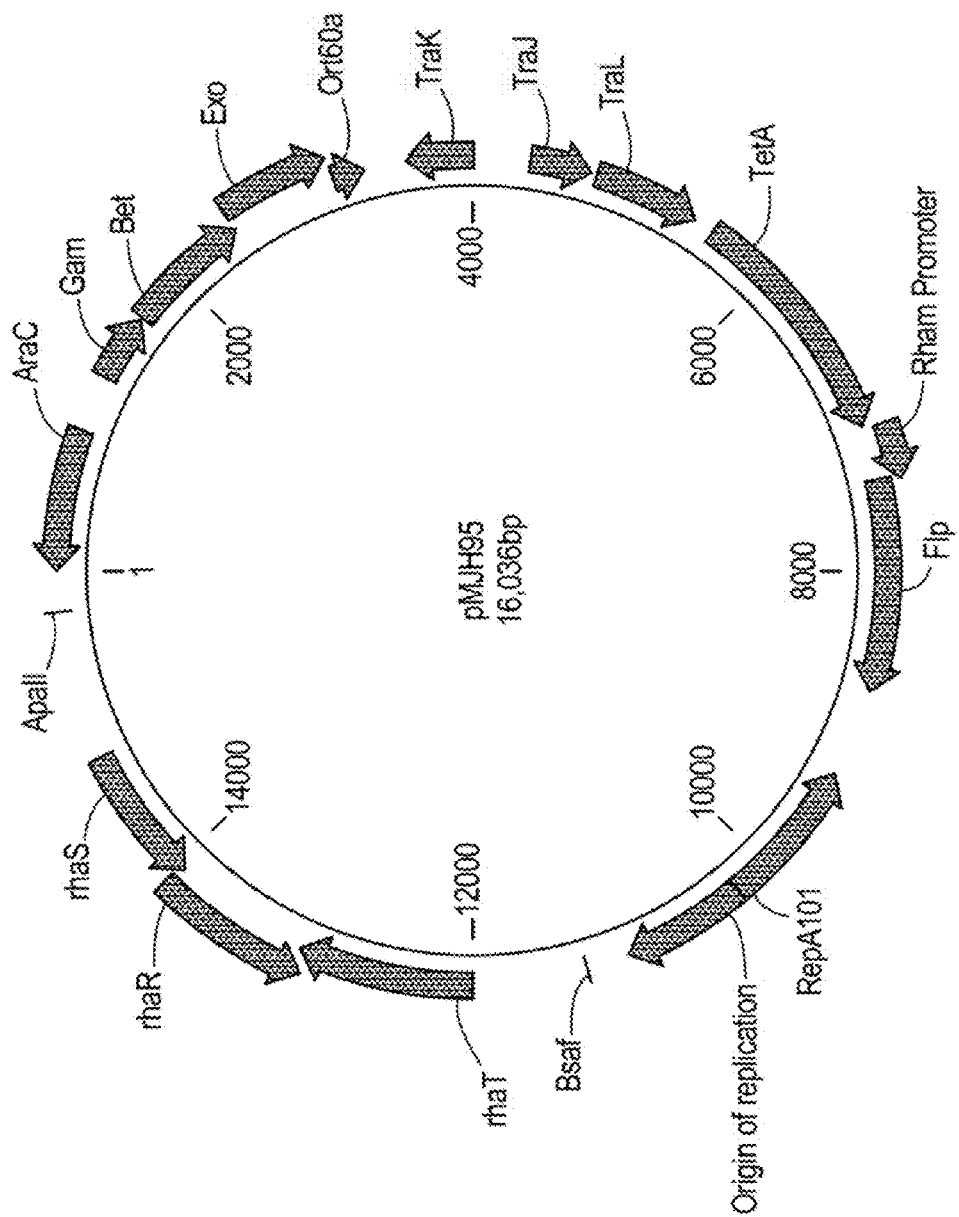
Figure 1D:
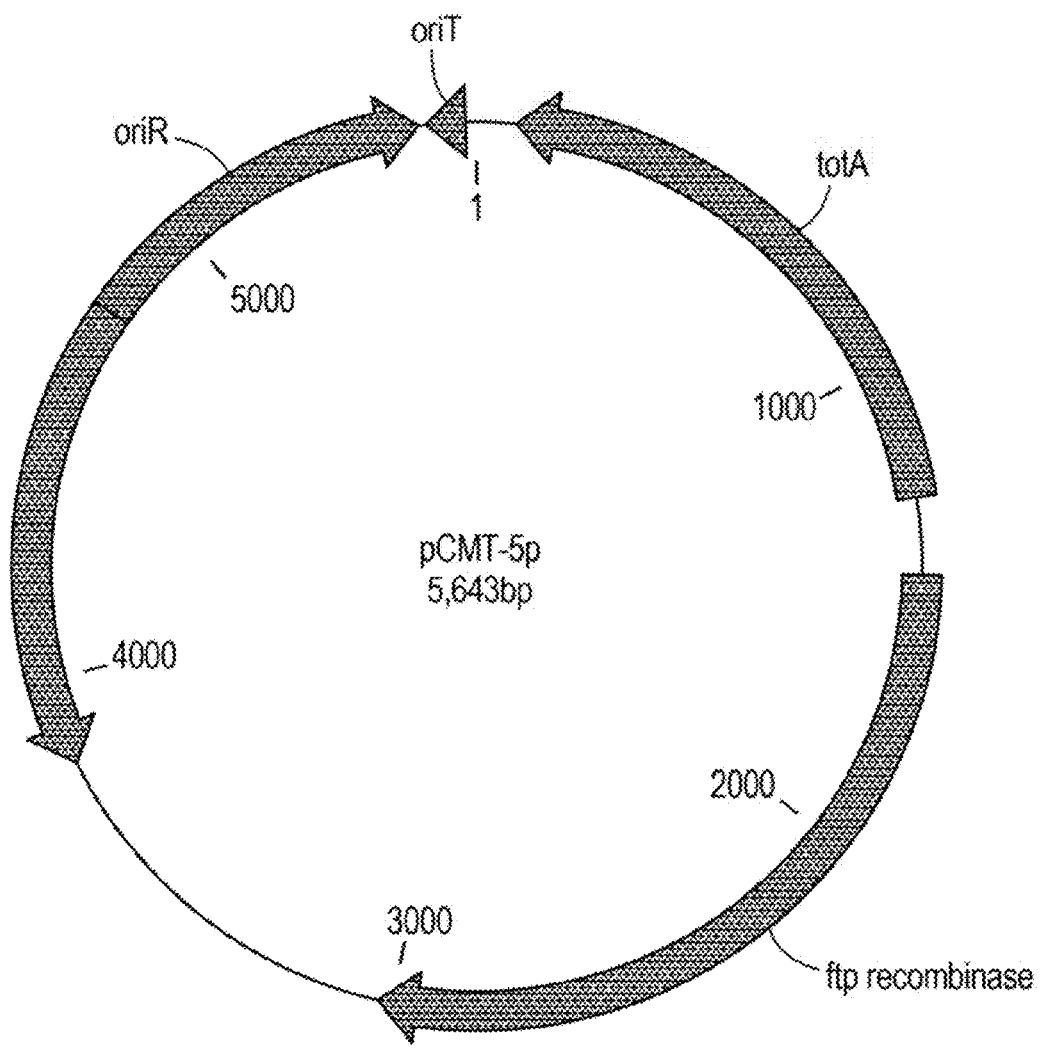

To construct a dual expression plasmid with arabinose-inducible Red cassette (exo, bet and gam) and rhamnose-inducible flippage (flp) gene under araPBAD and rhaPBAD promoters, respectively, we modified our recombinogenic plasmid pMJH46 by replacing the beta-lactamase (bla) and cat genes with rhaSRT and flp-tetA cassettes (FIGS. 1A, B, and C). The rhaSRT cassette amplified from genomic DNA of *E. coli* BL21. (DE3) using primers rhaSRT-BsaIF and rhaSRT-ApaLIR was cloned into a BsaI- and ApaLI-digested pMJH46 that resulted in plasmid pMJH52. To introduce rhamnose-inducible flp gene in pMJH52, the flp gene was amplified from pCP20 using primers Flp-pRhamF and Flp-pRhamR and was cloned into the pRham N-His vector under control of the rhaPBAD promoter that resulted in plasmid pPham-flp. This plasmid was then digested with XbaI and blunt-ended in order to insert a tetracycline resistance gene (tetA) that was PCR amplified from pMJH65 using primer tetAF and tetAR. After cloning this tetA cassette into the pRham-flp plasmid, resulting in plasmid pRham-flp-tetA, the flp-tetA cassette was digested with AlwNI and BsaAI, and blunt-ended for cloning into pMJH52. This flp-tetA cassette was then cloned into a BstZ17I and SfiI-digested and blunt-ended plasmid pMJH52. The resulting dual expression plasmid pMJH95 that contained arabinose-inducible λ-Red and rhamnose-inducible flip was verified by digestion with BsaI and ApaLI and agarose gel electrophoresis. The plasmid was introduced into *A. hydrophila* mutants to determine their efficiency in the excision of an antibiotic cassette flanked by FRT sequences.

Preparation of Linear Double Stranded DNA (dsDNA) Substrate for Recombineering.

The linear dsDNA fragments used for deletion of the ompLC gene from *E. ictaluri* with recombineering were generated by PCR amplification of the kanamycin resistance gene (kanR) cassette with its flanking FRT sequences using plasmid pKD4 as a template (10). All other linear dsDNA used for deletion of *E. ictaluri* genes eihA, dtrA and ptrA were PCR amplified from a kanR cassette located within the genome of this *E. ictaluri* Alg-08-183 ΔompLC mutant generated by recombineering. The linear dsDNA substrate used for recombineering in *A. hydrophila* were generated by PCR amplification of the cat gene or cat gene flanking with FRT sequences integrated within the genome of *A. hydrophila* ML09-119. Recombineering primers contained 50-60 bp of homology to the targeted genes at their 5' ends and 20-22 bp of homology to the cat cassette at their 3' ends. Primers were modified with four consecutive 5' phosphorothioates bonds to reduce the chance of degradation by exonucleases during recombination. PCR amplification of the respective antibiotic resistance gene cassette using these gene-targeted primers was performed using high fidelity Takara Ex Taq Polymerase (Clontech) and EconoTaq PLUS GREEN (Lucigen Corp.). At least 10 positive PCRs of 50 µl volume were pooled together and purified by phenol-chloroform extraction followed by ethanol precipitation (45) or using the Wizard DNA Clean-Up System (Promega, Madison, Wis.). Purified PCR products were resuspended in nuclease-free water and used for transformation into electrocompetent *E. ictaluri* and *A. hydrophila* strains harboring recombinogenic plasmids pMJH46 and pMJH65, respectively.

Deletion of *E. ictaluri* and *A. hydrophila* Genes by Recombineering.

Electrocompetent *E. ictaluri* and *A. hydrophila* harboring recombinogenic plasmids pMJH46 and pMJH65, respectively, were prepared as described follows. *E. ictaluri* and *A. hydrophila* strains were grown and selected for mutants at 28° C. or 30° C. in the presence of chloramphenicol and tetracycline, respectively. Overnight grown cultures were diluted 1:70 in 40 ml of Super Optimal broth (SOB) medium supplemented with appropriate antibiotics and 10 mM of L-arabinose and grown with vigorous shaking until the $OD_{600}$ attained a value of 0.45 or 0.6 for *E. ictaluri* and *A. hydrophila*, respectively. Cells were harvested by centrifugation at 5000×g for 8 min at 4° C., washed three times with ice-cold 10% glycerol and finally cells were concentrated 400-fold by resuspending with 100 µl of ice-cold GYT (10% glycerol, 0.125% yeast extract and 0.25% tryptone) medium or 10% glycerol. Freshly prepared electrocompetent cells were immediately used for electroporation. For deletion of targeted genes from *E. ictaluri* using recombineering, dsDNA substrate of appropriate concentrations were mixed with 50-55 µl of electrocompetent cells in a pre-chilled electroporation cuvette (0.1-cm gap), and pulsed at 1.8 kV, 25 µF and 200Ω using an Eppendorf Electroporator 2510 (Hamburg, Germany). For *A. hydrophila*, the same electroporation procedures were followed with the exception that cells were pulsed at 1.2 kV. Immediately after electroporation, 950 µl of SOC supplemented with 10 mM of L-arabinose (for catabolite repression) was added and incubated at an appropriate temperature with vigorous shaking for at least 4 hrs. Cells were then spread onto 2×YT agar plates supplemented with kanamycin and chloramphenicol for *E. ictaluri* and *A. hydrophila*, respectively, and incubated at an appropriate temperature to obtain mutants with the targeted deletions. The correct deletions of the targeted genes were confirmed by PCR and sequencing as previously described (10). To determine the effect of 1) phosphorothioate-modified primers, 2) the size of the gene-specific region of homology and 3) the concentration of the dsDNA substrates on recombination frequencies, each experiment was repeated independently at least three times.

Flp-Mediated Excision of Antibiotic Resistance Gene Cassettes to Generate Unmarked Mutants.

Before removal of the antibiotic resistance gene cassettes using Flp/FRT mediated recombination, recombinogenic plasmids were cured from the mutants of *E. ictaluri* and *A. hydrophila*. Plasmid pMJH46 was cured from *E. ictaluri* mutants by growing cells on TSB medium at 28° C. until the $OD_{600}$ attained a value of 1.0 and then heat-inducing cells by incubation at 43° C. for 1 hr with shaking at 250 rpm. Heat-induced cultures were serially diluted in sterile water and spread for isolated colonies onto BHI Blood Agar plates that were then incubated at 28° C. for 36 hours. To cure plasmid pMJH65 from *A. hydrophila* mutants, cultures were grown in TSB broth at 37° C. overnight and streaked onto TSA plates for isolated colonies. The loss of plasmid pMJH46 and pMJH65 from *E. ictaluri* and *A. hydrophila* mutants were confirmed by determining the lack of ability of individual colonies to grow on TSA plates supplemented with chloramphenicol and tetracycline, respectively. Plasmid pCP20 that contains the Flp recombinase (49) required for FRT sequence-specific recombination was electroporated into *E. ictaluri* mutants according to the methods described above. *E. ictaluri* mutants harboring pCP20 were selected on 2×YT agar plates supplemented with chloramphenicol. These *E. ictaluri* mutants were grown in TSB at 28° C. until $OD_{600}$ of 1.0 and temperature was shifted by incubating at 37° C. for 1 hr with shaking at 250 rpm to induce the removal of kanamycin resistance gene cassette by FLP recombinase. To obtain isolated colonies diluted cultures were plated onto BHI Blood Agar plates and incubated at 28° C. for up to 36 hours. Dual expression plasmid pMJH95 (pCMT-flp) constructed in this study was conjugally transferred to *A. hydrophila* mutants as described above and induced for the removal of chloramphenicol resistance gene cassette by incubating at 37° C. Colonies grown on non-selective plates that subsequently failed to grow on antibiotic selective plates were tested by PCR and sequencing to confirm the Flp-mediated excision of antibiotic resistance gene cassettes introduced by recombineering.

Cloning Large Genomic Inserts without PCR Amplification.

To construct a small, conjugally transferrable, and low copy-number plasmid backbone, the cat gene and p15A origin of replication (oriR) were PCR amplified from the genome of *A. hydrophila* ML09-119Δvgr3 (generated in this study) and pACYC184, respectively. The reverse primer used for amplification of the cat gene contains the 87 bp oriT sequence (Table 3) to facilitate the conjugal transfer of large insert clones to Gram-negative bacteria. The cat-oriT cassette and oriR sequence were fused together to construct a 2003 bp plasmid backbone cat-oriT-oriR (pMJH97) using SOE PCR with outermost primers. To clone the ymcABC operon of *A. hydrophila* ML09-119, the pMJH97 plasmid backbone was PCR amplified using primers that contain 60 and 63 bp, respectively, of homologous sequence specific to the upstream region of the ymcABC operon. To facilitate the restriction digestion of the regions flanking ymcABC and its contiguous cat-oriT-oriR cassette integrated within the genome, an Acc65I restriction site (GGTACC) was introduced between the 60 bp homologous sequence and cat gene priming site of the forward primer. Purified PCR products were introduced into *A. hydrophila* ML09-119 harboring plasmid pMJH65 by electroporation for genomic integration by recombineering. Colonies selected on 2×YT plates containing chloramphenicol were subjected to PCR to confirm the correct integration of the pMJH97 backbone plasmid into the genome, and amplicons of the expected size were selected for sequencing. Once the correct integration was confirmed, genomic DNA was extracted from ML09-119:: cat-oriT-oriR that was restriction digested with Acc65I. Blunt-ended and purified genomic DNA fragments were self-ligated, electroporated and selected on 2×YT plates with chloramphenicol for cloning into *E. coli* (E. cloni 10G, Lucigen Corp.). The cloned plasmid pYmcABC was verified by PCR and sequencing for the presence of the complete ymcABC operon as an insert. Once the complete ymcABC cloning was confirmed, the pYmcABC was introduced into *E. coli* SM10λpir electroporation and conjugally transferred to *A. hydrophila* as described above.

Nucleotide Sequence Accession Numbers.

The sequences of pMJH46 and pMJH65 were deposited to the NCBI GenBank sequence database under accession numbers JQ070344 and KF195927, respectively.

Results

Construction of Conjugally Transferable Recombinogenic Plasmids.

The expression of exo, bet and gam within bacterial cells substantially improves their recombination frequencies that can be exploited to modify bacterial genomes by recombineering (13). Though published reports indicate that some *E. ictaluri* strains are capable of accepting foreign DNA of up to 45 kb by electroporation (51), our repeated attempts failed to introduce the recombinogenic plasmid pKD46 (13) into primary disease isolates of *E. ictaluri* or *A. hydrophila*. To introduce the recombinogenic λ-Red cassette into *E. ictaluri*, a mobilizable plasmid was constructed by introducing the 'mob cassette' (oriT region, traJ and traK) along with a chloramphenicol resistance (cat) gene into pKD46, resulting in plasmid pMJH46 (FIG. 1A, accession no. JQ070344). The cat gene introduction broadens the applicability of this plasmid since some *E. ictaluri* strains are resistance to ampicillin (52); therefore, the original plasmid pKD46 expressing the bla gene is incompatible for these *E. ictaluri* isolates. We successfully transferred this recombinogenic plasmid pMJH46 into different *E. ictaluri* strains by conjugation with *E. coli* SM10λpir. In subsequent studies, the pMJH46 plasmid was modified by replacing the cat gene with tetA to make it compatible for the genomic modification of primary disease isolates of *A. hydrophila*. The resulting plasmid pMJH65 (FIG. 1B, accession number KF195927) was successfully introduced into highly virulent catfish isolate *A. hydrophila* ML09-119 (53) for genomic modifications through recombineering.

Deletion of *E. ictaluri* and *A. hydrophila* Genes by Recombineering.

To determine the feasibility of using this recombineering system in *E. ictaluri*, we deleted the ompLC gene that is required for phage ΦeiAU-183 attachment to *E. ictaluri* strain Alg-08-183 (54). The PCR screening of colonies grown on antibiotic selection plates showed that approximately 1% colonies were true mutants (data not shown). Unfortunately, a large number of colonies grown on 2×YT plates supplemented with kanamycin were determined to be false positive even though the suicide plasmid pKD4 (13) used as template was treated with DpnI before electroporation into *E. ictaluri*. To avoid the occurrence of background colonies, we subsequently used the genomic DNA of *E. ictaluri* Alg-08-183 ompLC::kanR mutant as the PCR template for amplification of the kanamycin resistance gene cassette. Using this chromosomal template to prepare amplicons we obtained 20 to 25 colonies per experiment on average, of which ~90% of them were true mutants. We deleted three additional genes including dtrA and ptrA of *E. ictaluri* Alg-08-183 (Hossain et al., 2012), and eihA of *E. ictaluri* R4383 (55) (Table 2). Using this recombineering approach, we also deleted 12 different genes from the primary disease isolate *A. hydrophila* ML09-119 (Table 2). PCR and sequencing confirmed that all genes that were targeted for deletion from *E. ictaluri* and *A. hydrophila* strains were successfully deleted by recombineering.

Effects of Primer Modification, Length of Homology and dsDNA Substrate Concentration in Recombination Frequency.

Figure 2:
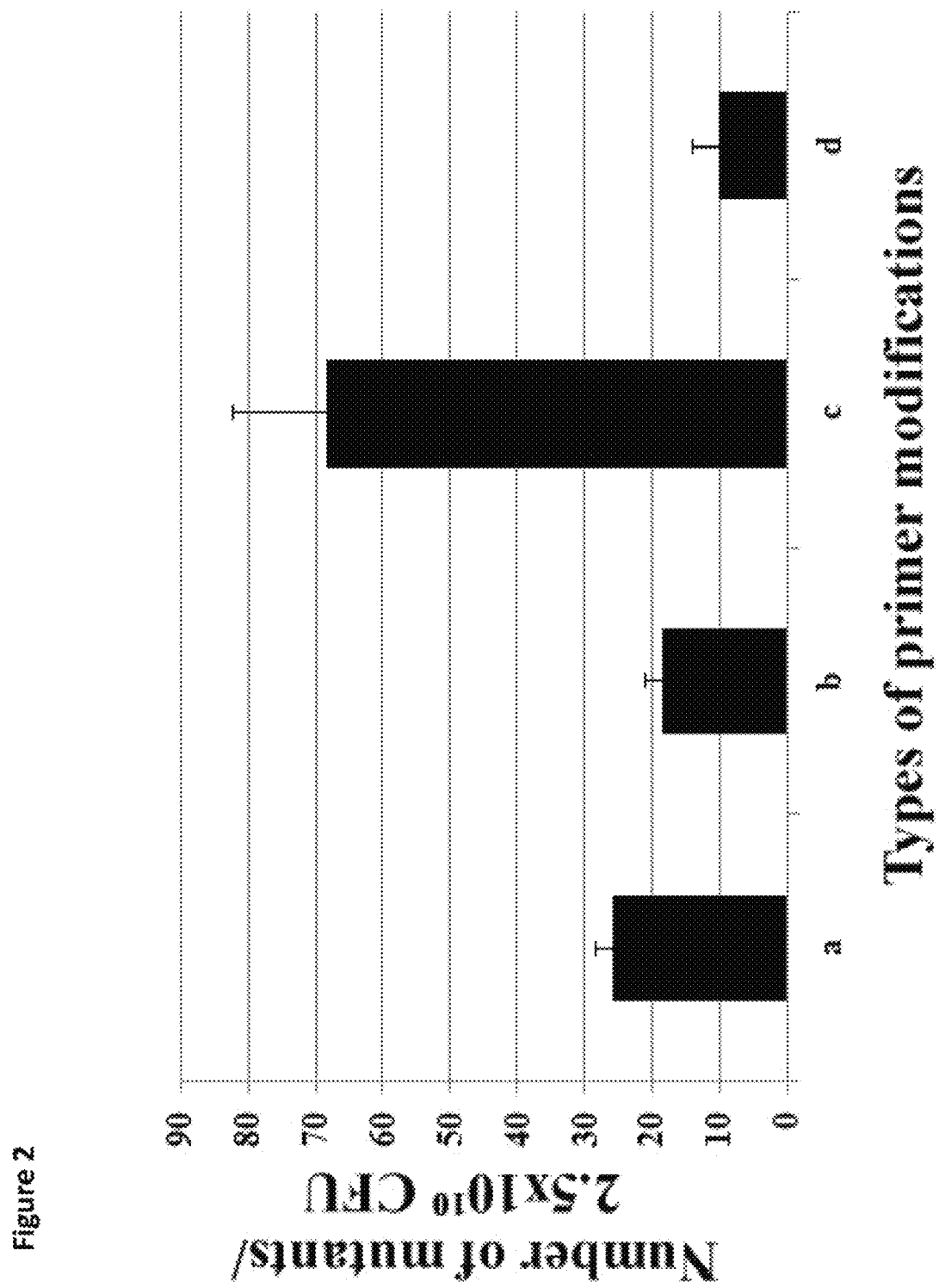
FIG. 2. Effect of primer modifications on the mutant frequency in *A. hydrophila*. Modified primers were generated by adding four consecutive phosphorothioate bonds at the 5' end of the primers. To generate type a PCR substrate, leading strand specific modified plasmid was used; type b, lagging strand specific primers were modified, type c and d both or none primers were modified, respectively. PCR products (type c) generated by modified forward and reverse primers provided significantly more mutants than other types of PCR substrates used for recombineering in this study (p-value=0.0026). Average number of mutants represents in the graph, derived from three independent recombineering experiments.

To determine the effect of primer modifications on recombination frequencies in *A. hydrophila*, four different combinations of primers were used for the preparation of dsDNA substrates to delete the waaL gene of *A. hydrophila* ML09-119. In one combination, both the leading and lagging strand-specific primers were modified with four consecutive 5' phosphothioate bonds, whereas in another combination both the strands specific primers were unmodified. In two other combinations the leading strand and lagging strand were modified with for consecutive 5' phosphothioates bonds, vice versa. We found that dsDNA substrate prepared with both of the modified primers provided significantly more mutants compared to other combinations (FIG. 2). Once we determined and modified primers provided significantly more mutants, all of our subsequent primers used for recombineering in *A. hydrophila* were modified on both strands.

To determine the effect of the length of the gene-specific homologous arms on recombination efficiency, three different dsDNA substrates that Included approximately 50 bp, 250 bp ord 500 bp of homologous sequence were used for deletion of the waaL gene. We found that the recombination frequencies were not significantly different due to the varying length of homologous arms flanking to the targeted gene (data not shown).

To determine the effect of dsDNA concentration on recombination frequencies in *A. hydrophila*, we used four different concentrations that included 0.75, 1.5, 3.0 and 5.0 µg of PCR products as a substrate for recombineering. Our findings demonstrated that gradual increment of the dsDNA substrate concentrations did not change the recombination frequency significantly (data not shown). The number of mutants we routinely obtained in this experiment was within the range of approximately 30-200.

Removal of Antibiotic Resistance Cassette by Flp Recombinase.

Temperature induction of *E. ictaluri* Alg-08-183ompLC::kanR, dtrA::kanR and *E. ictaluri* R4383 eihA::kanR mutant at 43° C. for 1 hr followed by plating on BHI blood agar plates resulted in the curing of the recombinogenic plasmid pMJH46 (data not shown). We found that only highly rich BHI medium supplemented with 5% Sheep Blood, unlike TSA, supported the growth of the high temperature-induced *E. ictaluri* strains. The introduction of plasmid pCP20, that contains the Flp recombinase (49) followed by their growth at 37° C. resulted in removal of the antibiotic marker from the *E. ictaluri* ompLC mutant PCR amplification of the targeted genes with their flanking primers indicated a 100% frequency for removal of the antibiotic selection marker. The antibiotic resistance markers from the *E. ictaluri* dtrA and eihA mutants were also removed using the Flp recombinase. We found that, in addition to the removal of the antibiotic resistance marker, heat induction efficiently cured the plasmid pCP20 from all mutant colonies tested. Cured mutants lacking the antibiotic resistance cassette could be subsequently targeted for deletion of additional genes. Since genes from *A. hydrophila* were replaced using the cat gene cassette, plasmid pCP20 containing the cat gene was not compatible for conducting Flp/FRT mediated recombination in *A. hydrophila* mutants. Therefore, we constructed a new flp recombinase plasmid pCMT-flp (FIG. 1D) that contained a tetA selectable marker that was conjugally transferred into *A. hydrophila* mutants for markerless mutant construction.

Dual Inducible Expression Plasmid for Red and Flp Recombination.

The construction of markerless mutants involves several steps including the introduction of λ-Red recombinogenic plasmid, curing of the plasmid after recombineering, and introduction of flp recombinase plasmid to remove the antibiotic resistance marker by flp/FRT recombination. If a double mutation is desired, then it would be necessary to cure the flp recombinase plasmid followed by re-introduction of the λ-Red recombinogenic plasmid. In this study, for faster and streamlined markerless mutant generation, we constructed a conjugally transferable, dual expression plasmid pMJH95 (FIG. 1C) that contains an arabinose-inducible red recombination cassette and a rhamnose-inducible Flp recombinase protein. Since the induction of genes under the transcriptional control of the rhaBAD promoter requires the RhaS and RhaR, and RhaT proteins for promoter activation and transport of rhamnose into the cells, respectively (56, 57), we cloned, the rhaSRT genetic cluster into the plasmid pMJH95 to facilitate rhamnose transport to enable induction of the rhaBAD promoter by rhaS. This plasmid was conjugally transferred to the *A. hydrophila* ML09-119hlyA mutant and after induction, flp recombinase removed the cat marker by FRT/flp recombination (data not shown). After introducing into *A. hydrophila* by conjugation, we constructed an *A. hydrophila* double mutant ΔaeroA-hlyA using this dual inducible plasmid.

Cloning without PCR Amplification of Large Inserts.

Figure 3:
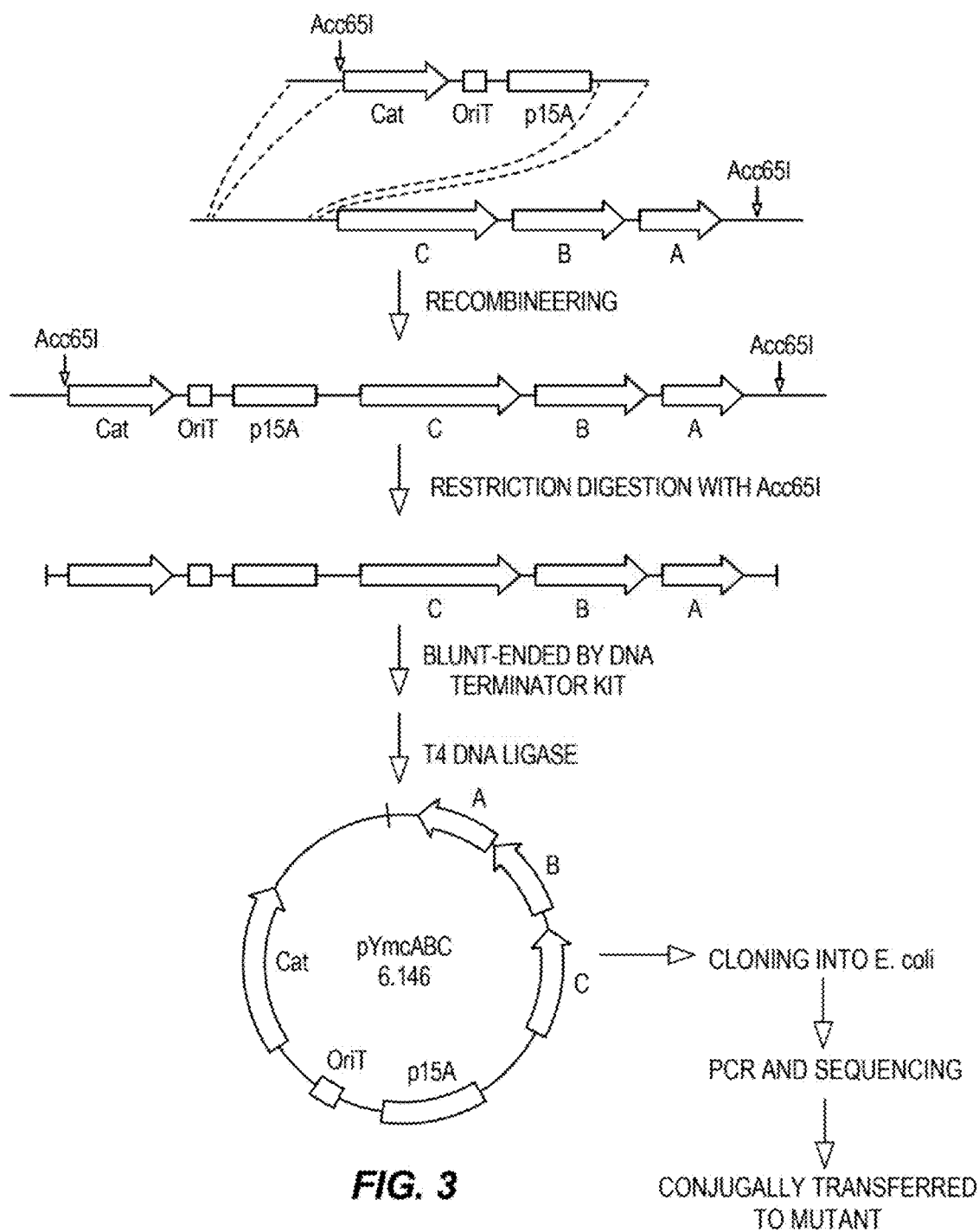
FIG. 3. Schematic representation of strategy use for PCR free cloning of large genetic insert using recombineering.

Since cloning of large inserts using traditional cloning techniques are challenging and PCR amplification of the targeted inserts can introduced unwanted mutations, we developed a novel technique to clone large genomic inserts of *A. hydrophila* that does not require any PCR amplifications of the targeted inserts (FIG. 3). As a proof of concept of this technique, we targeted for cloning the 3.6 kb ymcABC operon of *A. hydrophila* strain ML09-119. For this purpose, we constructed a small conjugally transferrable low copy-number plasmid backbone (pMJH97) and integrated it contiguously to the ymcABC operon of *A. hydrophila* ML09-119 by recombineering (data not shown). We confirmed the correct integration of the plasmid backbone upstream of the ymcABC operon by PCR and sequencing. We successfully cloned the complete ymcABC operon (FIG. 3) and conjugally transferred the plasmid construct into *A. hydrophila*.

Discussion

The genetic manipulation of primary pathogenic isolates, compare to domesticated laboratory isolates, can be challenging due to many factors including antibiotic resistance (58) (59), poor recombination efficiency and wide-spread occurrence of restriction-modification systems (43,60). Our attempts to genetically modify the fish pathogens *E. ictaluri* and *A. hydrophila* were inhibited due to our inability to introduce the λ Red recombineering system into these bacterial isolates. Similar difficulties were observed by several other researchers who reported reduced transformation efficiency of pKD46 in *E. coli* by electroporation (61), demonstrating the need for an alternative route to introduce the recombineering system, i.e., via conjugation. In this study we describe the development of a fast, efficient, and reliable technique for genetic modification of *E. ictaluri* and *A. hydrophila* (and presumably other Gram-negative bacteria) using a recombineering system that is readily transferrable by conjugation. The introduction of a mob cassette to pKD46 (13) permitted the resulting plasmid pMJH46 to transfer into different *E. ictaluri* strains by conjugation. Additional modified recombinogenic plasmids were constructed to make it compatible for knocking out genes from the emerging catfish pathogen *A. hydrophila*. Furthermore, we demonstrated the applicability of this method by creating multiple mutants in *E. ictaluri* and *A. hydrophila*.

Our first experiments using recombineering in *E. ictaluri* unfortunately were plagued by a large number of background colonies on the antibiotic selection plates that were not successful recombinants. These results were obtained even though we used suicide plasmid pKD4 as a template for PCR amplification of antibiotic cassette and treated the DNA with DpnI treatment, as has been shown to reduce the number of background colonies (62). The solution to reducing the high background of antibiotic resistant colonies was to use genomic DNA isolated from a successful genomic integrant (*E. ictaluri* Alg-08-183ompLC::kanR) constructed in this study as a template for PCR of the recombineering construct. Therefore, all of our subsequent recombineering experiments for gene deletion in *E. ictaluri* and *A. hydrophila* used genomic DNA as template for PCR amplification of antibiotic resistance gene cassettes.

We were able to use the Flp recombinase encoded on the temperature-sensitive plasmid pCP20 (49) to successfully remove a FRT-flanked antibiotic resistance cassette used for genome modification in *E. ictaluri*. Before introducing pMJH46 into *E. ictaluri* mutants, pMJH46 was cured by heat induction since both plasmids contain the cat gene. Unlike *E. coli* (13), *E. ictaluri* mutants required a highly rich medium (BHI supplemented with 5% sheep blood) to recover after heat-induction at 43° C., which may be due to the mesophilic growth temperature (28° C.) of *E. ictaluri*. Because of antibiotic resistance marker incompatibility, a new conjugally transferable flp recombinase plasmid, pCMT-flp, was constructed that can efficiently remove FRT-flanked antibiotic resistance gene cassettes. To avoid repeated curing of recombinogenic and flp recombinase plasmids to generate markerless mutants with multiple mutations, we constructed a dual expression plasmid pMJH95 with the Red cassette and flp gene under the control of arabinose- and rhamnose-inducible promoters, respectively. This plasmid can be used to delete genes by recombineering after arabinose-induction and then the FRT-flanked antibiotic resistance cassette can readily removed by rhamnose-induction of the flp recombinase.

In addition to developing techniques for genetic modification in *E. ictaluri* and *A. hydrophila*, we devised a novel technique for cloning large fragments of bacterial genomes without PCR amplification of the targeted region. This cloning system would be advantageous to clone larger fragments of genomic DNA without the need for PCR amplification, given the difficulties in producing larger amplicons and the potential for incorporating PCR-mediated errors. This method was validated by the cloning of a genetic operon from *A. hydrophila*, as an example of this method that can overcome the shortcomings of PCR-based methods for the cloning and conjugal transfer of genetic elements such as genomic islands, prophages, and other genetic clusters.

We have described a highly efficient and rapid procedure for the generation of markerless mutants in *E. ictaluri* and *A. hydrophila* by recombineering. The newly constructed conjugally transferable recombinogenic plasmids pMJH46, pMJH66 and pMJH95, and recombinase plasmid pCMT-flp can presumably be used for other Gram-negative bacteria for generating markerless mutants, especially for bacterial isolates that are recalcitrant to electroporation. Finally, the development of a PCR-free system for cloning and transfer will facilitate complementation of much larger genetic elements.

TABLE 2

List of bacterial strains and plasmids used in this study.

| Bacterial strains or plasmid | Features | References |
|---|---|---|
| *E. coli* | | |
| SM10λpir | thi-1thr leutonAlacYsupE recA::RP4-2-TcT::Mu Km$^r$ λpir | (46) |
| BW25113/pKD46 | F–, Δ(araD-araB)567, ΔlacZ4787(::rrnB-3), λ$^-$, rph-1, Δ(rhaD-rhaB)568, hsdR514, pKD46 | (13) |
| BT340 | F–, Δ(argF-lac)169, φ80dlacZ58(M15), glnV44(AS), λ$^-$, rfbC1, gyrA96(NalR), recA1 endA1, spoT1, thiE1, hsdR17, pCP20 | (13) |
| BW25141/pKD4 | F–, Δ(araD-araB)567, ΔlacZ4787(::rrnB-3), Δ(phoB-phoR)580, λ$^-$, galU95, ΔuidA3::pir$^+$, recA1, endA9(del-ins)::FRT, rph-1, Δ(rhaD-rhaB)568, hsdR514, pKD4 | (13) |
| *E. ictaluri* | | |
| Alg-08-183 | Pathogenic isolates from diseased catfish | (53) |
| R4383 | Highly hemolytic *E. ictaluri* strain from diseased catfish | (65) |
| Alg-08-183 ompLC::kanR | Replacement of hemolysin ompLC gene with kanR gene | This Study |
| Alg-08-183 drtA::kanR | Replacement of hemolysin dtrA gene with kanR gene | This Study |
| Alg-08-183 prtA::kanR | Replacement of hemolysin ptrA gene with kanR gene | This Study |
| R4383 eihA::KanR | Replacement of hemolysin eihA gene with kanR gene | This Study |
| R4383 ΔeihA | In-frame deletion of hemolysin gene eihA | This Study |
| Plasmids | | |
| pACYC184 | Include | reference |
| pKD46 | Temperature-sensitive recombinogenic plasmid | (13) |
| pKD4 | Template for recombineering substrate | (13) |
| pMJH46 | Conjugally transferrable recombinogenic plasmid | This Study |
| pMJH65 | Conjugally transferrable recombinogenic plasmid | This Study |
| pMJH95 | Conjugally transferrable recombinogenic and recombinase plasmid | This Study |

TABLE 2-continued

List of bacterial strains and plasmids used in this study.

| Bacterial strains or plasmid | Features | References |
|---|---|---|
| pCMT-flp | Temperature-sensitive Flp recombinase plasmid | This Study |
| pMJH97 | cat-oriT-oriR backbone plasmid for PCR-free cloning | This Study |
| pCP20 | Temperature-sensitive Flp recombinase plasmid | (51) |
| pGNS-BAC | Conjugally transferable BAC vector | (49) |

TABLE 3

List of primers used in this study.

| Primer Name | Sequence in 5'-3' direction |
|---|---|
| pKD4-ompLCf | AACTGGTAGATCATACCAACGCCAACGATGTTGTCGGTGCTGATACCGGCGTGTAGGCTGGAGCTGCTTC (SEQ ID NO: 43) |
| pKD4-ompLCr | GTTCAAAAAATTCCCGATGGAATCAAATTAGGCAGTGGCAGGTGTCAAAACATATGAATATCCTCCTTAGT (SEQ ID NO: 44) |
| ML44-RedF | ATGCTTACAACAAAAAATATGCCAGCCAATGCTGGGCTGGCAGCGTTTTCTGGTGTAGGCTGGAGCTGCTTC (SEQ ID NO: 45) |
| ML44-RedR | TTAGCAAGGGGGAAGATGCTCTGGTGGTGATGGTCTGTTTTTCTGATGATAGCATATGAATATCCTCCTTAGT (SEQ ID NO: 46) |
| Hemo-redF | TTCCTTTTAACTCTGCTTTGGCGCCCATGGGCGCTGATATGAGGCAATCTCTGTGTAGGCTGGAGCTGCTTC (SEQ ID NO: 47) |
| Hemo-redR | ACGGCGGCCCGCAGGCCGCCGTTGAGGATGGATAACGTCGCCACTATCCGGTCATATGAATATCCTCCTTAGT (SEQ ID NO: 48) |
| ML82-RedF | GTGATACGTAGACAAGGTGCGACCATCGTACTGTGGATATTACTGCTGTTTTGTGTAGGCTGGAGCTGCTTC (SEQ ID NO: 49) |
| ML82-RedR | TCAGCGGGTCACCTCTATCTTCAGCGTCTTTTGCAGCGCACTGACGTCCGGGTCATATGAATATCCTCCTTAGT (SEQ ID NO: 50) |
| RedtrackF | GATGTCTATCTGTTCAGCTC (SEQ ID NO: 51) |
| RedtrackR | GTACGCAATACCAATAGTG (SEQ ID NO: 52) |
| RE33-165F | TATGCAAGCTTGTAGTTCTTGCTGGTCTC (SEQ ID NO: 53) |
| RE33-165R | TATGCAAGCTTGTAACGCAACATTCTAAC (SEQ ID NO: 54) |
| k1 | CAGTCATAGCCGAATAGCCT (SEQ ID NO: 55) |
| k2 | CGGTGCCCTGAATGAACTGC (SEQ ID NO: 56) |
| Kt | CGGCCACAGTCGATGAATCC (SEQ ID NO: 57) |
| MobF | ATGCAGATATCGGATCCTTTTTGTCCG (SEQ ID NO: 58) |
| MobR | ACGCAGCAGTCAGTCACGATACAGCCGACCAGGCT (SEQ ID NO: 59) |
| CatF | TATCGTGACTGACTGCTGCGTGTAGACTTCCGTTGAACT (SEQ ID NO: 60) |
| CatR | ATGCAGATATCGCCTAATGAGTGAGCTAA (SEQ ID NO: 61) |
| MobicatF | AGAGTGCTGACAGATGAG (SEQ ID NO: 62) |
| MobicatR | ACGCAGCAGTCAGTCACGATAATGATGTGGTCTGTCCT (SEQ ID NO: 63) |
| MCF-int | CATGCGATATCACCGCTAACCTGTCTT (SEQ ID NO: 64) |
| CatR-int | CATGCGATATCTAATGAATCGGCCAAC (SEQ ID NO: 65) |

REFERENCES

1. Aubert, D. F., Hamad, M. A. and Valvano, M. A., (2014) A markerless deletion method for genetic manipulation of *Burkholderia cenocepacia* and other multidrug-resistant gram-negative bacteria. Methods Mol Biol, 1197, 311-327.
2. Cartman, S. T. and Minton, N. P. (2010) A mariner-based transposon system for in vivo random mutagenesis of *Clostridium difficile*. Appl Environ Microbiol, 76, 1103-1109.
3. Hadjifrangiskou, M., Gu, A. P., Pinkner, J. S., Kostakioti, M., Zhang, E. W., Greene, S. E. and Hultgren, S. J. (2012) Transposon mutagenesis identifies uropathogenic *Escherichia coli* biofilm factors. J Bacteriol, 194, 6195-6205.
4. Li, X.-t., Thomason, L. C., Sawitzke, J. A., Costantino, N. and Court, D. L. (2013) Positive and negative selection using the tetA-sacB cassette: recombineering and P1 transduction in *Escherichia coli*. Nucleic Acids Research.
5. Hirayama, Y., Sakanaka, M., Fukuma, H., Murayama, H., Kano, Y., Fukiya, S. and Yokota, A. (2012) Development of a Double-Crossover Markerless Gene Deletion System in *Bifidobacterium longum*: Functional Analysis of the a-Galactosidase Gene for Raffinose Assimilation. Applied and Environmental Microbiology, 78, 4984-4994.
6. Jost, B. H., Homchampa, P., Strugnell, R. A. and Adler, B. (1997) The sacB gene cannot be used as a counter-selectable marker in *Pasteurella multocida*. Molecular biotechnology, 8, 189-191.
7. Murphy, K. C. (1998) Use of bacteriophage lambda recombination functions to promote gene replacement in *Escherichia coli*. J Bacteriol, 180, 2063-2071.

8. Murphy, K. C., Campellone, K. G. and Poteete, A. R. (2000) PCR-mediated gene replacement in *Escherichia coli*. Gene, 246, 321-330.
9. Yu, D., Ellis, H. M., Lee, E.-C., Jenkins, N. A., Copeland, N. G. and Court, D. L. (2000) An efficient recombination system for chromosome engineering in *Escherichia coli*. Proceedings of the National Academy of Sciences, 97, 5978-5983.
10. Datsenko, K. A. and Wanner, B. L. (2000) One-step inactivation of chromosomal genes in *Escherichia coli* K-12 using PCR products. Proceedings of the National Academy of Sciences, 97, 6640-6645.
11. Copeland, N. G., Jenkins, N. A. and Court, D. L. (2001) Recombineering: a powerful new tool for mouse functional genomics. Nature reviews. Genetics, 2, 769-779.
12. Murphy, K. C. (1998) Use of Bacteriophage Recombination Functions To Promote Gene Replacement in *Escherichia coli*. Journal of Bacteriology, 180, 2063-2071.
13. Datsenko, K. A, and Wanner, B. L. (2000) One-step inactivation of chromosomal genes in *Escherichia coli* K-12 using PCR products. Proceedings of the National Academy of Sciences of the United States of America, 97, 6640-6645.
14. Cassuto, E., Lash, T., Sriprakash. K. S. and Radding, C. M. (1971) Role of Exonuclease and β Protein of Phage In Genetic Recombination, V. Recombination of DNA in Vitro. Proceedings of the National Academy of Sciences, 68, 1639-1643.
15. Matsuura, S.-i., Komatsu, J., Hirano, K., Yasuda. H., Takashima, K., Katsura, S. and Mizuno, A. (2001) Real-time observation of a single DNA digestion by exonuclease under a fluorescence microscope field. Nucleic Acids Research, 29, e79.
16. Little, J. W. (1967) An Exonuclease Induced by Bacteriophage. Journal of Biological Chemistry. 242, 679-686.
17. Court, D. L., Sawitzke, J. A. and Thomason, L. C. (2002) Genetic Engineering Using Homologous Recombination. Annual Review of Genetics, 36, 361-388.
18. Muniyappa, K. and Radding, C. M. (1986) The homologous recombination system of phage lambda. Pairing activities of beta protein. Journal of Biological Chemistry, 261, 7472-7478.
19. Karakousis, G., Ye, N., Li, Z., Chiu, S. K., Reddy, G. and Radding, C. M. (1998) The beta protein of phage binds preferentially to an intermediate in DNA renaturation. Journal of Molecular Biology, 276, 721-731.
20. Poteete, A. R., Fenton, A. C. and Murphy, K. C. (1988) Modulation of *Escherichia coli* RecBCD activity by the bacteriophage lambda Gam and P22 Abc functions. Journal of Bacteriology, 170, 2012-2021.
21. Jasin, M. and Schimmel, P. (1984) Deletion of an essential gene in *Escherichia coli* by site-specific recombination with linear DNA fragments. Journal of Bacteriology, 159, 783-786.
22. Matsuda, T., Freeman, T. A., Hilbert, D. W., Duff, M., Fuortes, M., Stapleton, P. P. and Daly, J. M. (2005) Lysis-deficient bacteriophage therapy decreases endotoxin and inflammatory mediator release and improves survival in a murine peritonitis model. Surgery, 137, 639-646.
23. Merabishvili, M., Pirnay, J.-P., Verbeken, G., Chanishvili, N., Tediashvili, M., Lashkhi, N., Glonti, T., Krylov, V., Mast, J., Van Parys, L. et al. (2009) Quality-Controlled Small-Scale Production of a Well-Defined Bacteriophage Cocktail for Use In Human Clinical Trials. PLoS ONE, 4, e4944.
24. Uzzau, S., Figueroa-Bossi, N., Rubino, S. and Bossi, L. (2001) Epitope tagging of chromosomal genes in *Salmonella*. Proceedings of the National Academy of Sciences, 98, 15264-15269.
25. Muyrers, J. P., Zhang, Y., Benes, V., Testa, G., Ansorge, W. and Stewart, A. F. (2000) Point mutation of bacterial artificial chromosomes by ET recombination. EMBO reports, 1, 239-243.
26. Arber, W, and Linn, S. (1969) DNA modification and restriction. Annual review of biochemistry, 38, 467-500.
27. Ando, T., Xu, Q., Torres, M., Kusugami, K., Israel, D. A. and Blaser, M. J. (2000) Restriction-modification system differences in *Helicobacter pylori* are a barrier to interstrain plasmid transfer. Mol Microbiol, 37, 1052-1065.
28. Arber, W, and Dussoix, D. (1962) Host specificity of DNA produced by *Escherichia coli*. I. Host controlled modification of bacteriophage lambda. Journal of molecular biology, 5, 18-36.
29. Sitaraman, R. and Leppla, S. H. (2012) Methylation-dependent DNA restriction in *Bacillus anthracis*. Gene, 494, 44-50.
30. Kurosawa, N. and Grogan, D. W. (2005) Homologous recombination of exogenous DNA with the *Sulfolobus acidocaldarius* genome; properties and uses. FEMS Microbiol Lett, 253, 141-149.
31. Donahue, J. P.; Israel, D. A., Peek, R. M., Blaser, M. J. and Miller, G. G. (2000) Overcoming the restriction barrier to plasmid transformation of *Helicobacter pylori*. Mol Microbiol, 37, 1066-1074.
32. Dawoud, T. M., Jiang, T., Mandal, R. K., Rieke, S. C. and Kwon, Y. M. (2014) Improving the efficiency of transposon mutagenesis in *Salmonella enteritidis* by overcoming host-restriction barriers. Molecular biotechnology, 56, 1004-1010.
33. Eden, P. A. and Blakemore, R. P. (1991) Electroporation and conjugal plasmid transfer to members of the genus *Aquaspirillum*. Archives of microbiology, 155, 449-452.
34. Flett, F., Mersinias, V. and Smith, C. P. (1997) High efficiency intergeneric conjugal transfer of plasmid DNA from *Escherichia coli* to methyl DNA-restricting streptomycetes. FEMS Microbiol Lett, 155, 223-229.
35. Elhai, J. and Wolk, C. P. (1988) Conjugal transfer of DNA to cyanobacteria. Methods in enzymology, 167, 747-754.
36. USDA. (2010) Catfish 2010 part I: reference of catfish health and production practices in the United States, 2009. USDA-APHIS-VS, CEAH, Ft. Collins, Colo.
37. Rogge, M. L., Dubytska, L., Jung, T. S., Wiles, J., Elkamel, A. A., Rennhoff, A., Oanh, D. T. and Thune, R. L. (2013) Comparison of Vietnamese and US isolates of *Edwardsiella ictaluri*. Diseases of aquatic organisms, 106, 17-29.
38. Hemstreet, B. (2010) An update on *Aeromonas hydrophila* from a fish health specialist for summer 2010. Catfish Journal, 24.
39. Hossain, M. J., Sun, D., McGarey, D. J., Wrenn, S., Alexander, L. M., Martino, M. E., Xing, Y., Terhune, J. S. and Liles, M. R. (2014) An Asian Origin of Virulent *Aeromonas hydrophila* Responsible for Disease Epidemics in United States-Farmed Catfish. mBio, 5.
40. Hossain, M. J., Waldbieser, G. C., Sun, D., Capps, N. K., Hemstreet, W. B., Carlisle, K., Griffin, M. J., Khoo, L., Goodwin, A. E., Sonstegard, T. S. et al. (2013) Implication of Lateral Genetic Transfer in the Emergence of *Aeromonas hydrophila* Isolates of Epidemic Outbreaks in Channel Catfish. PLoS ONE, 8, e80943.

41. Pridgeon, J. W, and Klesius, P. H. (2011) Molecular identification and virulence of three *Aeromonas hydrophila* isolates cultured from infected channel catfish during a disease outbreak in west Alabama (USA) in 2009, Diseases of aquatic organisms, 94, 249-253.
42. Zhang, X.-H., Yang, W.-M., Li, T.-T. and Li, A.-H. (2013) The genetic diversity and virulence characteristics of *Aeromonas hydrophila* isolated from fishponds with disease outbreaks in Hubei province. Acta Hydrobiologica Sinica, 37, 458-466.
43. Thomas, C. M. and Nielsen, K. M. (2005) Mechanisms of, and barriers to, horizontal gene transfer between bacteria. Nature reviews. Microbiology, 3, 711-721.
44. Simon, R., Priefer, U. and Puhler, A. (1983) A Broad Host Range Mobilization System for In Vivo Genetic Engineering: Transposon Mutagenesis in Gram Negative Bacteria. Nat Biotech, 1, 784-791.
45. Sambrook, J., Fritsch, E. F. and Maniatis, T. (1998) Molecular cloning: a laboratory manual. Cold Spring Harbor Laboratory Press, Cold Spring Harbor, N.Y.
46. He, P., Hao, K., Blom, J., Ruckert, C., Vater, J., Mao, Z., Wu, Y., Hou, M., He, P., He, Y. et al. (2012) Genome sequence of the plant growth promoting strain *Bacillus amyloliquefaciens* subsp. *plantarum* B9601-Y2 and expression of mersacidin and other secondary metabolites. J Biotechnol, 164, 281-291.
47. Kakirde, K. S., Wild J., Godiska, R., Mead, D. A., Wiggins, A. G., Goodman, R. M., Szybalski, W. and Liles, M. R. (2011) Gram negative shuttle BAC vector for heterologous expression of metagenomic libraries. Gene, 475, 57-62.
48. Szewczyk, E., Nayak, T., Oakley, C. E., Edgerton, H., Xiong, Y., Taheri-Talesh, N., Osmani, S. A. and Oakley, B. R. (2007) Fusion PCR and gene targeting in *Aspergillus nidulans*. Nat. Protocols, 1, 3111-3120.
49. Cherepanov, P. P. and Wackernagel, W. (1995) Gene disruption in *Escherichia coli*: TcR and KmR cassettes with the option of Flp-catalyzed excision of the antibiotic-resistance determinant. Gene, 158, 9-14.
50. Uzzau, S., Figueroa-Bossi, N., Rubino, S. and Bossi, L. (2001) Epitope tagging of chromosomal genes in *Salmonella*, Proceedings of the National Academy of Sciences of the United States of America, 98, 15264-15269.
51. Hossain, M. J., Rahman, K. S., Terhune, J. S. and Liles, M. R. (2012) An outer membrane porin protein modulates phage susceptibility in *Edwardsiella ictaluri*. Microbiol-Sgm, 158, 474-487.
52. Welch, T. J., Evenhuis, J., White, D. G., McDermott, P. F., Harbottle, H., Miller, R. A., Griffin, M, and Wise, D. (2009) IncA/C Plasmid-Mediated Florfenicol Resistance in the Catfish Pathogen *Edwardsiella ictaluri*. Antimicrobial Agents and Chemotherapy, 53, 845-846.
53. Hossain, M. J., Waldbieser, G. C., Sun, D., Capps, N. K., Hemstreet, W. B., Carlisle, K., Griffin, M. J., Khoo, L., Goodwin, A. E., Sonstegard, T. S. et al. (2013) Implication of Lateral Genetic Transfer in the Emergence of *Aeromonas hydrophila* Isolates of Epidemic Outbreaks in Channel Catfish. PLoS ONE, 8, e80943.
54. Hossain, M. J., Rahman Kh, S., Terhune, J. S. and Liles, M. R. (2012) An outer membrane porin protein modulates phage susceptibility in *Edwardsiella ictaluri*. Microbiology (Reading, England), 158, 474-487.
55. Williams, M. L., and Lawrence, M. L. (2005) Identification and characterization of a two-component hemolysin from *Edwardsiella ictaluri* Veterinary Microbiology, 108, 281-289.
56. Via, P., Badia, J., Baldoma, L., Obradors, N. and Aguilar, J. (1996) Transcriptional regulation of the *Escherichia coli* rhaT gene. Microbiology (Reading, England), 142 (Pt 7), 1833-1840.
57. Bhende, P. M. and Egan, S. M. (2000) Genetic Evidence that Transcription Activation by RhaS Involves Specific Amino Acid Contacts with Sigma 70. Journal of Bacteriology, 182, 4959-4969.
58. Lee, D. J., Bingle, L. E., Heurlier, K., Pallen, M. J., Penn, C. W., Busby, S. J. and Hobman, J. L. (2009) Gene doctoring: a method for recombineering in laboratory and pathogenic *Escherichia coli* strains. BMC microbiology, 9, 252.
59. Esteve, C., Alcaide, E. and Blasco, M. D. (2012) *Aeromonas hydrophila* subsp. *dhakensis* Isolated from Feces, Water and Fish in Mediterranean Spain. Microbes and Environments, 27, 367-373.
60. Monk, I. R., Shah, I. M., Xu, M., Tan, M. W, and Foster, T. J. (2012) Transforming the untransformable: application of direct transformation to manipulate genetically *Staphylococcus aureus* and *Staphylococcus epidermidis*. MBio, 3.
61. Serra-Moreno, R., Acosta, S., Hernalsteens, J., Jofre, J. and Muniesa, M. (2006) Use of the lambda Red recombinase system to produce recombinant prophages carrying antibiotic resistance genes. BMC Molecular Biology, 7, 31.
62. Sharan, S. K., Thomason, L. C., Kuznetsov, S. G. and Court, D. L. (2009) Recombineering: A Homologous Recombination-Based Method of Genetic Engineering. Nature protocols, 4, 206-223.

Example 2

Mutagenesis of Virulence Genes in an Epidemic Strain of *Aeromonas hydrophila* ML09-119 for Development of an Attenuated Vaccine Strain An epidemic strain of *A. hydrophila* (ML09-119) caused a devastating outbreak of Motile Aeromonad Septicemia of catfish (MAS) on the fish farms of Southeastern United States in 2009. *A. hydrophila* ML09-119 was reported to cause severe mortality in commercial catfish farms. Research has been done on the virulence of this epidemic strain on channel catfish including molecular identification of the specific strain and unique DNA sequences.

Previously our lab sequenced 11 *A. hydrophila* isolates, 6 of which are epidemic stains, while the others were historical *A. hydrophila* isolates not affiliated with an epidemic outbreak of disease that we describe as "reference" strains. A comparative genomic analysis indicated that 53 epidemic-associated genetic regions with 313 predicted genes were uniquely present in the epidemic isolates but absent from the reference isolates. Thirty four genes from this region were predicted to be related to the virulence of the epidemic strains. A functional metabolic island that encodes a complete pathway for myo-inositol catabolism was identified and demonstrated to be functional based on the ability of epidemic *A. hydrophila* isolate ML09-119 to use myo-inositol as a sole carbon source while the reference strain AL06-06 cannot. A novel O-antigen cluster was found in all the epidemic isolates and one reference isolates.

In this study, the gene iolA coding for the enzyme aldehyde dehydrogenase for myo-inositol catabolism was inactivated by traditional allelic exchange to generate the *A. hydrophila* ΔiolA$_{tra}$ mutant. The iolA-iolR genetic region was also mutagenized using a recombineering technique to obtain $\Delta iolA_{rec}$ mutants. An in vivo challenge in channel catfish showed that there was no mortality in the channel catfish that were challenged with $\Delta iolA_{tra}$ mutant, but there was mortality in the channel catfish challenged with $\Delta iolA_{rec}$ mutants similar to wild type ML09-119.

Eight mutants were created by knocking out an upstream portion of the iolA gene in the iolA-iolR promoter region. Results of the in vivo challenge in channel catfish showed that $\Delta iolA_{rec3}$, $\Delta iolA_{rec4}$ exhibited some decrease in mortality, but there were no significant difference in the mortality between the channel catfish challenged with $\Delta iolA_{rec3}$, $\Delta iolA_{rec4}$ and the channel catfish challenged with the wild type ML09-119. ELISA titer of the survivors of the $\Delta iolA_{tra}$ after 21 days showed that $\Delta iolA_{tra}$ can induce strong antibody response against the wild type *A. hydrophila* ML09-119, indicating that this mutant can serve as a promising vaccine candidate against the epidemic *A. hydrophila*.

Lipid A-Core ligase (waaL) and O-antigen polymerase (wzy) mutants were created by both traditional splicing PCR and conjugation technique and recombineering technique respectively, and termed $\Delta waaL_{tra}$ or $\Delta waaL_{Rec}$, $\Delta wzy_{tra}$ or $\Delta wzy_{Rec}$. An in vivo channel catfish challenge study was performed on channel catfish to study the role of O-antigen in the virulence of the epidemic strain of *A. hydrophila*. The results show that the channel catfish that were challenged with $\Delta waaL_{tra}$, $\Delta wzy_{tra}$ had 100% survival rate, but 0% survival rate was observed in the channel catfish that were challenged with $\Delta waaL_{Rec}$, $\Delta wzy_{Rec}$.

A ΔymcA mutant was created by knocking out the ymcA gene by a recombineering technique to study the role ymcA gene of the O-antigen in the virulence of *A. hydrophila*. A 68.13±16.75% survival rate was observed in the channel catfish that were challenged with ΔymcA mutant. Sub-challenge of the survivors of ΔymcA treatment group 21 days post first challenge showed that a 90.48±8.25% survival rate was observed. A significant difference was observed between the ΔymcA treatment group and the positive control group which were naive channel catfish challenged with wild type. ELISA titer of the survivors of the ΔymcA treatment group 21 days post first challenge showed that ΔymcA induced strong antibody response against the wild type *A. hydrophila* ML09-119 indicating that ΔymcA mutant can serve as a promising vaccine candidate.

A. DETERMINING THE ROLE OF THE MYO-INOSITOL PATHWAY IN *A. hydrophila* ML09-119 VIRULENCE Abstract In this study, the gene iolA coding for the enzyme aldehyde dehydrogenase for myo-inositol catabolism was inactivated by traditional allelic exchange to generate the *A. hydrophila* $\Delta iolA_{tra}$ mutant. The iolA-iolR genetic region was also mutagenized using a recombineering technique to generate $\Delta iolA_{rec}$ mutants. An in vivo challenge in channel catfish showed that there was no mortality in the channel catfish that were challenged with $\Delta iolA_{tra}$ mutant, but there was mortality in the channel catfish challenged with $\Delta iolA_{rec}$ mutants similar to wild type ML09-119.

Because of this observation, we hypothesized that the avirulent phenotype of the $\Delta iolA_{tra}$ mutant was due to a polar effect on the upstream and divergently transcribed iolR gene, which is known to be a negative transcriptional regulator in other bacteria. Eight mutants were created by knocking out the upstream of the iolA gene in the iolA-iolR promoter region. Results of the in vivo challenge in channel catfish showed that $\Delta iolA_{rec3}$, $\Delta iolA_{rec4}$ exhibited some decrease in mortality, but there were no significant difference in the mortality between the channel catfish challenged with $\Delta iolA_{rec3}$, $\Delta iolA_{rec4}$ and the channel catfish challenged with the wild type ML09-119. ELISA titer of the survivors of the $\Delta iolA_{tra}$ after 21 days showed that $\Delta iolA_{tra}$ can induce strong antibody response against the wild type *A. hydrophila* ML09-119, indicating that this mutant can serve as a promising vaccine candidate against the epidemic *A. hydrophila*.

Materials and Methods

Bacterial, Isolates and Plasmids.

The *A. hydrophila* ML09-119 and reference strain AL06-06 used in this study were picked out from single colony on the plate that were streaked using the −80° C. stock. The epidemic strain was from the west Alabama MAS outbreak in 2009, while the reference strain. The bacteria were routinely grown on fresh Trypticase Soy Broth (TSB) medium overnight before use. The *A. hydrophila* ML09-119 used for experiment was from the bacterial stocks of the fish disease lab in Auburn University. This epidemic strain was originally isolated from the kidneys of channel catfish naturally infected with *A. hydrophila*. The pure culture of epidemic strain was used first in a small test infection of 10 catfish. Moribund catfish that showed clinical signs of *A. hydrophila* ML09-119 was collected for necropsy. *A. hydrophila* was re-isolated from the fresh dying fish by poking a sterile plastic bacteriology loop into the kidney and inoculating a BHI plate. By doing this, it is expected than the virulence of the epidemic strain stock can be recovered. ML09-119 was then confirmed by biochemistry and selective media following the established identification procedures with modifications (Furuwatari, et al., 1994; Holt, et al., 1994), Briefly, the identification biochemical tests included Gram stain, cytochrome oxidase, glucose utilization, 0/129, sucrose, esculin hydrolysis, V-P, DL-lactate utilization and urocanic acid utilization, and then test on selective media M9 minimum media with inositol added. *E. coli* SM10-λ-pir (Simon et al., 1983) was used for the conjugal transfer of mobilizable plasmid to *A. hydrophila* ML09-119. The list of bacterial strains used in this study is presented in Table 4.

Construction of Defined *A. hydrophila* $\Delta iolA_{tra}$ Mutant by Traditional Splicing PCR and Conjugation Technique.

To investigate the role of myo-inositol utilization pathway in the virulence of epidemic *A. hydrophila* ML09-119 in channel catfish, a iolA knockout mutants, $\Delta iolA_{tra}$ were constructed using plasmid pDMS197, a sacB containing suicide plasmid (Edwards, Keller et al. 1998). The primers needed for this study were listed in the Table 5.

The two pairs of primers, AupF/AupR and AdnF/AdnR, were used to amplify approximately 350 bp upstream and downstream sequences of iolA gene, respectively using PCR kit (TaKara Ex Taq) to construct the ΔiolA mutant. The template used in this PCR was the genomic DNA of *A. hydrophila* ML09-119 which was extracted using a E.Z.N.A.® Bacterial DNA Kit (Omega Bio-Tek, USA). The chloramphenicol acetyltranferase gene (cat) was amplified from pMHH46 plasmid (Hossain et al 2013) using primers catF and catR. The primers AupR and AdnF, used for the amplification of upstream and downstream sequences of iolA gene contained the reverse complemented sequences of catF and catR primers which were added respectively at their 5' ends when the primers were designed. The Cat-cassette which was the chloramphenicol resistance gene ($Cm^R$) with two arms of the upstream and downstream homologous of iolA gene was created by fusing the two arms and the $Cm^R$ gene by splicing through overlap extension PCR (SOB) (Morton, Hunt et al. 1989). The primers for this PCR were Aup-intF and And-intR. The PCR products were purified by agarose gel purification.

The suicide plasmid pDMS197 was digested by restricted digestion enzyme XbaI (New England Biolabs, NEB, USA) following the protocol provided by the manufacturer. A 50 ul reaction was used for the digestion, including 25 ul of the suicide plasmid pDMS197 DNA, 3 ul of the XbaI restricted digestion enzyme, 5 ul of the 10×CutSmart™ Buffer, 1×BSA and 16 ul RNase free $H_2O$. The reaction system was incubated at 37° C. for one hour. The reaction system was then incubated at 65° C. for 20 min to stop the reaction. The digested product was purified by DNA Clean & Concentrator™ (Zymo research), and the concentration was measured by Qubit® dsDNA BR Assay Kit (Life technologies). The product was blunted using end-repair kit DNA terminator (Lucigen, USA) following the producer's instruction. The product was purified by DNA Clean & Concentrator™ (Zymo research) again before ligation.

The purified restriction enzyme XbaI digested and blunted suicide plasmid pDMS197 was ligated with the Gel purified Cat-cassette using Quick Ligase (NEB, USA) under the room temperature for 30 minutes. Briefly, 50 ng of blunted suicide plasmid pDMS197 and around 3-fold molar excess of the Cat-cassette insert was mixed together and the volume was adjusted to 10 ul with RNase free $H_2O$. 10 ul of the 2× Quick Ligation Buffer and 1 μl of Quick T4 DNA Ligase were added into the mixture. The mixture was centrifuged briefly and incubated at room temperature (25° C.) for 30 minutes before it was chilled on ice. A SB gel electrophoresis was done to confirm the ligation product (data not shown).

The making of the electrocompetent cells of E. coli SM10-λ-pir was following a published protocol (Inoue, et al., 1990) with minor changes. A 0.5 ml of the overnight culture of E. coli SM10-λ-pir bacteria was inoculated into 200 ml of Hanahan's Broth (SOB Medium) with 10 mM $MgCl_2$. The culture was incubated in the 37° C. water bathe incubator with shaking bed at 200 rpm for around 2.5 hours and the $OD_{600}$=0.4. The culture was chilled in ice for 10 min before loaded into 200 ml centrifuge tubes. The culture was centrifuged at 6000 rpm for 8 min at 4° C., the supernatant was discarded and the pellet was washed by resuspended with 10% glycerol and centrifuge again at 6000 rpm for 8 min. The wash step was repeated for 3 times before the pellet was gently resuspended in 200 ul GYT medium. The whole procedure was performed on ice.

The ligation product was then used in the electroporation (Chassy, et al., 1988; Dower et al, 1988) to create the plasmid pDMS197iolA, which contains a deletion of the entire iolA gene. 50 ul of the premade electrocompetent cells of the E. coli SM10-λ-pir was mixed gently with 2.5 ul of the ligation product and chilled on ice for 5 min. The mixture was transferred into ice cold cuvettes (Bulldog bio) before the cuvettes were loaded onto the Eppendorf® Eporator® (Eppendorf). Voltage was set up at 1800V. The mixture was mixed with recovery medium (SOC medium) right after the electronic pulse shock. The culture was transferred to a 2 ml test tube and incubated at 37° C. with shaking bed at 200 rpm for 2 hrs. The successful electroporated E. coli SM10-λ-pir with the plasmid pDMS197iolA was selected on 2XYT agar medium plate with 25 ul/ml chloramphenicol, 5 ul/ml tetracycline.

The suicide plasmids pDMS197iolA were independently introduced into A. hydrophila ML09-119 by conjugation with E. coli SM10-λ-pir bearing plasmid pDMS197iolA. A single colony was selected on the selective medium plate for SM10-λ-pir bearing plasmid pDMS197iolA for inoculation of 5 ml LB broth medium. The culture was incubated at 37° C. with shaking at 200 rpm until the $OD_{600}$ was above 1. A single colony of A. hydrophila ML09-119 was picked to inoculate 5 ml TSB broth medium. The culture was incubated at 30° C. with shaking at 200 rpm until the $OD_{600}$ was above 1. A 4 ml ML09-119 culture and 1 ml SM10-λ-pir bearing plasmid were mixed together. The 5 ml culture mixture was filtered through a MicroFunnel 300 SP (Micro-Funnel™) by vacuum pressure. 5 ml fresh LB broth medium was used for washing the cells onto the membrane. The membrane was transferred to the sheep blood agar medium after 2× wash step. The sheep blood agar medium was incubated at 30° C. overnight.

The membrane with the cell culture mixture was vortexed with 3 ml fresh TSB broth medium for selection. Single cross-over mutants were selected on TSA plate supplemented with chloramphenicol, tetracycline and colistin. Double-cross over mutants were obtained by plating onto LB (without NaCl) plates supplemented with 15% sucrose and 12.5 μg/ml chloramphenicol. Mutants grown on this selective plate were subjected to phenotypic and genotypic characterizations. The complete deletion of the iolA genes were confirmed by PCR followed by sequencing.

Construction of Defined A. hydrophila $\Delta iolA_{rec}$ Mutants by Recombineering.

A recombineering technique was used to create a precise deletion of the iolA gene and generate the $\Delta iolA_{Rec}$ mutant, in order to compare with the $\Delta iolA_{tra}$ created by the traditional technique by splicing through overlap extension PCR (SOE) (Horton, Hunt et al. 1989), as well as to better determine the role of myo-inositol utilization pathway in the virulence of epidemic A. hydrophila ML09-119 in channel catfish.

The chloramphenicol acetyltranferase (cat) gene was amplified from pMHH46 plasmid (Hossain et al 2013) using primers iolA5RecF and iolA5RecR to generate the cat-cassette with 50 bp of the upstream and downstream of the targeted iolA gene. The primers iolA5RecF contained 50 bp of the upstream of the targeted iolA gene and iolA5RecR contained the reverse complemented sequences of 50 bp of the upstream of the targeted iolA gene which were added respectively at the 5' ends of each respective primer. The PCR product was validated using gel electrophoresis before another 24×PCR was done using this PCR product to generate more cat-cassette insertion.

The PCR product was purified and concentrated using Wizard® DNA Clean-Up system (Promega, USA) following the protocol provided by the manufacturer. Briefly, the 24 different PCRs were pooled together in a 15 ml conical tube, and a Wizard® DNA Clean-Up kit (Promega, Madison, Wis.) was used to purify the PCR products according to the manufacturer's protocol. The concentration of the final concentrated PCR product was measured using Qubit® dsDNA BR Assay Kit (Life Technologies).

A. hydrophila ML09-119 containing the plasmid pMJH65, which was constructed for the purposes of introducing a recombineering cassette into gram-negative bacteria (Hossain et al, manuscript in preparation), was prepared for electroporation using a standard protocol (Inoue, et al., 1990) with minor changes. 0.5 ml of the overnight culture of ML09-119 bacteria was inoculated into 150 ml of Hanahan's Broth (SOB Medium) with 1.5 ml 1M Arabinose, 300 ul 25 mg/ml Tetracycline and 600 2M $MgCl_2$. The culture was incubated in the 30° C. water bath incubator with shaking at 200 rpm for around 4 hours and the $OD_{600}$=0.5. The culture was chilled on ice for 10 min before loaded into 200 ml centrifuge tubes. The culture was centrifuged at 6000 rpm for 8 min at 4° C. The supernatant was discarded and the pellet was washed by re-suspending with 10% glycerol and centrifuged again at 6000 rpm for 8 min. The wash step was repeated 4 times before the pellet was gently resuspended in 200 ul 10% glycerol. The whole procedure was performed on ice.

The concentrated and purified PCR product was then used in the electroporation (Chassy, et al., 1988; Dower et al, 1988) to create the precise iolA gene deletion mutant $\Delta iolA_{Rec}$. 50 ul of the premade electrocompetent cells of A. hydrophila ML09-119 (pMJH65) was mixed gently with 3 ug of the concentrated PCR product and chilled on ice for 5 min. The mixture was transferred into ice cold cuvettes (BulldogBio) before the cuvettes were loaded onto the Eppendorf® Eporator® (Eppendorf) with a voltage setting of 1200 V. The mixture was mixed with recovery medium (SOC medium) right after the pulse shock. The culture was transferred to a 2 ml test tube and incubated at 30° C. with shaking at 200 rpm overnight.

Figure 7:
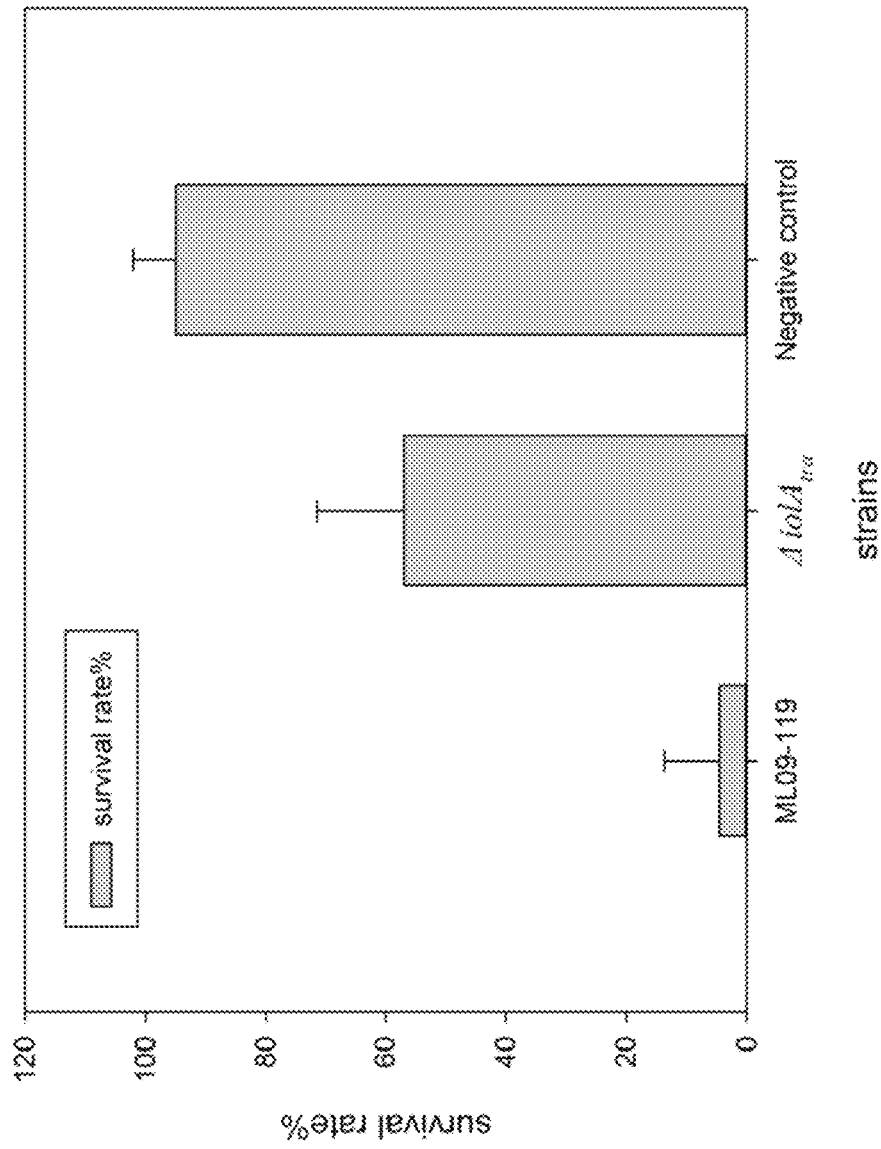
FIG. 7. Sub-challenge of the survivors in the $\Delta iolA_{tra}$ group with wild type. 21 days post challenge, all survivors of $\Delta iolA_{tra}$ group were I.P injected with $1 \times 10^6$ CFU/fish ML09-119. Naive channel catfish were I.P injected with the same dosage with ML09-119 as a positive control. Significant differences were observed between the ML09-119 group and $\Delta iolA_{tra}$ mutant group (P<0.05).

The successfully electroporated A. hydrophila ML09119 iolA deletion mutant was selected on a TSA agar medium plate with 25 ul/ml chloramphenicol. A similar strategy was followed for the construction of $\Delta iolA_{Rec2}$ through $\Delta iolA_{Rec8}$ which represent progressively larger deletions of the iolA-iolR promoter region, with each successive mutant having a deletion of the iolA gene and an additional 50 bp upstream of the iolA-iolR promoter region, respectively (FIG. 7).

Evaluating the Growth Response of A. hydrophila Mutants Using Myo-Inositol as a Sole Carbon Source.

A 2 ml TSB culture of the A. hydrophila isolate was started by inoculating the medium using a single colony of the bacteria. The culture was grown at 30° C. overnight with shaking at 200 rpm. The cell culture next day was centrifuged at 10,000×g for 10 min. The supernatant was poured out, and the pellet was resuspended in M9 minimal medium supplemented with 5.5 mM of myo-inositol (M9I). The centrifugation and re-suspension in M9I was repeated twice to remove any TSB residue. At last, the re-suspension of the bacteria, cells in M9I was adjusted to an $OD_{600}$ of 0.5. A 1:100 dilution of the suspension was achieved by 10 fold serial dilution from the original M9I suspension. A 100 ul of the dilution was used to inoculate 1.9 ml of M9I. The bacterial cultures were then incubated at 30° C. with shaking at 200 rpm for 144 hours and the $OD_{600}$ was recorded at 24 hrs intervals to record the growth condition of the bacteria strains in M9I. The results were used to evaluate the ability of each strain to use myo-inositol as a sole carbon source. A. hydrophila isolates ML09-119 and AL06-06 were used as positive and negative control, respectively, for the myo-inositol utilization assay.

Virulence Study of A. hydrophila Mutants in Channel Catfish.

All experiments conducted with vertebrate animals (catfish) were approved by the Institutional Animal Care and Use Committee (IACUC) review board at Auburn University in accordance with the animal welfare guidelines specified in the United States.

All the channel catfish (I. punctatus, Kansas Random Strain), used in this study were spawned at the hatchery of the Auburn University Fish Genetics Research Unit artificially prior to transferring to troughs or glass aquaria at the Auburn University Fish Pathology wet lab S6. Fish were maintained at recirculation systems (temperature around 25° C. and pH 7.5) using well water sources with constant aeration. Fish were fed daily with commercial feed. Water quality factors including temperature, pH, salt level, total ammonia level, total nitrite level were tested on daily basis to ensure that catfish fingerlings remained unstressed and naive to A. hydrophila. Catfish fingerlings were grown out in this system until their body weight (BW) reached 20±5 g.

A bacterial suspension of exponential phase growth was prepared by overnight culture of in 5 ml TSB broth medium with shaking at 200 rpm at 30° C. The next day 1 ml of the overnight bacterial culture was used to inoculate 100 ml fresh TSB broth culture which was incubated with shaking at 200 rpm at 30° C. for 4 hours. The bacterial culture was centrifuged at 6000 rpm for 10 min. The supernatant was discarded and the bacterial pellet was resuspended in fresh TSB media. The optical density of the bacterial culture was measured by the thermospectronic spectrophotometer (Thermo Spectronic, Rochester, N.Y., USA) at 600 nm and adjusted to an OD=1, which was expected to be $1\times10^9$ CFU/ml. After adjusting the bacterial suspension to an appropriate OD, a 1:100 dilution was performed using fresh TSB broth to get the desired concentration (around $1\times10^7$ CFU/ml) of A. hydrophila. Another 1:2 dilution was done with fresh TSB. This culture was put on ice and used for challenge within 3 hours. A plate count assay was conducted right after the fish challenge to calculate the accurate CFU/ml concentration used in this study. The bacterial culture used in the fish challenge were serial diluted and 100 ul of each dilution was spread on the TSA plates, with 3 replicates were done for each strain of bacteria.

Channel catfish in Auburn University Fish Pathology wet lab S-6 were randomly distributed into glass aquarium tanks. MS-222 (30 mg/l) was used during the handling of fish to calm the fish down to decrease the stress. Each tank contained 10 fish. A recirculating system was applied during the acclimation period, which was lasted for 10 days. Water temperature was originally 25° C. and salt level was kept around 1.8 ppt to decrease the stress caused by environmental changes as well as eliminating the chance of F. columnare infection. Water temperature was gradually brought up to 30±1° C., and salt was gradually brought down to 0.8 during the first 3 clay of the acclimation time. Every environmental factor was kept stable prior to the challenge. Fish were fed with commercial catfish fed once a day at 4% of their body weight. Water was changed once per day for the recirculating system with constant aeration. At the time of challenge, recirculating system was changed into flow through system, with the temperature at 30±1° C. Fish of each treatment tank were euthanized by immersing in a bucket with MS222 (30 mg/l), before 200 ul of ML09-119 bacterial culture was injected intraperitoneally into each fish. Fish were then put back to their cohabitation tanks. Fish of control groups were injected with pure TSB broth medium. Challenged fish were kept the same way as they were during the latter acclimating time. Mortalities were recorded daily for 14 days post challenge. Any moribund or dead fish were removed from the system daily for bacteriological identification and tissue sampling. Prior to sampling, fresh dying or dead fish were inspected externally and internally for any clinical signs. The identification of A. hydrophila isolated from anterior kidney of the fresh dying or dead fish was performed by the biochemistry and selective medium method described previously. Survivors of the challenge were kept for 28 days, before they are challenged again with the wild type ML09-119 to test if any protection effect was provided. The procedure of the re-challenge was similar to the previous challenge. At seven days post re-challenge, blood samples were then drawn from the survivors for the ELISA titer in the later experiment.

Immunogenicity of the Mutants and the Enzyme-Linked Immunosorbent Assay (ELISA).

Blood samples collected after the fish challenge were put in the room temperature for 2 hrs then 4° C. overnight allowing to clot completely. Serum of each blood sample was collected followed by centrifuging at 5000 rpm for 10 min. The supernatant of each sample was collected for Enzyme-linked Immunosorbent assay (ELISA) analysis.

Antibody responses of channel catfish to *A. hydrophila* were quantified by evaluating the presence of specific immunoglobulin to *A. hydrophila* wild type ML09-119 using indirect ELISA. Protein Detector™ ELISA kit was use to conduct the ELISA experiment.

The protocol followed was similar to the product introduction with minor changes. 96-well plastic plates were coated with 100 ul of a solution of 10 ug/ml ($10^7$ CFU/ml) *A. hydrophila* epidemic strain. *A. hydrophila* were suspended in carbonate-bicarbonate coating solution. The coating solution was prepared by diluting one time coating buffer tablet in 10 times of sterile reagent quality water. The plates with coating buffer and antigen were placed in 4° C. pH 9.6 overnight. The plates were washed 4 times with washing buffer provided by the kit the next day, followed by adding 1×BSA blocking buffer to block for 15 min at room temperature. After another wash step, the plates were used to do ELISA analysis. 100 ul 1% BSA blocking buffer was added into each well on the *A. hydrophila* ML09-119 coated plate. 200 ul of the 1/10 fish blood serum sample diluted with 1% BSA blocking buffer was added to the column A2-A11, A1 and A12 were served as positive and negative control. 100 ul of the solution from A1-A12 was transferred to B1-B12 and mixed carefully by pipetting 3-5 times, and this step was repeated across the plate until E1-E12. The final 100 ul from the wells in the row E after mixing was discarded. The plate was then incubated at room temperature for 1 hour. The plate was emptied, and residual liquid was tapped out. Plate was washed out by the washing buffer that came with the kit for 5 times. 100 ul of Rat Anti-catfish monoclonal antibody (Mab) was diluted 32 times and added into each well that contained the primary antibody, after which the plate was incubated at room temperature for 1 hour. After incubation the plated was emptied, and residual liquid was tapped out and the plate was washed out five times using the washing buffer that came with the kit 50 ul of tertiary antibody (goat anti-rat antibody conjugated with horseradish peroxidase) (0.1 ug/ml) was added into each wall that contained the secondary antibody. The plate was incubated at room temperature for 1 hour, after which the plate was washed as above. 50 ul of the substrate solution that came with the kit was added into each well that contained the tertiary antibody. The plated was incubated at room temperature for 5-15 min before the reaction as stopped by adding 50 ul of stop solution into each well for full color development and the plate was then read at $OD_{405}$. A reaction was defined as positive if its $OD_{450}$ value was at least two times the negative control. Ending points were the highest dilution with a positive reaction.

A criss-cross serial dilation analysis was done prior to the ELISA analysis of the samples to optimize the reagent concentration in the immunoassay procedure. 100 ul of 1% BSA blocking buffer was added into each well of the *A. hydrophila* ML09-119 coated plate. 200 ul of the 1/10 ML09-119 infected survivor fish blood serum sample diluted with 1% BSA blocking buffer was added to the respective columns and serially diluted across the plate to identify the best concentration range for the sample. Prior to adding the Mab, 100 ul of 1% BSA blocking buffer was added into each well, followed by 200 ul of the secondary Rat anti-channel catfish Mab. This Mab solution was serially diluted across the plate to identify the optimum concentration for the Mab.

Statistical Analysis.

Mortality data of this study was presented as mean±standard error (SE) and analyzed by one-way analysis of variance and Tukey's multiple range comparison using SAS software (SAS 9.2, SAS Institute Inc., Cary, N.C.). Significant level was set at 5% (p<0.05). Variances were considered significant when probability (P) values<0.05 were calculated.

Results

Evaluating the Growth Response of *A. hydrophila* Mutants Using Myo-Inositol as a Sole Carbon Source.

Figure 4:
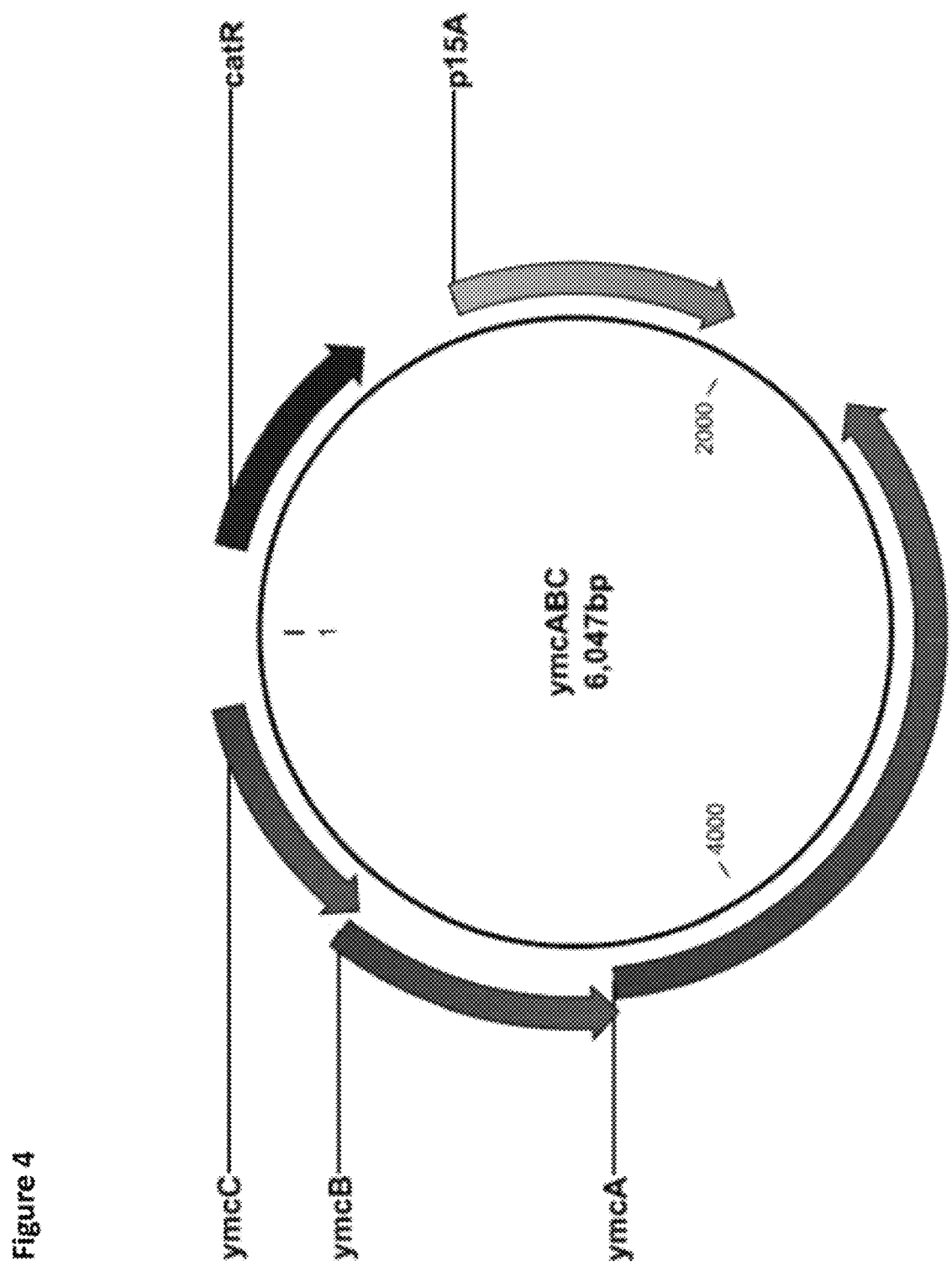
FIG. 4. Plasmid pYmcABC constructed by PCR-free cloning using recombineering.

The iolA gene encodes aldehyde dehydrogenase and terminally located in the inositol catabolic (iol) gene cluster of epidemic *A. hydrophila* isolates. It has been demonstrated that the iolA gene is required for the conversion of malonate semialdehyde to acetyl-CoA (Hossain et al., 2012). It was predicted that the iolA deletion mutants that were created in this study, which were created by replacing the iolA gene and 50 bp of upstream of the iolA gene with cat gene using both traditional technique and recombineering technique, would be unable to utilize myo-inositol as a sole carbon source. The growth assay was carried out with M9I for 144 hours, and it was determined that all of the iolA mutants were unable to utilize myo-inositol as a sole carbon source (FIG. 4), whereas wild type *A. hydrophila* ML09-119 reached stationary phase after 48 hours of incubation. The results of this myo-inositol assay were comparable to the results in previously published research (Hossain et al., 2012). Like *A. hydrophila* ML09-119 iolA mutants, wild type *A. hydrophila* AL06-06 that does not carry the iol cluster did not show any growth after 144 hours of incubation. The lack of the ability of the iolA mutant to utilize myo-inositol as a sole carbon source clearly demonstrated that an iolA mutation had been constructed and that IolA function is required for *A. hydrophila* utilization of myo-inositol as a sole carbon source.

Cumulative Survival Rate of the Channel Catfish Challenged with the iolA Mutants.

For better understanding of the virulence factors of the *A. hydrophila* epidemic strain and to identify possible live vaccine candidates, the iolA gene was knocked out by a traditional allelic exchange technique. It has been observed that all of the *A. hydrophila* epidemic strains *A. hydrophila* can utilize myo-inositol as a sole carbon source (Hossain, et al, 2013). Since iolA gene is required for the conversion of malonate semialdehyde to acetyl-CoA (Kohler, et al., 2011), the hypothesis is that the iolA gene can be the key virulence factor and by knocking out the iolA gene, the ML09-119 strain may be attenuated and serve as a vaccine candidate.

Figure 5:
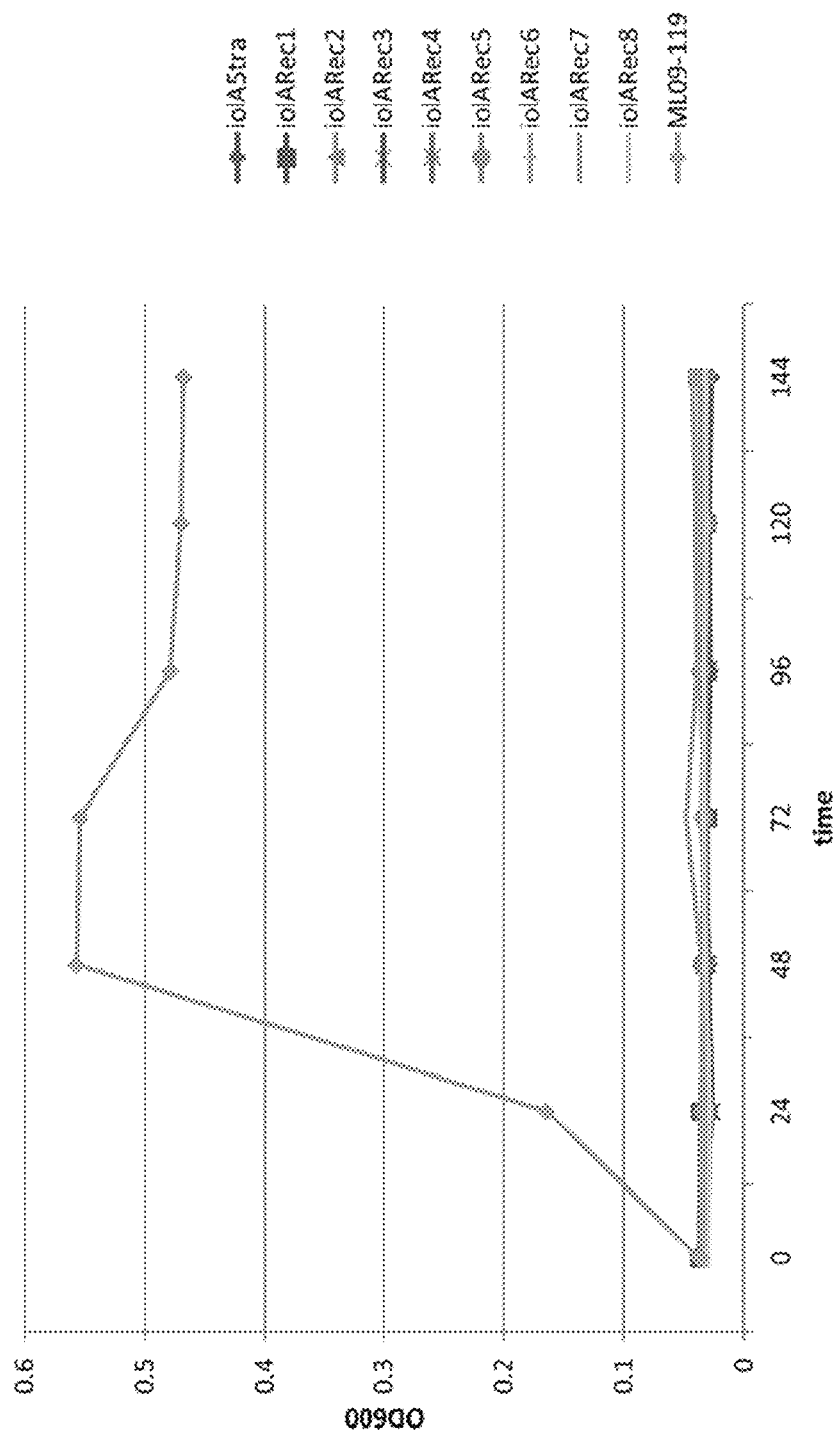
FIG. 5. Myo-inositol assay. Growth of bacterial strains in M9 medium containing myo-inositol as the sole carbon source for 144 hours. All the $\Delta iolA$ deletion mutants, both created by traditional SOE technique and the recombineering technique, were incapable of growth using myo-inositol as a sole carbon source. Wild type *A. hydrophila* ML09-119 reached stationary phase after 48 hours of incubation.

The results of the in vivo channel catfish i.p challenge with $\Delta iolA_{tra}$ showed that this mutant is avirulent. The channel catfish in the $\Delta iolA_{tra}$ treatment group had a 100±0% survival rate, while the wild-type strain-injected group had a 2.5%±0.08 survival rate. The percentage survival rates were transformed by arcsine square root transformation and then analyzed by SAS 9.2, and significant differences were observed between iolA and ML09-119 treatment groups (P<0.0001). This indicates that the $\Delta iolA_{tra}$ was an attenuated strain of ML09-119 (FIG. 5). However, the channel catfish i.p challenged with the $\Delta iolA_{Rec1}$ mutant, which was created by precisely knocking out the iolA gene using the recombineering method, was still fully virulent with a 2.5%±0.08 survival rate that was the same as the wild type positive control group (P>0.05). This indicated that the $\Delta iolA_{Rec1}$ was not an attenuated strain of ML09-119 (FIG. 5).

Figure 6:
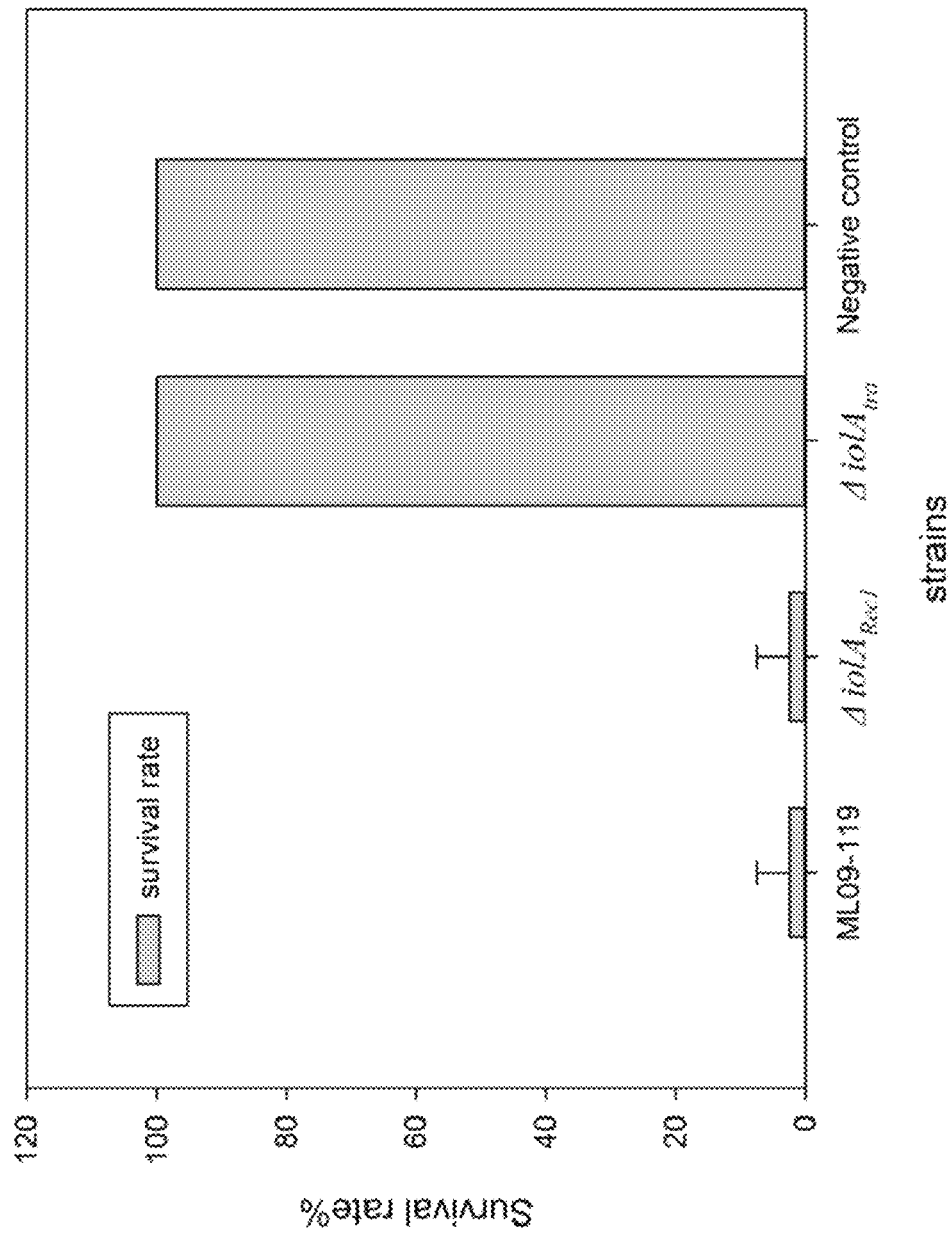
FIG. 6. Cumulative survival rate of the $\Delta iolA_{tra}$ and $\Delta iolA_{Rec1}$ mutants compared to wild type *A. hydrophila* ML09-119. Channel catfish that were i.p injected with $10^6$ CFU/fish of the $\Delta iolA_{tra}$ mutant had 100±0% survival rate, while 2.5%±0.08 survival rate was observed in the positive control treatment group in which channel catfish were i.p injected with $10^6$ CFU/fish wild type ML09-119 (P<0.0001). The $iolA_{Rec1}$ treatment group had a 2.5%±0.08 survival rate which was the same as the wild type positive control group (P>0.05).

Sub-challenge of the channel catfish survivors in the $\Delta iolA_{tra}$ treatment group with wild type ML09-119 showed a 56.9%±0.154 survival rate observed in the $\Delta iolA_{tra}$ group (FIG. 6). In contrast, there was a 4.4%±0.141 survival rate in the positive control group. All survivors of the $\Delta iolA_{tra}$ group were I.P injected with $1 \times 10^6$ CFU/fish ML09-119 again to determine if any immonogenicity developed. Naive channel catfish were I.P injected the same dosage with ML09-119 as a positive control. Significant differences were observed between the ML09-119 group and iolA mutant group (P<0.05) suggesting that a certain extent of immunogenicity to ML09-119 was developed by exposing catfish to the $\Delta iolA_{tra}$ mutant.

Investigation of the Virulence of the Different iolA Mutants.

The vast difference of the virulence between $\Delta iolA_{tra}$ and $iolA_{Rec1}$ mutants prompted us to remake the $\Delta iolA_{tra}$ mutant using the recombineering method to identify if any secondary mutation was introduce while the $\Delta iolA_{tra}$ mutant was constructed. The hypothesis for the difference between the $\Delta iolA_{tra}$ and iolARecI mutants is that there might be a second site mutation that happened during the construction of the $\Delta iolA_{tra}$ mutant that resulted in an attenuated strain.

Furthermore, it was noticed that during the construction of the $\Delta iolA_{tra}$ mutant that a part of the promoter region between the iolA and iolR genes was deleted as well (FIG. 7). This promoter region is hypothesized to contain the binding region for the transcriptional regulator protein IolR to regulate its own transcription, as it is expected to do for other genes in the IolR regulon (Kohler., et al. 2011). This prompted us to create the $\Delta iolA_{Rec2}$ through $\Delta iolA_{Rec8}$ mutants to determine if the loss of the IolR binding region (as yet undefined) will affect the expression of the iolR gene as result in an attenuated strain. The hypothesis is that by deleting the binding region for the transcriptional repressor IolR that this will increase the transcription of iolR, resulting in suppression of other possible virulence factor genes such as aerolysin (Zhang D, et al, 2013) that could possibly be co-regulated by IolR and be in the "IolR regulon". Thus the mutant will be attenuated.

Figure 8:
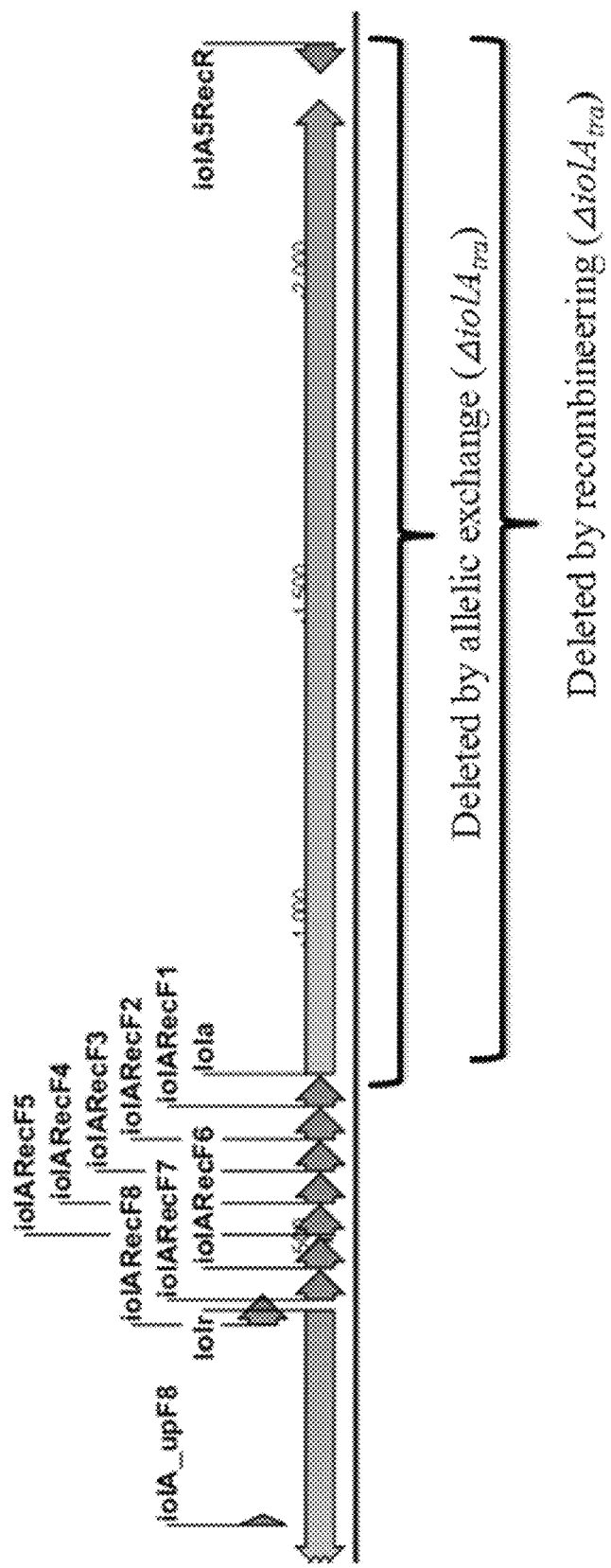
FIG. 8. The relative positions of the iolA and iolR gene

A pretrial was carried out to determine the virulence of each mutant as well as to help select specific mutants for vaccine and immunogenicity studies. The result of this pretrial showed that the remake of the $\Delta iolA_{tra}$ mutant using the recombineering method, $\Delta iolA_{rec}$, did not lose its virulence with a 0% survival rate, as did the $\Delta iolA_{Rec2}$, $\Delta iolA_{Rec5}$, $\Delta iolA_{Rec7}$, and $\Delta iolA_{Rec8}$ mutants. In contrast the $\Delta iolA_{tra}$ had a 83% survival rate, and the $\Delta iolA_{Rec3}$, $\Delta iolA_{Rec4}$, and $\Delta iolA_{Rec6}$ treatment groups had 25%, 33%, and 17% survival rates, respectively. (FIG. 8). These results indicate that there may be some variability in the virulence among these mutants and that there may be some contribution of the IolR regulon to A. hydrophila virulence. Even though this pretrial did not give a valid statistical analysis, it did provide a preliminary determination of the virulence of these iolA mutants. The $\Delta iolA_{Rec3}$ and $\Delta iolA_{Rec4}$ mutants were picked for the formal vaccine candidate and immunogenicity challenge study.

Vaccine Candidate and Immunogenicity Challenge Study.

Figure 9:
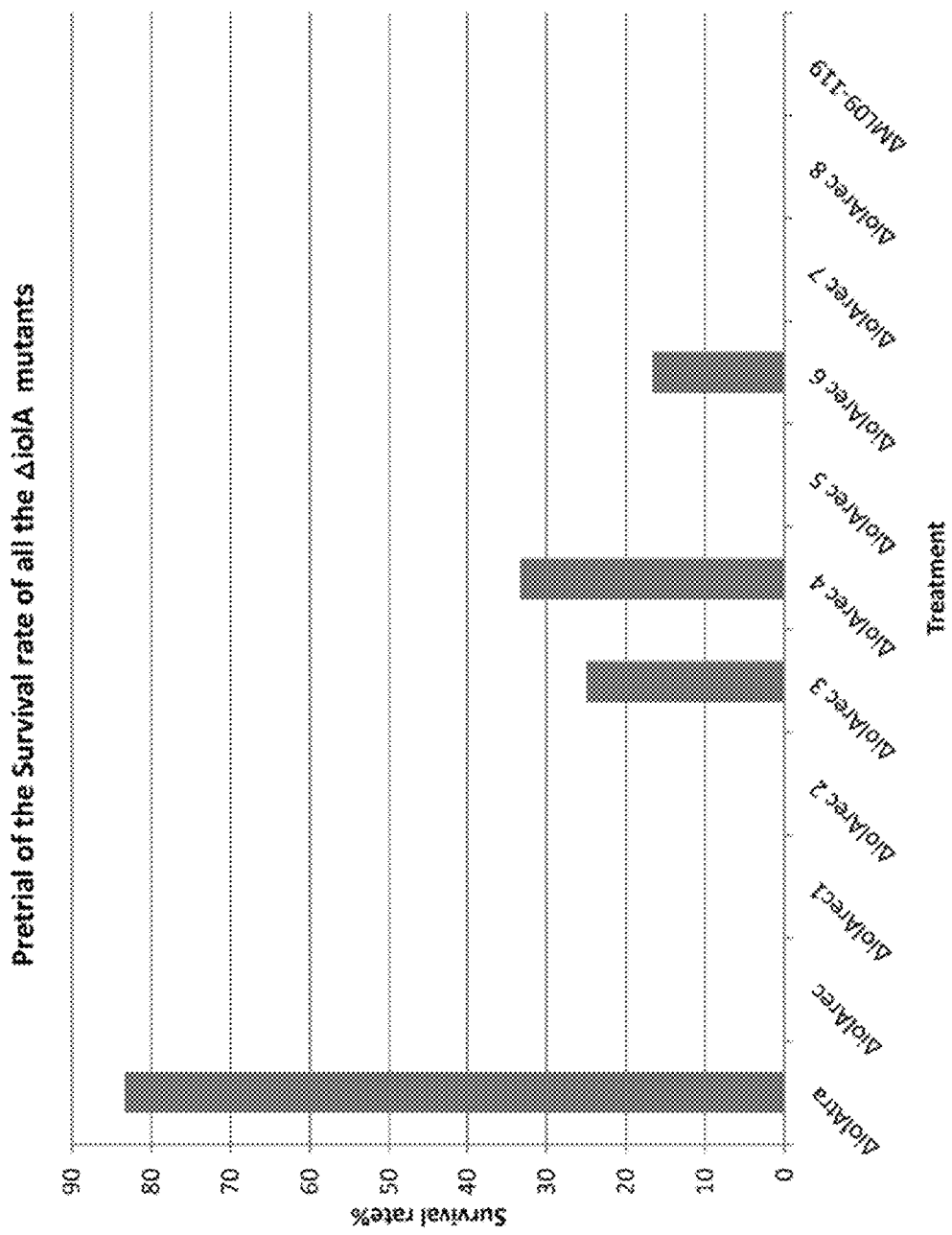
FIG. 9. Pre-trial challenge of the iolA mutants compared with wild type *A. hydrophila* ML09-119. A 0% survival rate was observed in the channel catfish i.p injected with the $\Delta iolA_{Rec}$ mutant, as did the $\Delta iolA_{Rec2}$, $\Delta iolA_{Rec5}$, $\Delta iolA_{Rec7}$, and $\Delta iolA_{Rec8}$ mutants. In contrast, the $\Delta iolA_{tra}$ mutant had an 83% survival rate, and there was 25%, 33.3%, and 16.7% survival rates observed for the $\Delta iolA_{Rec3}$, $\Delta iolA_{Rec4}$, and $\Delta iolA_{Rec6}$ treatment groups, respectively.
Figure 10:
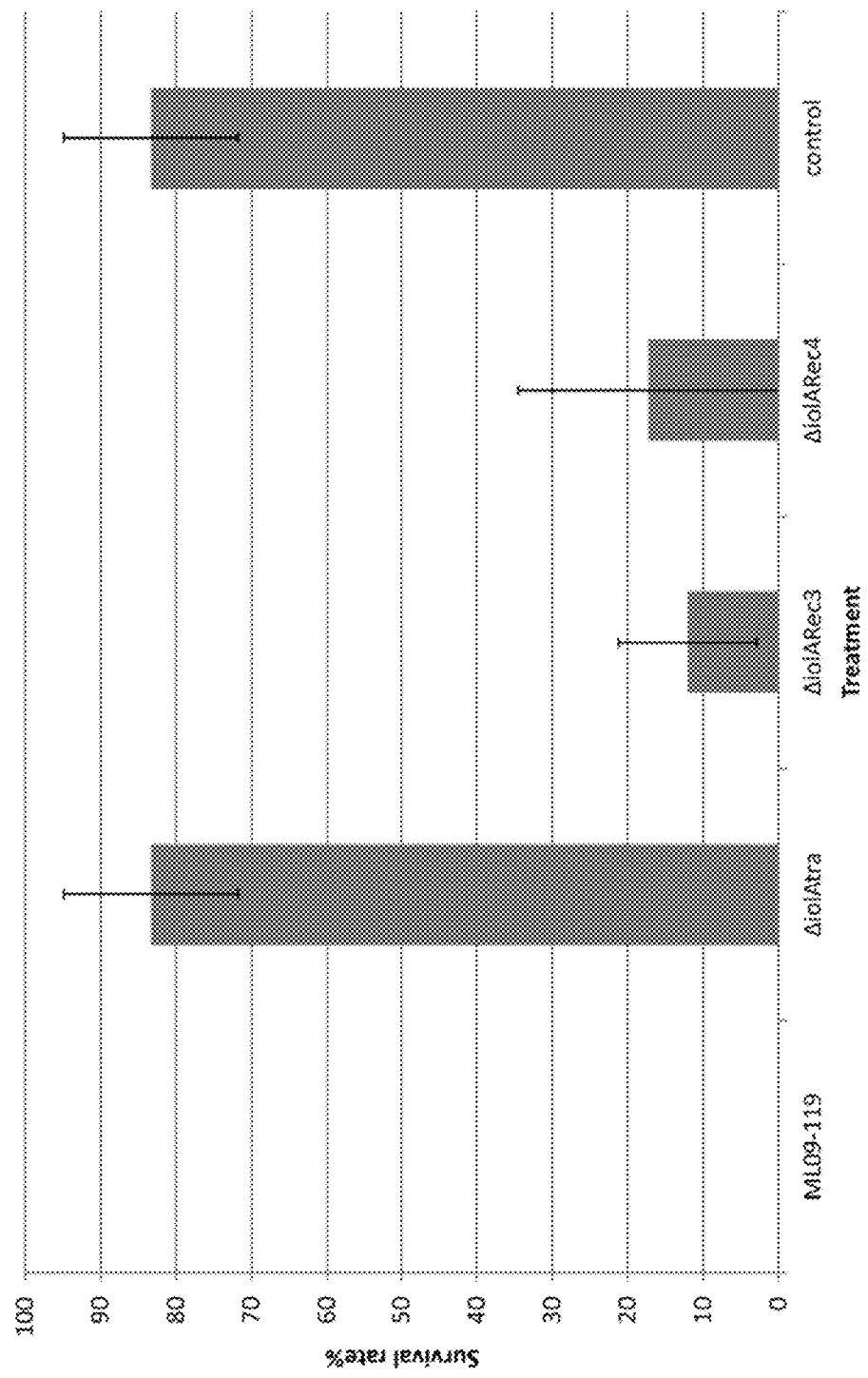
FIG. 10. Cumulative survival rate of the catfish challenged with the ΔiolA mutants. The channel catfish in the $\Delta iolA_{tra}$ treatment group had a 83.3±11.5% survival rate, while a 0±0% survival rate was observed in the ML09-119 treatment group (P<0.0001). Channel catfish challenged with the $\Delta iolA_{Rec3}$ or $\Delta iolA_{Rec4}$ mutants had a 12.1±9.1% and 17.3±17.2% survival rates, respectively.
Figure 12:
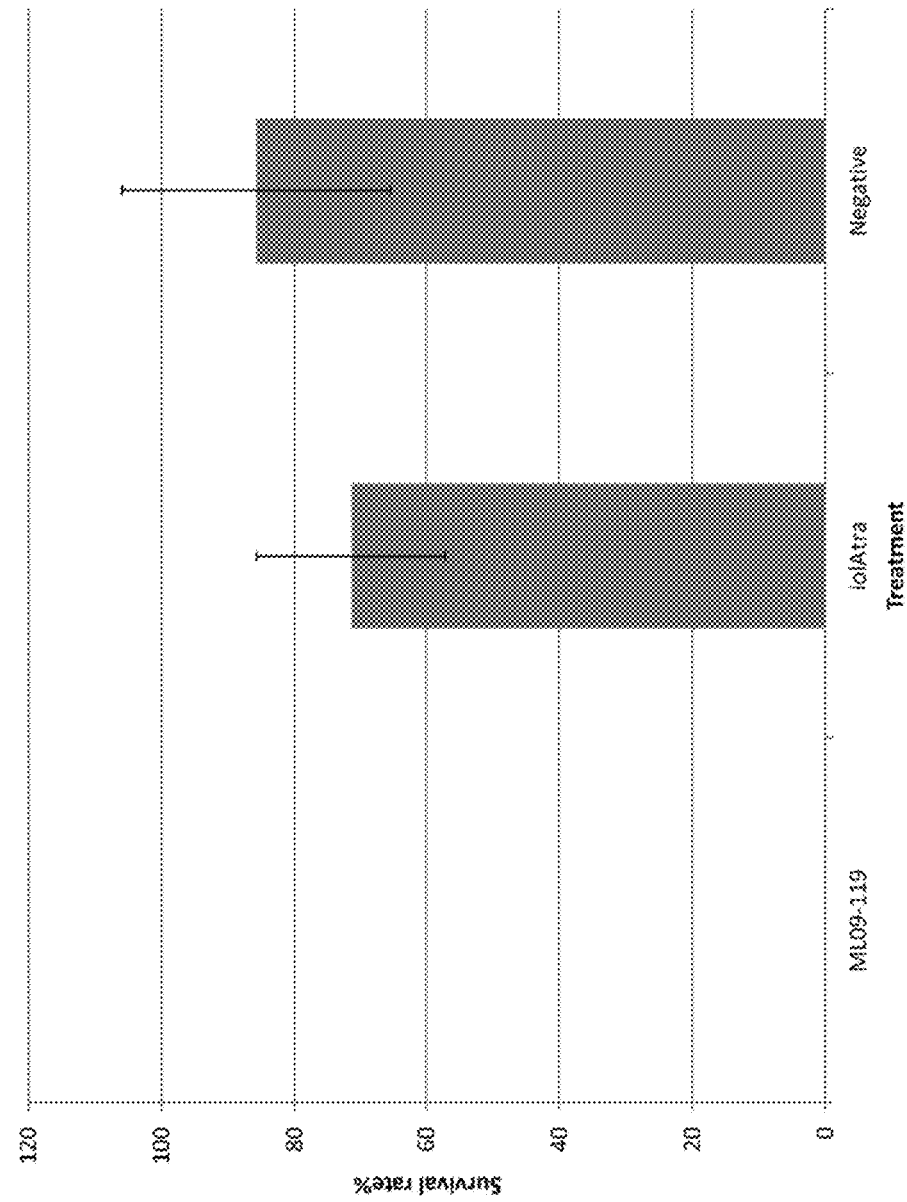
FIG. 12. Cumulative survival rate of the channel catfish survivors sub-challenged with ML09-119. Sub-challenge of the channel catfish survivors in the $\Delta iolA_{tra}$ treatment group with the wild type ML09-119 showed a 71.4±14.3% survival rate, compared to challenge of naïve fish that resulted in a 0±0% survival rate (P=0.00098).

To determine the virulence of the iolA mutants and to evaluate their efficacy as a live vaccine against A. hydrophila ML09-119, an in vivo channel catfish challenge study was conducted. The results of the in vivo channel catfish i.p challenge with $\Delta iolA_{tra}$ again showed that this mutant is attenuated in catfish with a 83.3±11.5% survival rate, while 0±0% survival rate was observed for the fish in the positive control treatment group (P<0.0001) (FIG. 9). However, channel catfish i.p challenged with $\Delta iolA_{Rec3}$ or $\Delta iolA_{Rec4}$ mutants, that have deletions of the iolA gene and 100 bp or 500 bp upstream of iolA gene, respectively, had 12.1±9.1% survival and 17.3±17.2% survival rates, respectively (FIG. 10). No significant difference was observed between the $iolA_{Rec3}$ or $iolA_{Rec4}$ and the wild type treatment group (P>0.05) (FIG. 10).

A sub-challenge of the channel catfish survivors was carried out 21 days post challenge. The $\Delta iolA_{tra}$ treatment group surviving fish that were challenged with the wild type ML09-119 showed a 71.4±14.3% survival rate, in contrast to the 0±0% survival rate observed in the naïve fish challenged with ML09-119 (P<0.05) (FIG. 11). This suggests that a certain extent of immunity against ML09-119 was developed by exposing catfish to the $\Delta iolA_{tra}$ mutant.

Enzyme-Linked Immunosorbent Assay (ELISA).

Figure 13:
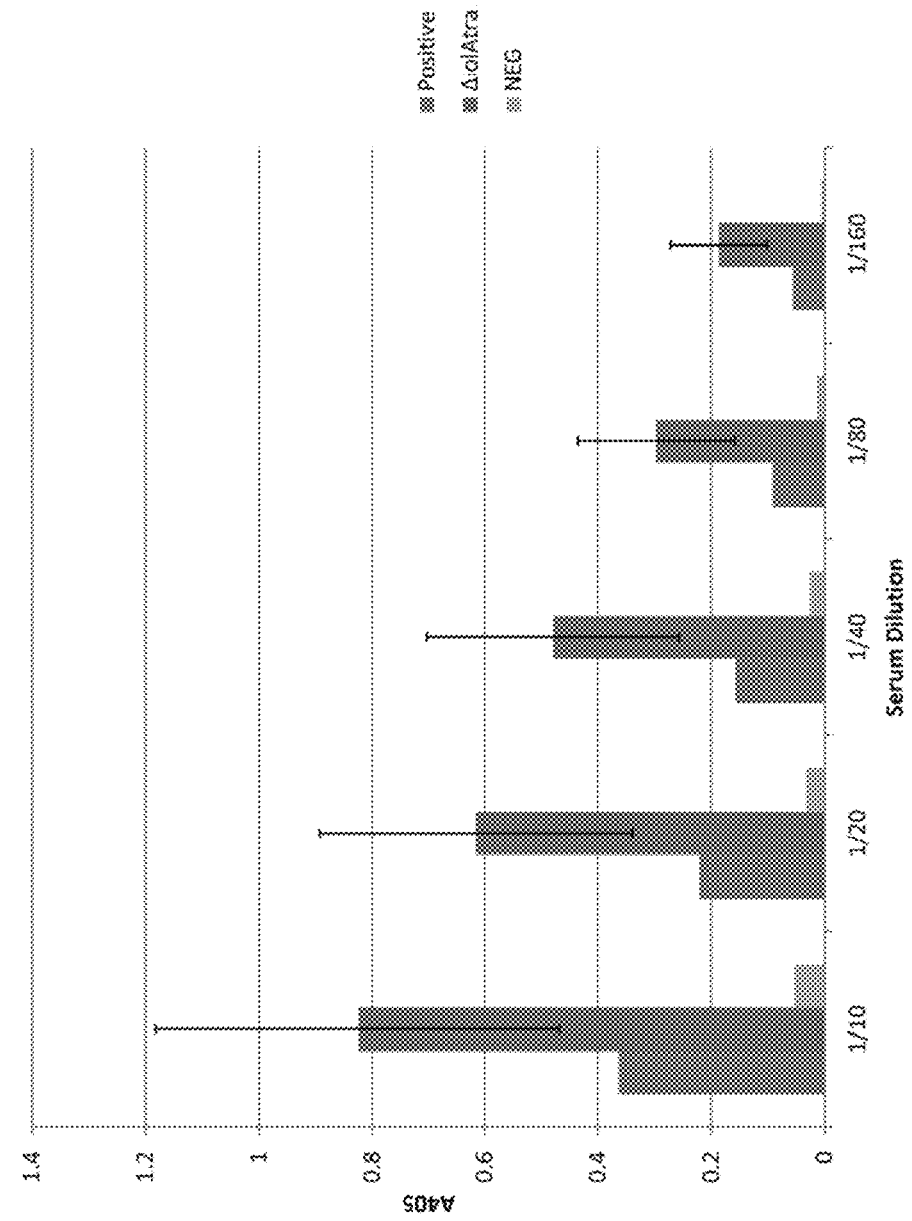
FIG. 13. Titers of $\Delta iol_{Atra}$ antibody against ML09-119 by ELISA. All the replicates of the $\Delta iolA_{tra}$ mutant induced strong antibody reaction to ML09-119. The levels of antibody to ML09-119 were highest in the serum from $\Delta iolA_{tra}$ mutant immunized channel catfish.

The Enzyme-linked Immunosorbent Assay (ELISA) was carried out to determine the efficacy of protective immunity induced by the $\Delta iolA_{tra}$ mutant immunized channel catfish were i.p injected with $1 \times 10^6$ CFU/fish of the mutant. We hypothesized that the $\Delta iolA_{tra}$ mutant expressed epitopes that would retain a similar immunogenicity as the wild type. Thus, a positive reaction should be observed in the titer of the ELISA assay. All of the replicates of the $\Delta iolA_{tra}$ mutant induced a strong antibody reaction to ML09-119 (FIG. 13). The levels of antibody to ML09-119 were highest in serum from the $\Delta iolA_{tra}$ mutant immunized channel catfish, indicating strong antibody induction by the $\Delta iolA_{tra}$ mutant.

Discussion

This study provided valuable insight into role of the myo-inositol pathway in the virulence of A. hydrophila ML09-119. One of the iolA gene deletion mutants created proved to be attenuated and can provide protection against A. hydrophila ML09-119 in an in vivo channel catfish challenge study. This mutant may be a promising live vaccine candidate against epidemic A. hydrophila.

The recent epidemic outbreak of the MAS, which caused by highly virulent A. hydrophila has drawn a lot attention since the catfish farming operations in the southeastern United States have not experienced a large-scale outbreak of MAS before (Hemstreet, 2010). In 2009 and in all subsequent years, catfish farmers in west Alabama have reported severe disease outbreaks which were then proved to be caused by a highly virulent strain of A. hydrophila, represented by strain ML09-119, to channel catfish (I. punctatus). From 2009-2011, Alabama catfish farmers lost more than 10 million pounds of catfish that were market-size and estimated to be more than $3 million due to this epidemic strain of A. hydrophila (Pridgeon et al., 2011; Liles et al., 2011). It is reported that A. hydrophila epidemic strain, ML09-119, is highly virulent to channel catfish, causing severe mortality within 24 h post exposure with certain amount of dose. Also, this epidemic A. hydrophila has expanded its geographic territory and caused frequent outbreaks in the summer months, resulting in millions of pounds of losses in Alabama, Mississippi and Arkansas. (Pridgeon and Klesius, 2011). Due to its highly virulent nature and huge economic loss so far, it is essential that the virulent factors be studied and an effective vaccine be developed.

A previous study showed that epidemic strains can utilize myo-inositol as a sole carbon source. All of the epidemic strains encode the myo-inositol catabolic pathway (Hossain et al, 2013). This prompted us to investigate the role of the myo-inositol pathway in the virulence of *A. hydrophila* ML09-119.

The $\Delta iolA_{tra}$ mutant was created using a traditional allelic exchange technique, and the in vivo channel catfish challenge study showed that this mutant is attenuated compared to its wild-type parent strain ML09-119. However, when we created a precise iolA gene deletion mutant $\Delta iolA_{Rec}$ using a more efficient and accurate recombineering technique, we observed that this mutant was still virulent in channel catfish. There are two hypotheses that could explain this difference in virulence between these two iolA mutants: 1) the truncation of the IolR binding region causes the over expression of iolR gene, repressing other virulence factors such as aerolysin, and/or 2) the $\Delta iolA_{tra}$ mutant has a secondary mutation responsible for some degree of virulence attenuation.

One difference between the $\Delta iolA_{tra}$ and the $\Delta iolA_{rec}$ mutants is that when the $\Delta iolA_{tra}$ was constructed part of the promoter region between the iolA and iolR genes was deleted. IolR is a transcriptional repressor for multiple genes in the myo-inositol pathway, including iolR (Kohler, et al. 2011). It is possible that when the $\Delta iolA_{tra}$ was constructed, the deleted promoter region contained a binding region for IolR (Kohler, et al. 2011). Without the binding region for the IolR repressor, the transcription of the iolR gene may be increased and the synthesis of more IolR might repress other genes that are related to the virulence of *A. hydrophila* in the IolR regulon such as aerolysin (Zhang et al., 2013; Cordero-Alba et al., 2012). We hypothesize that by deleting the region between the iolA and iolR gene that the expression of the iolR gene might change along with the virulence of the mutants. The results of RT-PCR using iolR-specific primers showed that there might be differences between the $\Delta iolA_{Rec4}$ and other $\Delta iolA_{Rec}$ mutants (data not shown); however, no quantification of these data has been performed to date. Our in vivo channel catfish challenge study showed that there is some attenuation within the $\Delta iolA_{Rec3}$ and $\Delta iolA_{Rec4}$ mutants; however, the statistical analysis did not support a difference at P<0.05, and additional experiments with more animals and groups may be needed in order to observe a statistically significant difference between the $\Delta iolA_{Rec3}$ or $\Delta iolA_{Rec4}$ mutants and wild type ML09-119.

Even though the reason for the attenuation of the $\Delta iolA_{tra}$ has not been completely characterized, the immunogenicity study showed that this mutant can provide around 70% survival rates for channel catfish at doses that result in no survival for naïve fish. The ELISA assay evaluating the antibody induced by the $\Delta iolA_{tra}$ mutant against *A. hydrophila* ML09-119 showed that the $\Delta iolA_{tra}$ mutant could induce strong antibody reaction. This indicates that $\Delta iolA5tra$ mutant can serve as a promising live vaccine candidate against the recent MAS epidemic outbreak. This study also raised some interesting studies for the future research including: (1) The reason of the attenuation of the $\Delta iolA_{tra}$ mutant; (2) The role of the iolR gene and what are the genes that are included in the IolR regulon; and (3) The delivery route for the live vaccine of the channel catfish against the *A. hydrophila* epidemic strain.

TABLE 4

Summary of bacterial strains and plasmids used in this study

| Bacterial strains and Plasmid | Relevant features | References |
|---|---|---|
| Bacterial strains | | |
| *A. hydrophila* ML09-119 | | Hossain et al., 2013 |
| *E. coli* SM10-λ-pir | thi-1thr leu tonA lacY supE recA::RP4-2-TcT::Mu Km$^r$ λpir | (Simon, Priefer et al. 1983) |
| Plasmids | | |
| pDMS197 | Suicide vector, sacB, Tet$^R$ | (Edwards, Keller et al. 1998) |
| pDMS197iolA | | This study |

TABLE 5

The primers used in this study

| primer ID | Primer sequence | Primer Application |
|---|---|---|
| iolA5RecF | 5'-T*G*A*A*ATTTAATTTTCAACAAATTCCGTGATCAT CAGCCAAGAGAGAGATC*GTAGACTTCCGTTGAACT*-3' (SEQ ID NO: 66) | Amplifying the cat-cassette for creating the $\Delta iolA_{Rec}$ |
| iolA5RecR | 5'-C*T*G*G*AGAGCGGGATAACCGAGGTGAGTCTGGAC GTGGCGCCTTCAGGAGA*GCCTAATGAGTGAGCTAA*-3' (SEQ ID NO: 67) | Amplifying the cat-cassette for creating the $\Delta iolA_{Rec}$ and serve as the reverse primer for the $\Delta iolA_{Rec2}$-$\Delta iolA_{Rec8}$ |
| iolARecF1 | 5'-A*A*A*T*TTAATTTTCAACAAATTCCGTGATCATCA GCCAAGAGAGAGATCG*AGTAGACTTCCGTTGAACT*-3' (SEQ ID NO: 68) | Amplifying the cat-cassette for c the $\Delta iolA_{Rec1}$ mutant |
| iolARecR1 | 5'-CGCCTTCAGGAGAGAGGGGCGACTGTCCCTCTCTTTT GTTACACTGTCCG*GCCTAATGAGTGAGCTAA*-3' (SEQ ID NO: 69) | Amplifying the cat-cassette for c the $\Delta iolA_{Rec1}$ mutant |
| iolARecF2 | 5'-T*G*C*T*GGATTGATCACAAAAAGGAATTTTTGTTT CACATAAGATTTTTATG*GTAGACTTCCGTTGAACT*-3' (SEQ ID NO: 70) | Amplifying the cat-cassette for c the $\Delta iolA_{Rec2}$ mutant |
| iolARecF3 | 5'-T*G*G*G*GGTTAAACCAGAACCAGGCCAACATCTGC GGGTATGGTGTCAAGA*GTAGACTTCCGTTGAACT*-3' (SEQ ID NO: 71) | Amplifying the cat-cassette for c the $\Delta iolA_{Rec3}$ mutant |

TABLE 5-continued

The primers used in this study

| primer ID | Primer sequence | Primer Application |
|---|---|---|
| iolARecF4 | 5'-A*C*C*A*TTCTTTCATATCATGAAAAACTGTAAACC<br>ATTTCGTAACGACAGACGTAGACTTCCGTTGAACT-3'<br>(SEQ ID NO: 72) | Amplifying the cat-cassette<br>for c the $\Delta iolA_{Rec4}$ mutant |
| iolARecF5 | 5'-G*C*T*T*CATTAACTGCTACAAGATCTCGTTTCCTG<br>TCTGCAGCAATGGAACAGTAGACTTCCGTTGAACT-3'<br>(SEQ ID NO: 73) | Amplifying the cat-cassette<br>for c the $\Delta iolA_{Rec5}$ mutant |
| iolARecF6 | 5'-A*A*T*G*CCAAATCAATTGATATTGTTCAGAAATCT<br>CAACCACTAAACCCCCGGTAGACTTCCGTTGAACT-3'<br>(SEQ ID NO: 74) | Amplifying the cat-cassette<br>for c the $\Delta iolA_{Rec6}$ mutant |
| iolARecF7 | 5'-C*T*G*T*TGCAATCATGTTTACCGGGGCGCCAGCCA<br>GTTACACTTCTTACTTCGTAGACTTCCGTTGAACT-3'<br>(SEQ ID NO: 75) | Amplifying the cat-cassette<br>for c the $\Delta iolA_{Rec7}$ mutant |
| iolARecF8 | 5'-T*C*T*G*CTAGATTCTTCGCCACTGTCATTATGCAC<br>TCCAATCTGTTGCAATCGTAGACTTCCGTTGAACT-3'<br>(SEQ ID NO: 76) | Amplifying the cat-cassette<br>for c the $\Delta iolA_{Rec8}$ mutant |
| Cat F | 5'-GTAGACTTCCGTTGAACT-3'<br>(SEQ ID NO: 77) | Amplifying the cat gene |
| CatR | 5'-GCCTAATGAGTGAGCTAA-3'<br>(SEQ ID NO: 78) | Amplifying the cat gene |
| iolA_upF8 | 5'-TTGCAGAATATGGTGAGGTT-3'<br>(SEQ ID NO: 79) | PCR and sequencing to<br>identify the mutant from<br>$\Delta iolA_{Rec6}$ to $\Delta iolA_{Rec8}$ |
| iolA_dnR8 | 5'-ATATGCCATTCAGTATGCCA-3'<br>(SEQ ID NO: 80) | PCR and sequencing to<br>identify the mutant from<br>$\Delta iolA_{Rec1}$-$\Delta iolA_{Rec8}$ |
| Aup_intF | 5'-CCAGCCAGTTACACTTCTTA-3'<br>(SEQ ID NO: 81) | fusing the two iolA gene<br>arms and the catR gene by<br>splicing through overlap<br>extension PCR (SOE) |
| And_intR | 5'-TTATCTTCAGGCTTGATGCT-3'<br>(SEQ ID NO: 82) | fusing the two iolA gene<br>arms and the catR gene by<br>splicing through overlap<br>extension PCR (SOE) |
| AupF | 5'-CACTCCAATCTGTTGCAATC-3'<br>(SEQ ID NO: 83) | Amplification of upstream<br>sequences of iolA gene |
| AupR | 5'-GATCTCTCTCTTGGCTGATGAGTTCAACGGAAGTCTA<br>C-3'<br>(SEQ ID NO: 84) | Amplification of upstream<br>sequences of iolA gene |
| AdnF | 5'-TCTCCTGAAGGCGCCATTAGCTCACTCATTAGGC-3'<br>(SEQ ID NO: 85) | Amplification of downstream<br>sequences of iolA gene |
| AdnR | 5'-GTAACACCACCGTGAGCAAG-3'<br>(SEQ ID NO: 86) | Amplification of downstream<br>sequences of iolA gene |

B. DETERMINING THE ROLE OF THE O-ANTIGEN IN *A. hydrophila* ML09-119 VIRULENCE

One difference between the $\Delta iolA_{tra}$ and the $\Delta iolA_{Rec}$ mutants is that when the $\Delta iol_{tra}$ was constructed part of the promoter region between the iolA and iolR genes was deleted. IolR is a transcriptional repressor for multiple genes in the myo-inositol pathway, including iolR (Kohler, et al. 2011). It is possible that when the $\Delta iolA_{tra}$ was constructed, the deleted promoter region contained a binding region for IolR (Kohler, et al. 2011). Without the binding region for the IolR repressor, the transcription of the iolR gene may be increased and the synthesis of more IolR might repress other genes that are related to the virulence of *A. hydrophila* in the IolR regulon such as aerolysin (Zhang et al., 2013; Cordero-Alba et al., 2012). We hypothesize that by deleting the region between the iolA and iolR gene that the expression of the iolR gene might change along with the virulence of the mutants. The results of RT-PCR using iolR-specific primers showed that there might be differences between the $\Delta iolA_{Rec4}$ and other $\Delta iolA_{Rec}$ mutants (data not shown); however, no quantification of these data has been performed to date. Our in vivo channel catfish challenge study showed that there is some attenuation within the $\Delta iolA_{Rec3}$ and $\Delta iolA_{Rec4}$ mutants; however, the statistical analysis did not support a difference at P<0.05, and additional experiments with more animals and groups may be needed in order to observe a statistically significant difference between the ΔiolA$_{Rec3}$ or ΔiolA$_{Rec4}$ mutants and wild type ML09-119.

Even though the reason for the attenuation of the ΔiolA$_{tra}$ has not been completely characterized, the immunogenicity study showed that this mutant can provide around 70% survival rates for channel catfish at doses that result in no survival for naïve fish. The ELISA assay evaluating the antibody induced by the ΔiolA$_{tra}$ mutant against *A. hydrophila* ML09-119 showed that the ΔiolA$_{tra}$ mutant could induce strong antibody reaction. This indicates that ΔiolA5tra mutant can serve as a promising live vaccine candidate against the recent MAS epidemic outbreak. This study also raised some interesting questions regarding whether additional genetic loci were contributing to virulence.

Introduction

Lipopolysaccharides (LPS) of Gram-negative bacteria are major virulent determinants and are composed of lipid A, an inner core oligosaccharide, and repeating O-antigen polysaccharides. The virulent nature of LPS is attributed due to the core oligosaccharide and O-antigen polysaccharides. LPS contributes significantly in bacterial pathogenesis by intestinal colonization (Nevola, Laux et al. 1987; West, Sansonetti et al. 2005), lessening macrophage activation (Lugo, Price et al, 2007), promoting intracellular growth (Nagy, Danino et al. 2006), and serum resistance (DeShazer, Brett et al. 1998). The truncation or deletion of the components of the LPS, particularly the O-antigen polysaccharide, diminishes the virulence properties of the bacterial pathogen and this attenuation is necessary for development of a live, attenuated vaccine strain.

In our previous study, through whole genome comparative genomic analysis, we determined the genetic basis of O-antigen biosynthesis from twelve different *A. hydrophila* isolates obtained from diseased fish (Hossain et al 2013), and observed a unique O-antigen biosynthetic pathway in ML09-119 and other epidemic strains and a total of 5 different O-antigen types among the sequenced strains.

Gene knockout and mutant generation is a tool developed from naturally existing mechanisms by which genetic material is exchanged between different bacteria and viruses (Rocha, et al. 2005). After the genes are transferred into the host bacteria, these genes are then incorporated onto the host genome by homologous gene recombination (Ishikawa, et al., 2013; Thomason, et al. 2007).

Recombineering is a precise technique for the manipulation of bacterial genes and other organisms (Yu et al., 2000). This technique is very accurate and fast in target gene deletion, insertion, or substitution events; thus, in a very short time mutants for the study of gene functions can be generated (Datsenko & Wanner, 2000; Datta et al., 2008; Rivero-Müller et al., 2007). A novel recombineering method was developed (Hossain et al., manuscript in preparation) in order to introduce a recombineering plasmid into epidemic *A. hydrophila* via conjugation and mutagenize genes to determine their respective roles in virulence.

In this study, the Lipid A-Core ligase gene (waaL) and O-antigen polymerase gene (wzy) knockout mutants, ΔwaaL$_{tra}$ or ΔwaaL$_{Rec}$, Δwzy$_{tra}$ or Δwzy$_{Rec}$ were created by both traditional allelic exchange and recombineering techniques. An in vivo channel catfish challenge study was conducted to study the role of O-antigen in the virulence of the epidemic strain of *A. hydrophila* ML09-119. A ΔymcA mutant was also created by knocking out the ymcA gene using the recombineering method to study the role of YmcA in the virulence of *A. hydrophila*.

Materials and Methods

Bacterial Isolates and Plasmids.

The *A. hydrophila* ML09-119 used in this study was picked out from single colony on a TSA plate that was inoculated from a −80° C. cryostock. The epidemic strain was from a west Alabama MAS disease outbreak in 2009. The bacteria were routinely grown on fresh TSB medium overnight before use. The *A. hydrophila* ML09-119 used for experiments was from the bacteria stocks of the fish disease lab in Auburn University. This epidemic strain was originally isolated from the kidneys of channel catfish naturally infected with *A. hydrophila*. The pure culture of the epidemic strain was used first in a small test infection of 10 catfish. Moribund catfish that showed clinical signs of *A. hydrophila* ML09-119 were collected for necropsy. *A. hydrophila* was re-isolated from a dying fish by poking a sterile plastic bacteriology loop into the kidney and inoculating a TSA plate. By doing this, it is expected than the virulence of the epidemic strain stock can be recovered. ML09-119 was then confirmed by biochemistry and selective media following the established identification procedures with modifications (Furuwatari, et al., 1994; Holt, et al., 1994). Briefly, the identification biochemical tests included Gram stain, cytochrome oxidase, glucose utilization, 0/129, sucrose, esculin hydrolysis, V-P, DL-lactate utilization and urocanic acid utilization, and then testing on the selective minimal medium M9 with myo-inositol added. *E. coli* SM10-λ-pir and *E. coli* CC118-λ-pir (Simon et al., 1983) were used for the conjugal transfer of the mobilizable mutagenesis plasmids to *A. hydrophila* ML09-119. The list of bacterial strains used in this study is presented in Table 6.

Construction of Defined *A. hydrophila* Lipid A-Core Ligase (waaL) and O-Antigen Polymerase (Wzy) Knockout Mutants, ΔwaaL$_{tra}$ & ΔWzy$_{tra}$, by Traditional Splicing PCR and Conjugation Technique.

Lipid A-Core ligase (waaL) and O-antigen polymerase (wzy) knockout mutants, ΔwaaL$_{tra}$ & Δwzy$_{tra}$ were constructed using suicide plasmid pDMS197 (Edwards, Keller et al. 1998). The primers needed for this study were listed in the Table 7.

The two pairs of primers, Li-upF/Li-upR and Li-dnF/Li-dnR, were used to amplify approximately 400 bp upstream and downstream sequences of waaL gene, respectively using EconoTaq PLUS GREEN 2× Master PCR kit (Lucigen, USA) to construct the ΔwaaL mutant. The template used in this PCR was the genomic DNA of *A. hydrophila* ML09-119 which was extracted using a E.Z.N.A.® Bacterial DNA Kit (Omega Bio-Tek, USA). The chloramphenicol acetyltransferase gene (cat) was amplified from pMHH46 plasmid (Hossain et al 2013) using primers catF and catR. The primers Li-upR and Li-dnF were used for the amplification of upstream and downstream sequences of waaL gene, and contained the reverse complemented sequences of catF and catR primers which were added respectively at their 5' ends. The CatR-cassette which was the chloramphenicol resistance gene (CM$^R$) with two arms of the upstream and downstream homologous of waaL gene was created by fusing the two arms and the CM$^R$ gene by splicing through overlap extension PCR (SOE) (Horton, Hunt et al. 1989). The primers for this PCR were Liup-intF and Lidn-intR. The PCR products were purified by agarose gel purification.

The suicide plasmid pDMS197 was digested by restricted digestion enzyme XbaI (New England Biolabs, NEB) following the protocol provided by the manufacturer. A 50 ul reaction was used for the digestion, including 25 ul of the suicide plasmid pDMS197 DNA, 3 ul of the XbaI restricted digestion enzyme, 5 ul of the 10×CutSmart™ Buffer, 1×BSA and 16 ul RNase free $H_2O$, the reaction system was incubated at 37° C. for one hour. The reaction system was then incubated at 65° C. for 20 min to stop the reaction. The digested product was purified by DNA Clean & Concentrator™ (Zymo research), and the concentration was measured by Qubit® dsDNA BR Assay Kit (Life technologies). The product was blunted using end-repair kit DNA terminator (Lucigen, USA) following the producer's instruction. The product was purified by DNA Clean & Concentrator™ (Zymo research) again before ligation.

The purified restriction enzyme XbaI digested and blunted suicide plasmid pDMS197 was ligated with the gel purified CatR-cassette using Quick Ligase (NEB, USA) incubated for 30 minutes. Briefly, 50 ng of blunted suicide plasmid pDMS197 and around 3-fold molar excess of the CatR-cassette insert was mixed together and the volume was adjusted to 10 ul with RNase free $H_2O$. 10 ul of the 2× Quick Ligation Buffer and 1 µl of Quick T4 DNA Ligase were added into the mixture. The mixture was centrifuged briefly and incubated at room temperature (25° C.) for 30 minutes before it was chilled on ice. A SB gel electrophoresis was done to confirm the ligation product (data not shown).

The making of the electrocompetent cells of *E. coli* CC118-λ-pir and SM10-λ-pir was following a published protocol (Iuoue, et al., 1990) with minor changes. A 0.5 ml of the overnight culture of *E. coli* CC118λ-pir and SM10-λ-pir bacteria was inoculated into 200 ml of Hanahan's Broth (SOB Medium) respectively with 10 mM $MgCl_2$. The culture was incubated in the 37° C. water bath incubator with shaking at 200 rpm for around 2.5 hours and the $OD_{600}$=0.4. The culture was chilled in ice for 10 min before loaded into 200 ml centrifuge tubes. The culture was centrifuged at 6000 rpm for 8 min at 4° C., the supernatant was discarded and the pellet was washed by resuspended with 10% glycerol and centrifuged again at 6000 rpm for 8 min. The wash step was repeated for 3 times before the pellet was gently resuspended in 200 ul GYT medium. The whole procedure was performed on ice.

The ligation product was then used in the electroporation (Chassy, et al., 1988; Dower et al, 1988) to create the plasmid pDMS197waaL, which contains a deletion of the entire waaL gene. 50 ul of the premade electrocompetent cells of the *E. coli* CC11810-λ-pir was mixed gently with 2.5 ul of the ligation product and chilled on ice for 5 min. The mixture was transferred into ice cold cuvettes (Bulldog bio) before the cuvettes were loaded onto the Eppendorf® Eporator® (Eppendorf). Voltage was set at 1800V. The mixture was mixed with recovery medium (SOC medium) right after the pulse shock. The culture was transferred to a 2 ml test tube and incubated at 37° C. with shaking at 200 rpm for 2 hrs. The successfully electroporated *E. coli* CC118-λ-pir with the plasmid pDMS197waaL was selected on 2XYT agar medium plate with 25 ug/ml chloramphenicol and 5 ug/ml tetracycline. A similar strategy was followed for the construction of pDMS197wsy, which contains a deletion of the entire wzy gene. *E. coli* CC118-λ-pir with the plasmids were grown in fresh LB medium with 25 ug/ml chloramphenicol and 5 ug/ml tetracycline. The plasmid was extracted using E.Z.N.A.® Plasmid Midi Kit (Omega Bio-Tek, USA) respectively to get more pure suicide plasmids pDMS197waaL and pDMS197wzy.

The suicide plasmids pDMS197waaL and pDMS197wzy were independently introduced into *A. hydrophila* ML09-119 by conjugation with *E. coli* SM10-λ-pir bearing plasmid pDMS197waaL or pDMS197wzy, respectively. A single colony was selected on the selective medium plate for SM10-λ-pir bearing plasmid pDMS197waaL or pDMS197wzy, respectively, for inoculation of 5 ml LB broth, medium. The culture was incubated at 37° C. with shaking at 200 rpm until the $OD_{600}$ was above 1. A single colony of *A. hydrophila* ML09-119 was picked to inoculate 5 ml TSB broth medium. The culture was incubated at 30° C. with shaking at 200 rpm until the $OD_{600}$ was above 1. A 4 ml ML09-119 culture and 1 ml SM10-λ-pir bearing plasmid pDMS197waaL or pDMS197wzy were mixed together, respectively. The 5 ml culture mixture was filtered through a MicroFunnel 300 SP (MicroFunnel™) by vacuum pressure and 5 ml of fresh LB broth medium was used for washing the cells onto the membrane. The membrane was transferred to the sheep blood agar medium after 2 washes. The sheep blood agar medium was incubated at 30° C. overnight.

The membrane with the cell culture mixture was vortexed with 3 ml fresh TSB broth medium for selection. Single cross-over mutants were selected oil TSA plate supplemented with chloramphenicol, tetracycline and colistin. Double-cross over mutants were obtained by plating onto LB (without NaCl) plates supplemented with 15% sucrose and 12.5 µg/ml chloramphenicol. Mutants grown on this selective plate were subjected to phenotypic and genotypic characterizations. The complete deletion of the waaL and wzy genes were confirmed by PCR followed by sequencing.

Construction of Defined *A. hydrophila* ΔymcA and $\Delta Wzy_{Rec}$ Mutant by Recombineering.

A recombineering technique was used to create a precise deletion of the ymcA gene and wzy gene and generate the ΔymcA and $\Delta wzy_{rec}$ mutants in order to determine the role of O-antigen in the virulence of epidemic *A. hydrophila* ML09-119 in channel catfish.

The chloramphenicol acetyltranferase (cat) gene was amplified from pMHH46 plasmid (Hossain et al 2013) using primers ymcARecF and ymcARecR to generate the cat-cassette with 50 bp of the upstream and downstream of the targeted ymcA gene. The primer ymcARecF contained 50 bp of the upstream of the targeted ymcA gene and the primer ymcARecR contained the reverse complemented sequences of 50 bp of the downstream of the targeted ymcA gene which were added respectively at the 5' ends of each respective primers. The PCR product was validated using agarose gel electrophoresis before another 24×PCR was done using this PCR product to generate more cat-cassette insertion.

The PCR product was purified and concentrated using Wizard® DNA Clean-Up system (Promega, USA) following the protocol provided by the manufacturer. Briefly, the 24 different PCRs were pooled together in a 15 ml conical tube, and a Wizard® DNA Clean-Up kit (Promega, Madison, Wis.) was used to purify the PCR products according to the manufacturer's protocol. The concentration of the final concentrated PCR product was measured using Qubit® dsDNA BR Assay Kit (Life Technologies).

*A. hydrophila* ML09-119 containing the plasmid pMJH65, which was constructed for the purposes of introducing a recombineering cassette into gram-negative bacteria (Hossain et al, manuscript in preparation), was prepared for electroporation using a standard protocol (Inoue, et al., 1990) with minor changes. 0.5 ml of the overnight culture of ML09-119 bacteria was inoculated into 150 ml of Hanahan's Broth (SOB Medium) with 1.5 ml 1M arabinose, 300 ul 25 mg/ml Tetracycline and 600 ul of 2M $MgCl_2$. The culture was incubated in the 30° C. water bath incubator with shaking at 200 rpm for around 4 hours and the $OD_{600}$=0.5. The culture was chilled on ice for 10 min before loaded into 200 ml centrifuge tubes. The culture was centrifuged at 6000 rpm for 8 min at 4° C. The supernatant was discarded and the pellet was washed by re-suspending with 10% glycerol and centrifuged again at 6000 rpm for 8 min. The wash step was repeated 4 times before the pellet was gently resuspended in 200 ul 10% glycerol. The whole procedure was performed on ice.

The concentrated and purified PCR product was then used in the electroporation (Chassy, et al., 1988; Dower et al, 1988) to create the precise ymcA gene deletion mutant ΔymcA. 50 ul of the premade electrocompetent cells of *A. hydrophila* strain ML09-119 (pMJH65) was mixed gently with 3 ug of the concentrated PCR product and chilled on ice for 5 min. The mixture was transferred into ice cold cuvettes (BulldogBio) before the cuvettes were loaded onto the Eppendorf® Eporator® (Eppendorf) with a voltage setting of 1200 V. The mixture was mixed with recovery medium (SOC medium) right after the pulse shock. The culture was transferred to a 2 ml test tube and incubated at 30° C. with shaking at 200 rpm overnight.

The successfully electroporated *A. hydrophila* ML09-119 ymcA gene deletion mutant was selected on a TSA agar medium plate supplied with 25 ug/ml chloramphenicol. A similar strategy was followed for the construction of $\Delta waaL_{rec}$ or $\Delta wzy_{Rec}$, which contains a deletion of waaL or wzy genes, respectively.

Virulence Study of *A. hydrophila* Mutants in Channel Catfish.

All experiments conducted with vertebrate animals (catfish) were approved by the Institutional Animal Care and Use Committee (IACUC) review board at Auburn University in accordance with the animal welfare guidelines specified in the United States.

All the channel catfish (*I. punctatus*, Kansas Random Strain), used in this study were spawned at the hatchery of the Auburn University Fish Genetics Research Unit artificially, prior to transferring to troughs or glass aquaria at the Auburn University Fish Pathology wet lab S-6. Fish were maintained at recirculation systems (temperature around 25° C. and pH 7.5) using well water sources with constant aeration. Fish were fed daily with commercial feed. Water quality factors including temperature, pH, salt level, total ammonia level, total nitrite level were tested on daily basis to ensure that catfish fingerlings remained unstressed and naive to *A. hydrophila*. Catfish fingerlings were grown out in this system until their body weight (BW) reached 20±5 g.

A bacterial suspension of exponential phase growth was prepared by overnight culture in 5 ml TSB broth medium on 200 rpm shaking at 200 rpm at 30° C. The next day 1 ml of the overnight bacterial culture was used to inoculate 100 ml fresh TSB broth culture which was incubated with shaking at 200 rpm at 30° C. for 4 hours. The bacterial culture was centrifuged at 6000 rpm for 10 min. The supernatant was discarded and the bacterial pellet was resuspended in fresh TSB media. The optical density of the bacterial culture was measured by the thermospectronic spectrophotometer (Thermo Spectronic, Rochester, N.Y., USA) at 600 nm and adjusted to an $OD_{600}=1$, which was expected to be $1 \times 10^9$ CFU/ml. After adjusting the bacterial suspension to an appropriate OD, A 1:100 dilution was performed using fresh TSB broth to get the desired concentration (around $1 \times 10^7$ CFU/ml) of *A. hydrophila*. Another 1:2 dilution was done with fresh TSB. This culture was put on ice and used for challenge within 3 hours. A plate count assay was conducted right after the fish challenge to calculate the accurate CFU/ml concentration used in this study. The bacterial cultures used in the fish challenge were serially diluted and 100 ul of each dilution was spread on the TSA plates with 3 replicates for each strain of bacteria.

Channel catfish in Auburn University Fish Pathology wet lab S-6 were randomly distributed into glass aquarium tanks. MS-222 (30 mg/l) was used during the handling of fish to calm the fish down to decrease the stress. Each tank contained 10 fish. A recirculating system was applied during the acclimation period, which was lasted for 10 days. Water temperature was originally 25° C. and salt level was kept around 1.8 ppt to decrease the stress caused by environmental changes as well as eliminating the chance of *F. columnare* infection. Water temperature was gradually brought up to 30±1° C., and salt was gradually brought down to 0.8 during the first 3 day of the acclimation time. Every environmental factor was kept stable prior to the challenge. Fish were fed with commercial catfish fed once a day at 4% of their body weight. Water was changed once per day for the recirculating system with constant aeration. At the time of challenge, recirculating system was changed into flow through system, with the temperature at 30±1° C. Fish of each treatment tank were euthanized by immersing in a bucket with MS-222 (30 mg/l), before 200 ul of ML09-119 bacterial culture was injected intraperitoneally into each fish. Fish were then put back to their cohabitation tanks. Fish of control groups were injected with pure TSB broth medium. Challenged fish were kept the same way as they were during the latter acclimating time. Mortalities were recorded daily for 14 days post challenge. Any moribund or dead fish were removed from the system daily for bacteriological identification and tissue sampling. Prior to sampling, fresh dying or dead fish were inspected externally and internally for any clinical signs. The identification of *A. hydrophila* isolated from anterior kidney of the fresh dying or dead fish was performed by the biochemistry and selective medium method described previously. Survivors of the challenge were kept for 28 days, before they are challenged again with the wild type ML09-119 to test if any protection effect was provided. The procedure of the re-challenge was similar to the preciously challenge. At seven days post re-challenge, blood samples were then drawn from the survivors for the ELISA titer in the later experiment.

Immunogenicity of the Mutants and Enzyme-Linked Immunosorbent Assay (ELISA).

Blood samples collected after the fish challenge were put in the room temperature for 2 hrs then 4° C. overnight allowing to clot completely. Serum of each blood sample was collected followed by centrifuging at 5000 rpm for 10 min. The supernatant of each sample was collected for Enzyme-linked Immunosorbent assay (ELISA) analysis. Antibody responses of channel catfish to *A. hydrophila* were quantified by evaluating the presence of specific immunoglobulin to *A. hydrophila* wild type ML09-119 using indirect ELISA. Protein Detector™ ELISA kit was use to conduct the ELISA experiment.

The protocol followed was similar to the product instructions with minor changes. Ninety six-well plastic plates were coated with 100 ul of a solution of 10 ug/ml ($10^7$ CFU/ml)) *A. hydrophila* epidemic strain. *A. hydrophila* were suspended in carbonate-bicarbonate coating solution. The coating solution was prepared by diluting one time coating buffer tablet in 10 times of sterile reagent quality water. The plates with coating buffer and antigen were placed in 4° C. pH 9.6 overnight. The plates were washed 4 times with washing buffer provided by the kit the next day, followed by adding 1×BSA blocking buffer to block for 15 min at room temperature. After another wash step, the plates were used to do ELISA analysis. 100 ul of 1% BSA blocking buffer was added into each well on the *A. hydrophila* ML09-119 coated plate. 200 ul of the ¹⁄₁₀ fish blood serum sample diluted with 1% BSA blocking buffer was added to the column A2-A11, A1 and A12 were served as positive and negative control. 100 ul of the solution from A1-A12 was transferred to B1-B12 and mixed carefully by pipetting 3-5 times. This step was repeated across the plate until E1-E12. The final 100 ul from the wells in the row E after mixing was discarded. The plate was then incubated at room temperature for 1 hour. The plated was emptied, and residual liquid was tapped out. The plate was washed out by the washing buffer that came with the kit for 5 times. 100 ul of Rat Anti-catfish monoclonal antibody (Mab) was diluted 32 times and added into each well that contained the primary antibody, after which the plate was incubated at room temperature for 1 hour. After incubation the plate was emptied, and residual liquid was tapped out and the plate was washed out five times by the washing buffer that came with the kit. 50 ul of tertiary antibody (goat anti-rat antibody conjugated with horseradish peroxidase) (0.1 ug/ml) was added into each wall that contained the secondary antibody. The plate was incubated at room temperature for 1 hour, after which the plate was washed as above. 5 minutes soaking time was given to the last wash. 50 ul of the substrate solution that came with the kit was added into each well that contained the tertiary antibody. The plated was incubated at room temperature for 5-15 min before the reaction as stopped by adding 50 ul of stop solution into each well for full color development and the plate was then read at $OD_{405}$. A reaction was defined as positive if its $OD_{450}$ value was at least two times the negative control. Ending points were the highest dilution with a positive reaction.

A criss-cross serial dilution analysis was done prior to the ELISA analysis of the samples to optimize the reagent concentration in the immunoassay procedure. 100 ul of 1% BSA blocking buffer was added into each well of the *A. hydrophila* ML09-119 coated plate. 200 ul of the 1/10 ML09-119 infected survivor fish blood serum sample diluted with 1% BSA blocking buffer was added to the respective columns and serially diluted across the plate to identify the best concentration range for the sample. Prior to adding the Mab, 100 ul of 1% BSA blocking buffer was added into each well, followed by 200 ul of the secondary rat anti-channel catfish Mab. This Mab solution was serially diluted across the plate to identify the optimum concentration for the Mab.

Results

Cumulative Survival Rate of the Channel Catfish Challenged with $\Delta waal_{tra}$ or $\Delta wzy_{tra}$ and $\Delta waal_{Rec}$ or $\Delta wzy_{Rec}$.

For better understanding of the virulence factors of the *A. hydrophila* epidemic strain and to identify possible live vaccine candidates, the waal and wzy genes that are expected to be required for O-antigen synthesis and assembly were knocked out by a traditional allelic exchange technique. The LPS of Gram-negative bacteria are major virulent determinant and are composed of lipid A, an inner core oligosaccharide and repeating O-antigen polysaccharide. The role of LPS in virulence is due to the core oligosaccharide and O-antigen polysaccharide, by contributing to intestinal colonization (Nevola, Laux et al. 1987; West Sansonetti et al. 2005), lessening macrophage activation (Lugo, Price et al. 2007), promoting intracellular growth (Nagy, Danino et al. 2006), and serum resistance (DeShazer, Brett et al. 1998). Since O-antigen significantly contributes to the virulence of many gram negative bacteria, the hypothesis is that the waal and wsy genes are virulence factors and by constructing targeted deletions of each of these genes that the resulting mutants of ML09-119 will be attenuated and can serve as promising vaccine candidates.

Figure 14:
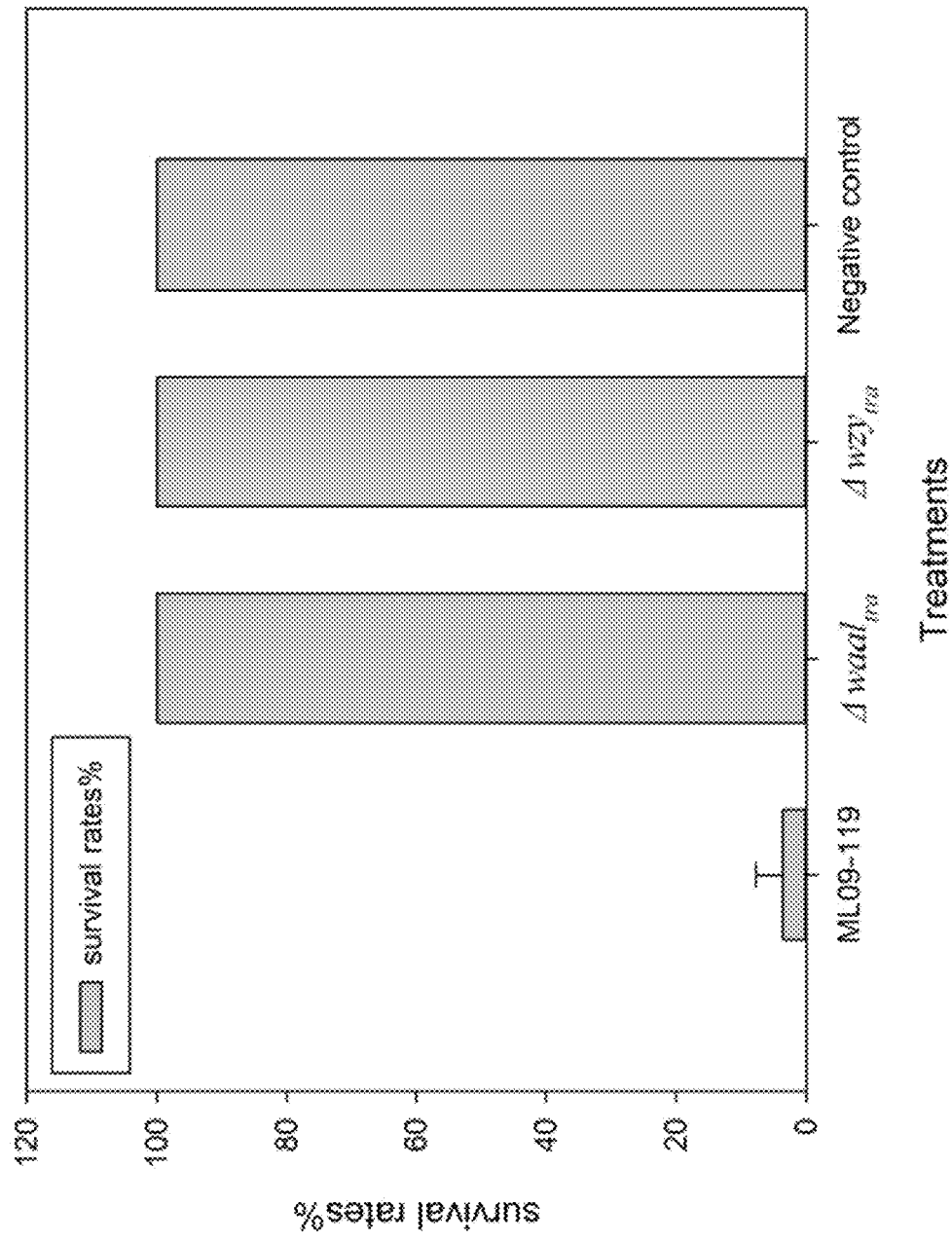
FIG. 14. Challenge with O-antigen mutants created by traditional Allelic exchange technique. The channel catfish in the $\Delta waal_{tra}$ and $\Delta wzy_{tra}$ treatment groups had 100±0% survival rate, while a 5±0.08% survival rate was observed in the positive control treatment ML09-119 group. A significant difference was observed between $\Delta waal_{tra}$ or $\Delta wzy_{tra}$ and ML09-119 treatment groups, P<0.0001.

The results of the in vivo channel catfish i.p challenge with $\Delta waal_{tra}$ and $\Delta wzy_{tra}$ showed that the $\Delta waal_{tra}$ and $\Delta wzy_{tra}$ are both avirulent. The channel catfish in the $\Delta waal_{tra}$ and $\Delta wsy_{tra}$ treatment groups had a 100±0% survival rate, while the wild-type strain-injected group had a 5±0.08% survival. The percentage survival rates were transformed by arcsine square root transformation and then analyzed by SAS 9.2, and significant differences were observed between $\Delta waal_{tra}$ or $\Delta wzy_{tra}$ and ML09-119 treatment groups (P<0.0001). This indicates that the $\Delta waal_{tra}$ and $\Delta wzy_{tra}$ are both attenuated strains of ML09-119 (FIG. 14). However, the channel catfish i.p challenged with the $\Delta waal_{Rec}$ and $\Delta wzy_{Rec}$ mutants, which were created by precisely knocking out the waal and wsy gene using the recombineering method, were still fully virulent with a survival rate comparable to the wild type ML09-119 (data not shown).

Sub-Challenge of the Channel Catfish Survivors in the $\Delta waal_{tra}$ and $\Delta wzy_{tra}$ Mutants Treatment Groups with Wild Type ML09-119 was Conducted.

Figure 15:
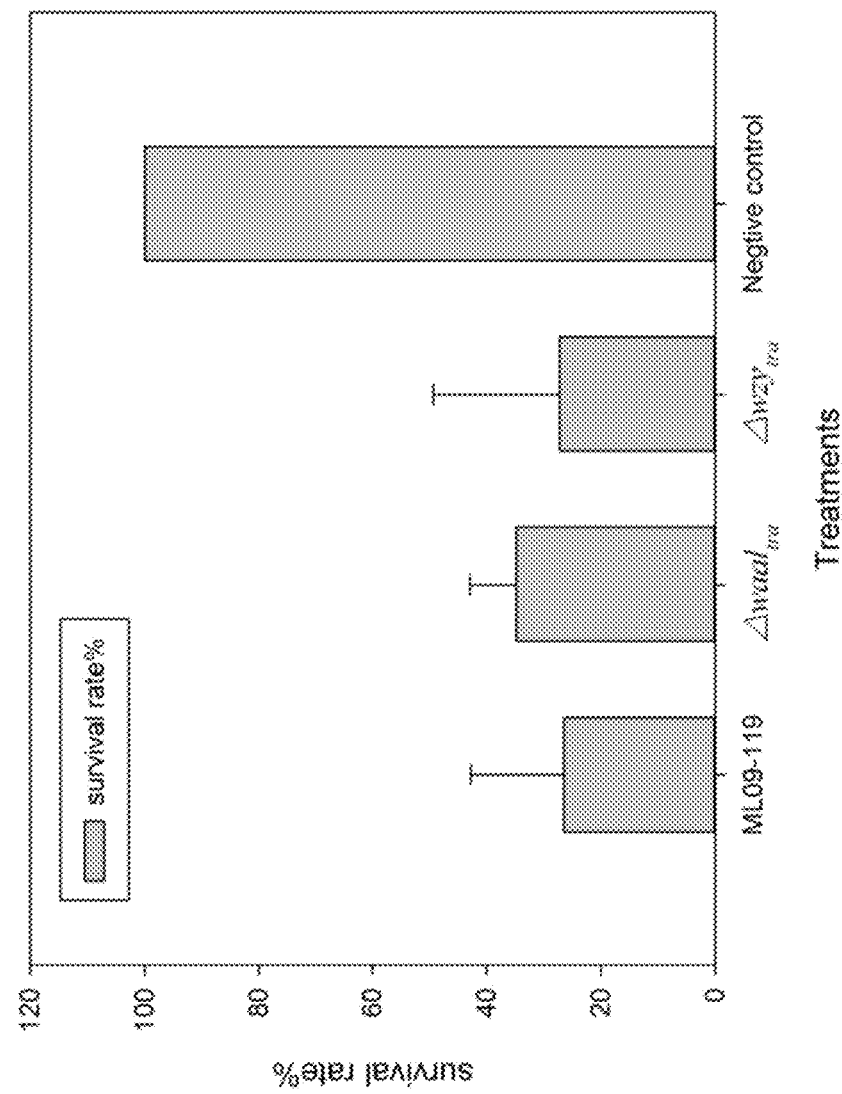
FIG. 15. Sub-challenge of the survivors of each treatment after 21 days with wild type ML09-119. The exact concentration of ML09-119 used in this experiment was not determined. However, significant differences were observed between the sham negative control group and the treatment groups (P=0.0044<0.05). No significant differences were observed between the treatment groups and the positive control group ($P_{\Delta waaltra}$>0.05 and $P_{\Delta waaltra}$=0.97). A 35±0.18% survival rate was observed in the $\Delta waal_{tra}$ group, and a 27±0.3% survival rate was observed in the $\Delta wzy_{tra}$ group.

Unfortunately, due to mistakes in the plate count technique, the exact concentration of ML09-119 used in this experiment was not determined. However, significant differences were still observed between the sham negative control group and the treatment groups (P<0.05). No significant differences were observed between the treatment groups and the positive control group ($P_{\Delta wzy}$>0.05 and $P_{\Delta waal}$>0.05). A 35±0.1% survival rate was observed in $\Delta waal$ group, and a 27±0.3% survival rate was observed in $\Delta wzy$ group, suggesting no immunity developed in either of the O-antigen mutant treatment groups (FIG. 15).

The investigation of the virulence of the $\Delta ymcA$ mutant and the vaccine candidate and immunogenicity challenge study. The vast difference in the virulence between the $\Delta waal_{tra}$ or $\Delta wzy_{tra}$ mutants and $\Delta waal_{Rec}$ or $\Delta wzy_{Rec}$ prompted us to investigate the molecular difference(s) between the mutations generated in these two groups. It was discovered that when the $\Delta waal_{tra}$ mutant was constructed, a part of the transcription termination site (TTS) of the ymcA gene, located downstream of the waal gene, was deleted. It is also possible that insertion of the $CM^R$ gene cassette has a polar effect on ymcA transcription. This prompted us to create the $\Delta ymcA$ mutant to determine if the ymcA gene contributes to the virulence of *A. hydrophila* ML09-119. The hypothesis was that by interrupting the ymcA gene, the $\Delta ymcA$ mutant will be attenuated; therefore, the $\Delta ymcA$ mutant was created using the recombineering technique.

Figure 16:
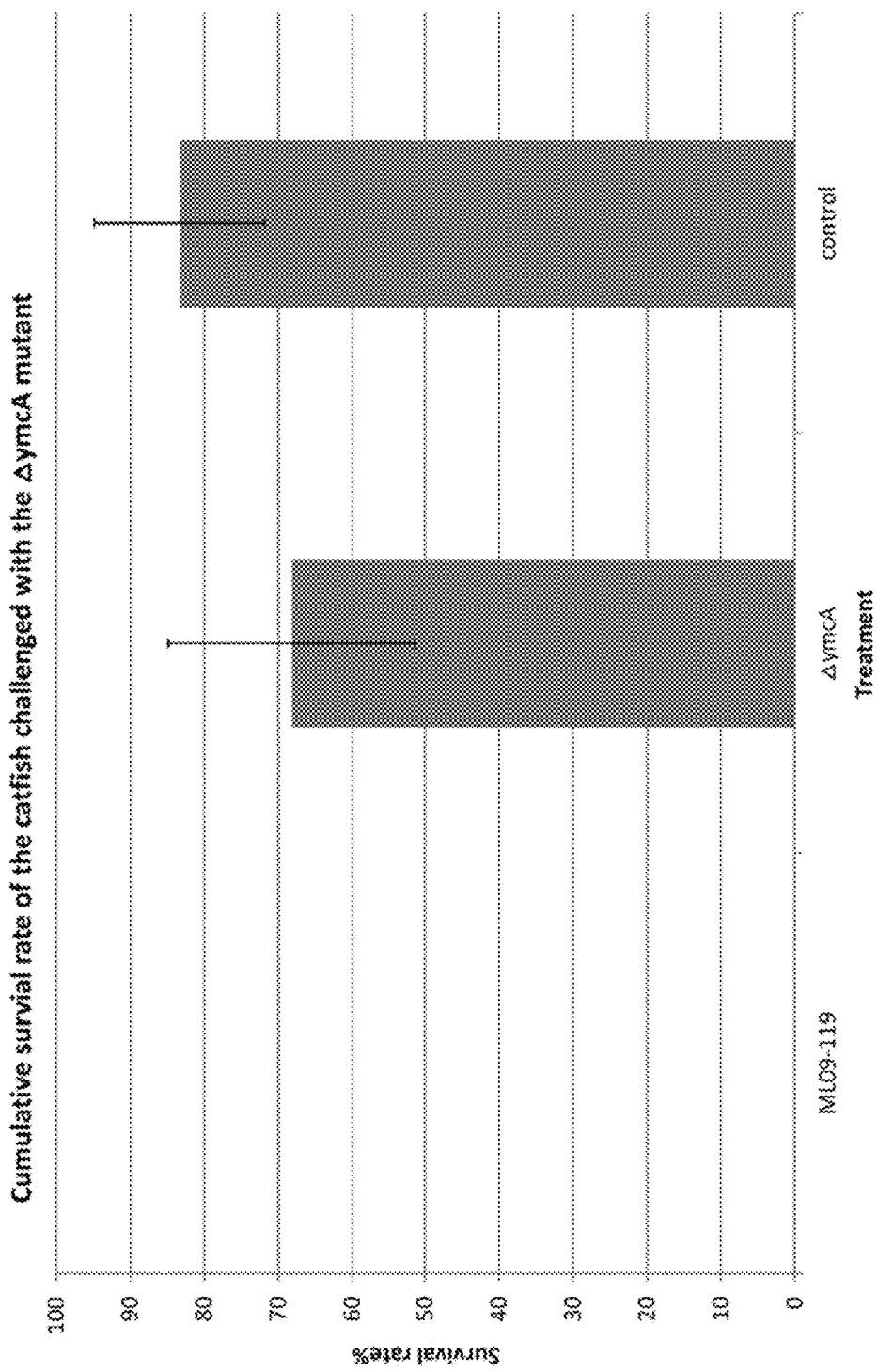
FIG. 16. Cumulative survival rate of the catfish challenged with the ΔymcA mutant. The channel catfish in the ΔymcA treatment group had a 68.1±16.8% survival rate, while a 0±0% survival rate was observed for wild-type ML09-119. Note that a 83.3±11.6% survival rate was observed in the negative control treatment group, with some deaths attributable to non-bacterial causes. A significant difference was observed between the ΔymcA and ML09-119 treatment groups, P=0.000186<0.05.

To determine the virulence of the $\Delta ymcA$ mutant and to evaluate the efficacy of the $\Delta ymcA$ mutant as a live vaccine against *A. hydrophila* ML09-119, an in vivo channel catfish challenge study was carried out. The results of the in vivo channel catfish i.p. challenged with $\Delta ymcA$ mutant showed that the $\Delta ymcA$ mutant was avirulent. The channel catfish in the $\Delta ymcA$ treatment group had a 68.1±16.8% survival rate, while a 0±0% survival rate was observed in the positive control treatment group. Note that a 83.3±11.6% survival rate was observed in the negative control treatment group. A significant difference was observed between the $\Delta ymcA$ treatment group and the *A. hydrophila* ML09-119 treatment group, $P_{\Delta ymcA}$=0.000186<0.05. This indicates that $\Delta ymcA$ is an attenuated mutant of ML09-119 (FIG. 16).

Figure 17:
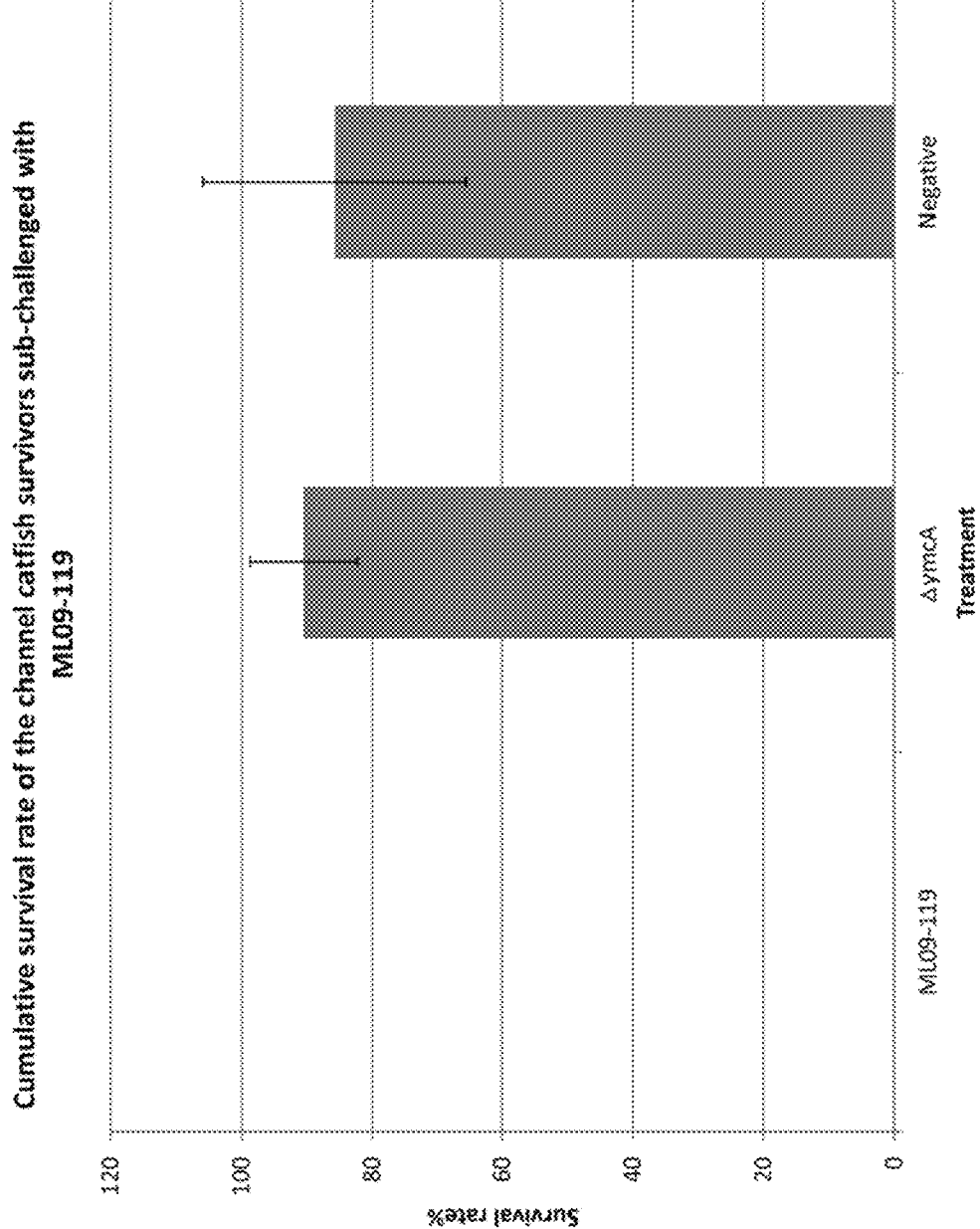
FIG. 17. Cumulative survival rate of the channel catfish survivors sub-challenged with ML09-119. The ΔymcA treatment group surviving fish that were challenged with the wild type ML09-119 showed a 90.5±8.3% survival rate, in contrast to the 0±0% survival rate observed in the naive channel catfish challenged with ML09-119. Significant differences were observed between the ML09-119 group and the ΔymcA mutant group, $P=4.52E^{-0.5}$<0.05.

A sub-challenge of the channel catfish survivors was carried out 21 days post challenge. The $\Delta ymcA$ treatment group surviving fish that were challenged with wild type ML09-119 showed a 90.5±8.3% survival rate, in contrast to the 0±0% survival rate observed in the naive channel catfish challenged with ML09-119 (FIG. 17). Significant differences were observed between the ML09-119 group and ΔymcA mutant group, $P_{\Delta ymcA}=4.52E^{-0.5}<0.05$. This suggested that protective immunity against ML09-119 was developed by exposing catfish to the ΔymcA mutant.

Enzyme-Linked Immunosorbent Assay (ELISA).

Figure 18:
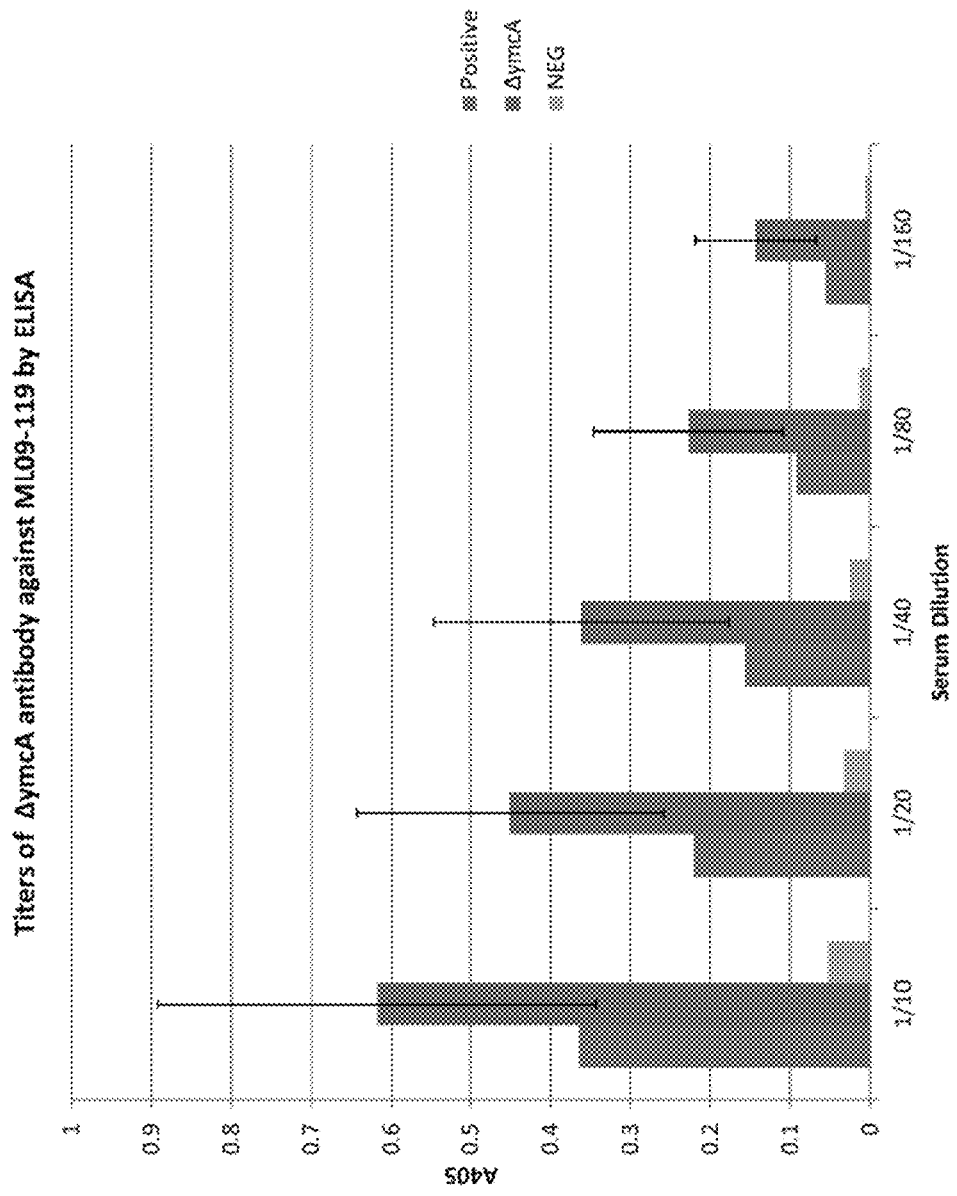
FIG. 18. Antibody titers offish exposed to ΔymcA against ML09-119 by ELISA. All of the replicates of the ΔymcA mutant-challenged fish induced a strong antibody reaction to ML09-119. The levels of antibody to ML09-119 were highest in the serum from ΔymcA mutant immunized channel catfish.

The Enzyme-linked Immunosorbent Assay (ELISA) was carried out to determine the efficacy of protective immunity induced by the ΔymcA mutant immunized channel catfish after being i.p injected with $1 \times 10^6$ CFU/fish of the mutant. Since LPS contributes significantly to bacterial pathogenesis via multiple mechanisms, and the ymcA gene has been reported to be required for the biosynthesis and assembly of the O-antigen (Peleg, et al., 2005), we hypothesized that the ymcA gene is a virulence factor in *A. hydrophila* ML09-119, the deletion of the ymcA gene, by removing the O-antigen, might result in an *A. hydrophila* strain that is sensitive to complement, is less invasive, and allows development of antibodies targeting *A. hydrophila* antigens that are present in more typical *A. hydrophila* strains that are opportunistic pathogens in different fish species. All of the replicates of the ΔymcA mutant induced a strong antibody reaction to ML09-119 (FIG. 18). The levels of antibody to ML09-119 were highest in serum from the catfish that were immunized with the ΔymcA mutant, indicating strong antibody induction by the ΔymcA mutant.

Discussion

This study provided valuable insight into role of the O-antigen in the virulence of *A. hydrophila* ML09-119. The ymcA gene deletion mutant was observed to be attenuated in its virulence and can provide protection against *A. hydrophila* ML09-119 in an in vivo channel catfish challenge study. This mutant may be a promising live vaccine candidate against epidemic *A. hydrophila*.

The recent epidemic outbreak of the MAS caused by highly virulent *A. hydrophila* has drawn a lot of attention since the catfish farming operations in the southeastern United States have not experienced a large-scale outbreak of MAS previously (Hemstreet, 2010). In 2009 and in all subsequent years, catfish farmers in west Alabama have reported severe disease outbreaks which were demonstrated to be caused by a highly virulent strain of *A. hydrophila*, represented by strain ML09-119, in catfish (*I. punctatus*). From 2009 to the present, Alabama catfish farmers lost more than 10 million pounds of catfish that were market-size and estimated to be more than $3 million due to this epidemic strain of *A. hydrophila* (Pridgeon et al., 2011; Liles et al., 2011). The *A. hydrophila* epidemic strain ML09-119 that has been used in research studies is highly virulent to channel catfish, causing severe mortality within 24 h post exposure at a dose of $>1 \times 10^6$ CPU by i.p injection. Also, this epidemic *A. hydrophila* strain has expanded its geographic territory and caused frequent outbreaks in the summer months, resulting in millions of pounds of losses in Alabama, Mississippi and Arkansas, (Pridgeon and Klesius, 2011). Due to its highly virulent nature and the resulting huge economic losses, it is essential that the virulent factors expressed by this epidemic *A. hydrophila* be studied and an effective vaccine be developed.

A previous study showed that epidemic strains possess an unique O-antigen cluster compared to reference strains (Hossain et al, 2013). This prompted us to investigate the role of the O-antigen in the virulence of the *A. hydrophila* ML09-119, since the O-antigen is known to contribute significantly in bacterial pathogenesis, such as intestinal colonization (Nevola, Laux et al. 1987; West, Sansonetti et al. 2005), lessening macrophage activation (Lugo, Price et al. 2007), promoting intracellular growth (Nagy, Danino et al. 2006), and serum resistance (DeShazer, Brett et al. 1998).

The $\Delta waal_{tra}$ and $\Delta wzy_{tra}$ mutants were created using a traditional allelic exchange technique, and the in vivo channel catfish challenge study showed that these mutants were attenuated compared to their wild type parent strain ML09-119 strain. However, when we created the precise waal and wzy gene deletion mutants $\Delta waal_{Rec}$ and $\Delta wzy_{Rec}$ mutants using a more efficient and accurate recombineering technique, we observed that those mutants were still virulent in channel catfish. It was found that during the construction of the Δwaal mutant that a region of the transcription termination site (TTS) between the waal gene and the ymcA gene was deleted, and the insertion of the gene cassette in the mutant may have a polar effect on ymcA transcription. The ymcA gene is reported to be required for the biosynthesis and assembly of the O-antigen (Peleg, et al. 2005). We therefore hypothesized that a ymcA mutant would be attenuated in its virulence. The in vivo channel catfish challenge study showed that the ΔymcA mutant is significantly attenuated in its virulence.

The immunogenicity study showed that this mutant can provide 90.5±8.3% protection for channel catfish in the in vivo channel catfish study, and the ELISA assay demonstrated that the ΔymcA mutant induced a strong antibody reaction. This indicates that ΔymcA mutant can serve as a promising live vaccine candidate against epidemic *A. hydrophila*. The fact that the ELISA titer of ΔymcA mutant is even higher than the positive control is probably due to that the serum for the positive control was collected months ago and stayed in the −20° C. for months, thereby losing some efficacy. We were not able to use fresh ML09-119 serum, since all of the channel catfish in the positive control group were dead and there were no survivors from which to collect blood samples.

Interestingly, there has not been any previous research investigating the contribution of YmcA to the virulence of any bacterial pathogens. There have been studies on the contribution of YmcA in *B. subtilis* on the formation of biofilms in multicellular bacterial assemblages (Branda, et al., 2004; Branda, et al., 2006; Kobayashi, 2007). However, in these studies the exact function of YmcA is not determined. One study on the human pathogen *Shigella flexneri* mentioned that the ymcA gene exists and speculates that it might encode a putative outer membrane lipoprotein that is highly conserved among *Shigella* and *E. coli* (Sun, et al., 2012). Since none of these studies have provided any conclusive evidence for the function of YmcA, this makes the finding in this study is even more valuable, given the evidence that the ymcA gene is required for virulence in epidemic *A. hydrophila*.

This study also raised some interesting studies for the future research including: (1) The exact function of YmcA; (2) The complementation of the ΔymcA mutant and determining if the complemented mutant is restored in its virulence; (3) The delivery route for the live vaccine of the channel catfish against the *A. hydrophila* the epidemic strain; (4) The protective effect of the ΔymcA mutant against other non-epidemic strains of *A. hydrophila*.

TABLE 6

Summary of bacterial strains and plasmids used in this study

| Bacterial strains and Plasmid | Relevant features | References |
|---|---|---|
| Bacterial strains | | |
| A. hydrophila ML09-119 | | Hossain et al., 2013 |
| A. hydrophila AL06-06 | | Hossain et al., 2013 |
| E. coli SM10-λ-pir | thi-1thr leu tonA lacY supE recA::RP4-2-TcT::Mu Km$^r$ λpir | (Simon, Priefer et al. 1983) |
| E. coli CC118-λ-pir | Δ(ara-leu) araD ΔlacX74 galE galKphoA20 thi-1 rpsE rpoB argE(Am) recA1 λpir | (Herrero, de Lorenzo et al. 1990) |
| Plasmids | | |
| pDMS197 | Suicide vector, sacB, Tet$^R$ | (Edwards, Keller et al. 1998) |
| pDMS197waaL | | This study |
| pDMS197wzy | | This Study |

TABLE 7

The primers used in this study

| Primer ID | Primer sequence | Primer Application |
|---|---|---|
| ymcARecF | 5'-T*A*G*A*GATATCAATATTCGTATTGCCAATCTCCT TGCTAATCGAGTACCAGA*GTAGACTTCCGTTGAACT*-3' (SEQ ID NO: 87) | Amplifying the cat-cassette for creating the ΔymcA |
| ymcARedR | 5'-C*A*A*C*TGCTCGCCCTTTTTGATGAAAAAAGATCG GCTCTATGCAACTTTTGAG*CCTAATGAGTGAGCTAA*-3' (SEQ ID NO: 88) | Amplifying the cat-cassette for creating the ΔymcA |
| ymcA_upF | 5'-CCGAATGGTAATCCACAGTT-3' (SEQ ID NO: 89) | PCR and Sequencing of ΔymcA for identification of the mutant |
| Ymca_dnR | 5'-TAGAACAGCTGGTCACGAGA-3' (SEQ ID NO: 90) | PCR and Sequencing of ΔymcA for identification of the mutant |
| Cat F | 5'-GTAGACTTCCGTTGAACT-3' (SEQ ID NO: 91) | Amplifying the cat gene |
| CatR | 5'-GCCTAATGAGTGAGCTAA-3' (SEQ ID NO: 92) | Amplifying the cat gene |
| Li-upF | 5'-ACTTAAGCTCGCCGAACTC (SEQ ID NO: 93) | Amplification of upstream sequences of WaaL gene |
| Li-upR | 5'-GCTGTCGAGGCCATGTGAGTTCAACGGAAGTCTAC-3' (SEQ ID NO: 94) | Amplification of upstream sequences of WaaL gene |
| Li-dnF | 5'-AAGATCGGCTCTATGCAACTTTAGCTCACTCATTAGG C-3' (SEQ ID NO: 95) | Amplification of downstream sequences of WaaL gene |
| Li-dnR | 5'-TGATTATGATGTAATGACTGG (SEQ ID NO: 96) | Amplification of downstream sequences of WaaL gene |
| Liup-intF | 5'-AGAAGCGGTGCTGATAACG (SEQ ID NO: 97) | fusing the two waal gene arms and the CM$^R$ gene by splicing through overlap extension PCR (SOE) |
| Lidn-intR | 5'-GGCAGTTACCATTCATGAGT (SEQ ID NO: 98) | fusing the two waal gene arms and the CM$^R$ gene by splicing through overlap extension PCR (SOE) |
| wzyupF | 5'-CCGCGACAACAACTCCTT (SEQ ID NO: 99) | Amplification of upstream sequences of wzy gene |
| wzyupR | 5'-GCACTTCCTGTATCAAGATTAGTTCAACGGAAGTCTA C-3' (SEQ ID NO: 100) | Amplification of upstream sequences of wzy gene |
| wzydnF | 5'-CTAGCTGTGGTGCCAGAATATTAGCTCACTCATTAGG C-3' (SEQ ID NO: 101) | Amplification of downstream sequences of wzy gene |
| wzydnR | 5'-CATTCAATATAGTGTCTGAA (SEQ ID NO: 102) | Amplification of downpstream sequences of wzy gene |

TABLE 7-continued

The primers used in this study

| Primer ID | Primer sequence | Primer Application |
|---|---|---|
| wzyup-inF | 5'-GTGACGCCACCGATGATA (SEQ ID NO: 103) | fusing the two wzy gene arms and the $CM^R$ gene by splicing through overlap extension PCR (SOE) |
| wzydn-inR | 5'-CTGATGTTATTATTGACCAAG (SEQ ID NO: 104) | fusing the two wzy gene arms and the $CM^R$ gene by splicing through overlap extension PCR (SOE) |

C. CONCLUSIONS

*A. hydrophila* ML09-119 has been reported to cause severe mortality in commercial catfish farms. In this study, the virulence factors of the myo-inositol pathway and of the O-antigen synthesis pathway were studied to determine their role in the virulence of *A. hydrophila* ML09-119. Mutants lacking factors in each of these pathways were created by both allelic exchange technique and recombineering technique. The efficacy of the mutant as a live vaccine candidate against *A. hydrophila* ML09-119 was evaluated by in vivo channel catfish challenge study.

In this study, the gene iolA coding for the enzyme aldehyde dehydrogenase for myo-inositol catabolism was inactivated by traditional allelic exchange to generate the *A. hydrophila* $\Delta iolA_{tra}$ mutant. An in vivo challenge in channel catfish showed that there was no mortality in the channel catfish that were challenged with $\Delta iolA_{tra}$ mutant, but there was mortality in the channel catfish challenged with $\Delta iolA_{rec}$ mutants similar to wild type ML09-119. Results of the in vivo challenge in channel catfish showed that $\Delta iolA_{rec3}$, $\Delta iolA_{rec4}$ exhibited some decrease in mortality, but there were no significant difference in the mortality between the channel catfish challenged with $\Delta iolA_{rec3}$, $\Delta iolA_{rec4}$ and the channel catfish challenged with the wild type ML09-119. ELISA titer of the survivor's of the $\Delta iolA_{tra}$ after 21 days showed that $\Delta iolA_{tra}$ can induce strong antibody response against the wild type *A. hydrophila* ML09-119, indicating that this mutant can serve as a promising vaccine candidate against the epidemic *A. hydrophila*.

In this study, Lipid A-Core ligase (waaL) and O-antigen polymerase (wzy) knockout mutants, $\Delta waaL$, $\Delta wzy$ were created by both traditional splicing PCR and conjugation technique and recombineering technique respectively, $\Delta waaL_{tra}$ or $\Delta waaL_{Rec}$, $\Delta wzy_{tra}$ or $\Delta wzy_{rec}$. An in vivo channel catfish challenge study was committed on channel catfish to study the role of O-antigen in the virulence of the epidemic strain of *A. hydrophila*. The results show that the channel catfish that were challenged with $\Delta waaL_{tra}$, $\Delta wzy_{tra}$ were avirulent, but $\Delta waaL_{Rec}$, $\Delta wzy_{Rec}$ were virulent.

In this study, a $\Delta ymcA$ mutant was created by knocking out the ymcA gene by recombineering technique. The results showed that $\Delta ymcA$ mutant was attenuated. Sub-challenge of the survivors of $\Delta ymcA$ treatment group 21 days post first challenge and ELISA titer of the survivors of the $\Delta ymcA$ treatment showed that this mutant can provide 90.5±8.3% protection against wild type *A. hydrophila* ML09-119 indicating that the $\Delta ymcA$ mutant can serve as a promising vaccine candidate.

Figure 20:
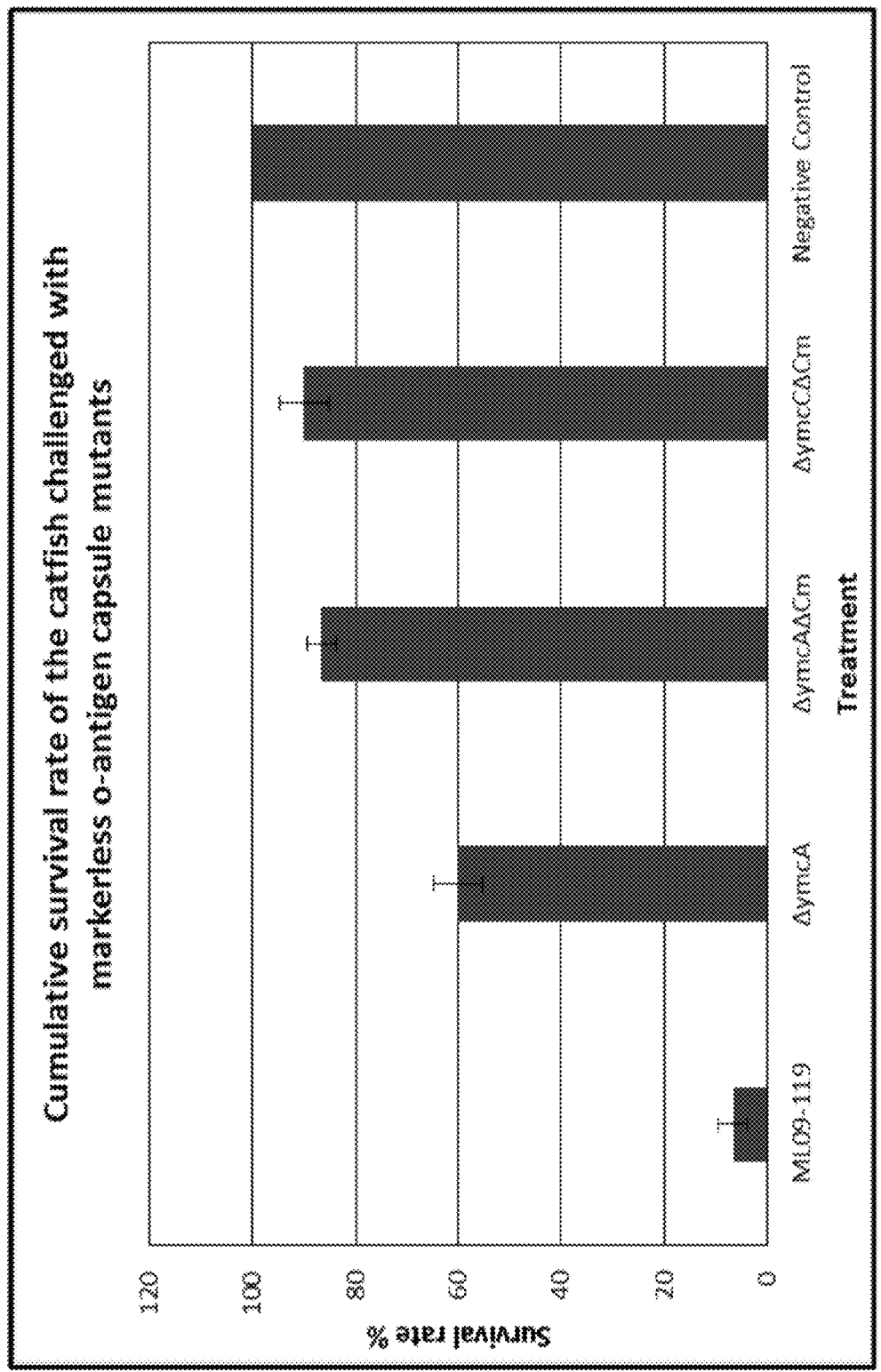
FIG. 20. Aquaria virulence studies of vAh strain ML09-119, the ΔymcA mutant (containing the chloramphenicol resistance cassette), and the markerless mutants of the O-antigen capsular genes ymcA and ymcC in channel catfish. For each treatment, 3 replicate groups of 10 fish each were injected intraperitoneally with 200 μl of bacterial cells adjusted to a fixed concentration (~$6.09\times10^6$ CFU/fish).

Markerless versions of the $\Delta ymcA$ and $\Delta ymcC$ mutants also were created using the flippase-mediated removal of the chloramphenicol resistance gene. These markerless mutants were injected IP into fingerling catfish and within 24 hours significant mortality was observed in the wild-type ML09-119-injected fish, but a significant reduction was observed in the mortality of fish injected with the $Cm^R$ $\Delta ymcA$, markerless $\Delta ymcA$, or the markerless $\Delta ymcC$ mutants compared to the wild-type control (P<0.05) (FIG. 20).

Figure 21:
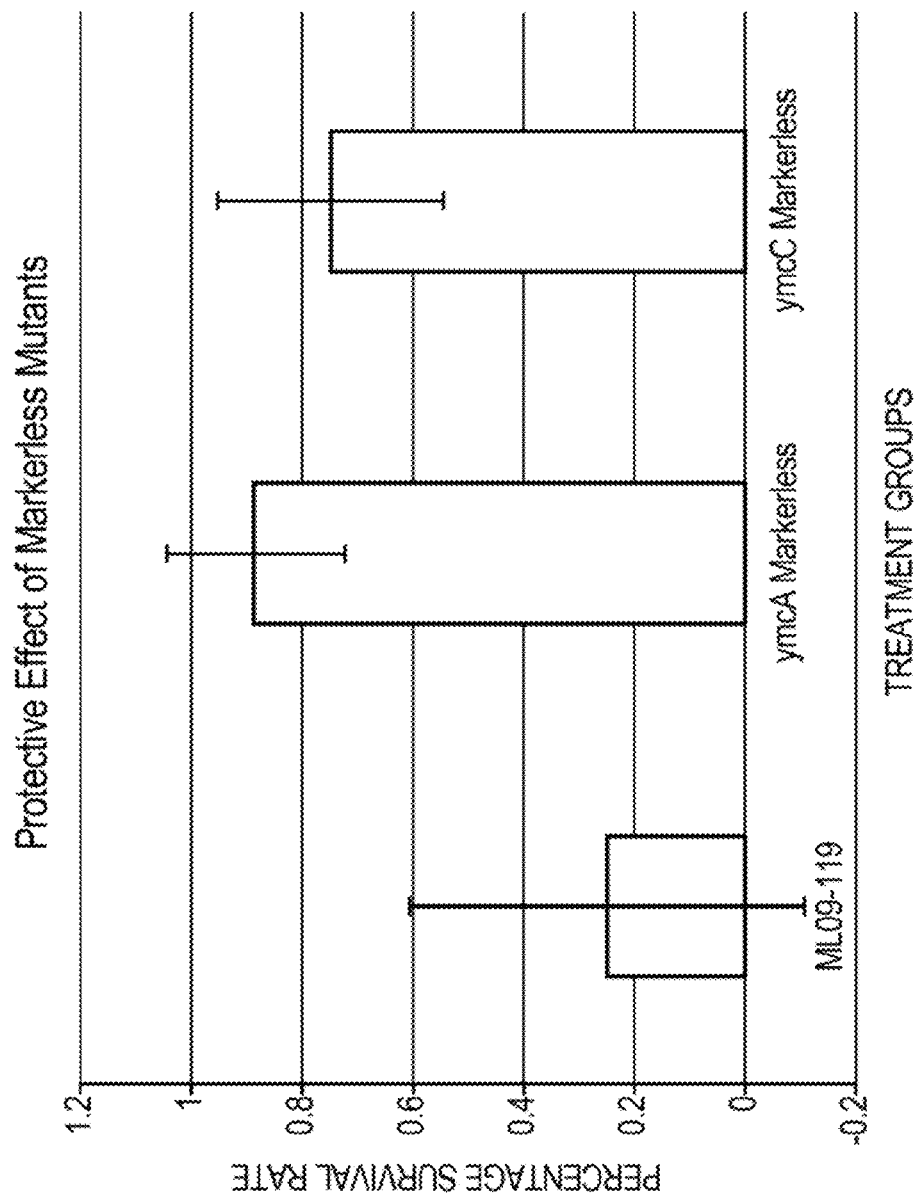
FIG. 21. Protective effect of ΔymcA and ΔymcC markerless mutants. Fingerling catfish that had previously been IP injected with $10^7$ CFU/fish for each respective mutant, as well as naïve fish, were challenged with ML09-119 at the dosage of $4\times10^6$ CFU/fish 21 days post-injection. Survival rate is recorded after 24 hours. The average survival rate of naïve fish was 25±35.4%, while the ΔymcA markerless treatment group's survival rate was 88.9±16.7%, and the ΔymcC markerless treatment group's survival rate was 75±20.4%, suggesting that both mutants can provide protection against epidemic vAh strain ML09-119.

Fingerling catfish that had previously been IP injected with $10^7$ CFU/fish for each respective mutant (i.e., the $\Delta ymcA$ markerless mutant and the $\Delta ymcC$ markerless mutant), as well as naïve fish, were challenged with ML09-119 at the dosage of $4 \times 10^6$ CFU/fish 21 days post-injection. Survival rate was recorded after 24 hours (FIG. 21). The average survival rate of naïve fish was 25±35.4%, while the $\Delta ymcA$ markerless treatment group's survival rate was 88.9±16.7%, and the $\Delta ymcC$ markerless treatment group's survival rate was 75±20.4%, suggesting that both mutants can provide protection against epidemic vAh strain ML09-119.

COMPREHENSIVE BIBLIOGRAPHY FOR EXAMPLE 2

Alexeyev, M. (1999). "The pKNOCK series of broad-host-range mobilizable suicide vectors for gene knockout and targeted DNA insertion into the chromosome of gram-negative bacteria." Biotechniques 26 (5): 824-827.

Allison, R. and H. Kelly (1963). "An epizootic of *Ichthyophthirius multifiliis* in a river fish population." The Progressive Fish-Culturist 25 (3): 149-150.

Alper, H., K. Miyaoku, et al. (2005). "Construction of lycopene-overproducing *E. coli* strains by combining systematic and combinatorial gene knockout targets." Nature biotechnology 23 (5): 612-616.

Anthony, J. (1963). "Parasites of eastern Wisconsin fishes." Transactions of the Wisconsin Academy of Sciences, Arts and Letters 52: 83-95.

Arias, C. R., W. Cai et al. (2012). "Catfish hybrid *Ictalurus punctatus×I. furcatus* exhibits higher resistance to columnaris disease than the parental species." Marine Ecology Progress Series 100 (1): 77-81.

Baba, T., T. Ara, et al. (2006). "Construction of *Escherichia coli* K-12 in-frame, single-gene knockout mutants: the Keio collection." Molecular systems biology 2 (1).

Bader, J. A. and J. M. Grizzle (1992). "Effects of ammonia on growth and survival of recently hatched channel catfish." Journal of Aquatic Animal Health 4 (1): 17-23.

Badgett, M. R., A. Auer, et al. (2002). "Evolutionary dynamics of viral attenuation." Journal of virology 76 (20): 10524-10529.

Baker, J. C. and J. L. Crites (1976). Parasites of channel catfish, *Ictalurus punctatus* Rafinesque, from the island region of Lake Erie. Proc. Helminthol. Soc. Wash.

Baxa, D., J. Groff, et al. (1990). "Susceptibility of nonictalurid fishes to experimental infection with *Edwardsiella ictaluri.*" Diseases of Aquatic Organisms 8 (2): 113-117.

Bebak, J., M. Matthews, et al. (2009). "Survival of vaccinated, feed-trained largemouth bass fry (*Micropterus salmoides floridanus*) during natural exposure to *Flavobacterium columnare*," Vaccine 27 (32): 4297-4301.

Beck, B. H., B. D. Farmer, et al. (2012). "Putative roles for a rhamnose binding lectin in *Flavobacterium columnare* pathogenesis in channel catfish *Ictalurus punctatus*." Fish & shellfish immunology 33 (4): 1008-1015.

Bengoechea, J. A., H. Najdenski, et al. (2004). "Lipopolysaccharide O antigen status of *Yersinia enterocolitica* O: 8 is essential for virulence and absence of O antigen affects the expression of other *Yersinia* virulence factors." Molecular microbiology 52 (2): 451-469.

Bergerhouse, D. L. (1994). "Lethal effects of elevated pH and ammonia on early life stages of hybrid striped bass," Journal of Applied Aquaculture 2 (3-4): 81-100.

Berman, T. and B. Magasanik (1966). "The Pathway of myo-inositol Degradation in *Aerobacter aerogenes* DEHYDROGENATION AND DEHYDRATION." Journal of Biological Chemistry 241 (4): 800-806.

Booth, N. J., J. B. Beekman, et al. (2009). "*Edwardsiella ictaluri* encodes an acid-activated urease that is required for intracellular replication in channel catfish (*Ictalurus punctatus*) macrophages." Applied and environmental microbiology 75 (21): 6712-6720.

Boyd, C. E. and C. S. Tucker (1992). "Water quality and pond soil analyses for aquaculture." Water quality and pond soil analyses for aquaculture.

Branda, S. S., F. Chu, et al. (2006). "A major protein component of the *Bacillus subtilis* biofilm matrix." Molecular microbiology 59 (4): 1229-1238.

Branda, S. S., J. E. González-Pastor, et al. (2004). "Genes involved in formation of structured multicellular communities by *Bacillus subtilis*." Journal of bacteriology 186 (12): 3970-3979.

Brüggemann, H., S. Bäumer, et al. (2003). "The genome sequence of *Clostridium tetani*, the causative agent of tetanus disease." Proceedings of the National Academy of Sciences 100 (3): 1316-1321.

Buentello, J. A., D. M. Gatlin III, et al. (2000). "Effects of water temperature and dissolved oxygen on daily feed consumption, feed utilization and growth of channel catfish (*Ictalurus punctatus*)." Aquaculture 182 (3): 339-352.

Cameron, D. E., J. M. Urbach, et al. (2008). "A defined transposon mutant library and its use in identifying motility genes in *Vibrio cholerae*." Proceedings of the National Academy of Sciences 105 (25): 8736-8741.

Chambrier, A. d. and T. Scholz (2008). "Tapeworms (Cestoda: Proteocephalidea) of firewood catfish *Sorubimichthys planiceps* (Siluriformes: Pimelodidae) from the Amazon River," Folia Parasitologica 55 (1): 17-28.

Chassy, B. M., A. Mercenier, et al. (1988). "Transformation of bacteria by electroporation." Trends in Biotechnology 6 (12): 303-309.

Chen, Y.-L, S. Kauffman, et al. (2008). "*Candida albicans* uses multiple mechanisms to acquire the essential metabolite inositol during infection." Infection and immunity 76 (6): 2793-2801.

Choi, S. H. and K. H. Kim (2011). "Generation of two auxotrophic genes knock-out *Edwardsiella tarda* and assessment of its potential as a combined vaccine in olive flounder (*Paralichthys olivaceous*)." Fish & shellfish immunology 31 (1): 58-65.

Cole, B. A. and C. E. Boyd (1986). "Feeding rate, water quality, and channel catfish production in ponds." The Progressive Fish-Culturist 48 (1): 25-29.

Collins, D. M. (2000). "New tuberculosis vaccines based on attenuated strains of the *Mycobacterium* tuberculosis complex." Immunology and cell biology 78 (4): 342-348.

Colt, J. and G. Tchobanoglous (1976). "Evaluation of the short-term toxicity of nitrogenous compounds to channel catfish, *Ictalurus punctatus*." Aquaculture 8 (3): 209-224

Cone, D. and P. Woo (1995). "Monogenea (Phylum Platyhelminthes)." Fish diseases and disorders. Volume 1: protozoan and metazoan infections. 289-327.

Coon, T. G. and H. R. Dames (1989). Catfish movement and habitat use in a Missouri River tributary. Proceedings of the Annual Conference Southeastern Association of Fish and Wildlife Agencies.

Cooper, R. K., E. B, Shotts Jr, et al. (1996). "Use of a mini-transposon to study chondroitinase activity associated with *Edwardsiella ictaluri*." Journal of Aquatic Animal Health 8 (4): 319-324.

Davison, J. (1999). "Genetic exchange between bacteria in the environment." Plasmid 42 (2): 73-91.

Declercq, A., F. Boyen, et al. (2013). "Antimicrobial susceptibility pattern of *Flavobacterium columnare* isolates collected worldwide from 17 fish species." Journal of fish diseases 36 (1): 45-55.

Declercq, A. M., F, Haesebrouck, et al. (2013). "Columnaris disease in fish: a review with emphasis on bacterium-host interactions." Vet Res 44 (27): 10.1186.

Deshazer, D., P. J. Brett, et al. (1998). "The type II O-antigenic polysaccharide moiety of *Burkholderia pseudomallei* lipopolysaccharide is required for serum resistance and virulence." Molecular microbiology 30 (5): 1081-1100.

Dickerson, H., D. Dawe, et al. (1995). "*Ichthyophthirius multifiliis* and *Cryptocaryon irritans* (Phylum Ciliophara)" Fish diseases and disorders. Volume 1: protozoan and metazoan infections. 181-227.

Dower, W. J., J. F. Miller, et al. (1988). "High efficiency transformation of *E. coli* by high voltage electroporation." Nucleic acids research 16 (13): 6127-6145.

Durborow, R. (1998). "Columnaris disease." A bacterial infection caused by *Flavobacterium Columnare* South Regional Aquaculture Centre SRAC, Texas A & M University, Publication (479).

Edwards, R. A., L. H. Keller, et al. (1998). "Improved allelic exchange vectors and their use to analyze 987P fimbria gene expression," Gene 207 (2): 149-157.

Esquivel, J. R., S. Z. Gomes, et al. (1998). "Growth of channel catfish, *Ictalurus punctatus*, in southern Brazil." Journal of Applied Aquaculture 8 (3): 71-78.

FAO (2012). "The state of world fisheries and aquaculture 2012." FAO Fisheries and Aquaculture Dept.

Flotemersch, J. E. (1996). Utilization of crayfish by channel catfish in a floodplain-river ecosystem, Mississippi State University. Department of Wildlife and Fisheries.

FROST, P. and A. NESS (1997). "Vaccination of Atlantic salmon with recombinant VP2 of infectious pancreatic necrosis virus (IPNV), added to a multivalent vaccine, suppresses viral replication following IPNV challenge," Fish & shellfish immunology 7(8): 609-619.

Galli-Taliadoros, L., J. Sedgwick, et al. (1995). "Gene knock-out technology: a methodological overview for the interested novice," Journal of immunological methods 181 (1): 1-15.

Gauchat-Feiss, D., J. Frey, et al. (1985). "Cloning of genes involved in myo-inositol transport in a *Pseudomonas* sp." Journal of bacteriology 162 (1): 324-327.

Goodwin, A. E. (1999). "Massive *Lernaea cyprinacea* infestations damaging the gills of channel catfish polycultured with bighead carp." Journal of Aquatic Animal Health 11 (4): 406-408.

Griffin, B. (1991). "Characteristics of a chondroitin AC lyase produced by *Cytophaga columnaris.*" Transactions of the American fisheries Society 120 (3): 391-395.

Griffiths, S. G. and K. Salonius (2007). Vaccine against salmonid rickettsial septicaemia based on arthrobacter cells, Google Patents.

Gudding, R., A. Lillehaug, et al. (1999). "Recent developments in fish vaccinology." Veterinary immunology and immunopathology 72 (1): 203-212.

Hanson, T. and M. D. Sites (2012). "2011 US Catfish Database." Fisheries.

Hargreaves, J. A. (2002). "Channel catfish farming in ponds: lessons from a maturing industry," Reviews in Fisheries Science 10 (3-4): 499-528.

Harris, N. J., J. W. Neal, et al. (2011). "Notes on hatchery spawning methods for bigmouth sleeper *Gobiomorus dormitor*." Aquaculture Research 42 (8): 1145-1152.

Hawke, J., R. Durborow, et al. (1998). "ESC—Enteric Septicemia of Catfish."

Hawke, J. P. (1979). "A bacterium associated with disease of pond cultured channel catfish, *Ictalurus punctatus.*" Journal of the Fisheries Board of Canada 36 (12): 1508-1512.

Hawke, J. P., A. C. McWHORTER, et al. (1981). "*Edwardsiella ictaluri* sp. nov., the causative agent of enteric septicemia of catfish." International Journal of Systematic Bacteriology 31 (4): 396-400.

He, J., J. Deng, et al. (2006). "A synergistic effect on the production of S-adenosyl-1-methionine in *Pichia pastoris* by knocking in of S-adenosyl-1-methionine synthase and knocking out of cystathionine-β synthase." Journal of biotechnology 126 (4): 519-527.

Hildreth, M. B. and R. D. Lumsden (1985). "Description of Otobothrium insigne plerocereus (Cestoda: Trypanorhyncha) and its incidence in catfish from the gulf coast of Louisiana," Proceedings of the Helminthological Society of Washington 52 (1): 44-50.

Hoffman, G. (1978). "Ciliates of freshwater fishes." Parasitic protozoa 11: 632-983.

Horton, R. M., H. D. Hunt, et al. (1989). "Engineering hybrid genes without the use of restriction enzymes: gene splicing by overlap extension," Gene 77 (1): 61-68.

Humphrey, J. D., C. Lancaster, et al. (1986). "Exotic bacterial pathogens *Edwardsiella tarda* and *Edwardsiella ictaluri* from imported ornamental fish *Betta splendens* and *Pontius conchouius*, respectively: isolation and quarantine significance," Australian Veterinary Journal 63 (11): 369-371.

Hung, K., R. Hayashi, et al. (1998). "The central role of CD4+ T cells in the antitumor immune response." The Journal of experimental medicine 188 (12): 2357-2368.

Inoue, H., H. Nojima, et al. (1990). "High efficiency transformation of *Escherichia coli* with plasmids." Gene 96 (1): 23-28.

Iredell, J. R., U. H. Stroeher, et al. (1998). "Lipopolysaccharide O-antigen expression and the effect of its absence on virulence in rfb mutants of *Vibrio cholerae* O1." FEMS Immunology & Medical Microbiology 20 (1): 45-54.

Ishikawa, M. and K. Hori (2013). "A new simple method for introducing an unmarked mutation into a large gene of non-competent Gram-negative bacteria by FLP/FRT recombination." BMC microbiology 13 (1): 86.

JANSSON, P. E., B. LINDBERG, et al. (1981). "Structural studies on the hexose region of the core in lipopolysaccharides from Enterobacteriaceae," European journal of biochemistry 115 (3): 571-577.

Jiang, X. M., B. Neal, et al. (1991). "Structure and sequence of the rfb (O antigen) gene cluster of *Salmonella* serovar *typhimurium* (strain LT2)." Molecular microbiology 5 (3): 695-713.

Karpf, A. R., (2006). "A potential role for epigenetic modulatory drugs in the enhancement of cancer/germ-line antigen vaccine efficacy." Epigenetics 1 (3): 116-120.

Kawsar, H. I., K. Ohtani, et al. (2004). "Organization and transcriptional regulation of myo-inositol operon in *Clostridium perfringens*," FEMS microbiology letters 235 (2): 289-295.

Kiernan, J. A. (1999). "Histological and histochemical methods: theory and practice." Shock 12 (6): 479.

Kinnucan, H. (1995). "Catfish aquaculture in the United States: five propositions about industry growth and policy." WORLD AQUACULTURE-BATON ROUGE- 26: 13-13.

Knepp, G. and G. F. Arkin (1973). "Ammonia toxicity levels and nitrate tolerance of channel catfish." The Progressive Fish-Culturist 35 (4): 221-224.

Kobayashi, K. (2007). "Gradual activation of the response regulator DegU controls serial expression of genes for flagellum formation and biofilm formation in *Bacillus subtilis*." Molecular microbiology 66 (2): 395-409.

Kohler, P. R., E.-L. Choong, et al. (2011). "The RpiR-like repressor IolR regulates inositol catabolism in *Sinorhizobium meliloti*." Journal of bacteriology 193 (19): 5155-5163.

Koonin, E. V., K. S. Makarova, et al. (2001). "Horizontal gene transfer in prokaryotes; quantification and classification 1." Annual Reviews in Microbiology 55 (1): 709-742.

Krings, E., K. Krumbach, et al. (2006). "Characterization of myo-inositol utilization by *Corynebacterium glutamicum*: the stimulon, identification of transporters, and influence on L-lysine formation." Journal of bacteriology 188 (23): 8054-8061.

Kröger, C., S. Srikumar, et al. (2011). "Bistability in myo-inositol utilization by *Salmonella enterica* serovar *Typhimurium*." Journal of bacteriology 193 (6): 1427-1435.

Lawler, R. E, (1960). "Observation on the life history of channel catfish, *Ictalurus punctatus* (Rafinesque)." Utah Lake, Utah. Job performance report. Federal Aid in Fish Restoration Project F-4-R-5.

Lawrence, M. L., M. M. Banes, et al. (2001). "Phenotype and virulence of a transposon-derived lipopolysaccharide O side-chain mutant strain of *Edwardsiella ictaluri*." Journal of Aquatic Animal Health 13 (4): 291-299.

Le, T. X. and Y. Munekage (2004). "Residues of selected antibiotics in water and mud from shrimp ponds in mangrove areas in Viet Nam." Marine pollution bulletin 49 (11): 922-929.

Lorenzen, N. and S. LaPatra (2005). "DNA vaccines for aquacultured fish." Revue Scientifique Et Technique-Office International Des Epizooties 24 (1): 201.

Lucas, J. S. and P. C. Southgate (2012). Aquaculture: Farming aquatic animals and plants, John Wiley & Sons.

Lugo, J. Z., S. Price, et al. (2007). "Lipopolysaccharide O-antigen promotes persistent murine bacteremia," Shock 27 (2): 186-191.

Maiden, M. C. (1998). "Horizontal genetic exchange, evolution, and spread of antibiotic resistance in bacteria." Clinical Infectious Diseases 27 (Supplement 1): S12-S20.

Martin, K. and T. Smith (2005). "The myo-inositol-1-phosphate synthase gene is essential in *Trypanosoma brucei*." Biochemical Society Transactions 33 (Pt 5): 983-985.

Matthews, R. (1994). "*Ichthyophthirius multifiliis* Fouquet, 1876: infection and protective response within the fish host." Parasitic diseases of fish. Samara Publishers, Dyfed, UK: 17-42.

Merino, S., X. Rubires, et al. (1996). "The O: 34-antigen lipopolysaccharide as an adhesin in *Aeromonas hydrophila*." FEMS microbiology letters 139 (2-3): 97-101.

Meyer, F. P. (1966). "A new control for the anchor parasite, *Lernaea cyprinacea*." The Progressive Fish-Culturist 28 (1): 33-39.

Meyer, F. P. and S. SNIESZKO (1970). A symposium on diseases of fishes and shellfishes. Seasonal fluctuations in the incidence of disease on fish farms. A symposium on diseases of fishes and shellfishes. Seasonal fluctuations in the incidence of disease on fish farms.

Mischke, C. C. (2003). "Evaluation of Two Bio-Stimulants for Improving Water Quality in Channel Catfish, *Ictalurus punctatus*, Production Ponds," Journal of Applied Aquaculture 14 (1-2): 163-169.

Mitchell, S. and H. Rodger (2011). "A review of infectious gill disease in marine salmonid fish." Journal of fish diseases 34 (6): 411-432.

Miwa, Y. and Y. Fujita (2001). "Involvement of two distinct catabolite-responsive elements in catabolite repression of the *Bacillus subtilis* myo-inositol (iol) operon." Journal of bacteriology 183 (20): 5877-5884.

Miyazaki, T. and J. Plumb (1985). "Histopathology of *Edwardsiella ictaluri* in channel catfish, *Ictalurus punctatus* (Rafinesque)*." Journal of fish diseases 8 (4): 389-392.

Morand, S., F. Robert, et al. (1995). "Complexity in parasite life cycles: population biology of cestodes in fish." Journal of animal ecology: 256-264.

Moriarty, D. J. (1997). "The role of microorganisms in aquaculture ponds." Aquaculture 151 (1): 333-349.

Morris, J. E. (1993). "Pond Culture of Channel Catfish in the North Central Region," North Central Regional Aquaculture Center In cooperation with USDA and the NCR Educational Materials Project.

Movahedzadeh, F., D. A. Smith, et al. (2004). "The *Mycobacterium* tuberculosis inol gene is essential for growth and virulence." Molecular microbiology 51 (4): 1003-1014.

MSU (2010). "Commercial Catfish Production: Disease," http://msucares.com/aquaculture/catfish/disease.html Murray, G. L., S. R. Attridge, et al. (2003). "Regulation of *Salmonella typhimurium* lipopolysaccharide O antigen chain length is required for virulence; identification of FepE as a second Wzz." Molecular microbiology 47 (5): 1395-1406.

Mylonas, C. C., A. Fostier, et al. (2010). "Broodstock management and hormonal manipulations of fish reproduction," General and comparative endocrinology 165 (3): 516-534.

Nagy, G., V. Danino, et al. (2006). "Down-regulation of key virulence factors makes the *Salmonella enterica* serovar Typhimurium rfaH mutant a promising live-attenuated vaccine candidate." Infection and immunity 74 (10): 5914-5925.

Nevola, J. J., D. C. Laux, et al. (1987). "In vivo colonization of the mouse large intestine and in vitro penetration of intestinal mucus by an avirulent smooth strain of *Salmonella typhimurium* and its lipopolysaccharide-deficient mutant." Infection and immunity 55 (12): 2884-2890.

Noga, E. J. (2010). Fish disease: diagnosis and treatment, John Wiley & Sons.

Norton, V. M. and K. B. Davis (1977). "Effect of abrupt change in the salinity of the environment on plasma electrolytes, urine volume, and electrolyte excretion in channel catfish, *Ictalurus punctatus*." Comparative Biochemistry and Physiology Part A: Physiology 56 (3): 425-431.

Ochman, H., J. G. Lawrence, et. al. (2000). "Lateral gene transfer and the nature of bacterial innovation." Nature 405 (6784): 299-304.

Overstreet, R. M., S. S. Curran, et al. (2002). "*Bolbophorus damnificus* n. sp. (Digenea: Bolbophoridae) from the channel catfish *Ictalurus punctatus* and American white pelican *Pelecanus erythrorhynchos* in the USA based on life-cycle and molecular data." Systematic Parasitology 52 (2): 81-96.

Padnos, M. and R. F. Nigrelli (1942). "*Trichodina spheroidesi* and *Trichodina halli* spp. nov. parasitic on the gills and skin of marine fishes, with special reference to the life-history of *T. spheroidesi*," Zoologica 27: 65-72.

Pádua, S., M. Martins, et al. (2013). "First record of *Chilodonella hexasticha* (Ciliophora: Chilodonellidae) in Brazilian cultured fish: A morphological and pathological assessment." Veterinary parasitology 191 (1): 154-160.

Paperna, I. (1972). "Infection by *Ichthyophthirius multifiliis* of fish in Uganda," The Progressive Fish-Culturist 34 (3): 162-164.

Paperna, I. (1991). "Diseases caused by parasites in the aquaculture of warm water fish." Annual Review of Fish Diseases 1: 155-194.

Peleg, A., Y, Shrifrin, et al. (2005). "Identification of an *Escherichia coli* operon required for formation of the O-antigen capsule." Journal of bacteriology 187 (15): 5259-5266.

Pflieger, W. L., M. Sullivan, et al. (1975). The fishes of Missouri, Missouri Department of Conservation Jefferson City.

Pirhonen, J. and C. B. Schreck (2003). "Effects of anaesthesia with MS-222, clove oil and $CO_2$ on feed intake and plasma cortisol in steelhead trout (*Oncorhynchus mykiss*)." Aquaculture 220 (1): 507-514.

Plumb, J. and D. Sanchez. (1983). "Susceptibility of five species of fish to *Edwardsiella ictaluri*." Journal of fish diseases 6 (3): 261-266.

Plumb, J. A. (1979). "Principal diseases of farm-raised catfish," Bulletin, Southern Cooperative Series, Alabama Agricultural Experiment Station, Auburn University, USA (225).

Plumb, J. A. and L. A. Hanson (2011). Health maintenance and principal microbial diseases of cultured fishes, John Wiley & Sons.

Polyak, I. K. (2007). Characterization of a virulence related hypothetical protein in *Edwardsiella ictaluri*, Faculty of the Louisiana State University and Agricultural and Mechanical College in partial fulfillment of the requirements for a degree of Master of Science In The Interdepartmental Program in Veterinary Medical Sciences through the Department of Pathobiological Sciences by Ildiko Katalin Polyak BS, Clark University.

Pridgeon, J. W. and P. H. Klesius (2010). "Identification and expression profile of multiple genes in channel catfish fry 10 min after modified live *Flavobacterium columnare* vaccination." Veterinary immunology and immunopathology 138 (1): 25-33.

Raupach, B. and S. H. Kaufmann (2001). "Bacterial virulence, proinflammatory cytokines and host immunity:

how to choose the appropriate *Salmonella* vaccine strain" Microbes and infection 3 (14): 1261-1269.

Reeves, P. R., M. Hobbs, et al. (1996). "Bacterial polysaccharide synthesis and gene nomenclature." Trends in microbiology 4 (12): 495-503.

Reynolds, T. B. (2009). "Strategies for acquiring the phospholipid metabolite inositol in pathogenic bacteria, fungi and protozoa: making it and taking it." Microbiology 155 (5): 1386-1396.

Rice, L. A. (1941). "The food of six Reelfoot Lake fishes." Tennessee Academy of Science 5: 22-26.

Robert, F. and C. Gabrion (1991). "Experimental approach to the specificity in first intermediate hosts of Bothriocephalids (Cestoda, Pseudophyllidae) from marine fish." Acta oecologica: (1990) 12 (5): 617-632.

Roberts, M. F. (2006). Inositol in bacteria and archaea. Biology of inositols and phosphoinositides, Springer: 103-133.

Robertson, D. A. (1985). A review of *Ichthyobodo necator* (Henneguy, 1883) an important and damaging fish parasite. Recent advances in aquaculture, Springer: 1-30.

Rocha, E. P., E. Cornet, et al. (2005). "Comparative and evolutionary analysis of the bacterial homologous recombination systems." PLoS genetics 1 (2).

Rocha, E. P., E, Cornet et al. (2005). "Comparative and evolutionary analysis of the bacterial homologous recombination systems." PLoS genetics 1 (2).

Rogge, M. L. and R. L. Thune (2011). "Regulation of the *Edwardsiella ictaluri* type III secretion system by pH and phosphate concentration through EsrA, EsrB, and EsrC." Applied and environmental microbiology 77 (13): 4293-4302.

Roubal, F., A. Bullock, et al. (1987). "Ultrastructural aspects of infestation by *Ichthyobodo necator* (Henneguy, 1883) on the skin and gills of the salmonids *Salmo salar* L. and *Salmo gairdneri* Richardson," Journal of fish diseases 10 (3): 181-192.

Sambrook, J., E. F. Fritsch, et al. (1989). Molecular cloning, Cold spring harbor laboratory press New York.

Schreier, T. M., J. J. Rack et al. (1996). "Efficacy of formalin, hydrogen peroxide, and sodium chloride on fungal-infected rainbow trout eggs," Aquaculture 140 (4): 323-331.

Sha, J., E. Kozlova, et al. (2002). "Role of various enterotoxins in *Aeromonas hydrophila*-induced gastroenteritis: generation of enterotoxin gene-deficient mutants and evaluation of their enterotoxic activity," Infection and immunity 70 (4): 1924-1935.

Sheehan, R. J, and W. M. Lewis (1986). "Influence of pH and ammonia salts on ammonia toxicity and water balance in young channel catfish," Transactions of the American fisheries Society 115 (6): 891-899.

Shimizu, T., K. Ohtani, et al. (2002). "Complete genome sequence of *Clostridium perfringens*, an anaerobic flesh-eater." Proceedings of the National Academy of Sciences 99 (2): 996-1001.

Shoemaker, C., O. Olivares-Fuster, et al. (2008). "*Flavobacterium columnare* genomovar influences mortality in channel catfish (*Ictalurus punctatus*)." Veterinary microbiology 127 (3): 353-359.

Shoemaker, C. A., P. H. Klesius, et al. (2002). "In vivo methods for utilizing the modified live *Edwardsiella ictaluri* vaccine against enteric septicemia in channel catfish," Aquaculture 203 (3): 221-227.

Shoemaker, C. A., P. H. Klesius, et al. (2007). "Immunization of eyed channel catfish, *Ictalurus punctatus*, eggs with monovalent *Flavobacterium columnare* vaccine and bivalent *F. columnare* and *Edwardsiella ictaluri* vaccine," Vaccine 25 (6): 1126-1131.

Shoemaker, C. A., P. H. Klesius, et al. (2009). "Use of modified live vaccines in aquaculture." Journal of the World Aquaculture Society 40 (5): 573-585.

Skirpstunas, R. T. and T. J. Baldwin (2002). "*Edwardsiella ictaluri* invasion of IEC-6, Henle 407, fathead minnow and channel catfish, enteric epithelial cells." Diseases of Aquatic Organisms 51 (3): 161-167.

Stevens, R. E. (1959). The white and channel catfishes of the Sautee-Cooper Reservoir and tailrace sanctuary. Proceedings of the Annual Conference Southeastern Association of Game and Fish Commissioners.

Stickley, A. and K. Andrews (1989). Survey of Mississippi catfish farmers on means, effort, and costs to repel fish-eating birds from ponds. Fourth Eastern Wildlife Damage Control Conference, 1989.

Stickney, R. R. (1996). Aquaculture of the United States: A Historical Survey, John Wiley & Sons.

Stickney, R. R. (2000). Encyclopedia of aquaculture, John Wiley and Sons,

Subasinghe, R. (2005). "Aquaculture topics and activities—State of world aquaculture." FAO 2005-2014 FAO Fisheries and Aquaculture Department [online].

Sun, Q., R. Lan, et al. (2012). "Identification of a divergent O-acetyltransferase gene oacIb from *Shigella flexneri* serotype 1b strains," Emerging Microbes & Infections 1 (9): e21.

Teichert-Coddington, D. R. and B. W. Green (1997). "Experimental and commercial culture of tilapia in Honduras." Tilapia aquaculture in the Americas 1: 142-162.

Thomas, C. M. and K. M. Nielsen (2005). "Mechanisms of, and barriers to, horizontal gene transfer between bacteria." Nature reviews microbiology 3 (9): 711-721.

Thomas, R. M., R. W. Titball, et al. (2007). "The immunologically distinct O antigens from *Francisella tularensis* subspecies *tularensis* and *Francisella novicida* are both virulence determinants and protective antigens." Infection and immunity 75 (1): 371-378.

Thomason, L., D. L. Court, et al. (2007). "Recombineering: genetic engineering in bacteria using homologous recombination." Current protocols in molecular biology: 1.16. 11-11.16. 24.

Thune, R. L., D. B. Fernandez, et al. (2007). "Signature-tagged mutagenesis of *Edwardsiella ictaluri* identifies virulence-related genes, including a *Salmonella* pathogenicity island 2 class of type III secretion systems." Applied and environmental microbiology 73 (24): 7934-7946.

Thane, R. L., L. A. Stanley, et al. (1993). "Pathogenesis of gram-negative bacterial infections in warm water fish." Annual Review of Fish Diseases 3: 37-68.

Tomasso, J., C. A. Goudie, et al. (1980). "Effects of environmental pH and calcium on ammonia toxicity in channel catfish." Transactions of the American fisheries Society 109 (2): 229-234.

Torkildsen, L., O. B. Samuelsen, et al. (2000). "Minimum inhibitory concentrations of chloramphenicol, florfenicol, trimethoprim/sulfadiazine and flumequiue in seawater of bacteria associated with scallops (*Pecten maximus*) larvae." Aquaculture 185 (1): 1-12.

Tucker, C. C. and E. H. Robinson (1990). Channel catfish farming handbook, Springer.

Tucker, C. S. and J. A. Hargreaves (2004). Biology and culture of channel catfish, Elsevier.

Tucker, C. S. and S. W. Lloyd (1985). "Evaluation of a commercial bacterial amendment for improving water quality in channel catfish ponds." Research repo Mississippi Agricultural and Forestry Experiment Station (USA).

Urawa, S. (1992). "Epidermal responses of chum salmon (*Oncorhynchus keta*) fry to the ectoparasitic flagellate *Ichthyobodo necator*." Canadian Journal of Zoology 70 (8): 1567-1575.

USDA (2010). "Catfish 2010 Part I: Reference of Catfish Health and Production Practices In the United States, 2009."

USDA (2010). "Catfish 2010 Part II: Health and Production Practices for Foodsize Catfish in the United States, 2009."

USDA (2014). "Catfish Production." the National Agricultural Statistics Service (MASS), Agricultural Statistics Board, United States Department of Agriculture (USDA).

Van Den Bosch, L., P. A. Manning, et al. (1997). "Regulation of O-antigen chain length is required for *Shigella flexneri* virulence," Molecular microbiology 23 (4): 765-775.

Vignesh, R., B. Karthikeyan, et al. (2011). "Antibiotics in aquaculture: an overview." South Asian Journal of Experimental Biology 1 (3): 114-120.

Wagner, B. A., D. J. Wise, et al. (2002). "The epidemiology of bacterial diseases in food-size channel catfish." Journal of Aquatic Animal Health 14 (4): 263-272.

Walters, G. and J. Plumb (1980). "Environmental stress and bacterial infection in channel catfish, *Ictalurus punctatus* Rafinesque." Journal of fish biology 17 (2): 177-185.

Wards, B., G. De Lisle, et al. (2000). "An esat6 knockout mutant of *Mycobacterium bovis* produced by homologous recombination will contribute to the development of a live tuberculosis vaccine." Tubercle and Lung Disease 80 (4): 185-189.

Wellborn, T. L. (1988). "Channel catfish: life history and biology." SRAC publication (USA).

West, N. P., P. Sansonetti, et al. (2005). "Optimization of virulence functions through glucosylation of *Shigella* LPS," Science 307 (5713): 1313-1317.

Wolters, W. R. and M. R. Johnson (1994). "Enteric septicemia resistance in blue catfish and three channel catfish strains." Journal of Aquatic Animal Health 6 (4): 329-334.

Wolters, W. R., D. J. Wise, et al. (1996). "Survival and antibody response of channel catfish, blue catfish, and channel catfish female×blue catfish male hybrids after exposure to *Edwardsiella ictaluri*." Journal of Aquatic Animal Health 8 (3): 249-254.

Xue, C. (2012). "*Cryptococcus* and Beyond—Inositol Utilization and Its Implications for the Emergence of Fungal Virulence." PLoS pathogens 8 (9): e1002869.

Yebra, M. J., M. Zúñiga, et al. (2007). "Identification of a gene cluster enabling *Lactobacillus casei* BL23 to utilize myo-inositol." Applied and environmental microbiology 73 (12): 3850-3858.

Yoshida, K.-I., D. Aoyama, et al. (1997). "Organization and transcription of the myo-inositol operon, iol, of *Bacillus subtilis*." Journal of bacteriology 179 (14): 4591-4598.

Zhang, D., J. W. Pridgeon, et al. (2013). "Expression and activity of recombinant proaerolysin derived from *Aeromonas hydrophila* cultured from diseased channel catfish." Veterinary microbiology 165 (3): 478-482.

Zhang, D., J. W. Pridgeon, et al. (2013). "Expression and activity of recombinant proaerolysin derived from *Aeromonas hydrophila* cultured from diseased channel catfish, " Veterinary microbiology 165 (3): 478-482.

Zhang, L., J. Radziejewska-Lebrecht, et al. (1997). "Molecular and chemical characterization of the lipopolysaccharide O-antigen and its role in the virulence of *Yersinia enterocolitica* serotype O: 8." Molecular microbiology 23 (1): 63-76.

Example 3

Methods for the Development of Markerless ML09-119ΔymcA Mutant

Conjugal transfer of recombinogenic plasmid pMJH65 into *Aeromonas hydrophila* strain ML09-119. The mobilizable recombinogenic plasmids pMJH65 bearing the λ-Red cassette were introduced into *E. coli* strain SM10λpir by electroporation according to a previously published method (1). Plasmid pMJH65 in *E. coli* strain SM10λpir was conjugally transferred into *A. hydrophila* strain ML09-119 by filter mating experiments according to the methods described previously (2). *A. hydrophila* transconjugants were selected on LB plates supplemented with tetracycline and colistin. The conjugal transfer of plasmid pMJH65 into *A. hydrophila* was confirmed by the positive growth of transconjugants in the presence of appropriate antibiotics and with PCR using primers p46-intF (5'-TGTTCCTTCTTCACTGTC-3') (SEQ ID NO:105) and p46intR (5'-GATGTACTTCACCAGCTC-3') (SEQ ID NO:106) (3).

Deletion of gene ymcA from *A. hydrophila* strain ML09-119 by recombineering. Electrocompetent *A. hydrophila* strain ML09-119 harboring recombinogenic plasmid pMJH65 was prepared as described follows. Overnight grown ML09-119 culture was diluted 1:70 in 40 ml of Super Optimal broth (SOB) medium supplemented with tetracycline (10 μg/ml) and 10 mM of L-arabinose, and grown with vigorous shaking until the $OD_{600}$ attained a value of 0.6 for *A. hydrophila*. Cells were harvested by centrifugation at 5000×g for 8 min at 4° C., washed three times with ice-cold 10% glycerol and cells were finally concentrated to 400-fold by resuspending with 100 μl of ice-cold 10% glycerol. Freshly prepared electrocompetent ML09-119 cells were immediately used for electroporation. Double stranded DNA (dsDNA) substrate used for deletion of ymcA gene from strain ML09-119 was generated by PCR using genomic DNA of *A. hydrophila* ML09-119vgr3A mutant (3) as a template using primers Lipo-FRT-F (5'-C*A*A*C*TGCTCGCCCTTTTTGATGAAAAAAGATCGGCTCTATGCAACTTTTGA GTGTAGGCTGGAGCTGCTTC-3') (SEQ ID NO:107) and Lipo-FRT-R (5'-T*A*G*A*GATATCAATATTCGATTGCCAATCTCCTTGCTAATCGAGTACCAGA CATATGAATATCCTCCTTAGT3') (SEQ ID NO:108) (3). For deletion of ymcA gene from *A. hydrophila* strain ML09-119 using recombineering, 1.0 μg of dsDNA substrate was mixed with 55 μl of electrocompetent ML09-119 cells in a pre-chilled electroporation cuvette (0.1-cm gap), and pulsed at 1.2 kV with 25 μF and 200Ω using Eppendorf Electroporator 2510 (Hamburg, Germany). Immediately after electroporation, 950 μl of SOC supplemented with 10 mM of L-arabinose was added and culture was incubated at 30° C. for overnight. Cells were then spread onto 2×YT agar plates supplemented with chloramphenicol (25.0 μg/ml) and incubated at 37° C. to obtain *A. hydrophila* ML09-119ΔymcA mutant and to cure the recombinogenic plasmid pMJH65 from the mutant. The correct deletion of ymcA gene from *A. hydrophila* strain ML09-119 was confirmed by PCR and sequencing using primers Liop_upF (5'-CCG AAT GGT AAT CCA CAG TT-3') (SEQ ID NO:109) and Liop_dnR (5'-TAG AAC AGC TGG TCA CGA GA-3') (SEQ ID NO:110). The removal of the recombinogenic plasmid pMJH65 from *A. hydrophila* ML09-119ΔymcA mutant was confirmed by the absence of its growth in TSB broth supplemented with tetracycline (10 µg/ml).

Flp-mediated excision of antibiotic resistance gene cassettes to generate unmarked mutants. *A. hydrophila* ML09-119ΔymcA mutant devoid of recombinogenic plasmid pMJH65 was mated with *E. coli* SM10λpir bearing FLP/FRT plasmid pMJH95 (3) according to the methods as described previously (2). The introduction of the plasmid pMJH95 into *A. hydrophila* ML09-119ΔymcA mutant was confirmed by its growth in the presence of tetracycline. Once the presence of plasmid pMJH95 was confirmed within *A. hydrophila* ML09-119ΔymcA mutant, culture was grown at 30° C. for overnight and induced for the removal of chloramphenicol resistance gene cassette by incubating at 37° C. for 6 hours. Broth culture was then streaked onto the TSA plates and incubated at 37° C. for overnight to obtain isolated colonies. Colonies grown on non-selective plates that subsequently failed to grow on antibiotic selective plates were tested by PCR and sequencing using primers Liop_upF (5'-CCG AAT GGT AAT CCA CAG TT3') (SEQ ID NO:111) and Liop_dnR (5'-TAG AAC AGC TGG TCA CGA GA-3') (SEQ ID NO:112) to confirm the Flp-mediated excision of antibiotic resistance gene cassettes introduced by recombineering. Sequence analysis demonstrated the precise deletion of ymcA gene and confirmed the generation of markerless ymcA mutant in *A. hydrophila* ML09-119.

REFERENCES FOR EXAMPLE 3

1. Sambrook J, Fritsch E F, Maniatis T. 1998. Molecular cloning: a laboratory manual. Cold Spring Harbor Laboratory Press, Cold Spring Harbor, N.Y.
2. Maurer K J, Lawrence M L, Fernandez D H, Thune R L. 2001. Evaluation and Optimization of a DNA Transfer System for *Edwardsiella ictaluri*. Journal of Aquatic Animal Health 13: 163-167.
3. Hossain M J, Thurlow C M, Sun D, Nasrin S, Liles M R. 2015. Conjugal Transfer of a Recombineering System to Generate and Complement Markerless Mutants. Manuscript in Preparation.

It will be readily apparent to one skilled in the art that varying substitutions and modifications may be made to the invention disclosed herein, without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

The invention claimed is:

1. An attenuated *Aeromonas* spp. bacterium that has been genetically modified by recombination to be deficient of one or more genes associated with O-antigen capsule synthesis or secretion, the gene being selected from the group consisting of:
   (a) a gene encoding YmcA polypeptide (SEQ ID NO:11) or a gene encoding a polypeptide having at least 95% sequence identity to the YmcA polypeptide (SEQ ID NO:11); and
   (b) a gene encoding YmcC polypeptide (SEQ ID NO:19) or a gene encoding a polypeptide having at least 95% sequence identity to the YmcC polypeptide (SEQ ID NO:19); and
   (c) both (a) and (b).

2. The attenuated *Aeromonas* spp. of claim 1, wherein the bacterium is selected from the group consisting of *Aeromonas hydrophila, Aeromonas caviae*, and *Aeromonas veronii*.

3. The attenuated *Aeromonas* spp. bacterium of claim 1, wherein the bacterium has been genetically modified by a method that includes (a) deleting at least a portion of the gene ymcA by recombination and inserting a selectable marker in place of the deleted portion of the ymcA gene, and (b) subsequently deleting the selectable marker to create a markerless bacterium deficient of gene ymcA.

4. The attenuated *Aeromonas* spp. bacterium of claim 3, wherein the bacterium has been genetically modified by (a) transferring a recombineering system into the bacterium, wherein the recombineering system deletes at least a portion of the ymcA gene and replaces the portion with the selectable marker flanked by two recombinase recognition target sites; (b) selecting the bacterium for expression of the selectable marker; (c) curing the selected bacterium of the recombineering system; (d) transferring a vector that expresses a recombinase into the selected bacterium, wherein the recombinase recognizes the two recombinase recognition target sites; (e) selecting the bacterium for lack of expression of the selectable marker; and (f) curing the selected bacterium of the vector that expresses the recombinase.

5. The attenuated *Aeromonas* spp. bacterium of claim 4, wherein the recombineering system comprises: a mobilizable recombineering vector; and a linear DNA molecule comprising the following contiguous sequences in 5' to 3' order: (i) a first nucleotide sequence of at least 10 nucleotides having sequence identity with the gene ymcA (SEQ ID NO:12), (ii) a second nucleotide sequence comprising the first of the recombinase recognition target sites, (iii) a third nucleotide sequence that expresses a selectable marker, (iv) a fourth nucleotide sequence comprising the second of the recombinase recognition target sites, and (v), a fifth nucleotide sequence of at least 10 nucleotides having sequence identity with the gene ymcA (SEQ ID NO:12) that is different than the first nucleotide sequence of (i), wherein after the recombinase is expressed, the recombinase recombines the recombinases recognition target sites to remove the selectable marker and the portion of the ymcA gene that is deleted is replaced with one recombinases recognition target site.

6. The attenuated *Aeromonas* spp. bacterium of claim 1, wherein the bacterium further has been genetically modified by recombination to be deficient of a gene encoding YmcB polypeptide (SEQ ID NO:17) or to be deficient of a gene encoding a polypeptide having at least 95% sequence identity to the YmcB polypeptide (SEQ ID NO:17).

7. A vaccine composition comprising the attenuated *Aeromonas* spp. bacterium of claim 1 and a carrier.

8. The vaccine composition of claim 7, wherein the attenuated *Aeromonas* spp. bacterium has been inactivated by chemical treatment or physical treatment.

9. A method for vaccinating an aquatic animal against infection by an *Aeromonas* spp. bacterium, the method comprising administering the vaccine composition of claim 7 to the aquatic animal.

10. The method of claim 9, wherein the aquatic animal is a channel catfish.

11. The method of claim 9, wherein the aquatic animal is administered the vaccine composition by intraperitoneal injection.

12. The method of claim 9, wherein the aquatic animal is administered the vaccine composition at a dose that delivers $10^4$-$10^8$ CFU of attenuated *Aeromonas* spp. bacteria per aquatic animal.

13. The method of claim 9, wherein the aquatic animal is administered the vaccine composition by immersing the aquatic animal in an aqueous medium comprising the vaccine composition.

14. The method of claim 13, wherein the aqueous medium has a concentration of $10^4$-$10^8$ CFU/ml of attenuated *Aeromonas* spp. bacteria.

15. An attenuated *Aeromonas* spp. bacterium that has been genetically modified by recombination to be deficient of:
   (a) a gene encoding YmcA polypeptide (SEQ ID NO:11) or a gene encoding a polypeptide having at least 95% sequence identity to the YmcA polypeptide (SEQ ID NO:11); and
   (b) a gene encoding YmcC polypeptide (SEQ ID NO:19) or a gene encoding a polypeptide having at least 95% sequence identity to the YmcC polypeptide (SEQ ID NO:19).

16. The attenuated *Aeromonas* spp. of claim 15, wherein the bacterium is selected from the group consisting of *Aeromonas hydrophila, Aeromonas caviae*, and *Aeromonas veronii*.

17. The attenuated *Aeromonas* spp. bacterium of claim 15, wherein the bacterium has been genetically modified by a method that includes (a) deleting at least a portion of the gene ymcA by recombination and inserting a selectable marker in place of the deleted portion of the ymcA gene, and (b) subsequently deleting the selectable marker to create a markerless bacterium deficient of gene ymcA.

18. The attenuated *Aeromonas* spp. bacterium of claim 15, wherein the bacterium further has been genetically modified by recombination to be deficient of a gene encoding YmcB polypeptide (SEQ ID NO:17) or to be deficient of a gene encoding a polypeptide having at least 95% sequence identity to the YmcB polypeptide (SEQ ID NO:17).

19. A vaccine composition comprising the attenuated *Aeromonas* spp. bacterium of claim 15 and a carrier.

20. The vaccine composition of claim 19, wherein the attenuated *Aeromonas* spp. bacterium has been inactivated by chemical treatment or physical treatment.

* * * * *

SEQUENCE LISTING

```
<160> NUMBER OF SEQ ID NOS: 42

<210> SEQ ID NO 1
<211> LENGTH: 1736
<212> TYPE: DNA
<213> ORGANISM: Artificial
<220> FEATURE:
<223> OTHER INFORMATION: Conjugally transferable red recombinase vector
      pMJH65 oriT

<400> SEQUENCE: 1
cagccgacca ggctttccac gcccgcgtgc cgctccatgt cgttcgcgcg gttctcggaa        60
acgcgctgcc gcgtttcgtg attgtcacgc tcaagcccgt agtcccgttc gagcgtcgcg       120
cagaggtcag cgagggcgcg gtaggcccga tacggctcat ggatggtgtt tcgggtcggg       180
tgaatcttgt tgatggcgat atggatgtgc aggttgtcgg tgtcgtgatg cacggcactg       240
acgcgctgat gctcggcgaa gccaagccca gcgcagatgc ggtcctcaat cgcgcgcaac       300
gtctccgcgt cgggcttctc tcccgcgcgg aagctaacca gcaggtgata ggtcttgtcg       360
gcctcggaac gggtgttgcc gtgctgggtc gccatcacct cggccatgac agcgggcagg       420
gtgattgcct cgcagttcgt gacgcgcacg tgacccaggc gctcggtctt gccttgctcg       480
tcggtgatgt acttcaccag ctccgcgaag tcgctcttct tgatggagcg catgggacg       540 tgcttggcaa tcacgcgcac cccccggccg ttttagcggc taaaaaagtc atggctctgc       600 cctgggcgg accacgccca tcatgacctt gccaagctcg tcctgcttct cttcgatctt       660
cgccagcagg gcgaggatcg tggcatcacc gaaccgcgcc gtgcgcgggt cgtcggtgag       720
```

```
ccagagtttc agcaggccgc ccaggcggcc caggtcgcca ttgatgcggg ccagctcgcg        780
gacgtgctca tagtccacga cgcccgtgat tttgtagccc tggccgacgg ccagcaggta        840
ggccgacagg ctcatgccgg ccgccgccgc cttttcctca atcgctcttc gttcgtctgg        900
aaggcagtac accttgatag gtgggctgcc cttcctggtt ggcttggttt catcagccat        960
ccgcttgccc tcatctgtta cgccggcggt agccggccag cctcgcagag caggattccc       1020
gttgagcacc gccaggtgcg aataagggac agtgaagaag gaacaccgc tcgcgggtgg        1080
gcctacttca cctatcctgc ccggctgacg ccgttgggta caccaaggaa agtctacacg       1140
aacccttggg caaaatcctg tatatcgtgc gaaaaaggat ggatataccg aaaaaatcgc       1200
tataatgacc ccgaagcagg gttatgcagc ggaaaagcgc tgcttccctg ctgttttgtg       1260
gaatatctac cgactggaaa caggcaaatg caggaaatta ctgaactgag gggacaggcg       1320
agagacgatg ccaaagagct acaccgacga gctggccgag tgggttgaat cccgcgcggc       1380
caagaagcgc cggcgtgatg aggctgcggt tgcgttcctg gcggtgaggg cggatgtcga       1440
ggcggcgtta gcgtccggct atgcgctcgt caccatttgg gagcacatgc gggaaacggg       1500
gaaggtcaag ttctcctacg agacgttccg ctcgcacgcc aggcggcaca tcaaggccaa       1560
gcccgccgat gtgcccgcac cgcaggccaa ggctgcggaa cccgcgccgg cacccaagac       1620
gccggagcca cggcggccga agcaggggg caaggctgaa aagccggccc cgctgcggc        1680
cccgaccggc ttcaccttca acccaacacc ggacaaaaag gatccctcga gatccc          1736
```

<210> SEQ ID NO 2
<211> LENGTH: 138
<212> TYPE: PRT
<213> ORGANISM: Enterobacteria phage lambda

<400> SEQUENCE: 2

Met Asp Ile Asn Thr Glu Thr Glu Ile Lys Gln Lys His Ser Leu Thr
1               5                   10                  15

Pro Phe Pro Val Phe Leu Ile Ser Pro Ala Phe Arg Gly Arg Tyr Phe
            20                  25                  30

His Ser Tyr Phe Arg Ser Ser Ala Met Asn Ala Tyr Tyr Ile Gln Asp
        35                  40                  45

Arg Leu Glu Ala Gln Ser Trp Ala Arg His Tyr Gln Gln Leu Ala Arg
    50                  55                  60

Glu Glu Lys Glu Ala Glu Leu Ala Asp Asp Met Glu Lys Gly Leu Pro
65                  70                  75                  80

Gln His Leu Phe Glu Ser Leu Cys Ile Asp His Leu Gln Arg His Gly
                85                  90                  95

Ala Ser Lys Lys Ser Ile Thr Arg Ala Phe Asp Asp Val Glu Phe
            100                 105                 110

Gln Glu Arg Met Ala Glu His Ile Arg Tyr Met Val Glu Thr Ile Ala
        115                 120                 125

His His Gln Val Asp Ile Asp Ser Glu Val
    130                 135

<210> SEQ ID NO 3
<211> LENGTH: 226
<212> TYPE: PRT
<213> ORGANISM: Enterobacteria phage lambda

<400> SEQUENCE: 3

Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
            20                  25                  30

Thr Ala Ser Glu Val His Asn Val Ile Ala Lys Pro Arg Ser Gly Lys
        35                  40                  45

Lys Trp Pro Asp Met Lys Met Ser Tyr Phe His Thr Leu Leu Ala Glu
    50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
        115                 120                 125

Glu Leu Lys Cys Pro Phe Thr Ser Arg Asp Phe Met Lys Phe Arg Leu
    130                 135                 140

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
        195                 200                 205

Lys Met Asp Glu Ala Leu Ala Glu Ile Gly Phe Val Phe Gly Glu Gln
    210                 215                 220

Trp Arg
225

<210> SEQ ID NO 4
<211> LENGTH: 261
<212> TYPE: PRT
<213> ORGANISM: Enterobacteria phage lambda

<400> SEQUENCE: 4

Met Ser Thr Ala Leu Ala Thr Leu Ala Gly Lys Leu Ala Glu Arg Val
1               5                   10                  15

Gly Met Asp Ser Val Asp Pro Gln Glu Leu Ile Thr Thr Leu Arg Gln
            20                  25                  30

Thr Ala Phe Lys Gly Asp Ala Ser Asp Ala Gln Phe Ile Ala Leu Leu
        35                  40                  45

Ile Val Ala Asn Gln Tyr Gly Leu Asn Pro Trp Thr Lys Glu Ile Tyr
    50                  55                  60

Ala Phe Pro Asp Lys Gln Asn Gly Ile Val Pro Val Val Gly Val Asp
65                  70                  75                  80

Gly Trp Ser Arg Ile Ile Asn Glu Asn Gln Gln Phe Asp Gly Met Asp
                85                  90                  95

Phe Glu Gln Asp Asn Glu Ser Cys Thr Cys Arg Ile Tyr Arg Lys Asp
            100                 105                 110

Arg Asn His Pro Ile Cys Val Thr Glu Trp Met Asp Glu Cys Arg Arg
        115                 120                 125

Glu Pro Phe Lys Thr Arg Glu Gly Arg Glu Ile Thr Gly Pro Trp Gln
    130                 135                 140

```
Ser His Pro Lys Arg Met Leu Arg His Lys Ala Met Ile Gln Cys Ala
145                 150                 155                 160

Arg Leu Ala Phe Gly Phe Ala Gly Ile Tyr Asp Lys Asp Glu Ala Glu
            165                 170                 175

Arg Ile Val Glu Asn Thr Ala Tyr Thr Ala Glu Arg Gln Pro Glu Arg
            180                 185                 190

Asp Ile Thr Pro Val Asn Asp Glu Thr Met Gln Glu Ile Asn Thr Leu
            195                 200                 205

Leu Ile Ala Leu Asp Lys Thr Trp Asp Asp Asp Leu Leu Pro Leu Cys
210                 215                 220

Ser Gln Ile Phe Arg Arg Asp Ile Arg Ala Ser Ser Glu Leu Thr Gln
225                 230                 235                 240

Ala Glu Ala Val Lys Ala Leu Gly Phe Leu Lys Gln Lys Ala Ala Glu
            245                 250                 255

Gln Lys Val Ala Ala
            260

<210> SEQ ID NO 5
<211> LENGTH: 363
<212> TYPE: PRT
<213> ORGANISM: Saccharomyces cerevisiae

<400> SEQUENCE: 5

Asn Thr Ile Ile Ser Asn Ser Leu Ser Phe Asp Ile Val Asn Lys Ser
1               5                   10                  15

Leu Gln Phe Lys Tyr Lys Thr Gln Lys Ala Thr Ile Leu Glu Ala Ser
            20                  25                  30

Leu Lys Lys Leu Ile Pro Ala Trp Glu Phe Thr Ile Ile Pro Tyr Tyr
            35                  40                  45

Gly Gln Lys His Gln Ser Asp Ile Thr Asp Ile Val Ser Ser Leu Gln
50                  55                  60

Leu Gln Phe Glu Ser Ser Glu Glu Ala Asp Lys Gly Asn Ser His Ser
65                  70                  75                  80

Lys Lys Met Leu Lys Ala Leu Leu Ser Glu Gly Glu Ser Ile Trp Glu
            85                  90                  95

Ile Thr Glu Lys Ile Leu Asn Ser Phe Glu Tyr Thr Ser Arg Phe Thr
            100                 105                 110

Lys Thr Lys Thr Leu Tyr Gln Phe Leu Phe Leu Ala Thr Phe Ile Asn
            115                 120                 125

Cys Gly Arg Phe Ser Asp Ile Lys Asn Val Asp Pro Lys Ser Phe Lys
130                 135                 140

Leu Val Gln Asn Lys Tyr Leu Gly Val Ile Ile Gln Cys Leu Val Thr
145                 150                 155                 160

Glu Thr Lys Thr Ser Val Ser Arg His Ile Tyr Phe Phe Ser Ala Arg
            165                 170                 175

Gly Arg Ile Asp Pro Leu Val Tyr Leu Asp Glu Phe Leu Arg Asn Ser
            180                 185                 190

Glu Pro Val Leu Lys Arg Val Asn Arg Thr Gly Asn Ser Ser Ser Asn
            195                 200                 205

Lys Gln Glu Tyr Gln Leu Leu Lys Asp Asn Leu Val Arg Ser Tyr Asn
            210                 215                 220

Lys Ala Leu Lys Lys Asn Ala Pro Tyr Ser Ile Phe Ala Ile Lys Asn
225                 230                 235                 240
```

```
Gly Pro Lys Ser His Ile Gly Arg His Leu Met Thr Ser Phe Leu Ser
                245                 250                 255

Met Lys Gly Leu Thr Glu Leu Thr Asn Val Val Gly Asn Trp Ser Asp
            260                 265                 270

Lys Arg Ala Ser Ala Val Ala Arg Thr Thr Tyr Thr His Gln Ile Thr
        275                 280                 285

Ala Ile Pro Asp His Tyr Phe Ala Leu Val Ser Arg Tyr Tyr Ala Tyr
    290                 295                 300

Asp Pro Ile Ser Lys Glu Met Ile Ala Leu Lys Asp Glu Thr Asn Pro
305                 310                 315                 320

Ile Glu Glu Trp Gln His Ile Glu Gln Leu Lys Gly Ser Ala Glu Gly
                325                 330                 335

Ser Ile Arg Tyr Pro Ala Trp Asn Gly Ile Ile Ser Gln Glu Val Leu
            340                 345                 350

Asp Tyr Leu Ser Ser Tyr Ile Asn Arg Arg Ile
        355                 360

<210> SEQ ID NO 6
<211> LENGTH: 48
<212> TYPE: DNA
<213> ORGANISM: Saccharomyces cerevisiae

<400> SEQUENCE: 6
gaagttccta ttccgaagtt cctattctct agaaagtata ggaacttc                  48

<210> SEQ ID NO 7
<211> LENGTH: 1134
<212> TYPE: DNA
<213> ORGANISM: Aeromonas hydrophila

<400> SEQUENCE: 7
gtgctgttca gtccgctggc catcgacatc tacctgcccg ccatcccgca gatggccgag     60
cagctggggg ccgaggtgac cctgatgcag ggtaccatca cctggttcct gttcagcatg    120
ggactggggc agctgctggt ggggccgctg ccgatcgct acggccgcaa gcccatcgcc     180
cttggcggtg tgttgctcta cggtctgagc gccctggggg ccgttttgc cgcgagcctc     240 ggcgagctga tgctggcgcg ggtgctgcaa ggcttcggtg cctgtgccac ctcggtggcc    300
gccttctcgg tggtgcgtga cagctacggc cccaagaaga gcgtcagat gatctcctac     360 ctgaacggtg ccatctgctt tattccggcg ctggcccct gctcggtgg ctggctcacc     420 gccaaggcgg gctggtcggc caacttctgg ttcatggccg ttatgcggt catcgtcggt     480 agctggctgc tgtggcggat gccggagacc cgtccggaag agaccagcag cagcggcccg    540
ctcatcagct ggtcgcgcta cagcccggtg ctgcgctccc cgagcttcct gttcaacgcg    600
acgctgtgca tgctggcgat ggcggtgatc ctggcctatg tcaccgcggc gccggtgcaa    660
ctgatggtga agctggggct ggacatgagc ggcttcagct actggttcac tgccaacgcg    720
gcactcaaca tcctggcctg cttcctggcg ccccgtttca tcgccagagt ggggccaaga    780
cgcacccctg catcggcct gctggtgctg ctgctctccg ccatcgcctt gaccctggcc    840
atgcacatcg agcatccgct ggccatgatg gggccggtgt cctctccag catcggcttt    900 gccatgatcc tgggcgccgc cgccggcatg gcgctggcac cgttcggcca ctgcgccggc    960
accgccgccg ccctgctcgg tctgttccag atgagcggct caggtgcgct ggtgggcttc   1020
atcggcgtgc tgatgcacga tccgctcagc cagctggcgt tgcacatgtg gctgctgctg   1080 cccccctttgc tgatgctgat gacccgccag ggccggcgct tgtgtttgca ataa         1134
```

<210> SEQ ID NO 8
<211> LENGTH: 377
<212> TYPE: PRT
<213> ORGANISM: Aeromonas hydrophila

<400> SEQUENCE: 8

Met Leu Phe Ser Pro Leu Ala Ile Asp Ile Tyr Leu Pro Ala Ile Pro
1               5                   10                  15

Gln Met Ala Glu Gln Leu Gly Ala Glu Val Thr Leu Met Gln Gly Thr
            20                  25                  30

Ile Thr Trp Phe Leu Phe Ser Met Gly Leu Gly Gln Leu Leu Val Gly
        35                  40                  45

Pro Leu Ala Asp Arg Tyr Gly Arg Lys Pro Ile Ala Leu Gly Gly Val
    50                  55                  60

Leu Leu Tyr Gly Leu Ser Ala Leu Gly Ala Gly Phe Ala Ala Ser Leu
65                  70                  75                  80

Gly Glu Leu Met Leu Ala Arg Val Leu Gln Gly Phe Gly Ala Cys Ala
                85                  90                  95

Thr Ser Val Ala Ala Phe Ser Val Val Arg Asp Ser Tyr Gly Pro Lys
            100                 105                 110

Lys Ser Gly Gln Met Ile Ser Tyr Leu Asn Gly Ala Ile Cys Phe Ile
        115                 120                 125

Pro Ala Leu Ala Pro Leu Leu Gly Gly Trp Leu Thr Ala Lys Ala Gly
    130                 135                 140

Trp Ser Ala Asn Phe Trp Phe Met Ala Gly Tyr Ala Val Ile Val Gly
145                 150                 155                 160

Ser Trp Leu Leu Trp Arg Met Pro Glu Thr Arg Pro Glu Glu Thr Ser
                165                 170                 175

Ser Ser Gly Pro Leu Ile Ser Trp Ser Arg Tyr Ser Pro Val Leu Arg
            180                 185                 190

Ser Pro Ser Phe Leu Phe Asn Ala Thr Leu Cys Met Leu Ala Met Ala
        195                 200                 205

Val Ile Leu Ala Tyr Val Thr Ala Ala Pro Val Gln Leu Met Val Lys
    210                 215                 220

Leu Gly Leu Asp Met Ser Gly Phe Ser Tyr Trp Phe Thr Ala Asn Ala
225                 230                 235                 240

Ala Leu Asn Ile Leu Ala Cys Phe Leu Ala Pro Arg Phe Ile Ala Arg
                245                 250                 255

Val Gly Pro Arg Arg Thr Leu Arg Ile Gly Leu Leu Val Leu Leu Leu
            260                 265                 270

Ser Ala Ile Ala Leu Thr Leu Ala Met His Ile Glu His Pro Leu Ala
        275                 280                 285

Met Met Gly Pro Val Phe Leu Ser Ser Ile Gly Phe Ala Met Ile Leu
    290                 295                 300

Gly Ala Ala Ala Gly Met Ala Leu Ala Pro Phe Gly His Cys Ala Gly
305                 310                 315                 320

Thr Ala Ala Ala Leu Leu Gly Leu Phe Gln Met Ser Gly Ser Gly Ala
                325                 330                 335

Leu Val Gly Phe Ile Gly Val Leu Met His Asp Pro Leu Ser Gln Leu
            340                 345                 350

Ala Leu His Met Trp Leu Leu Leu Pro Pro Leu Leu Met Leu Met Thr
        355                 360                 365

Arg Gln Gly Arg Arg Leu Cys Leu Gln
    370                 375

<210> SEQ ID NO 9
<211> LENGTH: 1555
<212> TYPE: DNA
<213> ORGANISM: Aeromonas hydrophila

<400> SEQUENCE: 9

| | |
|---|---:|
| acttaaattg aagagtttga tcatggctca gattgaacgc tggcggcagg cctaacacat | 60 |
| gcaagtcgag cggcagcggg aaagtagctt gctacttttg ccggcgagcg cggacgggt | 120 |
| gagtaatgcc tggaaattg cccagtcgag ggggataaca gttggaaacg actgctaata | 180 |
| ccgcatacgc cctacggggg aaagcagggg accttcgggc cttgcgcgat tggatatgcc | 240 |
| caggtgggat tagctagttg gtgaggtaat ggctcaccaa ggcgacgatc cctagctggt | 300 |
| ctgagaggat gatcagccac actggaactg agacacggtc cagactccta cgggaggcag | 360 |
| cagtggggaa tattgcacaa tgggggaaac cctgatgcag ccatgccgcg tgtgtgaaga | 420 |
| aggccttcgg gttgtaaagc actttcagcg aggaggaaag gttggcgcct aatacgtgtc | 480 |
| aactgtgacg ttactcgcag aagaagcacc ggctaactcc gtgccagcag ccgcggtaat | 540 |
| acggagggtg caagcgttaa tcggaattac tgggcgtaaa gcgcacgcag gcggttggat | 600 |
| aagttagatg tgaaagcccc gggctcaacc tgggaattgc atttaaaact gtccagctag | 660 |
| agtcttgtag agggggtag aattccaggt gtagcggtga atgcgtaga gatctggagg | 720 |
| aataccggtg gcgaaggcgg cccccctggac aaagactgac gctcaggtgc gaaagcgtgg | 780 |
| ggagcaaaca ggattagata ccctggtagt ccacgccgta acgatgtcg atttggaggc | 840 |
| tgtgtccttg agacgtggct tccggagcta acgcgttaaa tcgaccgcct ggggagtacg | 900 |
| gccgcaaggt taaaactcaa atgaattgac ggggcccgc acaagcggtg gagcatgtgg | 960 |
| tttaattcga tgcaacgcga agaaccttac ctggccttga catgtctgga atcctgcaga | 1020 |
| gatgcgggag tgccttcggg aatcagaaca caggtgctgc atggctgtcg tcagctcgtg | 1080 |
| tcgtgagatg ttgggttaag tcccgcaacg agcgcaaccc ctgtcctttg ttgccagcac | 1140 |
| gtaatggtgg gaactcaagg gagactgccg gtgataaacc ggaggaaggt ggggatgacg | 1200 |
| tcaagtcatc atggccctta cggccagggc tacacacgtg ctacaatggc gcgtacagag | 1260 |
| ggctgcaagc tagcgatagt gagcgaatcc caaaaagcgc gtcgtagtcc ggatcggagt | 1320 |
| ctgcaactcg actccgtgaa gtcggaatcg ctagtaatcg caaatcagaa tgttgcggtg | 1380 |
| aatacgttcc cgggccttgt acacaccgcc cgtcacacca tggagtgggt tgcaccaga | 1440 |
| agtagatagc ttaaccttcg ggagggcgtt taccacggtg tgattcatga ctggggtgaa | 1500 |
| gtcgtaacaa ggtaaccctta ggggaacctg gggttggatc acctccttac cttaa | 1555 |

<210> SEQ ID NO 10
<211> LENGTH: 1552
<212> TYPE: DNA
<213> ORGANISM: Edwardsiella ictaluri

<400> SEQUENCE: 10

| | |
|---|---:|
| tttaattgaa gagtttgatc atggctcaga ttgaacgctg cggcaggct taacacatgc | 60 |
| aagtcgggcg gtagcaggga gaaagcttgc tttctccgct gacgagcggc ggacgggtga | 120 |
| gtaatgtctg gggatctgcc tgatggaggg ggataactac tggaaacggt agctaatacc | 180 |
| gcataacgtc gcaagaccaa agtgggggac cttcgggcct catgccatca gatgaaccca | 240 |

```
gatgggatta gctagtaggt gaggtaatgg ctcacctagg cgacgatccc tagctggtct    300
gagaggatga ccagccacac tggaactgag acacggtcca gactcctacg ggaggcagca    360
gtggggaata ttgcacaatg ggcgcaagcc tgatgcagcc atgccgcgtg tatgaagaag    420
gccttcgggt tgtaaagtac tttcagtagg gaggaaggtg tgagcgttaa tagcgttcac    480
aattgacgtt acctacagaa gaagcaccgg ctaactccgt gccagcagcc gcggtaatac    540
ggagggtgca agcgttaatc ggaattactg ggcgtaaagc gcacgcaggc ggtttgttaa    600
gttggatgtg aaatccccgg gcttaacctg gaactgcatc caagactgg  caagctagag    660
tctcgtagag ggaggtagaa ttccaggtgt agcggtgaaa tgcgtagaga tctggaggaa    720
taccggtggc gaaggcggcc tcctggacga agactgacgc tcaggtgcga aagcgtgggg    780
agcaaacagg attagatacc ctggtagtcc acgctgtaaa cgatgtcgat ttggaggttg    840
tgcccttgag gcgtggcttc cgaagctaac gcgttaaatc gaccgcctgg ggagtacggc    900
cgcaaggtta aaactcaaat gaattgacgg gggcccgcac aagcggtgga gcatgtggtt    960
taattcgatg caacgcgaag aaccttacct actcttgaca tccagcgaat cctgtagaga   1020
tacgggagtg ccttcgggaa cgctgagaca ggtgctgcat ggctgtcgtc agctcgtgtt   1080
gtgaaatgtt gggttaagtc cgcaacgagc gcaacccctt atcctttgtt gccagcggtt   1140
aggccgggaa ctcaaaggag actgccagtg ataaactgga ggaaggtggg gatgacgtca   1200
agtcatcatg gcccttacga gtagggctac acacgtgcta caatggcgta tacaaagaga   1260
agcgacctcg cgagagcaag cggacctcat aaagtacgtc gtagtccgga ttggagtctg   1320
caactcgact ccatgaagtc ggaatcgcta gtaatcgtgg atcagaatgc cacggtgaat   1380
acgttcccgg gccttgtaca caccgcccgt cacaccatgg gagtgggttg caaaagaagt   1440
aggtagctta accttcggga gggcgcttac cactttgtga ttcatgactg gggtgaagtc   1500
gtaacaaggt aaccgtaggg gaacctgcgg ttggatcacc tccttacctg aa            1552
```

<210> SEQ ID NO 11
<211> LENGTH: 426
<212> TYPE: PRT
<213> ORGANISM: Aeromonas hydrophila

<400> SEQUENCE: 11

```
Met Trp Gly Val Thr Phe Arg Thr Asn Phe Asn Asp Leu Lys Pro Val
1               5                   10                  15

His Ile Asp Gln Pro Arg Pro Ile Tyr Gln Leu Asp Gln Val Pro Ala
            20                  25                  30

Thr Met Thr Asp Val Lys Trp Gln Ala Leu Thr Ala Asp Leu Lys Glu
        35                  40                  45

Asn Ala Gly Trp Gln Asp Thr Glu Phe Tyr Thr Thr Thr Asn Thr Val
    50                  55                  60

Thr Val Ile Gly Thr Gln Ser Lys Tyr Arg Asn Lys Gly Glu Ala Ile
65                  70                  75                  80

Lys Arg Thr Ser Leu Leu Ala Ala Asn Tyr Leu Pro Ser Thr Val Asp
                85                  90                  95

Glu Leu Asn Val Ile Glu Arg Lys Ala Asn Phe Gln Leu Gln Glu Thr
            100                 105                 110

Arg Ile Asp Leu Pro Ser Val Arg Arg Ala Asn Val Val Gln Val Leu
        115                 120                 125

Gly Glu Glu Gln His Glu Lys Ser Thr Val Gln Ala Ala Gly Lys Thr
    130                 135                 140
```

```
Tyr Gly Lys Ser Ile Tyr Ala Ser Glu Arg Lys Thr Tyr Ser Tyr Ser
145                 150                 155                 160

Phe Asp Pro Asp Leu Thr Gln Ser Phe Gly Gly Ala Glu Ser Phe Tyr
            165                 170                 175

Met Tyr Gln Leu Gly Ile Asn Ala Asn Ala Asp Trp Arg Ile Asn Glu
        180                 185                 190

Asn Asn Ser Leu Gln Gly Thr Leu Phe Val Asn Leu Met Asn Asn Tyr
    195                 200                 205

Asp Glu Phe Asn Tyr Lys Ala Pro Pro Asp Gly Ala Ala Leu Pro
210                 215                 220

Arg Val Arg Thr Trp Ile Arg Glu Tyr Val Asp Ser Ser Asn Val Leu
225                 230                 235                 240

Leu Asn Asn Leu Gln Leu Thr His Met Gln Pro Leu Ala Gln Asp Trp
                245                 250                 255

Tyr Gly Gln Ala Tyr Gly Gly Tyr Leu Glu Met Met Tyr Ala Gly Val
            260                 265                 270

Gly Ser Glu Val Leu Tyr Arg Pro Tyr Gly Lys Thr Trp Ala Ile Gly
        275                 280                 285

Leu Asp Ala Asn Trp Val Lys Gln Arg Asp Trp Asn Asn Thr Leu Lys
    290                 295                 300

Met Ala Asp Tyr Asp Val Met Thr Gly His Ile Thr Ala Tyr Trp Gln
305                 310                 315                 320

Leu Pro Phe Met Ser Asn Val Thr Ala Lys Val Ser Val Gly Gln Tyr
                325                 330                 335

Leu Ala Gly Asp Lys Gly Ala Thr Phe Asp Phe Ser Lys Arg Phe Asp
            340                 345                 350

Ser Gly Val Val Leu Gly Gly Tyr Ala Thr Phe Thr Asn Val Ser Ala
        355                 360                 365

Glu Glu Tyr Gly Glu Gly Ser Phe Thr Lys Gly Ile Tyr Val Thr Ile
    370                 375                 380

Pro Phe Asp Leu Met Leu Leu Lys Pro Thr Thr Ala Lys Gly Ser Ile
385                 390                 395                 400

Gly Trp Val Pro Leu Thr Arg Asp Gly Gly Gln Met Leu Ser Arg Lys
                405                 410                 415

Asn Gly Leu Tyr Gly Leu Thr Glu Leu Gln
            420                 425

<210> SEQ ID NO 12
<211> LENGTH: 1281
<212> TYPE: DNA
<213> ORGANISM: Aeromonas hydrophila

<400> SEQUENCE: 12
atgtgggggg tgacttttcg gactaacttt aatgatctga aaccagtcca tattgaccaa      60
cctagaccta tttatcaact tgaccaggtt cctgccacta tgactgacgt gaagtggcaa     120
gcgctaaccg ctgatttgaa agagaatgct ggttggcagg atacagagtt ttacacaacc     180
accaatactg tgactgtcat cggtacgcag agcaagtatc gtaataaggg tgaggcgata     240
aagagaacct ctttgttagc agcaaattat ttgcctagta cagttgatga gctgaatgtt     300
attgaacgta aggcgaactt ccagttgcaa gagactcgca tcgatctccc atctgttcgt     360
cgtgcaaatg tggtacaggt attgggtgaa aacagcatg aaaaatcgac ggtgcaggct     420
gcagggaaaa cctatgggaa atctatctat gcatctgagc gcaaaactta ttcatactct     480
tttgatccag atctgacgca atcatttggt ggtgctgagt cttttttatat gtatcagtta     540
```

```
ggcattaatg ccaatgcgga ttggcgtata aatgaaaata acagcttgca gggtacgctg      600
tttgtcaatc tgatgaataa ctacgatgag ttcaattata aagcccctcc tccagatggc      660
gctgccttac cacgagttcg acgtggatt cgtgagtatg tcgattcctc caatgtatta       720
ctcaacaact tgcagttaac ccatatgcaa ccacttgctc aagattggta cgggcaagct      780
tatggcggat atttggagat gatgtatgcc ggcgtcggga gtgaggtact ttatcgtcca      840
tatggtaaga cttgggctat tggtcttgat gcaaactggg tgaaacagcg agactggaac      900 aatacccctga aaatggctga ttatgatgta atgactgggc atattactgc gtattggcag     960
ttaccattca tgagtaatgt caccgccaaa gtctccgtag gtcagtattt ggctggtgac     1020
aaaggcgcga cattcgactt ctccaaaagg tttgattcgg gtgttgtctt ggggggtat     1080 gcaacattta ccaatgtctc agcagaggag tatggtgaag gtagctttac caaaggaatt     1140
tatgtcacga taccgtttga tctgatgctg ctcaagccaa caaccgcgaa aggaagcatt     1200
ggatgggttc ctttgacacg ggatggaggc cagatgttga gtcgcaagaa tggcctttac     1260
ggtttgacag agttgcagta a                                               1281
```

<210> SEQ ID NO 13
<211> LENGTH: 343
<212> TYPE: PRT
<213> ORGANISM: Escherichia coli

<400> SEQUENCE: 13

```
Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240
```

```
Arg Val Arg Lys Asn Gly Val Ala Ala Pro Ser Ala Thr Ser Gln Leu
            245                 250                 255

Ser Thr Arg Ala Leu Glu Gly Ile Phe Glu Ala Thr His Arg Leu Ile
        260                 265                 270

Tyr Gly Ala Lys Asp Asp Ser Gly Gln Arg Tyr Leu Ala Trp Ser Gly
            275                 280                 285

His Ser Ala Arg Val Gly Ala Ala Arg Asp Met Ala Arg Ala Gly Val
        290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Thr Gly Ala Met Val
                325                 330                 335

Arg Leu Leu Glu Asp Gly Asp
            340
```

<210> SEQ ID NO 14
<211> LENGTH: 34
<212> TYPE: DNA
<213> ORGANISM: Escherichia coli
<220> FEATURE:
<221> NAME/KEY: misc_feature
<222> LOCATION: (14)..(16)
<223> OTHER INFORMATION: n is a, c, g, or t
<220> FEATURE:
<221> NAME/KEY: misc_feature
<222> LOCATION: (19)..(21)
<223> OTHER INFORMATION: n is a, c, g, or t

<400> SEQUENCE: 14
ataacttcgt atannntann ntatacgaag ttat                              34

<210> SEQ ID NO 15
<211> LENGTH: 105
<212> TYPE: PRT
<213> ORGANISM: Aeromonas hydrophila

<400> SEQUENCE: 15

```
Met Ala Ser Glu Leu Leu Ala Ile Ile Ser Ile Ile Phe Gln Leu
1               5                   10                  15

Gln Pro Lys Trp Gln Pro Trp Arg Leu Ile Phe Asn Ser Thr Glu Glu
            20                  25                  30

Ser Ser Trp Thr Met Lys Gln Ala Ile Asn Phe Lys Leu Thr Ala Thr
        35                  40                  45

Thr Arg Ile Ala Arg Ile Pro Leu Thr Pro Ala Ile Phe Ile Leu Thr
    50                  55                  60

Lys Trp Ile Phe Asn Ile Ala Ala Phe Gly Tyr Ile Ser Pro Ala Asp
65                  70                  75                  80

Thr Asp Ser Lys Ile Lys Trp Thr Ile Ala Phe Thr Ser Cys His Lys
                85                  90                  95

Leu Thr Val Lys Glu Ser Gly Pro His
            100                 105
```

<210> SEQ ID NO 16
<211> LENGTH: 672
<212> TYPE: DNA
<213> ORGANISM: Aeromonas hydrophila

<400> SEQUENCE: 16
atgttttctc ttcgtttgtt tatgtctttg gggttattac tcttgagtgg ctgttccgcc    60

```
accagttcag atacctatgc aactctccgc tatgccttt  tggggtagta tgatgtggag    120
gtaacgactg aaaaagtgcg tgacttgcct tatgccagcg cctatctacg agtgggtgat    180
agcccacagg ctttggtagt gcttgcgttt gcagatcctg atggttcatt gagctgggtg    240
agttctgata taagctttt  tgttaccaaa tcaggtcgac tgcacaagac ggtgggtttg    300
gaaaatgatc tctatttagt ggcatcatct tggcctgatc cattgcagaa atggtaagt     360 gtacctgata tatctttgaa tctagatgcg atgtcttggc agtatactgc cgaatgggaa    420
aaggattatg tgagtggata taacatgcag gctaagttta tatcttctgt gaaggaaacg    480
ttgttaattc ttgataaatc acatgatgtt actttaattg atgaattggt cagtgttgga    540
caggataaga actcttggca taattactat tggtttgaac ctagtacggg tagagtatta    600
aaaagccaac agcaactggg gccggactta ccggttattg aaatgataat attaaagccg    660
tacgcattat ga                                                        672
```

<210> SEQ ID NO 17
<211> LENGTH: 248
<212> TYPE: PRT
<213> ORGANISM: Aeromonas hydrophila

<400> SEQUENCE: 17

```
Met Lys Arg Tyr Leu Met Val Ser Leu Ile Pro Phe Phe Ala Leu Ala
1               5                   10                  15

Gln Ala Asp Val Asn Val Ile Phe Ala Arg His Ala Thr Ala Lys Ile
            20                  25                  30

Glu Leu His Asp Gly Ala Arg Leu Ala Asp Leu Leu Phe Asn Val Gln
        35                  40                  45

Leu Pro Asp Asn Ile Tyr Trp Arg Thr Ala Gln Ile Ser Asn Glu Lys
50                  55                  60

Thr Ile Ala Val Phe Gln Val Thr Lys Glu Lys Leu Leu Lys Asp Leu
65                  70                  75                  80

Lys Ser Leu Gln Val Leu Trp Met Arg Glu Gly Asp Lys Gly Ala Leu
                85                  90                  95

Ile Gln Ser Thr Gln Gln Leu Leu Gln Glu Leu Asp Lys Val Pro Val
            100                 105                 110

Ser Gly Arg Leu Ser Ile Ala Leu Asp Pro Ala Lys Ser Arg Ile Asp
        115                 120                 125

Pro Asn Gly Asn Pro Gln Leu Lys Gly Gln Tyr Thr Leu Phe Leu Ala
    130                 135                 140

Ser Arg Pro Asp Phe Ile Tyr Leu Val Gly Leu Ile Asn Gly Arg Ser
145                 150                 155                 160

Lys Gln Pro Leu Gln Ala Gly Ala Ser Leu Ala Ser Tyr Trp Gln Asp
                165                 170                 175

Tyr Arg Leu Leu Ala Gly Ala Ala Gln Asn Glu Ala Phe Leu Ile Gln
            180                 185                 190

Pro Asp Gly Ala Ile Ser Arg Val Pro Val Ala Asn Trp Asn Lys Leu
        195                 200                 205

His Arg Glu Pro Met Ala Gly Ala Thr Met Phe Val Gly Phe Asp Pro
    210                 215                 220

Gln Leu Leu Pro Glu Gln Tyr Arg Asp Ile Asn Ile Arg Ile Ala Asn
225                 230                 235                 240

Leu Leu Ala Asn Arg Val Pro Glu
                245
```

<210> SEQ ID NO 18
<211> LENGTH: 1584
<212> TYPE: DNA
<213> ORGANISM: Aeromonas hydrophila

<400> SEQUENCE: 18

| | | | | | |
|---|---|---|---|---|---|
| atgaagagat | acttgctttg | gctgctgctg | attggcatca | gtcatgctgt | tcccttgcgg | 60 |
| gccagcgaat | ccacccttga | agcgccggag | cgggtcgtac | tccagctgcg | ctggctgcat | 120 |
| cagccccagt | tcgttggcta | tcacatggcc | aaggccaagg | gcttttatgc | cagtgccggg | 180 |
| ctggacgtcg | agatacggcc | cggcggcaag | gacatcagcc | cggtagaaga | ggtgctgagc | 240 |
| gggcgggccg | acttcggggt | cggcaacacc | gaggtgctca | ccagctacgc | cagcggccag | 300 |
| ccgctgttgg | cgcttgccag | cgtctatcag | cactccccgt | ccatctttct | ggctcgccgt | 360 |
| gacagcggca | ttctcaccgt | tgacgacatg | cgtggcaaac | ggatcatgat | gttttcggcc | 420 |
| catcaggacg | ccgaactgct | ggccactctc | ttctatcagg | gctcaatga | gcaccagctc | 480 |
| atcccgctgc | ccacctcggt | caacatcgag | gatctcatcg | agggccgggt | cgacatcttc | 540 |
| aacgcctacc | tcagcaacga | acccttctat | ctggaggagc | gcggcattcc | cgtctccgtc | 600 |
| atcaatccgc | gcaactacgg | catcgatttc | tacagcgaca | tcctgttcac | cacccaggcg | 660 |
| caggagcgcg | cccatccgga | tcgggtagcc | aggtttcggg | ccgcgagcct | ggcgggctgg | 720 |
| cgctacgccc | tcgcccaccc | gcaggaggcc | atcgccctgc | tgcgcaagga | gtatggcgtc | 780 |
| aaccgcagtc | aagcccacat | ggagtacgag | ctgcaggtga | gcaaggagat | gatccagccg | 840 |
| ctctatgtgg | agatcgggta | tatgaatccc | gatcgcatga | cccacatcat | gcagcagctg | 900 |
| gtcgagatcg | gctggtgtc | caaaccggtc | tccttgcacg | agtttctcta | tcaggcccct | 960 |
| tccgagcagt | ggattttctg | gcgtccctgg | ttcctgctga | gctggcagc | ctgcgtgctg | 1020 |
| atcctgctgc | tggccctcta | tctattgatg | tgcaaccagc | ggctcaatcg | cgagattgcc | 1080 |
| ctgcgccgcc | agcgggagga | ggagatctgg | cagctggccc | gccgcgaccc | gctcaccggc | 1140 |
| ctgcccaacc | ggctgagcct | gatggagcgg | ctcgatgccc | agatcaaggg | cccggcccct | 1200 |
| ggctgcctgc | tgttttgcga | tctcgacgac | ttcaagcagg | tcaacgacaa | cttcggccac | 1260 |
| agccacggcg | atgccctcct | ctgccagctg | gcggagcgga | tcagccgcag | cctcgggcca | 1320 |
| cagcacttct | tcgccagact | ggccggcgac | gagttcgtgc | tgctgttgcc | gggccacgac | 1380 |
| caggcgcagg | ccgacgccat | cgccgagcag | atcagggtca | ccatgcagtc | gccattcgag | 1440 |
| gtggaaggag | ttccgctggc | ggtcggcatc | agcgtcggca | tcagccagta | ccagccgggc | 1500 |
| tggcgccccg | agcagtggct | gatccaggcc | gatcgcgcca | tgtaccagga | caaggggggct | 1560 |
| ccgctggcaa | cgcccccagg | ctga | | | | 1584 |

<210> SEQ ID NO 19
<211> LENGTH: 223
<212> TYPE: PRT
<213> ORGANISM: Aeromonas hydrophila

<400> SEQUENCE: 19

Met Phe Ser Leu Arg Leu Phe Met Ser Leu Gly Leu Leu Leu Ser
1               5                   10                  15

Gly Cys Ser Ala Thr Ser Ser Asp Thr Tyr Ala Thr Leu Arg Tyr Ala
            20                  25                  30

Phe Leu Gly Val Asp Asp Val Glu Val Thr Thr Glu Lys Val Arg Asp
        35                  40                  45

Leu Pro Tyr Ala Ser Ala Tyr Leu Arg Val Gly Asp Ser Pro Gln Ala
        50                  55                  60

Leu Val Val Leu Ala Phe Ala Asp Pro Asp Gly Ser Leu Ser Trp Val
 65                  70                  75                  80

Ser Ser Asp Asn Lys Leu Phe Val Thr Lys Ser Gly Arg Leu His Lys
                 85                  90                  95

Thr Val Gly Leu Glu Asn Asp Leu Tyr Leu Val Ala Ser Ser Trp Pro
            100                 105                 110

Asp Pro Leu Gln Lys Met Val Ser Val Pro Asp Ile Ser Leu Asn Leu
            115                 120                 125

Asp Ala Met Ser Trp Gln Tyr Thr Ala Glu Trp Glu Lys Asp Tyr Val
130                 135                 140

Ser Gly Tyr Asn Met Gln Ala Lys Phe Ile Ser Ser Val Lys Glu Thr
145                 150                 155                 160

Leu Leu Ile Leu Asp Lys Ser His Asp Val Thr Leu Ile Asp Glu Leu
                165                 170                 175

Val Ser Val Gly Gln Asp Lys Asn Ser Trp His Asn Tyr Tyr Trp Phe
            180                 185                 190

Glu Pro Ser Thr Gly Arg Val Leu Lys Ser Gln Gln Gln Leu Gly Pro
            195                 200                 205

Asp Leu Pro Val Ile Glu Met Ile Ile Leu Lys Pro Tyr Ala Leu
            210                 215                 220

<210> SEQ ID NO 20
<211> LENGTH: 672
<212> TYPE: DNA
<213> ORGANISM: Aeromonas hydrophila

<400> SEQUENCE: 20

```
atgtttctc ttcgtttgtt tatgtctttg gggttattac tcttgagtgg ctgttccgcc      60
accagttcag ataccatgc aactctccgc tatgcctttt tgggggtaga tgatgtggag     120
gtaacgactg aaaaagtgcg tgacttgcct tatgccagcg cctatctacg agtgggtgat    180
agcccacagg ctttggtagt gcttgcgttt gcagatcctg atggttcatt gagctgggtg   240
agttctgata taagctttt tgttaccaaa tcaggtcgac tgcacaagac ggtgggtttg   300
gaaaatgatc tctatttagt ggcatcatct tggcctgatc cattgcagaa atggtaagt   360
gtacctgata tatcttgaa tctagatgcg atgtcttggc agtatactgc cgaatgggaa   420
aaggattatg tgagtggata taacatgcag gctaagttta tatcttctgt gaaggaaacg  480
ttgttaattc ttgataaatc acatgatgtt acttaattg atgaattggt cagtgttgga   540
caggataaga actcttggca taattactat tggtttgaac ctagtacggg tagagtatta  600
aaaagccaac agcaactggg gccggactta ccggttattg aaatgataat attaaagccg   660
tacgcattat ga                                                       672
```

<210> SEQ ID NO 21
<211> LENGTH: 573
<212> TYPE: PRT
<213> ORGANISM: Aeromonas hydrophila

<400> SEQUENCE: 21

Met Ile Lys Asn Ile Asn Gly Val Phe Gly Val Leu Phe Ala Ala Tyr
 1               5                  10                  15

Trp Leu Leu Gly Met His Phe Phe Met His Asn Pro Gly Gly Ala Gly
            20                  25                  30

-continued

```
Leu Tyr Leu Pro Phe Asn Ala Trp Gly Trp Ile Phe Ala Ser Leu Val
         35                  40                  45

Ile Gly Leu Gly Leu Trp Gln Val Thr Leu Gln Gln Arg Leu Val Phe
 50                  55                  60

Ser Ser Leu Gln Gly Trp Leu Trp Leu Gly Ala Leu Leu Leu Leu Leu
 65                  70                  75                  80

Pro Met Ala Tyr Pro Gly Phe Asp Leu Lys Asp Tyr Ala Ile Pro Arg
                 85                  90                  95

Leu Leu Gly Leu Phe Thr Gly Leu Leu Phe Leu Phe Cys Leu Tyr Gln
            100                 105                 110

Trp Gln Leu Val Arg Ala Ser Arg Asp Gln Leu Phe Tyr Leu Leu Leu
            115                 120                 125

Gly Ala Val Ala Ile Glu Ala Leu Leu Gly Met Val Gln Tyr Tyr Leu
130                 135                 140

Leu Ile Pro Gly Asn Trp Leu Gly Tyr Asp Thr Arg Ala Asn Arg Pro
145                 150                 155                 160

Tyr Gly Ile Phe Gln Gln Pro Asn Val Met Ala Thr Phe Met Ala Thr
                165                 170                 175

Gly Leu Val Leu Ala Gly Trp Leu Glu Leu Arg Gly Asn Ala Asn Pro
            180                 185                 190

Trp Leu Lys Gly Leu Arg Tyr Gly Val Ile Leu Ala Ala Ser Leu Leu
            195                 200                 205

Leu Val Ala Leu Gln Ser Arg Val Gly Gln Leu Gly Gly Leu Leu Ala
210                 215                 220

Leu Leu Leu Leu Val Pro Ala Leu His Arg Gln Glu Arg Leu Ala Gln
225                 230                 235                 240

Val Leu Gly Leu Val Ala Leu Gly Val Gly Leu Gly Ile Ala Ser Gln
                245                 250                 255

Tyr Gly Ile Ser Gly Val Lys Arg Gly Leu Glu Ala Tyr Gln Ser Gly
            260                 265                 270

Gly Met Arg Ser Ile Tyr Trp Pro Tyr Ala Ala Lys Leu Ile Ala Gln
            275                 280                 285

Ser Pro Trp Val Gly Trp Gly Tyr Gly Ser Phe Glu Thr Thr Phe Leu
290                 295                 300

His His Tyr Met Ala Asp Lys Ala Leu Asn Pro Ala Met Val Gln Ile
305                 310                 315                 320

Glu Tyr Asn Leu Asp His Pro His Asn Glu Phe Leu Tyr Trp Ala Val
                325                 330                 335

Glu Gly Gly Leu Ala Pro Met Ile Gly Met Val Leu Met Gly Gly Ala
            340                 345                 350

Leu Leu Trp Arg Val Ser Lys Ala Gly Trp Val Lys Gly Gly Ala Leu
            355                 360                 365

Leu Ala Leu Val Thr Pro Ile Leu Leu His Thr Gln Thr Glu Tyr Pro
370                 375                 380

Leu Tyr His Ala Ile Ala Leu Trp Trp Ala Leu Leu Leu Val Tyr
385                 390                 395                 400

Val Leu Asp Ala Glu Val Glu Glu Gly Leu Gln Ala Ser Gly Arg Ala
                405                 410                 415

Ser Trp Arg Glu Tyr Val Tyr Arg Pro Trp Leu Leu Leu Arg Phe Val
            420                 425                 430

Ala Ile Ile Ile Pro Leu Leu Val Val Pro Phe Met Leu Thr Ala Ile
            435                 440                 445
```

```
His Thr Ala Trp Val Val Thr Lys Tyr Glu Arg Gly Gly Tyr Lys Glu
    450                 455                 460
Pro Thr Leu Leu Asp Val Val Asn Pro Met Ala Trp Leu Thr Arg
465                 470                 475                 480
Val Glu Phe Asp Val Asn Ser Val Arg Leu Met Val Gly Leu Gln Ala
                485                 490                 495
Asn Asn His Ala Glu Leu Glu Ala Tyr Leu Glu Trp Gly Gln Ala Phe
            500                 505                 510
Val Arg His Thr Pro Arg Ala Asn Ile Tyr Ala Asn Met Val Ile Ala
        515                 520                 525
Leu Asp Ala Leu Gly Arg Lys Glu Glu Ala Arg Ala Leu Arg Arg Glu
    530                 535                 540
Ala Leu Ala Leu Tyr Pro Gly Asp Pro Leu Leu Thr Gly Ser Ala Ala
545                 550                 555                 560
Thr Ser Val Ala Thr Ala Leu Glu Arg Lys Pro Ser Ala
                565                 570

<210> SEQ ID NO 22
<211> LENGTH: 1722
<212> TYPE: DNA
<213> ORGANISM: Aeromonas hydrophila

<400> SEQUENCE: 22
atgattaaaa acataaatgg cgtgtttggt gtactctttg ctgcttattg gttgttgggc        60
atgcactttt tcatgcacaa ccccggtggg gccgggctct atctgccgtt caacgcctgg       120
ggctggatct tcgccagcct ggtcatcggt ctgggactgt ggcaggtgac gctgcagcag       180
cggctggtgt tctcctcttt gcagggctgg ctctggctgg gggcgttgct gctgctgctg       240
cccatggcct atcccggctt tgacctgaaa gactatgcga ttccccgttt gctggggctg       300
tttaccggtc tgctgtttct gttctgtctc taccagtggc agctggtgcg gcgtctcgt        360
gaccagctgt tctatctgct gctgggggcg gtggccatcg aggcgctgct gggcatggtg       420
cagtactacc tgctgatccc gggtaactgg ctggggtatg cacccgcgc caaccgcccc        480
tacggcatct tcaacaacc caatgtgatg gcgaccttca tggcgaccgg gcttgtgctg        540
gccggctggc tggagctgcg cggtaatgcc aaccctggc tcaaggggct gcgctatggg        600
gtgatcctgg cggccagcct gctgctggtg gcgctgcaat cccgggtggg gcagttgggg       660
ggcctgctgg cgctgctcct gctcgtgccc gcattgcatc gtcaggagcg gctggcacag       720
gtactgggtc tggttgctct cggtgtcggg ctggggatcg cctcccagta cgggatcagc       780
ggtgtcaaac gcgggctgga ggcctatcag tccggcggca tgcgctccat ctactggccc       840
tacgccgcca agctgattgc ccagtctccg tgggttggct ggggttacgg cagctttgaa       900
accacctttt tgcaccacta catggccgac aaggcgctga accggccat ggtacagatt        960
gaatacaacc tcgatcaccc ccacaacgag ttcctctact gggcggtgga aggggggctg      1020
gctcctatga tcgcatggt gctgatgggc ggtgctctgt tgtggcgcgt gagcaaggcc       1080
ggttgggtca agggggggc gctgctggcc ctggtgaccc cgatcctgct gcatacccag       1140
accgagtatc cgctttatca cgccatcgcc ctgtggtggg ccctgctgct gctggtgtat       1200
gtactggatg cggaagtgga ggaggggctg caagcctcgg gccgtgccag ctggcgcgag      1260
tatgtctatc gccccctggtt gttgctgcgc ttcgtggcca tcatcattcc actgctggtg       1320
gtgcccttca tgctgaccgc cattcatact gcctgggtgg tcaccaagta cgagcgcggc       1380
ggctacaagg agccaaccct gctgctcgac gtcgtcaatc ccatggcctg gttgacccgg      1440
```

```
gtcgagtttg acgtcaactc ggtgcggttg atggtgggct tgcaggccaa caatcacgca      1500
gagctggagg cgtatttaga gtggggtcag gcgtttgtgc gccacacgcc gagagccaac      1560
atctacgcca acatggtgat cgcgctggat gcgctgggac gaaaagagga ggcccgggca      1620
ctgcgccgcg aggcgctggc gctctatccg ggtgatccct tgctgaccgg ctcggccgcc      1680
acctccgtgg ccacggcgct ggaacgcaaa ccctcggcct ga                         1722
```

<210> SEQ ID NO 23
<211> LENGTH: 242
<212> TYPE: PRT
<213> ORGANISM: Aeromonas hydrophila

<400> SEQUENCE: 23

```
Met Ala Ala Gln Phe Gly Gly Leu Ala Ser Leu Ala Gly Val Asn Leu
1               5                   10                  15

Ser Gly Gly Gly Gly Leu Asp Lys Thr Ala Ile Ala Val Glu Ile Gly
                20                  25                  30

Lys Ser Arg Gln Phe Leu Ser His Phe Ile Arg Gln His Gln Leu Glu
            35                  40                  45

Val Pro Leu Met Ala Val Ile Lys Ala Asp Lys Val Thr Gly Glu Leu
        50                  55                  60

Leu Val Asp Lys Asn Ile Tyr Asp Val Asp Thr Lys Lys Trp Val Arg
65                  70                  75                  80

Glu Val Pro Pro Ser Lys Ser Val Glu Pro Thr Asp Trp Glu Leu Val
                85                  90                  95

Lys Ala Phe Arg Ala Leu Ala Ser Ile Ser Gln Asp Thr Lys Ser Gly
            100                 105                 110

Leu Val Thr Val Ala Val Glu Tyr Tyr Ser Pro Glu Thr Ala Lys Gln
        115                 120                 125

Trp Val Asp Trp Leu Val Ala Asp Leu Asn Glu Gly Met Lys Leu Arg
    130                 135                 140

Asp Gln Thr Asp Ala Ile Arg Asn Ile Ser Tyr Leu Lys Ala Gln Leu
145                 150                 155                 160

Glu Lys Thr Pro Val Ala Asp Met Gln Lys Val Phe Tyr Gln Leu Ile
                165                 170                 175

Glu Glu Gln Thr Lys Thr Leu Met Leu Thr Glu Val Asn Gln Glu Tyr
            180                 185                 190

Val Phe Lys Thr Leu Asp Pro Ala Val Val Ala Glu Glu Lys Ala Lys
        195                 200                 205

Pro Lys Arg Ala Leu Ile Ala Val Leu Gly Thr Leu Leu Gly Gly Met
    210                 215                 220

Leu Gly Val Met Ile Ala Leu Val Arg His Ser Ile Gly Arg Pro Pro
225                 230                 235                 240

Arg His
```

<210> SEQ ID NO 24
<211> LENGTH: 729
<212> TYPE: DNA
<213> ORGANISM: Aeromonas hydrophila

<400> SEQUENCE: 24

```
atggctgccc agtttggtgg tcttgctagc ttggctggtg taaatctcag tggtggcggc      60
ggtctggaca aaacggctat tgcggtcgaa attgggaaat cccgccaatt cttaagtcac     120
tttatccgcc aacaccagct ggaagtgccg ttgatggcgg ttattaaagc tgacaaggtg     180
```

```
accggtgagt tacttgttga taaaaacatc tacgatgtcg acaccaaaaa gtgggtgcgt    240
gaggtgccac ctagcaagtc ggttgaacca accgactggg agctggttaa ggcatttcgc    300
gcacttgcca gtatcagcca ggataccaaa tcagggttgg ttacggtggc tgtggagtac    360
tactctccgg agactgccaa gcagtgggtt gactggttgg tggccgatct caatgaaggc    420
atgaagttgc gggatcaaac tgatgcgata cgtaacatta gctatctcaa agcacaactt    480
gaaaaaaccc ctgtcgctga tatgcagaag gtgttctatc aactgatcga ggagcagact    540
aaaaccttga tgttgactga agtgaatcaa gagtacgttt ttaaaaccct tgatcctgcc    600
gtggttgctg aggaaaaagc gaaaccaaaa cgggcgttga tcgccgtatt ggggacgctg    660
cttggcggca tgctaggcgt tatgattgca ctggtacgcc attcaatcgg tcgtccacct    720
cgtcattga                                                            729
```

<210> SEQ ID NO 25
<211> LENGTH: 874
<212> TYPE: PRT
<213> ORGANISM: Aeromonas hydrophila

<400> SEQUENCE: 25

```
Met Lys His Lys Gly Leu Leu Ser Leu Ala Leu Phe Gly Gly Pro
  1               5                  10                  15

Leu Leu Ala Ala Pro Gln Val Thr Pro Glu Met Ile Ala Lys Phe Lys
             20                  25                  30

Gln Leu Ser Pro Ala Gln Gln Ala Leu Ala Ala Gln Tyr Gly Ile
         35                  40                  45

Asp Ser Ser Gln Leu Gly Thr Asn Thr Ser Gln Ser Ser Ile Thr Pro
     50                  55                  60

Val Asn Thr Ala Pro Val Ala Ala Pro Arg Glu Val Asp Tyr Asn Lys
 65                  70                  75                  80

Glu Ser Gln Arg Pro Leu Val Ala Gly Val Ala Gln Glu Gly Ala Leu
                 85                  90                  95

Gln Pro Phe Gly Tyr Ser Val Phe Ala Gly Glu Pro Leu Thr Asp Ala
            100                 105                 110

Pro Val Val Asp Met Pro Val Ala Asp Asp Tyr Val Met Gly Pro Gly
            115                 120                 125

Asp Glu Ile Arg Ile Gln Leu Tyr Gly Lys Glu Asn Ala Ser Tyr Thr
        130                 135                 140

Leu Ala Ile Gly Arg Glu Gly Phe Ile Asp Phe Pro Ser Leu Gly Pro
145                 150                 155                 160

Ile Ala Ala Ser Gly Gln Thr Phe Gln Gln Leu Arg Ser Glu Leu Glu
                165                 170                 175

Asn Arg Ile Lys Glu Gln Lys Ile Gly Val Glu Ala Phe Ile Ser Phe
            180                 185                 190

Gly Ala Leu Arg Thr Met Gln Val Phe Val Met Gly Asp Ala Tyr Arg
        195                 200                 205

Pro Gly Ala Tyr Asn Val Asn Gly Met Ala Thr Val Thr Gln Ala Leu
    210                 215                 220

Gln Ala Ala Gly Gly Ile Asp Thr Val Gly Ser Leu Arg Lys Ile Gln
225                 230                 235                 240

Val Lys Arg Ala Gly Gln Lys Val Ile Asp Val Asp Leu Tyr Lys Met
                245                 250                 255

Leu Val Trp Gly Asp Thr Ser Gln Asp Ile Arg Leu Arg Ser Gly Asp
            260                 265                 270
```

```
Thr Val Phe Ile Pro Ala Lys Ser Ser Glu Val Ser Ile Asp Gly Leu
            275                 280                 285

Val Lys Arg Pro Ala Thr Tyr Glu Leu Thr Ser Pro Ala Ala Leu Val
290                 295                 300

Asn Val Leu Gly Leu Ala Gly Gly Met Lys Ala Ala Leu Lys Glu
305                 310                 315                 320

Val Ser Val Thr Arg Tyr Ser Glu Thr Gly Met Arg Val Phe Asn Leu
                325                 330                 335

Asn Leu Ser Arg Pro His Asp Arg Gln Phe Val Val Arg Asp Gly Asp
                340                 345                 350

Lys Val Thr Val Lys Pro Ser Ser Thr Glu Tyr Ser Gln Ala Ile Val
                355                 360                 365

Val Lys Gly Ala Val Arg Glu Gly Val Phe Ser Phe Gln Pro Gly
                370                 375                 380

Met Arg Ile Ser Arg Val Leu Gln Ser Ala Asp Arg Asp Leu Thr Ser
385                 390                 395                 400

Val Thr Asp Leu Asn Tyr Ala Leu Ile Val Arg Glu Val Asp Ala Gln
                405                 410                 415

Arg Asn Ile Glu Val Leu Gln Phe Asn Leu Gly Arg Val Leu Gln Met
                420                 425                 430

Pro Gly Gly Glu Asp Asp Ile Arg Leu Gln Pro Arg Asp Gln Val Leu
                435                 440                 445

Ile Phe Ser Asn Glu Ala Thr Asp Arg Leu Lys Gln Leu Ala Ser Ser
                450                 455                 460

Gln Thr Ser Ser Ala Ser Ile Asp Asn Gln Ala Asn Gln Arg Ile Gly
465                 470                 475                 480

Gln Gln Val Asn Thr Val Asp Asp Ser Thr Gly Ala Asp Val Ser Leu
                485                 490                 495

Ala Gln Leu Ala Lys Glu Asp Lys Met Thr Leu Ala Ser Val Ser Asn
                500                 505                 510

Thr Thr Lys Thr Ala Ala Met Val Gly Ala Ser Arg Gln Ala Leu Leu
                515                 520                 525

Ala Pro Val Ile Glu Arg Leu Lys Ala Gln Ala Ala Gln Gly Lys Pro
                530                 535                 540

Val Gln Ile Ala Glu Val Arg Gly Glu Val Lys Tyr Pro Gly Val Tyr
545                 550                 555                 560

Pro Leu Thr Pro Tyr Ser Arg Thr His Asp Leu Ile Met Ala Ala Gly
                565                 570                 575

Gly Phe Asn Glu Gln Ala Asn Val Ile Glu Leu Ser Arg Val Ser Glu
                580                 585                 590

Arg Gly Asn Asp Ile Ala Ile Glu Asn Gln His Leu Asp Leu Ala Thr
                595                 600                 605

Ala Asn Arg Val Thr Gly Ser Pro Leu Val Gln Ser Lys Asp Ser Leu
610                 615                 620

Asn Val Leu Pro His Pro Gln Trp Arg Glu Ala Thr Val Gln Val
625                 630                 635                 640

Phe Gly Glu Val Lys Tyr Pro Gly Thr Tyr Thr Val Arg Arg Gly Glu
                645                 650                 655

Arg Leu Gln Asp Leu Ile Gln Arg Val Gly Gly Ile Thr Pro Tyr Ala
                660                 665                 670

Asn Pro Asn Gly Ala Val Phe Ala Arg Glu Ala Leu Arg Lys Gln Glu
                675                 680                 685
```

```
Ala Glu Arg Ile Ala Met Leu Arg Asp Glu Leu Lys Gln Glu Ile Ala
            690                 695                 700

Thr Met Thr Leu Arg Arg Gln Ser Ser Ile Thr Asn Tyr Thr Ser Ser
705                 710                 715                 720

Pro Ala Asp Ala Met Thr Val Val Asn Gln Leu Glu Asn Ser Lys Ala
                725                 730                 735

Val Gly Arg Met Thr Ile Asp Met Pro Ala Ile Leu Ser Gly Asp Lys
            740                 745                 750

Gln Ala Asp Val Met Leu Gln Asp Gly Asp Lys Leu Tyr Val Pro Ala
        755                 760                 765

Leu Gln Asn Val Val Ser Ile Gln Gly Met Val Gln Phe Pro Ser Ser
770                 775                 780

His Val Tyr Asp Gly Asn Leu Ser Val Asn Asp Tyr Leu Ser Arg Ala
785                 790                 795                 800

Gly Gly Thr Lys Lys Gln Ala Asp Thr Asp Arg Ile Tyr Val Ile Lys
                805                 810                 815

Ala Asn Gly Ser Val Met Leu Pro Gly Asp Ser Trp Phe Gly Gly Arg
            820                 825                 830

Lys Gly Leu Glu Pro Gly Asp Thr Ile Val Val Pro Val Asp Ser Asp
        835                 840                 845

Tyr Leu Asp Asn Leu Ser Ile Met Thr Ser Ala Thr Gln Ile Leu Tyr
850                 855                 860

Gln Leu Gly Val Ala Trp Ser Ala Ile Lys
865                 870

<210> SEQ ID NO 26
<211> LENGTH: 2625
<212> TYPE: DNA
<213> ORGANISM: Aeromonas hydrophila

<400> SEQUENCE: 26
atgaaacata agggattgtt actctcgttg gcattgttcg gggggccgct cttggctgca      60
ccgcaagtga cgcctgagat gattgctaaa tttaaacagc tgtctccagc ccaacagcag     120
gcacttgctg ctcaatatgg tattgactca tcccaattgg gaacgaatac cagccaaagc     180
agtattactc cggtcaatac tgcgcctgtg gctgctccac gtgaagtgga ttacaacaaa     240
gagtctcagc ggccttttgg tcgctggtgt gcgcaagagg gggcgttgca gccttttggt     300
tatagcgttt ttgctgggga acctctgaca gatgcgcccg tggtggatat gccggttgca     360
gacgattatg tgatgggacc gggtgacgaa atccggattc agctctatgg caaggagaat     420
gcgagttata ccctggcgat tggccgtgag ggatttatcg atttcccttc ccttggccct     480
attgccgcca gtggccagac tttccagcaa ctacgtagtg aattggaaaa ccgaatcaaa     540
gagcaaaaaa ttggtgtaga agcgtttatc agttttggcg ctctgcgtac catgcaagtt     600
tttgtgatgg gcgatgctta cgcccccggc gcctataacg tcaatggtat ggctaccgtg     660
acccaggccc tgcaggctgc gggtggtatc gatacgtag ggtcgctgcg taagatccaa     720
gtcaagcgtg cagggcaaaa agtgatcgat gtcgacctct acaaaatgtt ggtatggggc     780
gacactagcc aggatatccg tctgcgctcc ggtgatacgg tgtttatccc tgctaaaagc     840
agtgaagtga gtattgatgg tttggttaaa cgccctgcga cttatgaatt gaccagtccc     900
gcagccctgg ttaatgtgct tgggttggcg gcggcatga aggccgctgc actcaaagaa     960
gtttcggtga cccgttatag tgaaaccggg atgcgggtat ttaacctgaa tttgtcaagg    1020
ccacatgatc gtcagtttgt tgtgcgtgat ggtgacaagg tcacggtcaa accgagcagt    1080
```

-continued

```
accgaatata gccaggcgat tgtggtaaaa ggtgccgtgg ttcgtgaagg cgtcttcagc    1140
ttccagccgg gaatgcggat cagtcgtgtg ttgcaaagtg ccgaccgcga tctgacatcg    1200
gtcactgact tgaattatgc cctgattgtg cgtgaggtgg atgcgcaacg taatatcgag    1260
gtgctgcaat tcaatctagg ccgtgtgttg caaatgccgg gcggggaaga tgacattcgt    1320
ttgcagccgc gggatcaggt gcttattttt agcaatgagg cgaccgaccg gctgaaacag    1380
ctggcgagca gccagacctc ttcggcaagt attgacaatc aggctaatca gcgcattggt    1440
cagcaagtca atacggtaga cgacagtact ggtgctgatg ttagccttgc tcagctggct    1500
aaagaagata agatgacttt ggctagtgta tctaacacga cgaagactgc ggcgatggtt    1560
ggggcctctc gtcaagcttt gctcgctccg gttattgagc gtttgaaagc acaagcagcg    1620
caaggtaaac cggtacagat tgctgaagtt cgcggtgagg ttaaatatcc ggggtctat    1680 cccttgacgc cttatagccg tacccatgat ttaatcatgg ccgcgggtgg gtttaacgaa    1740
caggcgaatg tgattgagtt atctcgcgtg agtgagcgag ggaatgatat tgcaattgaa    1800
aatcagcatc tggatttggc aaccgcaaat cgggtaaccg ttcgccgtt ggtgcaatca     1860 aaagacagct tgaacgtgtt gcctcatccc caatggcgtg aagaagctac cgtacaggtg    1920
tttggcgagg tgaagtatcc gggaacctat acggtgcgtc gtggagaacg tttgcaggat    1980
ttgatccagc gtgtcggtgg tattactccc tatgccaatc cgaatggtgc tgtctttgct    2040
cgtgaagcgc tgcgtaaaca ggaagccgaa cgcatcgcta tgttgcgtga tgaactcaag    2100
caagagattg cgaccatgac actgcgtcgt caatccagca tcaccaacta caccagctct    2160
cctgctgatg cgatgacagt ggttaatcag ctggagaaca gcaaggctgt cggtcgtatg    2220
actatcgata tgccagcgat tttgtctgga gacaagcagg ctgatgtgat gctgcaagat    2280
ggcgacaagc tttatgtgcc tgcgttacaa aatgtggtct ctattcaggg gatggtgcaa    2340
ttcccctctt cccatgttta cgatgggaac ctgagtgtca atgattacct gagtcgtgct    2400
gggggaacca agaagcaggc tgataccgac cgcatctacg tgatcaaggc aaatggtagc    2460
gtgatgctgc caggtgacag ctggtttggt ggtcgcaaag gcctggagcc gggtgatacc    2520
atcgtggtac ctgttgattc tgattatctg gataacctga gcatcatgac ctcagcaacc    2580
cagatcctct atcaattggg tgtcgcgtgg agtgcaatca agtaa                   2625
```

<210> SEQ ID NO 27
<211> LENGTH: 360
<212> TYPE: PRT
<213> ORGANISM: Aeromonas hydrophila

<400> SEQUENCE: 27

```
Met Ser Glu Lys Thr Pro Val Ile Pro Asn Gln Trp Ala Gln Ala His
1               5                   10                  15

Ala Ser Asp Glu Ile Asp Leu Arg Glu Leu Val Leu Val Leu Trp Arg
            20                  25                  30

Gln Lys Val Leu Ile Leu Leu Ile Thr Gly Ala Phe Ala Val Ala Gly
        35                  40                  45

Ile Ile Tyr Ala Met Thr Ala Arg Gln Val Trp Thr Ser Gln Ala Leu
    50                  55                  60

Val Ser Glu Pro Ser Val Ser Gln Val Ala Leu Gln Leu Ala Val
65                  70                  75                  80

Asp Lys Ile Gln Thr Ile Met Ser Ser Asn Gly Ala Pro Pro Ser Ala
                85                  90                  95
```

```
Gly Val Phe Ser Ser Leu Glu Lys Ser Ala Ile Tyr Lys Ser Phe Ile
            100                 105                 110
Ser Ala Phe Asn Ser Met Asn Asn Lys Arg Ala Phe Leu Met Gln Glu
        115                 120                 125
Gly Val Tyr Ala Ala Glu Met Glu Lys Ser Gly Val Ser Asp Lys Arg
    130                 135                 140
Ser Lys Leu Val Leu Met Arg Glu Leu Ala Asp Thr Ile Ser Ala Lys
145                 150                 155                 160
Ala Leu Asp Lys Ile Ser Gln Asp Ile Thr Leu Asn Val Ser Ala Glu
                165                 170                 175
Thr Pro Glu Leu Ala Leu Gln Arg Leu Glu Lys Tyr Ile Glu Phe Val
            180                 185                 190
Gln Gln Gln Gln Leu Lys Arg Lys Asn Ala Glu Leu Gln Ser Ile Leu
        195                 200                 205
Gln Asn Arg Ile Lys Thr Leu Thr Ala Gln Tyr Asp Ser Val Lys Ala
    210                 215                 220
Asp Thr Leu Leu Lys Arg Gln Glu Glu Leu Gln Arg Val Gly Tyr Ser
225                 230                 235                 240
Leu Arg Ile Ser Lys Ala Ala Gly Val Asp Val Pro Leu Glu Arg Ile
                245                 250                 255
Asp Ser Gln Glu Val Phe Asn Ile Gln Leu Gly Ala Lys Gly Leu Ala
            260                 265                 270
Glu Lys Val Lys Ile Leu Asn Glu Ile Lys Val Pro Glu Leu Leu Asn
        275                 280                 285
Pro Glu Leu Gly Ile Ile Arg Leu Gln Leu Ser Ser Leu Lys Ala Leu
    290                 295                 300
Lys Phe Glu Asn Ala Asp Phe Gln Ser Phe Asn Ile Ile Asp Ser Pro
305                 310                 315                 320
Glu Glu Pro Phe Thr Arg Asp Gln Pro Lys Arg Pro Leu Ile Val Val
                325                 330                 335
Leu Ala Thr Leu Leu Gly Gly Met Leu Gly Val Thr Ile Val Leu Val
            340                 345                 350
Arg His Ala Phe Arg Arg Ala Asp
            355                 360

<210> SEQ ID NO 28
<211> LENGTH: 1083
<212> TYPE: DNA
<213> ORGANISM: Aeromonas hydrophila

<400> SEQUENCE: 28
atgagcgaga aaacgccggt tattcctaac cagtgggcgc aagcacacgc atcagatgag      60
atagatctac gagagctggt gttggtgctg tggcgtcaaa agtattgat  attgttgata     120 accggtgcat tgctgttgc  tgggattatt tacgccatga cagcgcgtca ggtatggact     180
agtcaggccc ttgtttcgga gccgtcagtt tctcaagtag cggcactaca attggctgtg     240
gataaaatac aaacaataat gtccagtaac ggagctcctc catcggcagg tgtgttttcc     300
tcgcttgaga atccgctat  atacaaaagt tttatctcag cttttaatag catgaataat     360
aagagagcgt ttttgatgca agaaggtgtc tacgcagccg agatgaaaaa tcaggagta      420 tccgataagc gcagtaaaact tgtgttaatg agggagttag ctgataccat atctgctaag     480
gctctggata aataagcca  agatataact ttaaatgtct ctgctgaaac gcctgagctt     540
gctctgcaac ggctagaaaa gtatattgaa tttgttcaac agcagcaact aaaacgcaaa     600
```

```
aatgcagagt tacaatctat attgcaaaac agaataaaaa cgttgactgc acaatatgat    660
agtgtcaagg ctgatacttt actaaaaagg caggaagaac ttcagcgggt tggatatagt    720
ttgcgtatca gtaaggcggc tggtgtagat gtgcctcttg aacggattga tagtcaagag    780
gttttcaata tccaattagg ggcgaaaggc ttggctgaaa aagtgaaaat attaaatgag    840
attaaagttc ctgaacttct taatcctgaa ttagggataa ttcgtttgca attaagtagt    900
ttaaaagcgt tgaagtttga aaatgctgac tttcagtctt ttaatattat cgattcacca    960
gaggaaccgt ttacccgtga ccagcccaaa cgcccgttaa ttgttgtatt ggctaccctg   1020
ctggggggca tgttgggggt tacgattgtg ctggtacggc atgcctttcg tcgagcagat   1080
tga                                                                 1083
```

<210> SEQ ID NO 29
<211> LENGTH: 503
<212> TYPE: PRT
<213> ORGANISM: Aeromonas hydrophila

<400> SEQUENCE: 29

```
Met Asp Ile Val Gln Asn Tyr Ile Gly Gly Ala Ile Thr Ala Ser Leu
1               5                   10                  15

Ser Glu Arg Ile Ala Pro Ile Phe Asn Pro Ala Gln Gly Glu Pro Ile
            20                  25                  30

Arg Gln Val Phe Leu Ser Thr Ala Asp Glu Val Arg Gln Ala Ile Ala
        35                  40                  45

Val Ala His Ala Ala Phe Pro Ala Trp Ser His Thr Pro Pro Leu Arg
    50                  55                  60

Arg Ala Arg Ile Leu Phe Gln Phe Lys Ala Leu Leu Glu Thr Lys Arg
65                  70                  75                  80

Asp Glu Leu Ala Arg Leu Ile Ser Glu Glu His Gly Lys Val Phe Ser
                85                  90                  95

Asp Ala Gln Gly Glu Leu Thr Arg Gly Ile Glu Val Val Glu Phe Ala
            100                 105                 110

Cys Gly Ile Thr His Leu Gln Lys Gly Glu His Ser Ala Asn Val Gly
        115                 120                 125

Thr Gly Val Asp Cys His Ser Leu Met Gln Pro Leu Gly Val Cys Thr
    130                 135                 140

Gly Ile Thr Pro Phe Asn Phe Pro Ala Met Val Pro Met Trp Met Phe
145                 150                 155                 160

Pro Ile Ala Leu Ala Thr Gly Asn Thr Phe Val Leu Lys Pro Ser Glu
                165                 170                 175

Lys Asn Pro Ser Leu Ala Leu Arg Leu Ala Gln Leu Leu Gln Glu Ala
            180                 185                 190

Gly Leu Pro Asp Gly Val Phe Asn Val Val Asn Gly Asp Lys Glu Ala
        195                 200                 205

Val Asp Val Leu Leu Thr Asp Glu Arg Val Gln Ala Val Ser Phe Val
    210                 215                 220

Gly Ser Thr Pro Ile Ala Glu Tyr Ile Tyr Ser Val Ala Ser Ala His
225                 230                 235                 240

Gly Lys Arg Cys Gln Ala Leu Gly Gly Ala Lys Asn His Cys Ile Val
                245                 250                 255

Met Pro Asp Ala Asp Ile Glu Gln Thr Leu Ser Ala Ile Met Gly Ala
            260                 265                 270

Ala Tyr Gly Ala Ala Gly Glu Arg Cys Met Ala Leu Ser Val Ala Val
        275                 280                 285
```

```
Ala Val Gly Asp Glu Val Ala Asp Asn Leu Val Ser Gly Ile Lys Asn
            290                 295                 300
Arg Ile Ala Gln Met Arg Val Gly Pro Gly Ile Thr Glu Gly Arg Glu
305                 310                 315                 320
Asn Asp Met Gly Pro Val Ile Ser Ala Gln His Arg Ala Lys Ile Ile
                325                 330                 335
Glu Tyr Ile Asp Gln Gly Val Glu Gln Gly Ala Thr Leu Cys Ile Asp
                340                 345                 350
Gly Arg Asn Phe Thr Val Pro Thr His Lys Gln Gly Phe Phe Val Gly
            355                 360                 365
Pro Thr Leu Phe Asp Arg Val Thr Pro Glu Met Ser Ile Tyr Gln Glu
        370                 375                 380
Glu Ile Phe Gly Pro Val Leu Cys Ile Val Arg Ala Pro Asp Tyr Arg
385                 390                 395                 400
Thr Ala Val Thr Leu Ile Asn Arg His Gln Tyr Gly Asn Gly Thr Ala
                405                 410                 415
Ile Phe Thr Arg Asp Gly Asp Thr Ala Arg Gln Phe Ser Glu Glu Val
                420                 425                 430
Gln Ala Gly Met Val Gly Ile Asn Val Pro Ile Pro Val Pro Met Ala
            435                 440                 445
Phe His Ser Phe Gly Gly Trp Lys Arg Ser Ile Phe Gly Pro Leu Asn
        450                 455                 460
Val His Gly Asn Asp Gly Val Arg Phe Tyr Thr Arg Met Lys Thr Ile
465                 470                 475                 480
Thr Ser Arg Trp Pro Thr Ser Val Arg Leu Glu Gln His Thr Gly Ser
                485                 490                 495
Phe Thr Met Pro Thr Met Gly
            500

<210> SEQ ID NO 30
<211> LENGTH: 1512
<212> TYPE: DNA
<213> ORGANISM: Aeromonas hydrophila

<400> SEQUENCE: 30
atggacatcg tacagaatta catcggtggc gccatcaccg ccagtctcag cgagcgtatt      60
gcccccatct tcaatccggc gcagggcgaa ccgatacgtc aggtatttct gagcacggcc     120
gatgaagttc gccaggccat tgccgttgcc cacgcggcct ccctgcatg gtcgcacaca     180 cctccactgc gtcgagccag aatcctgttt cagttcaaag cattgctgga aaccaaacgg     240
gatgagttag cccgcctcat cagcgaagag catggcaagg tattctctga tgctcagggt     300
gaactgaccc gtggtataga agtagtgaaa tttgcctgtg cattactca tctgcaaaaa     360 ggcgaacact ccgccaacgt cggcaccggt gtcgactgcc actctctgat gcaaccctc     420 ggtgtatgca ccgggattac accattcaac tttccggcca tggtacccat gtggatgttc     480
cccatcgctc tggctaccgg taacaccttc gtactcaagc cttcagagaa gaatccctca     540
ttggcgttac gattggcgca gttgcttcag gaggcagggc tgccggatgg gtatttaac      600 gtagtcaatg tgacaaaga ggcagtggat gtactgctga ccgatgaacg agtccaggcg     660
gtgagctttg tgggctccac tcccatagcc gaatacatat attccgttgc atcagcgcat     720
ggcaagcgtt gccaggcgct gggggcgcc aaaaatcact gcatcgtgat gccagatgca     780
gatatagaac agactctttc agccatcatg ggcgctgcct acggtgcagc cggtgaacgc     840
```

```
tgcatggcgc tatctgttgc cgtcgcagtg ggcgatgaag tggctgataa cctggtttcc    900
ggaatcaaaa atcgcattgc ccagatgcga gttgggccag ggatcaccga aggccgggag    960
aatgatatgg gtccggtgat ttccgcccag catagagcca aaatcattga gtacattgat   1020
cagggggtag aacaggggc aacgctttgc attgatggcc gcaattttac cgttcccact   1080
cacaaacagg gcttcttcgt tggcccaacg ctattcgacc gggtcacccc ggagatgagt   1140
atctatcagg aagagatttt cggcccagta ttgtgcatag tccgcgctcc tgactaccgc   1200
accgcagtca cattaatcaa tcgccaccaa tacggtaacg gcaccgccat cttcacccgc   1260
gacggtgata cagcccgtca gtttagcgaa gaagtacagg cagggatggt tggaatcaat   1320
gtgcctatcc cggtgccaat ggcattccat agcttcgggg gatggaaacg ctccatcttt   1380
ggaccattga atgtacacgg taacgatggt gttcggtttt acacccgaat gaagaccatc   1440
acgagccgct ggcccactag cgtacgactt gaacagcata ctggcagctt taccatgccg   1500
acgatgggat aa                                                      1512
```

```

<210> SEQ ID NO 31
<211> LENGTH: 644
<212> TYPE: PRT
<213> ORGANISM: Aeromonas hydrophila

<400> SEQUENCE: 31

Met Gln Gln Ile Arg Met Thr Met Ala Gln Ala Leu Val Lys Phe Leu
1               5                   10                  15

Asp Gln Gln Phe Val Glu Ile Asp Gly Ala Gln His Lys Phe Val His
            20                  25                  30

Gly Ile Phe Thr Ile Phe Gly His Gly Asn Val Leu Gly Leu Gly Gln
        35                  40                  45

Ala Leu Glu Gln Asp Ala Gly Gly Leu Lys Val Tyr Gln Gly Cys Asn
    50                  55                  60

Glu Gln Gly Met Ala His Ile Ala Leu Gly Phe Thr Lys Gln His Lys
65                  70                  75                  80

Arg Lys Arg Ile Cys Ala Val Thr Ser Ser Val Gly Pro Gly Ala Ala
                85                  90                  95

Asn Met Val Thr Ala Ala Ala Thr Ala Thr Ala Asn Arg Leu Pro Leu
            100                 105                 110

Leu Leu Leu Pro Gly Asp Leu Phe Ala Ser Arg Gln Pro Asp Pro Val
        115                 120                 125

Leu Gln Gln Val Glu Gln Tyr His Asp Ala Ser Ile Ser Thr Asn Asp
    130                 135                 140

Cys Phe Arg Pro Val Ser Arg Tyr Trp Asp Arg Ile Ser Arg Pro Glu
145                 150                 155                 160

Gln Leu Met Ser Ala Leu Ile Asn Ala Met Arg Val Leu Thr Asp Pro
                165                 170                 175

Ala Asp Thr Gly Ala Val Thr Leu Cys Leu Pro Gln Asp Val Gln Gly
            180                 185                 190

Glu Ala Tyr Asp Tyr Pro Val Ser Phe Phe Ala Arg Arg Val His Arg
        195                 200                 205

Ile Glu Arg Arg Pro Pro Ser Glu Ala Met Leu Ala Asp Ala Val Ser
    210                 215                 220

Leu Ile Glu Gly Lys Arg Lys Pro Leu Leu Val Cys Gly Gly Gly Val
225                 230                 235                 240

Arg Tyr Ser Glu Ala His Gly Ala Leu Arg Asp Phe Val Glu Arg Phe
                245                 250                 255
```

```
Asn Ile Pro Phe Ala Glu Thr Gln Ala Gly Lys Gly Ala Ile Glu Ala
            260                 265                 270

Glu His Ser Leu Asn Val Gly Gly Leu Gly Thr Thr Gly Cys Leu Ala
            275                 280                 285

Ala Asn Arg Leu Ala Ala Glu Ala Asp Leu Ile Ile Gly Val Gly Thr
            290                 295                 300

Arg Phe Thr Asp Phe Thr Thr Ala Ser Lys Ser Leu Phe Ser His Pro
305                 310                 315                 320

Glu Val Gln Phe Leu Thr Ile Asn Val Ala Ser Phe Asp Ala His Lys
            325                 330                 335

Leu Asp Ala Val Pro Val Ala Asp Ala Arg Val Ala Leu Glu Ile
            340                 345                 350

Leu Gly Glu Gln Leu Gly Ala Arg Ala Tyr Arg Cys Asp Tyr Glu Gly
            355                 360                 365

Glu Ile Ile Ala Ala Arg Ala Glu Trp Glu Ser Glu Trp Gln Arg Leu
            370                 375                 380

Ala Asn Ile Gln Val Asp Lys Asn Phe Val Pro Glu Val Ala Gly Gln
385                 390                 395                 400

Leu Asp Ala Leu Leu Pro Glu Tyr Met Asp Ser Leu Ala Thr Arg Leu
            405                 410                 415

Thr Gln Thr Arg Val Leu Gly Leu Leu Asp Lys Trp Leu Glu Pro Asp
            420                 425                 430

Ala Ile Val Val Gly Ala Ala Gly Ser Leu Pro Gly Asp Leu Gln Arg
            435                 440                 445

Met Trp Arg Pro Arg His Pro Asp Thr Tyr His Leu Glu Tyr Gly Tyr
            450                 455                 460

Ser Cys Met Gly Tyr Glu Ile Ala Ala Ala Ile Gly Ala Arg Ile Ala
465                 470                 475                 480

Ser Pro Ala Gln Pro Val Tyr Ala Phe Val Gly Asp Gly Ser Tyr Leu
            485                 490                 495

Met Leu His Thr Glu Leu Gln Thr Ala Val Gln Glu Gly Leu Lys Ile
            500                 505                 510

Val Val Leu Leu Phe Asp Asn Ala Gly Phe Gly Cys Ile Asn Asn Leu
            515                 520                 525

Gln Met Gly Gln Gly Met Gly Ser Phe Gly Thr Glu Asn Arg Tyr Arg
            530                 535                 540

Asn Pro Asp Ser Gly Val Leu Asn Gly Pro Leu Val Arg Val Asp Phe
545                 550                 555                 560

Ala Lys Asn Ala Glu Ser Tyr Gly Cys Thr Ser Tyr Arg Val His Asp
            565                 570                 575

Glu Val Glu Leu Glu Ala Ala Leu Gly Ala Ala Arg Asp Gln Gly
            580                 585                 590

Pro Val Leu Ile Asp Ile Lys Val Leu Pro Lys Thr Met Thr His Ser
            595                 600                 605

Tyr Glu Ala Trp Trp His Thr Gly Thr Ala Gln Ile Ala Asp Lys Pro
            610                 615                 620

Glu Ile Glu Ala Ala Val Ala Ile Arg Asp Met Leu Ala Thr Arg
625                 630                 635                 640

Ala Arg Gln Tyr

<210> SEQ ID NO 32
<211> LENGTH: 1935
<212> TYPE: DNA
```

<213> ORGANISM: Aeromonas hydrophila

<400> SEQUENCE: 32

```
atgcagcaga tcagaatgac gatggcccag gcgctggtga agtttcttga tcagcagttc      60
gtggaaattg atggggcaca acataagttt gtacatggca tttttaccat ctttggccat     120
gggaatgtgt tggggttggg tcaggcgcta gagcaagatg caggtggatt gaaggtttat     180
cagggggtgta acgagcaggg gatggctcat atagccctcg ggtttaccaa acagcacaaa    240
cgcaagcgga tctgtgctgt cacctcttcc gttgggccgg gggctgccaa tatggtgact     300
gcggctgcta ctgctaccgc taatcgcctt cctttgttgc tattgcccgg agatctgttt     360
gccagtcgcc agcctgatcc tgtgttgcaa caggtagagc agtaccatga tgccagcatt     420
agtactaatg attgctttcg tcccgtatct cgttattggg acagaatctc tcgaccggag     480
cagttgatga gtgccctgat caatgccatg cgggtgctca cggatcctgc cgataccggt     540
gccgtcacgc tctgtttgcc tcaggatgtg caaggcgagg cctatgatta ccccgtttct     600
ttctttgcca ggcgagtaca ccggatcgaa cgccgccctc ccagtgaggc catgttggcc     660
gatgcggttt ccctgattga aggcaagcgt aaaccgctgc tggtatgtgg aggtggggtg     720
cgttatagcg aagctcatgg cgcgctgcgt gactttgtcg agcgcttcaa tattcctttt     780
gccgagactc aggctggtaa gggggccata gaggcggagc attcgctcaa tgttgggggg     840
cttggcacta ccggttgcct ggctgctaac cgcctggcag ccgaggcgga tttgatcatt     900
ggggtgggta cccgtttcac cgatttcaca acagcttcca agtcattgtt tagtcatcct     960
gaggtacaat ttttgaccat aaatgtcgcc agcttcgatg ctcacaagct ggatgccgtg    1020
cctgtggttg cggatgctcg ggtggctctg gagatacttg gtgagcagct tggtgctcgg    1080
gcttatcgct gcgattatga aggggaaatt attgccgccc gtgccgagtg gaaaagtgaa    1140
tggcagcggt tagccaatat tcaggttgac aagaattttg tgccagaagt cgctgggcaa    1200
cttgatgctt tactgccgga gtatatggat agcctggcta ccagactgac tcaaactcgg    1260
gtgttgggat tgctggacaa gtggcttgag ccagatgcaa ttgtcgtggg ggctgcaggt    1320
tctttgcccg tgatctgca gcgcatgtgg cggccacggc acccagatac ctatcatctc    1380
gagtatggat attcctgcat gggttatgag attgcagccg ctatcggggc ccgcattgca    1440
tcaccagcac aacctgtcta tgcgtttgtc ggtgacggct cctacctgat gctgcacaca    1500
gaactgcaga cggccgtaca agagggtctg aagatcgtgg tcttgttgtt cgacaatgca    1560
ggatttggtt gcattaataa cctgcaaatg gggcaaggga tgggaagttt tggtaccgaa    1620
aaccgatatc gaaatccgga tagcggtgtt ttgaatggtc ctctggtacg agttgatttt    1680
gccaagaacg cagagagtta cggttgtacc agctatcggg tgcacgacga ggtggaattg    1740
gaggctgcac tgggggcggc agctcgtgac caaggaccgg tactgatcga tatcaaggtg    1800
ctgccaaaaa ccatgaccca tagttacgaa gcgtggtggc atacaggtac tgctcagata    1860
gcagacaaac ccgaaatcga ggctgcggcg gtcgcgattc gtgacatgtt ggcgacccga    1920
gcccgccaat actga                                                    1935
```

<210> SEQ ID NO 33
<211> LENGTH: 328
<212> TYPE: PRT
<213> ORGANISM: Aeromonas hydrophila

<400> SEQUENCE: 33

```
Met Phe Asn Ile Ala Leu Phe Gly Ala Gly Arg Ile Gly Gln Val His
1               5                   10                  15

Ala Val Asn Ile Ala Asp His Asn Glu Thr Arg Leu Tyr Ser Val Ile
            20                  25                  30

Asp Pro His Gln Glu Gly Ala Leu Thr Leu Ala Ala Lys His Gly Ala
        35                  40                  45

Lys Val Gln Ser Cys Glu Glu Ala Met Val Asp Pro Gln Ile His Gly
    50                  55                  60

Val Leu Ile Ala Ser Thr Asp Thr His Ala Asp Leu Ile Glu His
65                  70                  75                  80

Ala Ala Arg Ala Gly Lys Thr Ile Phe Cys Glu Lys Pro Val His Leu
                85                  90                  95

Asp Leu Ala Arg Val Arg Asp Cys Leu Ala Thr Val Ala Ala Cys Asn
            100                 105                 110

Val Pro Leu Phe Val Gly Phe Asn Arg Arg Phe Asp Pro Gln Phe Arg
        115                 120                 125

Arg Val Lys Thr Asp Ala Gln Ala Gly Cys Ile Gly Lys Pro Glu Ser
    130                 135                 140

Leu Leu Ile Ile Ser Arg Asp Pro Ser Pro Pro Ala Glu Tyr Val
145                 150                 155                 160

Arg Val Ser Gly Gly Met Phe Arg Asp Met Thr Ile His Asp Phe Asp
                165                 170                 175

Met Ala Arg Phe Ile Met Gly Glu Glu Pro Val Ser Val Tyr Ala Gln
            180                 185                 190

Gly Ser Asn Leu Val Asp Pro Ala Ile Gly Glu Ala Gly Asp Ile Asp
        195                 200                 205

Thr Ala Phe Ile Val Leu Arg Tyr Ala Ser Gly Ala Met Ala Thr Ile
    210                 215                 220

Val Asn Ser Arg Arg Ser Ser Tyr Gly Tyr Asp Gln Arg Leu Glu Leu
225                 230                 235                 240

His Gly Ser Glu Gly Leu Leu Cys Ala Gly Asn Ile Leu Glu Asn Gln
                245                 250                 255

Val Gln His Tyr Gly Lys Gln Gly Cys Thr Ser Ala Leu Pro Glu His
            260                 265                 270

Phe Phe Leu Gln Arg Tyr Lys Ser Ala Tyr Ala Glu Trp Glu His
        275                 280                 285

Phe Val Ala Val Leu Arg Gly Glu Ala Val Pro Asp Cys Ser Gly Asp
    290                 295                 300

Asp Gly Glu Arg Ala Leu Tyr Leu Ala Asp Lys Ala Leu Glu Ser Leu
305                 310                 315                 320

Arg Ser Gln Arg Glu Ile Val Leu
                325

<210> SEQ ID NO 34
<211> LENGTH: 987
<212> TYPE: DNA
<213> ORGANISM: Aeromonas hydrophila

<400> SEQUENCE: 34
atgtttaata tcgcgttatt tggtgccggt cggattggtc aggttcatgc ggtcaacatc      60
gcggatcaca tgaaactcg tctttattct gtcatcgacc ctcatcagga gggggctttg     120
actttggccg ccaagcacgg tgccaaggta caaagttgtg aagaagcaat ggttgatccc     180
cagattcatg gggtgctgat tgcctcggcg acggataccc atgccgatct cattgaacat     240
```

```
gcggcacgtg ctggaaaaac aatcttttgc gaaaaaccgg tgcatctgga tttagctcgg      300
gtccgtgatt gccttgcgac ggtagcagct tgcaacgttc ctctctttgt tggtttcaac      360
cgccgctttg acccacagtt ccgccgcgtg aaaaccgacg cccaggccgg tgtatcggc       420 aaaccggaat cgctgctgat catctcccgc gatccgtctc caccaccggc ggagtatgtc      480
cgcgtctctg gcggcatgtt ccgcgatatg accattcacg actttgatat ggcgcgcttc      540
atcatgggtg aagagccggt gtcggtgtat gcccagggca gcaacctggt ggatccggca      600
attggcgagg cgggagacat cgacaccgct tttattgttc tgagatatgc ctccggcgca      660
atggcgacca tcgttaacag ccgccgctcc tcttacggct acgaccagcg tctggagcta      720
catggctccg aagggctgct ctgcgcgggc aatattcttg aaaatcaggt gcagcactac      780
ggaaaacagg gctgcaccag cgcgctgccg aacacttct tcctgcaacg ctacaaatcc       840
gcttacgccg cggaatggga acactttgtt gcggtattgc gcggcgaagc ggtgcctgac      900
tgcagcggcg atgatggtga acgtgcgctg tacctcgcgg ataaagcgct ggagtcgctg      960
cgtagccagc gcgagattgt cctctaa                                         987
```

<210> SEQ ID NO 35
<211> LENGTH: 377
<212> TYPE: PRT
<213> ORGANISM: Aeromonas hydrophila

<400> SEQUENCE: 35

```
Met Lys Glu Val Cys Ile Gly Leu Ile Gly Thr Gly Tyr Ile Gly Lys
1               5                   10                  15

Ala His Ala Ile Ala Tyr Ala Gln Ala Pro Thr Val Phe Asn Leu Arg
            20                  25                  30

Gly Lys Leu Val Arg Glu Met Val Ala Glu Val Asn Pro Thr Leu Ala
        35                  40                  45

Ala Ala Arg Ala Gln Ala Phe Gly Phe Asn Arg Ser Thr Gly Asp Trp
    50                  55                  60

Arg Ala Leu Val Ala Asp Pro Ala Ile Asp Val Val Asp Ile Cys Ser
65                  70                  75                  80

Pro Asn His Leu His Lys Glu Met Ala Leu Glu Ala Ile Arg His Gly
                85                  90                  95

Lys His Val Tyr Ser Glu Lys Pro Leu Ala Leu Asn Ala His Asp Ala
            100                 105                 110

Arg Glu Met Val Glu Ala Ala Lys Arg Ala Gly Val Lys Thr Leu Val
        115                 120                 125

Gly Phe Asn Tyr Met Lys Asn Pro Thr Ala Gln Leu Ala Lys Glu Ile
    130                 135                 140

Ile Ala Arg Gly Glu Ile Gly Glu Val Ile His Phe Tyr Gly Thr His
145                 150                 155                 160

Asn Glu Asp Tyr Met Ala Asp Pro Leu Ser Pro Ile His Trp His Cys
                165                 170                 175

Phe Lys Glu Thr Ala Gly Leu Gly Ala Leu Gly Asp Leu Ala Ala His
            180                 185                 190

Ile Ile Asn Met Ala Gln Tyr Leu Val Gly Glu Ile Glu Gln Val Cys
        195                 200                 205

Gly Asp Leu Lys Ile Val Pro Glu Arg Pro Ala Lys Ala Gly Ser
    210                 215                 220

Ser Glu Met Ile Ala Val Glu Asn Glu Asp Gln Ala His Ala Met Val
225                 230                 235                 240
```

```
Arg Phe Ala Gly Gly Ala Gln Gly Val Ile Glu Thr Ser Arg Val Ala
                245                 250                 255

Cys Gly Arg Lys Met Gly Leu Ser Tyr Val Ile Thr Gly Thr Lys Gly
            260                 265                 270

Ala Ile Ser Phe Thr Gln Glu Arg Met Ala Glu Leu Lys Leu Tyr Leu
        275                 280                 285

His Asp Asp Pro Val Asn Arg Gln Gly Phe Arg Thr Leu Leu Val Gly
    290                 295                 300

Pro Ala His Pro Asp Tyr Gly Ala Phe Cys Met Gly Ala Gly His Gly
305                 310                 315                 320

Ile Gly Phe Asn Asp Gln Lys Thr Val Glu Val Arg Asp Leu Val Asp
                325                 330                 335

Gly Ile Ala Ala Asp Ala Pro Met Trp Pro Asp Phe Glu Glu Gly Trp
            340                 345                 350

Lys Val Ser Arg Val Leu Asp Ala Ile Ala Leu Ser His Gln Gln Gly
        355                 360                 365

Arg Trp Leu Asn Val Asn Asp Ile Val
    370                 375

<210> SEQ ID NO 36
<211> LENGTH: 1134
<212> TYPE: DNA
<213> ORGANISM: Aeromonas hydrophila

<400> SEQUENCE: 36
atgaaagagg tttgtattgg attaattggc accgggtata tcggcaaggc gcatgccatc      60
gcctatgccc aggccccgac ggtcttcaac ctgcgcggca agctggtgcg tgagatggtg     120
gccgaggtaa acccgacgct ggcggcagcg cgcgcgcagg cgtttggctt taaccgttca     180
acgggagact ggcgggcgct ggtggccgac ccggccattg atgtggtgga tatttgctcg     240
cccaaccatc tgcataaaga gatggcgctg gaagcgatcc gccacggcaa gcacgtttac     300
tcggaaaaac cgctggcgct gaacgcccac gacgcgcgtg agatggtcga ggccgcgaag     360
cgggcagggg tgaaaaccct ggtggggttc aactacatga aaaacccgac ggcgcagctg     420
gcgaaagaga ttatcgcccg cggcgaaata ggcgaggtga tccacttcta cggcacccac     480
aacgaagact atatggctga cccgcttttcg cccattcact ggcactgctt caaagagact     540
gccgggctgg gggcgctggg cgatctggcg gcgcatatca tcaatatggc gcagtacctg     600
gtgggggaga ttgagcaggt ttgcggcgac ctgaagattg tggtcccgga acgtccggcg     660
aaggccgggt cgtcggagat gattgccgtc gaaaacgaag atcaggccca cgcaatggtg     720
cgtttcgcgg gcggggcgca gggtgtgatt gaaacctccc gcgtcgcctg cggccgcaag     780
atggggttgt catatgtgat caccggaacg aaaggcgcca tcagcttcac tcaggagcgc     840
atggccgagc tgaagctcta tctgcatgac gatccggtca accgtcaggg attccgcacg     900
ctgctggtcg gcccggcaca cccggactac ggcgcgttct gtatgggcgc aggccacggt     960
attggcttta acgatcaaaa aacggtggaa gtgcgtgacc tggtggatgg cattgccgcc    1020
gacgcaccga tgtggccgga ctttgaagag ggctggaagg tctcgcgcgt gctggacgcc    1080
atcgcactct cacaccagca aggccgctgg ctgaacgtga atgacattgt ctga          1134

<210> SEQ ID NO 37
<211> LENGTH: 634
<212> TYPE: PRT
<213> ORGANISM: Aeromonas hydrophila
```

```
<400> SEQUENCE: 37

Met Glu Lys Gln Phe Asp Val Ile Cys Met Gly Arg Val Ala Val Asp
1               5                   10                  15

Leu Tyr Ser Gln Gln Ile Gly Ala Arg Leu Glu Asp Val Ser Ser Phe
            20                  25                  30

Ala Lys Tyr Leu Gly Gly Ser Gly Asn Val Ala Tyr Gly Thr Ala
        35                  40                  45

Arg Gln Gly Leu Arg Ser Ser Met Leu Ala Arg Val Gly Asp Glu His
    50                  55                  60

Met Gly Arg Phe Leu Arg Glu Glu Leu Asn Gln Val Gly Cys Asp Thr
65                  70                  75                  80

Ser His Leu Ile Thr Asp Lys Thr Arg Leu Thr Ala Leu Val Leu Leu
                85                  90                  95

Gly Ile Lys Asp Arg Asp Thr Phe Pro Leu Ile Phe Tyr Arg Asp Asn
            100                 105                 110

Cys Ala Asp Met Ala Ile Thr Ala Ser Asp Val Asp Glu Asn Tyr Ile
        115                 120                 125

Ala Ser Ala Arg Cys Leu Ala Ile Thr Gly Thr His Leu Ser His Pro
130                 135                 140

Gln Thr Arg Glu Ala Val Leu Thr Ala Leu Gly Tyr Ala Arg Arg His
145                 150                 155                 160

Gly Val Arg Thr Val Leu Asp Ile Asp Tyr Arg Pro Val Leu Trp Gly
                165                 170                 175

Leu Thr Ser Leu Gly Asp Gly Glu Thr Arg Phe Ile Ala Ala Asp Gln
            180                 185                 190

Val Thr Arg Glu Leu Gln Glu Val Leu His Leu Phe Asp Val Ile Val
    195                 200                 205

Gly Thr Glu Glu Glu Phe His Ile Ala Gly Gly Ser Thr Asp Thr Leu
210                 215                 220

Leu Ala Leu Ala Gln Val Arg Ala Val Ser Gln Ala Thr Leu Val Cys
225                 230                 235                 240

Lys Arg Gly Ala Leu Gly Cys Ser Val Tyr Thr Gly Ala Ile Pro Ala
                245                 250                 255

Arg Leu Asp Asp Gly Leu Thr Val Thr Gly Val Arg Val Glu Val Leu
            260                 265                 270

Asn Val Leu Gly Ala Gly Asp Ala Phe Met Ser Gly Leu Leu Arg Gly
        275                 280                 285

Tyr Leu Asn Asp Glu Gly Trp Glu Gln Ala Cys Arg Tyr Ala Asn Ala
    290                 295                 300

Cys Gly Ala Leu Val Val Ser Arg His Gly Cys Ala Pro Ala Met Pro
305                 310                 315                 320

Ser Lys Ile Glu Leu Asp Asp Tyr Leu Ala Arg Ala Ala Leu Val Pro
                325                 330                 335

Arg Pro Asp Leu Asp Pro Arg Leu Asn His Leu His Arg Val Thr Thr
            340                 345                 350

Arg Arg Arg Glu Trp Pro Glu Leu Cys Val Met Ala Phe Asp His Arg
        355                 360                 365

Ser Gln Leu Glu Asp Met Ala Leu Gln Cys Gly Ala Ser Leu Lys Arg
370                 375                 380

Ile Pro Ala Leu Lys Gln Leu Ile Leu Gln Ala Ser Arg Glu Ala Ala
385                 390                 395                 400

Ser Arg Ala Gly Leu Ala Gly Lys Ala Gly Leu Leu Cys Asp Gly Thr
                405                 410                 415
```

```
Phe Gly Gln Asp Ala Leu Asn Ala Ile Thr Gly Glu Gly Trp Trp Ile
            420                 425                 430

Gly Arg Pro Ile Glu Leu Pro Gly Ser Arg Pro Leu Glu Met Glu His
        435                 440                 445

Gly Asn Ile Gly Thr Gln Leu Ile Ser Trp Pro Gln Glu His Val Val
    450                 455                 460

Lys Cys Leu Val Phe Phe His Pro Glu Asp Ala His Gly Leu Arg Leu
465                 470                 475                 480

Glu Gln Glu Gln Lys Ile Ala Glu Val Tyr His Ala Cys Cys Gln Ser
                485                 490                 495

Gly His Glu Leu Leu Glu Val Ile Leu Pro Ala Ser Met Pro Arg
            500                 505                 510

Ser Asp Glu Leu Tyr Leu Arg Ala Ile Ser Arg Phe Tyr Asn Leu Gly
        515                 520                 525

Ile Tyr Pro Asp Trp Trp Lys Leu Pro Pro Leu Thr Ser Asp Gly Trp
    530                 535                 540

Thr Ala Leu Ser Glu Ile Ile Pro Arg Arg Asp Pro His Cys Arg Gly
545                 550                 555                 560

Val Val Ile Leu Gly Leu Asp Ala Pro Ala Glu Gln Leu Arg Ala Gly
                565                 570                 575

Phe Asn Ala Ala Ala Gly His Glu Leu Val Lys Gly Phe Ala Val Gly
            580                 585                 590

Arg Thr Leu Phe Gly Glu Ala Ser Arg Ala Trp Leu Lys His Asp Ile
        595                 600                 605

Asp Asp Ala Gln Leu Val Ala Arg Ile Arg Asp Asn Tyr Leu Gln Leu
    610                 615                 620

Ile Ala Trp Trp Arg Glu Arg Gly His Ala
625                 630

<210> SEQ ID NO 38
<211> LENGTH: 1905
<212> TYPE: DNA
<213> ORGANISM: Aeromonas hydrophila

<400> SEQUENCE: 38
gtggaaaagc agtttgatgt gatatgcatg ggccgcgtgg cggtagacct ctacagtcag      60
cagattggtg cgcggctgga ggatgtgtcg agctttgcca atatctcgg cggctcgtcc     120 ggcaacgtgg cgtacggcac ggcgcggcag gggttgcgtt cgtcgatgct ggcccgcgtg     180
ggcgacgagc atatgggccg gttcctgcgc gaagagctaa atcaggtggg ctgtgatacc     240
agccatctga tcaccgataa aacacgcctc acggcgctgg tactactcgg cattaaagac     300
cgggacacct ttcctctgat tttttatcgc gataactgcg cggatatggc cattacggcc     360
agcgatgtgg acgaaaacta catcgcctcc gcacggtgtc ttgccatcac cgggactcac     420
ctttctcatc gcagacccg cgaggcggtg ctgacggcgc tggctacgc ccgtcgtcac     480 ggcgtgcgca cggtgctgga cattgattac cgcccggtgc tgtggggct gacctcctta     540 ggcgacggcg aaacgcgctt tatcgctgcc gatcaggtca cccgtgaact tcaggaggtg     600
ctgcacctct tcgacgtcat tgtcggcacc gaggaggagt tcacattgc gggcggcagc     660 acggacaccc tgctggcgct ggcgcaggtg cgtgccgtga gccaggccac gctggtctgc     720
aaacgcggcg cgcttggctg ttcggtctat accggtgcca ttccggcccg tctggatgac     780
ggcctgacgg tgaccggcgt gcgcgtggag gtgctgaacg tcctcggcgc gggcgatgcc     840
```

```
tttatgtccg gcctgctacg cggctacctg aacgacgagg gctgggagca ggcgtgccgc    900
tatgccaacg cctgcggcgc gctggtggtc tcgcgccacg gctgcgcccc ggcgatgccg    960
agcaaaattg agctggatga ttatctcgcg cgcgccgcgc tcgttccacg cccggatctc   1020
gacccgcgtc tgaaccatct gcaccgggtc accacccgtc gccgcgaatg gccggaattg   1080
tgcgtaatgg cgttcgatca tcgcagccag cttgaagata tggcgctgca gtgcggggcg   1140
tcgctcaaac gtattccggc gctcaagcag ctgatcctgc aggccagccg cgaggcggcg   1200
agccgtgccg ggctggcagg caaagcgggc ctgctatgtg acggtacgtt tggtcaggac   1260
gcgctcaacg ccattaccgg tgaagggtgg tggatcgggc ggcccattga gctgccgggc   1320
tcccgtccgc tggagatgga gcacggcaac atcggcaccc agcttatcag ctggccgcag   1380
gagcatgtgg tgaagtgcct ggtctttttc cacccggaag atgcccacgg cctgcgcctg   1440
gagcaggagc agaaaattgc cgaggtctac cacgcctgct gccagtccgg gcatgagctg   1500
ctgctggagg tgatattgcc cgccagcatg ccgcgcagcg atgaacttta tctgcgtgcc   1560
atctcccgct tctacaacct gggtatttac ccggactggt ggaaattgcc gccgctgacg   1620
tccgatggct ggacggcact gagcgagatt atcccgcgtc gggatccgca ctgccgtggg   1680
gttgtgatcc tcgggctgga tgcgccggcc gagcagctgc gtgccgggtt taacgccgcg   1740
gcagggcacg aactggtgaa aggatttgcc gtggggcgca cgctgtttgg cgaagcttcc   1800
cgtgcatggc tgaaacacga tatcgacgat gcgcagctgg tggcgcgcat ccgggacaat   1860
tacctgcagc ttatcgcctg gtggcgcgag cgcggacacg cataa                  1905
```

<210> SEQ ID NO 39
<211> LENGTH: 296
<212> TYPE: PRT
<213> ORGANISM: Aeromonas hydrophila

<400> SEQUENCE: 39

```
Met Ser Val Gln Leu Gly Ile Asn Pro Leu Thr Trp Thr Asn Asp Asp
1               5                   10                  15

Leu Pro Ser Leu Gly Ala Glu Thr Pro Leu Glu Thr Cys Leu Ser Glu
            20                  25                  30

Gly Lys Glu Ala Gly Phe Ala Gly Phe Glu Leu Gly Asn Lys Phe Pro
        35                  40                  45

Arg Glu Ala Arg Leu Leu Gly Leu Ile Leu Gln Arg His Asp Leu Gln
    50                  55                  60

Leu Val Ser Gly Trp Tyr Ser Gly Arg Leu Leu Glu Arg Ser Val Glu
65                  70                  75                  80

Glu Glu Ile Ala Ala Val Gln Ser His Leu Thr Leu Arg Glu Leu
                85                  90                  95

Gly Ala Lys Val Leu Val Phe Ala Glu Val Ser Gly Cys Ile His Gly
            100                 105                 110

Glu Gln Gln Thr Pro Val His Leu Arg Pro Arg Phe Pro Gln Ala Arg
        115                 120                 125

Trp Lys Glu Tyr Gly Glu Lys Leu Thr Glu Phe Ala Arg Tyr Thr Gln
    130                 135                 140

Gln Gln Gly Val Gln Ile Ala Tyr His His Met Gly Thr Val Ile
145                 150                 155                 160

Glu Ser Ala Asp Asp Val Asp Asn Leu Met Thr His Thr Gly Glu Glu
                165                 170                 175

Val Gly Leu Leu Leu Asp Thr Gly His Leu Thr Phe Ala Gly Ala Asp
            180                 185                 190
```

```
Pro Leu Ala Val Ala Gln Arg Trp Ala Ser Arg Ile Asn His Val His
    195                 200                 205

Cys Lys Asp Val Arg Ala Asp Val Leu Ala Asp Val Lys Asn Arg Lys
    210                 215                 220

Thr Ser Phe Leu Asp Ala Val Leu Ser Gly Val Phe Thr Val Pro Gly
225                 230                 235                 240

Asp Gly Cys Val Asp Tyr Pro Pro Ile Met Gln Leu Leu Lys Ala Gln
                245                 250                 255

Asp Tyr His Gly Trp Leu Val Val Glu Ala Glu Gln Asp Pro Ala Ile
                260                 265                 270

Ala His Pro Phe Thr Tyr Ala Ser Met Gly Tyr Gln Asn Leu His Arg
            275                 280                 285

Phe Ala Gln Asp Ala Gly Leu Ile
    290                 295

<210> SEQ ID NO 40
<211> LENGTH: 891
<212> TYPE: DNA
<213> ORGANISM: Aeromonas hydrophila

<400> SEQUENCE: 40
atgagtgtgc aattaggcat taccccctg acgtggacta acgacgatct gccttccctt      60
ggtgccgaaa cgccgctgga gacctgtctg agcgagggga agaggctgg ttttgccggt     120 ttcgaactgg gcaacaaatt cccgcgtgaa gcgcgcctgc ttggcctcat tttgcagcgc     180
cacgatctgc agctggtctc tggctggtac tccggccgcc tgctggagcg cagcgtggaa     240
gaggagattg cagccgtgca gtcccacctg acgctgttgc gtgagctggg ggcaaaggtg     300
ctggtatttg cggaggtgag cggctgcatt cacggcgagc agcagacgcc ggtgcatctg     360
cgcccgcgct ccccgcaggc acgctggaaa gagtatggcg agaagctcac ggaatttgcc     420
cgctacactc agcagcaggg ggtgcagatt gcctatcacc accatatggg gacggtgatt     480
gagtccgccg acgacgtgga caacctgatg acccatactg gcgaagaggt cgggttgctg     540
ctggacaccg tcacctgac ctttgccggg gccgatccgc tggcggtggc gcagcgctgg     600
gcgtcgcgca tcaaccacgt tcactgcaaa gacgtgcgtg ccgatgtgct ggcggatgtc     660
aaaaaccgca aaaccagctt cctcgatgcg gtgctgagcg gcgtatttac cgtgccaggc     720
gacggctgcg tggattatcc ggccgatcatg caactgctga agcgcagga ttatcacggc     780 tggctggtgg tggaggcgga gcaggatccg gcgattgctc accccttac ctatgcatca     840 atgggctatc agaatttgca tcgttttgcg caggacgctg ggcttatctg a              891

<210> SEQ ID NO 41
<211> LENGTH: 273
<212> TYPE: PRT
<213> ORGANISM: Aeromonas hydrophila

<400> SEQUENCE: 41

Met Ser Lys Leu Leu Ser Arg His His Ser Pro Asp Gly Gln Gly Arg
1               5                   10                  15

Thr Gln Cys Ile Thr Pro Ala Ser Ala Gly Trp His Val Gly Phe
                20                  25                  30

Glu Val Tyr Glu Leu Ala Ala Ser Gln Arg Ile Glu Phe Ala Thr Gly
            35                  40                  45

Glu Asp Glu Leu Cys Leu Val Leu Val Ala Gly Leu Ala Thr Ile Ser
50                  55                  60
```

Thr Pro His Ala Arg Tyr Pro Arg Ile Gly Glu Arg Met Ser Pro Phe
65                  70                  75                  80

Glu Arg Lys Lys Pro Trp Ala Val Tyr Ile Thr Arg Gly Asp Ser Cys
            85                  90                  95

Cys Val Val Ala Glu Thr Pro Leu Glu Leu Ala Val Cys Arg Ala Pro
                100                 105                 110

Gly Lys Gly Thr Asn Pro Ser Arg Leu Ile Leu Pro Gln Asp Ile Gly
            115                 120                 125

Ala Glu Ala Arg Gly Arg Gly Asn Asn Arg Arg Phe Val His Asn Ile
130                 135                 140

Leu Pro Asp Thr Ala Leu Ala Asp Ser Leu Leu Val Val Glu Val Phe
145                 150                 155                 160

Thr Glu Glu Gly Cys Thr Ser Ser Tyr Pro Ser His Lys His Asp Thr
                165                 170                 175

Asp Asn Val Pro Asp Glu Thr Tyr Leu Glu Glu Thr Tyr Tyr His Arg
                180                 185                 190

Ile Asn Pro Pro Gln Gly Phe Cys Phe Gln Arg Val Tyr Thr Asp Asp
            195                 200                 205

Arg Thr Leu Asp Glu Ser Met Ala Val Tyr Asp Lys Asp Val Val Met
210                 215                 220

Ala Pro Arg Gly Tyr His Pro Val Ala Thr Leu Ala Gly Tyr Asp Asn
225                 230                 235                 240

Tyr Tyr Leu Asn Val Met Ala Gly Pro Val Arg Lys Trp Leu Phe Ser
                245                 250                 255

Trp Glu Ala Asp His Gln Trp Ile Asn Thr Glu Ser Tyr Ala His Thr
                260                 265                 270

Arg

<210> SEQ ID NO 42
<211> LENGTH: 822
<212> TYPE: DNA
<213> ORGANISM: Aeromonas hydrophila

<400> SEQUENCE: 42
atgtctaaac tcttgtcccg ccatcactct cctgatggac agggcagaac tcagtgcatc      60
acgcctgcgt ctgccggttg gcatcatgtg ggcttcgaag tgtatgaatt ggcggctagc     120
cagcgtatcg agtttgcgac tggtgaggat gaactctgcc tggtattggt ggctggtctt     180
gcgaccattt cgacgccaca tgctcgctat ccgcgtatag gtgagcggat gagtccgttt     240
gagcgaaaaa agccttgggc ggtttacatc acccgtggtg atagctgttg cgtggtggca     300
gaaacgccgt tagagcttgc cgtgtgccgg gctccgggta aaggtaccaa tccgtcccgt     360
ctgatactgc cacaagacat tggcgcagag gcgcgtgggc gcggtaataa tcgtcgcttt     420
gtgcacaata ttctgccaga tactgcccct gccgatagtt tgttggtggt ggaggtgttt     480
accgaagagg gttgtaccag ttcatatccg agtcataagc acgacactga caacgtccct     540
gatgagactt atctggaaga gacttactac cacaggatca atccgcctca agggttctgt     600
ttccagcgtg tgtataccga tgatcggact ctggatgaat ccatggctgt ttatgacaag     660
gatgtggtca tggctcccag aggctaccac ccggtagcta cgttggcggg ttacgataat     720
tactatctga atgtcatggc tgggccggta cgcaaatggt tgtttagctg ggaggccgac     780
catcagtgga tcaatacaga gtcctatgcg cataccagat aa                         822